(12) United States Patent
Taub

(10) Patent No.: US 10,925,852 B2
(45) Date of Patent: Feb. 23, 2021

(54) TALC-BOUND COMPOSITIONS AND USES THEREOF

(71) Applicant: THE TRUSTEES OF COLUMBIA UNIVERSITY IN THE CITY OF NEW YORK, New York, NY (US)

(72) Inventor: Robert Norman Taub, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/740,938

(22) PCT Filed: Jun. 27, 2016

(86) PCT No.: PCT/US2016/039504
§ 371 (c)(1),
(2) Date: Dec. 29, 2017

(87) PCT Pub. No.: WO2017/003908
PCT Pub. Date: Jan. 5, 2017

(65) Prior Publication Data
US 2018/0185321 A1 Jul. 5, 2018

Related U.S. Application Data

(60) Provisional application No. 62/186,870, filed on Jun. 30, 2015.

(51) Int. Cl.
| | | |
|---|---|---|
| *A61K 31/337* | (2006.01) | |
| *A61K 47/52* | (2017.01) | |
| *A61P 35/00* | (2006.01) | |
| *A61K 31/407* | (2006.01) | |
| *A61K 31/704* | (2006.01) | |
| *A61K 33/24* | (2019.01) | |
| *A61K 38/14* | (2006.01) | |
| *A61K 47/02* | (2006.01) | |
| *A61K 31/7068* | (2006.01) | |
| *A61K 9/00* | (2006.01) | |
| *A61K 47/68* | (2017.01) | |

(52) U.S. Cl.
CPC .......... *A61K 31/337* (2013.01); *A61K 9/0012* (2013.01); *A61K 9/0019* (2013.01); *A61K 31/407* (2013.01); *A61K 31/704* (2013.01); *A61K 31/7068* (2013.01); *A61K 33/24* (2013.01); *A61K 38/14* (2013.01); *A61K 47/02* (2013.01); *A61K 47/52* (2017.08); *A61K 47/6809* (2017.08); *A61P 35/00* (2018.01); *A61K 2300/00* (2013.01)

(58) Field of Classification Search
CPC .. A61K 31/337; A61K 47/6809; A61K 47/52; A61K 9/0012; A61K 9/0019; A61K 31/407; A61K 31/704; A61K 31/7068; A61K 33/24; A61K 38/14; A61K 47/02; A61P 35/00
USPC ......................................................... 514/649
See application file for complete search history.

(56) References Cited

U.S. PATENT DOCUMENTS

| | | | |
|---|---|---|---|
| 5,525,338 A | 6/1996 | Goldenberg | |
| 5,607,659 A | 3/1997 | Gustayson et al. | |
| 6,077,499 A | 6/2000 | Griffiths et al. | |
| 6,120,768 A | 9/2000 | Griffiths et al. | |
| 7,794,691 B2 | 9/2010 | Morgenstern et al. | |
| 7,935,346 B2 | 5/2011 | Paganelli et al. | |
| 8,562,947 B2 | 10/2013 | De Santis et al. | |
| 8,846,001 B2 | 9/2014 | Velikyan et al. | |
| 2003/0091565 A1 | 5/2003 | Beltzer et al. | |
| 2009/0162315 A1 | 6/2009 | Terman et al. | |
| 2010/0055093 A1 | 3/2010 | Shepard et al. | |
| 2010/0184848 A1* | 7/2010 | Wine | A61K 9/0014 514/454 |
| 2010/0255103 A1* | 10/2010 | Liong | A61K 9/5094 424/489 |
| 2010/0285088 A1 | 11/2010 | Sargeant et al. | |
| 2013/0039848 A1 | 2/2013 | Bradbury et al. | |
| 2013/0115295 A1 | 5/2013 | Wang et al. | |
| 2013/0130286 A1 | 5/2013 | Silverstein et al. | |
| 2014/0072643 A1 | 3/2014 | Desai et al. | |
| 2014/0199403 A1* | 7/2014 | Desai | A61K 31/337 424/491 |

FOREIGN PATENT DOCUMENTS

| | | | |
|---|---|---|---|
| WO | WO1993/025240 | 12/1993 | |
| WO | WO1994/004702 | 3/1994 | |
| WO | WO2003/105762 | 12/2003 | |
| WO | WO-2004093916 A1 * | 11/2004 | ......... A61K 31/4188 |
| WO | WO2006/003123 | 1/2006 | |

(Continued)

OTHER PUBLICATIONS

Paganelli et al. (Clin Cancer Res, 2007, 13, 5646s-5651s) (Year: 2007).*

(Continued)

*Primary Examiner* — Yevgeny Valenrod
(74) *Attorney, Agent, or Firm* — Dentons US LLP

(57) ABSTRACT

Provided herein are compositions and methods for treatment of a disease, disorder, or condition, such as a proliferative disease, disorder, or condition. One aspect provides a composition including a therapeutic agent and a substrate. Another aspect provides methods for treating a disease, disorder, or condition.

5 Claims, 38 Drawing Sheets

(56) References Cited

FOREIGN PATENT DOCUMENTS

| WO | WO2014/030002 | 2/2014 |
|----|---------------|--------|
| WO | WO2015/112636 | 7/2015 |

OTHER PUBLICATIONS

Healthgrades Editorial Staff (Abdominal Cancer, https://www.healthgrades.com/conditions/abdominal-cancer, retrieved from the internet on Dec. 19, 2018) (Year: 2018).*
Coester et al International Journal of Pharmaceutics 2000, 196, 147-149 (Year: 2000).*
Chinol et al European Urology, 2003, 44, 556-559 (Year: 2003).*
Chinol et al Nucl. Med. Commun. 1997, 18(2), 176-182 (Year: 1997).*
Ahn et al., Mesoporous silica nanoparticle-based cisplatin prodrug delivery and anticancer effect under reductive cellular environment, Journals of Materials Chemistry B, 2013, vol. 1, pp. 2829-2836 and Supplement 5 pages.
Bentzen, Preventing or reducing late side effects of radiation therapy: radiobiology meets molecular pathology, Nature Reviews Cancer, 2006, vol. 6; pp. 702-713.
Bolzati et al., Avidin-biotin system: a small library of cysteine biotinylated derivatives designed for the $[^{99m}Tc(N)(PNP)]^{2+}$ metal fragment, Nuclear Medicine and Biology, 2006, vol. 34, pp. 511-522.
Büller et al., Enoxaparin followed by once-weekly idrabiotaparinux versus enoxaparin plus warfarin for patients with acute symptomatic pulmonary embolism: a randomised, double-blind, double-dummy, non-inferiority trial, The Lancet, 2012, vol. 379, Issue 9811, pp. 123-129.
Caliceti et al., Poly(ethylene glycol)-avidin bioconjugates: suitable candidates for tumor pretargeting, Journal of Controlled Release, 2002, vol. 83, pp. 97-108.
Canonico, The use of human Fibrin Glue in the surgical operations, Acta Bio Medica, 2003, vol. 74, Supplement 2, pp. 21-25.
Chinol et al., Localization of Avidin in Superficial Bladder Cancer: A Potentially New Approach for Radionuclide Therapy, European Urology, 2003, vol. 44, pp. 556-559.
Desantis et al., AvidinOX™ for highly efficient tissue-pretargeted radionuclide therapy, Cancer Biotherapy and Radipharmaceuticals, 2010, vol. 25, No. 2, pp. 143-148.
Dillon et al., RNAI as an experimental and therapeutic tool to study and regulate physiological and disease processes, Annual Review of Physiology, 2005, vol. 67, pp. 147-173.
Drecoll et al., Treatment of Peritoneal Carcinomatosis by Targeted Delivery of the Radio-Labeled Tumor Homing Peptide 213Bi-DTPA-[F3]2 into the Nucleus of Tumor Cells, PLOS One, May 2009, vol. 4, Issue 5, pp. 1-9.
Dunn-Dufault et al., A solid-phase technique for preparation of no-carrier-added technetium-99m radiopharmaceuticals: application to the streptavidin/biotin system, Nuclear Medicine and Biology, 2000, vol. 27, Issue 8, pp. 803-807.
Dykxhoorn et al., The silent revolution: RNA interference as basic biology, research tool, and therapeutic, Annual Review of Medicine, 2005, vol. 56, pp. 401-423.
Elhai et al., Conjugal transfer of DNA to cyanobacteria, Methods in Enzymology, 1988, vol. 167, pp. 747-754.
Europe Supplementary Search Report dated Jan. 22, 2019 in related Application No. EP16818530.4 filed Jun. 27, 2016 (10 Pages).
Fanning et al., Gene-expressed RNA as a therapeutic: Issues to consider, using ribozymes and small hairpin RNA as specific examples, Handbook Experimental Pharmacology, 2006, vol. 173, pp. 289-303.
Fysh et al., Pleurodesis outcome in malignant pleural mesothelioma, Thorax 2013, vol. 68, No. 6, pp. 594-596.
Ghadessy et al., Directed evolution of polymerase function by compartmentalized self-replication, Proc Natl Acad Sci USA, 2001, vol. 98, No. 8, pp. 4552-4557.

Gibble et al., Fibrin glue: the perfect operative sealant?, Transfusion, 1990, vol. 30, No. 8, pp. 741-747.
Handagama et al., Incorporation of intravenously injected albumin, immunoglobulin G, and fibrinogen in guinea pig megakaryocyte granules, The Journal of Clinical Investigation, 1989, vol. 84, No. 1, pp. 73-82.
Heffner et al., Recent advances in the diagnosis and management of malignant pleural effusions, Mayo Clinic Proceedings, 2008, vol. 83, No. 2, pp. 235-250.
Helene, Control of gene expression by triple helix-forming oligonucleotides, The antigene strategy, Annals of the New York Academy of Sciences, 1992, vol. 660, pp. 27-36.
International Search Report and Written Opinion dated Apr. 13, 2015 in related PCT Application No. PCT/US15/12303 filed Jan. 21, 2015 (7 pages).
International Search Report and Written Opinion dated Sep. 19, 2016 in related International Application No. PCT/US16/39504 filed Jun. 27, 2016 (10 pages).
Knox et al., Phase II Trial of yttrium-90-DOTA-biotin Pretargeted by NR-LU-10 Antibody/Streptavidin in Patients With Metastatic Colon Cancer, Clin Cancer Res, Feb. 2000, vol. 6, Issue 2, pp. 406-414.
Lebold et al., Nanostructured silica materials as drug-delivery systems for doxorubicin: single molecule and cellular studies, Nano Letters, 2009, vol. 9, No. 8, pp. 2877-2883 and Supplement 10 pages.
Lee et al., Applications of fibrin sealant in surgery, Surgical Innovation, 2005, vol. 12, No. 3, pp. 203-213.
Lee et al., Biomarker discovery from the plasma proteome using multidimensional fractionation proteomics, Current Opinion in Chemical Biology, 2006, vol. 10, pp. 42-49.
Lee et al., Selective apoptosis of lung cancer cells with talc, European Respiratory Journal, 2010, vol. 35, No. 2, pp. 450-452.
Lewis et al., A facile, water-soluble method for modification of proteins with DOTA. Use of elevated temperature and optimized pH to achieve high specific activity and high chelate stability in radiolabeled immunoconjugates, Bioconj Chem, Nov.-Dec. 1994, vol. 5, No. 6, pp. 565-576.
Li et al., In Vivo Delivery of Silica nanorattle encapsulated docetaxel for liver cancer therapy with low toxicity and high efficacy, ACS Nano, 2010, vol. 4, No. 11, pp. 6874-6882 and Supplement 7 pages.
Lindegren et al., Pretargeted Radioimmunotherapy with α-Particle Emitting Radionuclides, Current Radiopharmaceuticals, Jul. 2011, vol. 4, Issue 3, pp. 248-260.
Link et al., Beyond toothpicks: new method for isolating mutant bacteria, Nature Reviews, 2007, vol. 5, No. 9, pp. 680-688.
Maguire et al., Efficient 1-step Radiolabeling of Monoclonal Antibodies to High Specific Activity With 225Ac for α-Particle Radioimmunotherapy of Cancer, Sep. 2014, J Nucl Med, vol. 55, Issue 9, pp. 1492-1498.
Maher, DNA triple-helix formation: An approach to artificial gene repressors?, BioEssays, 1992, vol. 14, No. 12, pp. 807-815.
Miederer et al., Realizing the potential of the Actinium-225 radionuclide generator in targeted alpha-particle therapy applications, Adv Drug Deliv Rev, 2008, vol. 60, Issue 12, pp. 1371-1382.
Minelli et al., Engineering nanocomposite materials for cancer therapy, Small-Journal, 2010, vol. 21, pp. 2336-2357.
Nagai et al., Asbestos surface provides a niche for oxidative modification, Cancer Science, 2011, vol. 102, No. 12, pp. 2118-2125.
Paganelli et al., IART (Intra-operative avidination for radionuclide therapy) for accelerated radiotherapy in breast cancer patients. Technical aspects and preliminary results of a phase II study with 90Y-labelled biotin, Ecancermedicalscience, 2010, vol. 4, Issue 166, 13 pages.
Pagel et al., Anti-CD45 pretargeted radioimmunotherapy using bismuth-213: high rates of complete remission and long-term survival in a mouse myeloid leukemia xenograft model, Blood, 2011, vol. 118, No. 3, pp. 703-711.
Pushparaj et al., Short Interfering RNA (siRNA) as a Novel Therapeutic, Clinical and Experimental Pharmacology and Physiology, 2006, vol. 33, Nos. 5-6, pp. 504-510.
Reynolds et al., Rational siRNA design for RNA interference, Nature Biotechnology, 2004, vol. 22, No. 3, pp. 326-330.

(56) References Cited

OTHER PUBLICATIONS

Sabatino et al., A New Biotin derivative-DOTA Conjugate as a Candidate for Pretargeted Diagnosis and Therapy of Tumors, J Med Chem, Jul. 2003, vol. 46, Issue 14, pp. 3170-3173.
Sagner et al., Rapid filter assay for the detection of DNA polymerase activity: identification of the gene for the DNA polymerase from *Thermus aquaticus*, Gene, 1991, vol. 97, pp. 119-121.
Sakahara et al., Avidin-biotin system for delivery of diagnostic agents, Adv Drug Deliv Rev, Apr. 1999, vol. 37, No. 1-3, pp. 89-101.
Salmaso et al., Preparation and characterization of active site protected poly(ethylene glycol)-avidin bioconjugates, Biochimica et Biophysica Acta, 2005, vol. 1726, Issue 1, pp. 57-66.
Sriram et al., Advances in pleural disease, Drug Discovery Today, Disease Mechanisms, 2007, vol. 4, No. 2, pp. 103-108.
Studier, Protein production by auto-induction in high-density shaking cultures, Protein Expression and Purification, 2005, vol. 41, Issue 1, pp. 207-234.

Turhanen et al., A novel strategy for the synthesis of enzymatically stable biotin—DOTA conjugates for in vivo use, Med Chem Comm, Jul. 25, 2011, vol. 2, pp. 886-888.
Vaidya et al., Targeted intraoperative radiotherapy versus whole breast radiotherapy for breast cancer (TARGIT-A trial): an international, prospective, randomised, non-inferiority phase 3 trial, Lancet, Jul. 2010, vol. 376, No. 9735, pp. 91-102.
Wan et al., pH-disintegrable polyelectrolyte multilayer-coated mesoporous silica nanoparticles exhibiting triggered co-release of cisplatin and model drug molecules, Macramolecular Rapid Communications, 2011, vol. 32, pp. 1082-1089.
Wilbur et al., Streptavidin in Antibody Pretargeting. 5. Chemical modificationo f recombinant streptavidin for labeling with the a-particle emitting radionuclides $^{213}$Bi and $^{211}$At, Bioconjug Chem., 2008, vol. 19, No. 1, pp. 158-170.
Yao et al., Avidin Targeting of Intraperitoneal Tumor Xenografts, JNCI Natl Cancer Inst, Jan. 1998, vol. 90, Issue 1, pp. 25-29.

\* cited by examiner

|  | 1650.3ug | 198.4ug |
|---|---|---|
| 1st Wash with PBS | 307.4 | 31.4 |
| 2nd Wash with PBS | 67.3 | 27.6 |
| 3rd Wash with PBS | 40.3 | 32.7 |
| 1st Wash with EDTA | 13.2 | 15.8 |
| 2nd Wash with EDTA | 12.3 | 19.8 |
| 3rd Wash with EDTA | 13.2 | 13 |

HRP AVIDIN Left Over in Supernatant After o/n Incubation with Talc, OD

| | Amount of HRP AVIDIN Added to Talc | | | | | |
|---|---|---|---|---|---|---|
| | 40ng/ml | 20ng/ml | 10ng/ml | 5ng/ml | 2.5ng/ml | 1.25ng/ml | 0.63ng/ml |
| 1mg Talc | 1.559 | 0.619 | 0.324 | 0.186 | 0.117 | 0.074 | 0.073 |
| 5mg Talc | 1.069 | 0.344 | 0.203 | 0.121 | 0.084 | 0.066 | 0.066 |
| 10mg Talc | 0.916 | 0.255 | 0.144 | 0.134 | 0.084 | 0.082 | 0.075 |
| 20mg Talc | 0.703 | 0.256 | 0.162 | 0.165 | 0.108 | 0.113 | 0.128 |

FIG. 8A

| HRP AVIDIN | OD |
|---|---|
| 40ng/ml | 3.802 |
| 20ng/ml | 2.814 |
| 10ng/ml | 1.500 |
| 5ng/ml | 0.725 |
| 2.5ng/ml | 0.325 |
| 1.25ng/ml | 0.256 |
| 0.63ng/ml | 0.171 |
| PBS | 0.049 |

FIG. 8B

HRP AVIDIN Binded with Talc After o/n Incubation, OD

| | Amount of HRP AVIDIN Added to Talc | | | | | | |
|---|---|---|---|---|---|---|---|
| | 40ng/ml | 20ng/ml | 10ng/ml | 5ng/ml | 2.5ng/ml | 1.25ng/ml | 0.63ng/ml |
| 1mg Talc | 2.76 | 1.12 | 0.78 | 0.47 | 0.34 | 0.37 | 0.43 |
| 5mg Talc | 2.84 | 1.10 | 0.98 | 0.97 | 0.53 | 0.54 | 0.80 |
| 10mg Talc | 3.68 | 2.79 | 1.78 | 1.66 | 0.86 | 1.14 | 0.96 |
| 20mg Talc | 3.66 | 3.33 | 3.27 | 3.39 | 2.97 | 2.83 | 3.13 |

FIG. 9A

| HRP AVIDIN | OD |
|---|---|
| 40ng/ml | 3.954 |
| 20ng/ml | 3.610 |
| 10ng/ml | 2.168 |
| 5ng/ml | 1.067 |
| 2.5ng/ml | 0.464 |
| 1.25ng/ml | 0.358 |
| 0.63ng/ml | 0.235 |
| PBS | 0.047 |

FIG. 9B

| Treatment | % Survival |
|---|---|
| Cells +62.5uM CARBO | 80 |
| Cells +1.25mg Talc | 47.64 |
| Cells+1.25mg Talc/62.5 | 47.87 |

# TALC-BOUND COMPOSITIONS AND USES THEREOF

CROSS-REFERENCE TO RELATED APPLICATIONS

The present application claims the benefit of priority to PCT International Application No. PCT/US16/39504 filed 27 Jun. 2016, which claims the benefit of U.S. Provisional Application Ser. No. 62/186,870, filed 30 Jun. 2015; each of which is incorporated herein by reference in its entirety.

STATEMENT REGARDING FEDERALLY SPONSORED RESEARCH OR DEVELOPMENT

Not Applicable.

MATERIAL INCORPORATED-BY-REFERENCE

Not Applicable.

FIELD OF THE INVENTION

The present disclosure generally relates to kits, compositions, or methods for the treatment of a disease, disorder, or condition, such as a proliferative disease, disorder, or condition, including a therapeutic composition bound to a substrate.

BACKGROUND OF THE INVENTION

Malignant pleural mesothelioma (MPM) is a rare tumor that usually forms on the tissue lining organs. The cancer is treatable but not curable. A common cause of MPM is exposure to asbestos (a silicate mineral), and although asbestos use has decreased, the cases of MPM is expected to rise. MPM can present as a pleural effusion or as localized plaque-like pleural lesions. Pleural effusion, a condition where liquid buildup in between lung walls leads to shortness of breath, affects 95% of MPM patients. MPM is conventionally treated by stripping of the pleura if possible followed by evacuation of the effusion by suction and injecting a solution of talc particles into the residual cavity to inflame the surfaces, thereby allowing the parietal and visceral pleura to adhere to each other, closing the cavity and preventing the recurrence of the effusion. Follow-up treatment includes systemic chemotherapy to remove residual cancerous cells (e.g., free-floating persistent microscopic tumor cells). But these follow-up treatments are not selective in their targeting or may not penetrate into the now poorly vascularized, inflamed, tumor-contaminated pleural space or pleurodesed surfaces. Recurrence of tumors from cancerous cells left behind can be a common outcome.

SUMMARY OF THE INVENTION

Among the various aspects of the present disclosure is the provision of a composition for treatment of a proliferative disease, disorder, or condition. In some embodiments, the compositions can include a therapeutic agent and a substrate, where the therapeutic agent is contained in or on the substrate and the substrate includes silica, silicate, or talc.

In some embodiments, the composition includes a chemotherapeutic agent. In some embodiments the therapeutic agent includes an antitumor antibiotic, anthracycline, aziridine-containing composition, nucleoside analog, taxane, or diterpene. In some embodiments, the therapeutic agent further includes a platin. In some embodiments, therapeutic agent includes bleomycin, doxorubicin, gemcitabine, mitomycin, or paclitaxel.

In some embodiments, the composition includes a therapeutic agent and a substrate; and the therapeutic agent or the substrate has specific or non-specific affinity for a target tissue associated with the disease, disorder, or condition.

In some embodiments, the substrate includes talc.

Another aspect provides a method of treating a disease, disorder, or condition in a subject.

In some embodiments, the disease, disorder, or condition comprises a proliferative disease, disorder, or condition. In some embodiments, the disease, disorder, or condition includes one or more selected from the group consisting of: a cancer, malignant pleural mesothelioma, peritoneal carcinomatosis, leukemia, lymphoma, non-small cell lung cancer, testicular cancer, lung cancer, abdominal cancer, ovarian cancer, uterine cancer, cervical cancer, pancreatic cancer, colorectal cancer, breast cancer, prostate cancer, gastric cancer, colon cancer, skin cancer, stomach cancer, liver cancer, liver metastasis, esophageal cancer, bladder cancer, appendiceal carcinoma, gastric carcinoma, pancreatic carcinoma, peritoneal mesothelioma, pseudomyxoma peritonei, blood vessel proliferative disorder, fibrotic disorder, mesangial cell proliferative disorder, psoriasis, actinic keratoses, seborrheic keratoses, warts, keloid scars, eczema, viral-associated hyperproliferative disease, papilloma viral infection, mesothelioma, Meigs Syndrome, sarcoma, appendiceal carcinoma, pseudomyxoma peritonei, prostate cancer, prostate cancer lymph node dissection beds, rectovesical pouch tumor bed, ovarian cancer resection bed and peritoneal spread, uterine cancer resection cavities, pleural and peritoneal mesothelioma resection bed and peritoneal seeding, colorectal carcinoma, appendiceal carcinoma, pancreatic carcinoma, liver metastases, gastric carcinoma, renal carcinoma, retroperitoneal tumors, retroperitoneal sarcoma, retroperitoneal carcinoma, breast cancer, breast cancer lumpectomy, breast cancer lumpectomy dissection cavity, breast cancer lymph node, breast cancer lymph node dissection cavity, melanoma, melanoma node dissection cavity, sarcoma, sarcoma resection cavities, head or neck cancer, head or neck cancer resection cavity, neck cancer lymph node, neck lymph node dissection cavities, scalp lesion, glioblastoma, glioblastoma resection cavity, brain surface tumor lesion, resected brain surface tumor lesion, non resected brain surface tumor lesion, trunk sarcoma, trunk sarcoma resection cavity, extremity sarcoma, and extremity sarcoma resection cavity, or a combination thereof. In some embodiments, the proliferative disease, disorder, or condition includes a cancer.

In some embodiments, the method includes administering the composition to the pleural space of the subject. In some embodiments, the method includes administering the composition to the subject post-operatively in or near a surgically operated area. In some embodiments, the method includes administering the composition to the subject post-operatively in a cavity where proliferative cells or tissue were surgically removed. In some embodiments, the method includes administering the composition to the subject in an amount effective to inhibit replication of cancer cells; inhibit spread of the disease, disorder, or condition; reduce tumor size; decrease tumor vascularization; increase tumor permeability; reduce recurrence of tumor growth; prevent recurrence of tumor growth; reduce a number of cancerous cells in the subject; or ameliorate a symptom of the disease, disorder, or condition.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 1A shows Biotin Rhodamine binding to talc.

FIG. 2A shows 100 µM Avidin and Avidin Rhodamine in reaction after washing with 3× with 1 ml 1×PBS.

FIG. 2B shows 100 µM Avidin and Avidin Rhodamine in reaction after washing with 3× with 1 ml 1×PBS followed by washing 3× with 0.2% EDTA.

FIG. 2C shows 10 µM Avidin and Avidin Rhodamine after washing with 3× with 1 ml 1×PBS.

FIG. 2D shows 10 µM Avidin and Avidin Rhodamine after washing with 3× with 1 ml 1×PBS followed by washing 3× with 0.2% EDTA (0.5 ml).

FIG. 2E shows 1 µM Avidin and Avidin Rhodamine after washing with 3× with 1 ml 1×PBS.

FIG. 2F shows 1 µM Avidin and Avidin Rhodamine after washing with 3× with 1 ml 1×PBS followed by washing 3× with 0.2% EDTA.

FIG. 2G shows 100 nM Avidin and Avidin Rhodamine after washing with 3× with 1 ml 1×PBS.

FIG. 2H shows 100 nM Avidin and Avidin Rhodamine after washing with 3× with 1 ml 1×PBS followed by washing 3× with 0.2% EDTA.

FIG. 2I shows 10 nM Avidin and Avidin Rhodamine after washing with 3× with 1 ml 1×PBS.

FIG. 2J shows 10 nM Avidin and Avidin Rhodamine after washing with 3× with 1 ml 1×PBS followed by washing 3× with 0.2% EDTA.

FIG. 8A shows Optical Density (OD) values for HRP Avidin remaining in supernatant following overnight incubation with talc.

FIG. 8B shows Optical Density (OD) values for HRP Avidin at varying concentrations.

FIG. 9A shows Optical Density (OD) values for HRP Avidin remaining in supernatant following overnight incubation with talc.

FIG. 9B shows Optical Density (OD) values for HRP Avidin.

DETAILED DESCRIPTION OF THE INVENTION

Figure 1A:
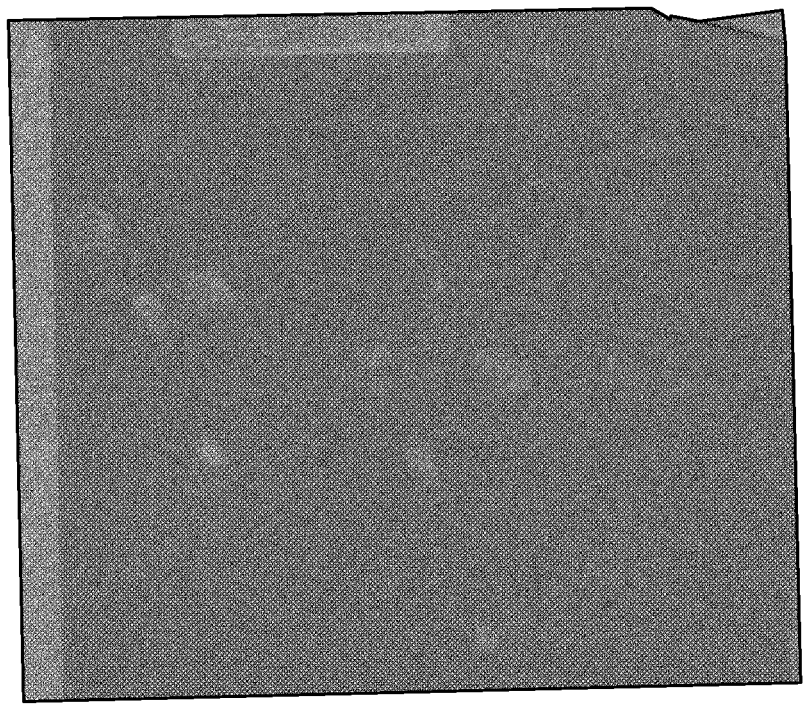
FIG. 1A-FIG. B are a series of microscopy images depicting the binding capacity of proteins to Talc using a FITC filter and a Rhodamine filter.

The present disclosure is based, at least in part, on the discovery that a combination of a therapeutic agent coupled to a molecule or substrate can be used to precisely deliver targeted therapy to a tissue of a subject in need thereof. Such an approach can provide a therapeutic agent-based targeted therapy. Various approaches described herein can prolong the life of a subject with a neoplastic disorder, such as intracavitary cancer, or supplement or replace chemotherapy.

Various technologies described herein can target cancerous cells after pleurodesis. In in one embodiment, talc (a type of mineral), or a similar silicate, functionalized with a therapeutic agent can be injected into the pleural cavity of a subject after pleurodesis. Because many therapeutic agents have an affinity for talc, therapy can be selectively targeted to a tumor-contaminated pleural space. In some embodiments, a therapeutic agent bound to a substrate (e.g., talc) can be used as a targeting agent. When pleurodesis is performed, the substrate (e.g., talc) and the therapeutic agent can be trapped in the potential pleural space formed. Accordingly, targeted therapy of a pleurodesed space can be performed (e.g., repeatedly performed) without compromising surrounding tissue, or without excessive systemic toxicity.

By linking a therapeutic agent to a molecule or substrate (e.g., talc itself or to molecules or particles that can be mixed with talc), the pleurodesed areas containing the therapeutic agent can be targeted to the areas with which they come in contact. It follows from the above that if therapeutic agent-conjugated molecules or particles (e.g., therapeutic agent-talc) can be deposited in a tissue in a controlled uniform manner, the dosage given to a subject can be precisely controlled at the site.

Various compositions and methods described herein can include the use of cytotoxic agents or chemotherapeutic agents bound to silica or talc, thus effectively killing cells in their vicinity but not significantly or substantially harming more distant tissues or bone marrow.

In one embodiment, therapeutic agent-conjugated talc can be injected into the pleural space of a subject for precisely targeting therapy of mesothelioma or other cancers occupying the pleural space needing such treatment.

The approach of combining the use of therapeutic agent-bound silica or talc in pleurodesis, so as to serve as a third party target for chemotherapy-mediated cell death has not been previously reported.

The present disclosure is based, at least in part, on the discovery that a combination of a ligand coupled to (an endogenous or exogenous) molecule or substrate and a receptor coupled to a radioisotope (or vice versa, a receptor coupled to molecule or substrate and a ligand coupled to a radioisotope) can be used to precisely deliver targeted radiotherapy to a tissue of a subject in need thereof. Such an approach can provide a ligand-based pre-target for a subsequent administration of receptor-radioisotope complex. Such an approach can be amenable to a broad array of natural and artificial materials including, but not limited to, polylactic materials, glass, or other surgical, prosthetic, implantable materials, or endogenous tissues. Various approaches described herein can prolong the life of a subject with a neoplastic disorder, such as intracavitary cancer, or supplement or replace chemotherapy.

Various technologies described herein can target cancerous cells after pleurodesis. In in one embodiment, talc (a type of mineral), or a similar silicate, functionalized with a ligand (e.g., avidin or streptavidin) can be injected into the pleural cavity of a subject after pleurodesis, and the subject can then be treated with a receptor-conjugated radioisotope (e.g., a biotin-conjugated radioisotope). Because biotin has a high affinity for avidin or streptavidin, radioisotopes can be selectively targeted to a tumor-contaminated pleural space given the presence of the avidin or streptavidin target. In some embodiments, a ligand (e.g., avidin or streptavidin) bound to substrate (e.g., talc) can be used as a pretargeting agent. When pleurodesis is performed, the substrate (e.g., talc) can be trapped in the potential pleural space formed, and the ligand (e.g., avidin or streptavidin) can serve as a target for ligand-coupled radioisotopes (e.g., biotinylated radioisotopes) (e.g., at a binding constant 10 E-15 for biotin-avidin). Accordingly, targeted radiotherapy of a pleurodesed space can be performed (e.g., repeatedly performed) without compromising surrounding tissue, or without excessive systemic toxicity.

By linking a ligand (e.g., avidin or related molecules) to a molecule or substrate (e.g., talc itself or to molecules or particles that can be mixed with talc), the pleurodesed areas containing the ligand can be positioned to bind tightly to any circulating receptor-containing small molecules (e.g., biotin-radioisotope) with which they come in contact, with an extraordinarily high association constant (e.g., 10 E-15). It follows from the above that if biodegradable ligand-conjugated molecules or particles (e.g., avidin-talc) can be deposited in a tissue in a controlled uniform manner, they can precisely determine the shape and intensity of radiotherapy delivered by alpha-emitting receptor-conjugated radioisotopes (e.g., biotin-radioisotope) attracted to the site.

Various systems described herein can include the use of receptor-conjugated alpha emitting isotopes, for example Radium 223 or Bismuth 212, which emit energetic alpha particles over a short range (e.g., about 110 microns or less), thus effectively killing cells in their vicinity but not significantly or substantially harming more distant tissues or bone marrow. In some embodiments, an isotope can be safely given repeatedly as often as weekly or monthly with no rise in side effects attributable to the drug.

In one embodiment, avidin- or streptavidin-conjugated silica or talc can be injected into the pleural space of a subject to attract biotin-labeled alpha emitting isotopes (e.g., Radium 223, Bismuth 212, Yttrium 190) for precisely targeted radiotherapy of mesothelioma or other cancers occupying the pleural space needing such treatment.

The approach of combining the use of streptavidin- or avidin-labeled silica or talc in pleurodesis, so as to serve as a third party target for radioisotope-mediated cell death has not been previously reported.

In one embodiment, a ligand (e.g., avidin or streptavidin) can be coupled directly or indirectly to fibrinogen. The ligand-fibrinogen complex can then be incorporated into a fibrin "glue", or a fibrin mesh or gel, and activated with thrombin. After activation, the ligand-fibrin glue, mesh, or gel can be used as a support, sealant, clot-promoting agent, or surgical adhesive. Thus can be provided pretargeting of difficult to reach surgical areas for postoperative radiation supplied by, e.g., intravenously injecting a receptor-radioisotope (e.g., a biotinylated alpha emitting radioisotope).

In another embodiment, a ligand (e.g., avidin or streptavidin) can be coupled to gelatin, such as can be present in a conventional surgical gelfoam (e.g., in the form of a powder or gauze). The stability of the ligand-gelfoam complex may be incrementally enhanced and adjusted by crosslinking the proteins by exposing the mixture to ultraviolet light. The gelfoam can then be used as is, or optionally incorporated into a fibrin "glue", or a fibrin mesh or gel, and activated with thrombin. The avidin-gelfoam material can itself serve as a support, sealant, clot-promoting agent, or surgical adhesive. Thus can be provided pretargeting of difficult to reach surgical areas for postoperative radiation supplied by, e.g., intravenously injecting a receptor-radioisotope (e.g., a biotinylated alpha emitting radioisotope).

Also provided are compositions, systems, or methods in which the ligand is not coupled to a molecule or substrate prior to administration to a subject. In some embodiments, a "bare" ligand has specific or non-specific binding affinity for a biological tissue associated with a disease, disorder, or condition described herein. For example, a ligand such as avidin having a highly positive charge can adhere to a negatively charged tissue, such as a peritoneal surface. Avidin administered to at or near the peritoneal membrane (e.g., by injection), where it binds. A receptor-radioisotope complex (e.g., a biotinylated radioisotope) can be directly introduced into the cavity (e.g., by radiologically guided catheter), where it would bind to avidin (or other ligand) on exposed surfaces. Intravenous avidin could simultaneously "clear" some or all isotope escaping from the peritoneal cavity.

Above exemplary compositions, systems, or methods are further described herein.

Molecule or Substrate

As described herein, a molecule or substrate, or plurality or combination thereof, can be coupled to a therapeutic agent (e.g., chemotherapeutic agent) so as to provide a therapeutic effect (e.g., a cytotoxic effect) in an area in or around the molecule or substrate.

As described herein, a molecule or substrate, or plurality or combination thereof, can be coupled to a ligand (e.g., avidin, streptavidin) so as to attract a radioisotope coupled to a corresponding receptor (e.g., biotin). Such an approach can provide targeted radiotherapy in a subject via selective binding of the ligand and receptor. A molecule can be a plurality of molecules. A substrate can be a plurality of substrates.

A molecule can be a molecule endogenous or exogenous to the subject. A molecule as described herein can be a microsphere or other particle. A molecule as described herein can be a microsphere or other particle introduced into talc. A molecule or a plurality of molecules coupled or attached to part of a ligand/receptor pair can be any molecule present in or introduced into a subject having a proliferative disease, disorder, or condition.

A substrate can be any natural or artificial material. Exemplary substrates include, but are not limited to, talc, fibrin, polymeric materials, plastics, plastic fillers, latex particles, gels, polylactic materials, microspheres, glass, proteinaceous materials, carbohydrate materials, or other surgical, prosthetic, or implantable materials, such as a mesh, suture, tissue scaffold, or other such materials.

A molecule or substrate can be an endogenous tissue of the subject (e.g., a peritoneal membrane).

Silicates, Talc.

A molecule or a plurality of molecules coupled or attached to part of a ligand/receptor pair or a therapeutic agent can be, for example, silica, silicate, or talc.

Talc is understood to be a metamorphic mineral composed of hydrated magnesium silicate with the chemical formula $H_2Mg_3(SiO_3)_4$ or $Mg_3Si_4O_{10}(OH)_2$. Talc is understood to have a tri-octahedral layered structure, similar to that of pyrophyllite, but with magnesium in the octahedral sites of the composite layers. As used herein, talc can mean a hydrated magnesium silicate (e.g., $H_2Mg_3(SiO_3)_4$ or $Mg_3Si_4O_{10}(OH)_2$), a variant thereof, or a similar silicate. For example, a molecule or a plurality of molecules coupled or attached to part of a ligand/receptor pair or a therapeutic agent can be a soft mineral similar to talc, such as steatite, pinite, pyrophyllite (a.k.a. French chalk). As another example, a molecule or a plurality of molecules coupled or attached to part of a ligand/receptor pair or a therapeutic agent can be a talc-schist, such as steatite.

Talc and asbestos are both naturally occurring silicate minerals. Asbestos is understood as a set of naturally occurring silicate minerals that share an eponymous asbestiform habit of long, thin crystals (e.g., serpentine, chrysotile, amphibole, amosite, crocidolite, tremolite, actinolite, anthophyllite, richterite, winchite). Surface features and binding characteristics of asbestos (see generally, Nagai et al. 2011 Cancer Science 102(12), 2118-2125) can be useful for characterizing binding of talc, or another silicate, to one part of a ligand/receptor pair (e.g., avidin or streptavidin) or a therapeutic agent (e.g., chemotherapeutic agent). While under no obligation to provide a mechanism, and in no way limited the scope of the present disclosure, it is presently thought that talc has a high capacity to absorb and accommodate biomolecules (e.g., a ligand or a receptor) on its surface area. Accordingly, talc or other silicates should have a high capacity for linkage to a ligand or a receptor or a therapeutic agent, as described herein. Such predictive mechanism has been confirmed by preliminary talc-avidin and talc-chemotherapeutic agent binding studies.

Fibrin.

A molecule or substrate can be fibrin. One part of a ligand/receptor pair or a therapeutic agent can be coupled or attached to fibrin. Fibrin is generally understood as a fibrous, non-globular protein involved in the clotting of blood, which can be formed by the action of protease thrombin on fibrinogen (a glycoprotein), which causes the latter to polymerize. Fibrin sealant has been used with increasing frequency in a variety of surgical field for its unique hemostatic and adhesive abilities, such as mimicking the last step of the coagulation cascade independently of a subjects coagulation status (see generally, Lee, 2005, Surg Innov, 12(3), 203-213; Gibble and Ness, 1990, Transfusion, 30(8), 741-747; Canonico, 2003, Acta Bio Medica, 74 Supp 2, 21-25; Handagama et al., 1989, J Clin Invest, 84, 73-82). Except as otherwise noted herein, therefore, the process of the present disclosure can be carried out in accordance with such uses of fibrin or fibrin glue.

In some embodiments, fibrin or fibrinogen can be coupled to a therapeutic agent. In some embodiments, fibrin or fibrinogen can be coupled to avidin. Fibrinogen can be dispensed as a "glue", where after being applied, it can be treated with thrombin (so as to polymerize and form fibrin) to produce a biotinylated clot. A subject can be given intravenous avidin to displace any unbound biotin, and some time later (e.g., about 24 hours later), a biotinylated radioisotope can be given, which would then bind to the avidin immobilized on the fibrinogen clot.

In some embodiments, fibrin or fibrinogen can be biotinylated. For example, a protein such as fibrinogen (e.g., about 10 to about 20 mg/ml) can be dialyzed against 1.0 M NaCl/0.03 M N-Tris[hydroxymethyl]methyl-2aminoethane sulfonic acid, pH 7.42. Biotinyl-epsilon-aminocaproic acid N-hydroxysuccinate ester (about 50 mg/ml in dimethylformamide) can be added (e.g., in a 1:100 dilution, vol/vol), and the mixture incubated (e.g., at 20° C. for 30 min, then at 4° C. for 90 min). Samples can then be dialyzed extensively against the NaCl/TES buffer, and finally against 0.15 M NaCl/0.0 I M NaPO4, pH 7.4, at 20° C.

The biotinylated fibrinogen can then be dispensed as a "glue", where after being applied, it can be treated with thrombin (so as to polymerize and form fibrin) to produce a biotinylated clot. Some time later (e.g., one day), the subject can be given intravenous avidin which would be expected to bind to the biotinylated fibrinogen. Unbound avidin can be expected to be cleared after some amount of time (e.g., about 2 hours, about 3 hours, or up to 24 hours). Some portion of the avidin would remain at the site of the biotinylated fibrin glue, but would present binding sites for addition of biotin, which would represent a "pretarget" for the biotinylated isotope. Biotinylated radioactive isotopes can then be injected, which would then bind to the molecule immobilized on the fibrinogen clot. Such a "double-decker" approach can allow for amplification of the number of sites to which the radioactive isotopes can bind.

A molecule (e.g., talc) coupled to a ligand (e.g., avidin) or a therapeutic agent (e.g., a chemotherapeutic agent) can be mixed, coated or suspended in or on another composition, such as a fibrin/gelatin matrix (e.g., an FDA-approved fibrin/gelatin matrix).

Gelatin or Gelfoam.

A molecule or a plurality of molecules coupled or attached to part of a ligand/receptor pair can be, for example, a gelatin. It has been discovered that positively charged avidin can form multiple linkages with a gelatin matrix, such as that used in a gelfoam. The avidin-gelatin bond can withstand repeated washing with serum. A gelfoam can be understood to be a particulate embolic agent that can temporarily occlude blood vessels for a period of time (e.g., up to five weeks) by absorbing liquid and plugging the vessel. A gelfoam can be a frequently used surgical hemostatic device. A gelfoam can be composed of water-insoluble gelatin particles that may travel distally and occlude smaller capillaries. A ligand described herein, such as avidin, can be mixed with gelatin particles so as to form a gelfoam of gelatin bound to ligand (e.g., gelatin-avidin complex). Gelfoam can be commercially available (e.g., Gelfoam®, Pfizer/Baxter). Conventional use of gelfoam is understood in the art. Except as otherwise noted herein, therefore, methods and compositions of the present disclosure (e.g., ligand-gelatin complex in a gelfoam) can be carried out in accordance with such processes.

For example, gelatin can be coupled to a ligand (e.g., avidin or streptavidin). The gelatin can be present in a conventional surgical gelfoam (e.g., in the form of a powder or gauze). The gelfoam can then be used as is, or optionally incorporated into a fibrin "glue", or a fibrin mesh or gel, and activated with thrombin. The avidin-gelfoam material can itself serve as a support, sealant, clot-promoting agent, or surgical adhesive. Thus can be provided pretargeting of difficult to reach surgical areas for postoperative radiation supplied by, e.g., intravenously injecting a receptor-radioisotope (e.g., a biotinylated alpha emitting radioisotope).

In some embodiments, the ligand-molecule or substrate complex can be exposed to ultraviolet light for a period of time sufficient to stabilize or strength the coupling there between. For example, the stability of the ligand-gelfoam complex may be incrementally enhanced and adjusted by crosslinking the proteins by exposing the mixture to ultraviolet light.

It has been discovered that gelfoam loaded with avidin may lose some of the attached material when exposed to serum. This may be a problem if the loaded gauze is placed in juxtaposition with tissues for long periods. It has further been discovered that exposing gelfoam (e.g., gauze or pellets) to ultraviolet light for varying periods of time can stabilize the bond between gelfoam and avidin while retaining an ability to bind biotin. In some embodiments, no reagents are needed other than gelfoam and avidin.

Substrate.

A therapeutic agent can be coupled to a substrate. One part of a ligand/receptor pair can be coupled or attached to a substrate. A substrate can include an implantable devices, for example: drug-delivering vascular stents (e.g., self-expanding stents typically made from nitinol, balloon-expanded stents typically prepared from stainless steel, cobalt chrome, and others); other vascular devices (e.g., grafts, catheters, valves, artificial hearts, heart assist devices); implantable defibrillators, especially defibrillator leads; blood oxygenator devices (e.g., tubing, membranes); surgical devices (e.g., sutures, staples, anastomosis devices, vertebral disks, bone pins, suture anchors, hemostatic barriers, clamps, screws, plates, clips, vascular implants, tissue adhesives and sealants, tissue scaffolds); membranes; cell culture devices; chromatographic support materials; biosensors; shunts for hydrocephalus; wound management devices; endoscopic devices; infection control devices; orthopedic devices (e.g., for joint implants, fracture repairs); dental devices (e.g., dental implants, fracture repair devices), urological devices (e.g., penile, sphincter, urethral, bladder, prostrate, vaginal, fallopian, and renal devices, and catheters); colostomy bag attachment devices; ophthalmic devices (e.g., ocular coils); glaucoma drain shunts; synthetic prostheses (e.g., breast); intraocular lenses; respiratory, peripheral, cardiovascular, spinal, neurological, dental, gastro-intestinal, gastro-esophageal (e.g., for Barrett's Esophagus or pre-cancerous esophageal tissue or cells), ear/nose/throat (e.g., ear drainage tubes) devices; renal devices; iliac devices; cardiac devices; aortic devices (e.g., grafts or stents); and dialysis devices (e.g., tubing, membranes, grafts).

Non-limiting examples of substrates include urinary catheters (e.g., surface-coated with antimicrobial agents such as vancomycin or norfloxacin), intravenous catheters (e.g., treated with additional antithrombotic agents such as heparin, hirudin, or coumadin), tissue grafts including small diameter grafts, tissue scaffolds including artificial or natural materials, vascular grafts, artificial lung catheters, atrial septal defect closures, electro-stimulation leads for cardiac rhythm management (e.g., pacer leads), glucose sensors (long-term and short-term), degradable, non-degradable, or partially degradable coronary stents, blood pressure and stent graft catheters, birth control devices, benign prostate and prostate cancer implants, bone repair/augmentation devices, breast implants, cartilage repair devices, dental implants, implanted drug infusion tubes, intravitreal drug delivery devices, nerve regeneration conduits, oncological implants, electrostimulation leads, pain management implants, spinal/orthopedic repair devices, wound dressings, embolic protection filters, abdominal aortic aneurysm grafts, heart valves (e.g., mechanical, polymeric, tissue, percutaneous, carbon, sewing cuff), valve annuloplasty devices, mitral valve repair devices, vascular intervention devices, left ventricle assist devices, neuro aneurysm treatment coils, neurological catheters, left atrial appendage filters, hemodialysis devices, catheter cuff, anastomotic closures, vascular access catheters, cardiac sensors, uterine bleeding patches, uterine stent or stent-like devices, cervix treatment devices, urological catheters/stents/implants, gastro-esophageal stents, treatments for lower esophageal sphincter, in vitro diagnostics, aneurysm exclusion devices, and neuropatches.

Non-limiting examples of substrates include vena cava filters, urinary dilators, endoscopic surgical tissue extractors, endoscopic drug or fluid delivery devices, atherectomy catheters or devices, imaging catheters or devices (e.g., Intravascular Ultrasound (IVUS), Magnetic Resonance Imaging (MRI), or Optical Coherence Tomography (OCT) catheters or devices), thrombis or clot extraction catheters or devices (e.g., thrombectomy devices), percutaneous transluminal angioplasty catheters or devices, PTCA catheters, stylets (vascular and non-vascular), guiding catheters, drug infusion catheters, esophageal stents, pulmonary stents, bronchial stents, circulatory support systems, angiographic catheters, transition sheaths and dilators, coronary and peripheral guidewires, hemodialysis catheters, neurovascular balloon catheters or devices, tympanostomy vent tubes, cerebro-spinal fluid shunts, defibrillator leads, percutaneous closure devices, drainage tubes, thoracic cavity suction drainage catheters, electrophysiology catheters or devices, stroke therapy catheters or devices, abscess drainage catheters, biliary drainage products, dialysis catheters, central venous access catheters, and parental feeding catheters or devices.

Non-limiting examples of substrates include catheters, implantable vascular access ports, blood storage bags, vascular stents, blood tubing, arterial catheters, vascular grafts, intraaortic balloon pumps, sutures (e.g., cardiovascular), total artificial hearts and ventricular assist pumps, extracorporeal devices such as blood oxygenators, blood filters, hemodialysis units, hemoperfusion units, plasmapheresis units, hybrid artificial organs such as pancreas or liver and artificial lungs, as well as filters adapted for deployment in a blood vessel in order to trap emboli (also known as "distal protection devices" or "distal embolic protection devices").

As another example, a ligand (e.g., avidin or streptavidin) or a therapeutic agent (e.g., chemotherapeutic agent) can be coupled to a biodegradable or non-biodegradable substrate, such as sutures, clips or meshes, implanted adjacent to or within delicate, relatively inaccessible surgically operated areas (e.g., pancreatic head, superior mesenteric artery region) or tumor-cell-contaminated surgical fields (e.g., surface of kidney in contact with a resected retroperitoneal sarcoma). Such an approach can pre-target the region for postoperative therapy (e.g., chemotherapy) while reducing the risk of injury (e.g., radiation or cellular toxicity) to other areas of the tissue or organ (e.g., liver or kidney).

As another example, a ligand or a therapeutic agent can be coupled to a fibrin sealant sprayed on a synthetic bioabsorbable sheet made of mixture of polyabsorable material such as a mixture of polygycolic and acid and polylactic acid (e.g., Resomer®, GMP). As another example, a ligand can be coupled to a PGA fabric, nonwoven homopolymer (e.g., Neovell, Gunze, Kyoto Japan) that hydrolozyes and disintegrates by about 50% in about 10 days, with remaining product disintegrating in about 15 weeks. As another example, a ligand or a therapeutic agent can be coupled to a transparent fibrin glue film dressing that can be sprayed onto a surface. As another example, a ligand or a therapeutic agent can be coupled to an aerosolized fibrin sealant (Bolheal, Chemo-Sero-Therapeutic Research Institute, Kumamoto. Japan). As another example, a ligand or a therapeutic agent can be coupled to an acrylic spray, such as a polymer sprayed to seal lungs (e.g., Optispray). As another example, a ligand can be coupled to a collagen or chitosan patch (e.g., chitosan g210, Pronova Biopolymer). As another example, a ligand or a therapeutic agent can be coupled to a hydrocolloid dressing (a dispersion of gelatin, pectin and carboxymethylcellulose together with other polymers and adhesives). As another example, a ligand or a therapeutic agent can be coupled to a collagen filler, such as used to hold moisture in ostomy appliances. As another example, a ligand or a therapeutic agent can be coupled to a bioengineered human collagen dermal fillers (e.g., CosmoDerm I, CosmoDem II, CosmoPlast), which contain collagen fillers and lidocaine. As another example, a ligand or a therapeutic agent can be coupled to a Bovine collagen (e.g., Zyderm I, Zyderm II, and Zyplast). As another example, a ligand can be coupled to sheets of collagen coated with fibrinogen, thrombin, or aprotinin (e.g., TachoComb®, Nycomed Pharma; TachoSil®, Takeda Pharmaceuticals).

A molecule or substrate can be composed of any suitable biocompatible, bioerodable, or bio-tolerant material including, but not limited to, gold, tantalum, iridium, platinum, nitinol, stainless steel, platinum, titanium, tantalum, nickel-titanium, cobalt-chromium, magnesium, ferromagnetic, nonferromagnetic, alloys thereof, fiber, cellulose, various biodegradable or non-biodegradable polymers, or combinations thereof. For example, a substrate can be composed of MP35N or MP20N (trade names for alloys of cobalt, nickel, chromium, and molybdenum, Standard Press Steel Co., Pa.). A substrate can be a metal (e.g., transition, actinide, or lanthanide metal). A substrate can be non-magnetic, magnetic, ferromagnetic, paramagnetic, or superparamagnetic. A substrate can further include strength-reinforcement materials that include but are not limited to, thickened sections of base material, modified surface properties (e.g., for promotion of endothelial progenitor cells), modified geometries, intermediate material, coating, fibers (such as composites, carbon, cellulose or glass), Kevlar, or other material(s).

A molecule or substrate can be composed of a biodegradable, a bioerodable, a non-biodegradable material, a non-bioerodable material, or a combination thereof. A molecule or substrate can be permanent or temporary. A temporary molecule or substrate can be resident for a period of time such as about one day, about 10 days, about 15 days, about 30 days, about 60 days, about 90 days, or longer.

A molecule or substrate can be composed, in whole or in part, of a non-biodegradable polymer such as polyetheretherketone (PEEK), PEEK derivatives, polyethyleneteraphthalate, polyetherimide, polymide, polyethylene, polyvinylfluoride, polyphenylene, polytetrafluroethylene-co-hexafluoropropylene, polymethylmethacrylate, polyetherketone, poly (ethylene-co-hexafluoropropylene), polyphenylenesulfide, polycarbonate, poly (vinylidene fluoride-co-hexafluoropropylene), poly (tetrafluoroethylene-co-ethylene), polypropylene, or polyvinylidene fluoride.

A molecule or substrate can be composed, in whole or in part, of a biodegradable materials, such as polycaprolactone, poly (D,-lactide), polyhydroxyvalerate, polyanhydrides, polyhydroxybutyrate, polyorthoesters, polyglycolide, poly (L-lactide), copolymers of lactide and glycolide, polyphosphazenes, or polytrimethylenecarbonate.

Therapeutic Agent.

As described herein, a therapeutic agent (e.g., a chemotherapeutic agent) can be coupled to a molecule or substrate. Such an approach can provide targeted therapy in a subject via binding of the therapeutic agent and molecule or substrate.

A therapeutic agent can be any agent or drug that treats any disease, disorder, or condition. A therapeutic agent can be a cytotoxic therapeutic agent.

A therapeutic agent can be a chemotherapeutic agent. A chemotherapeutic agent can be one or more anti-cancer drugs that are given as part of a standardized chemotherapy regimen. A chemotherapeutic agent can be given with a curative intent, or it may aim to prolong life or to reduce symptoms (palliative chemotherapy). A chemotherapeutic agent can be given with other therapeutic agents.

A therapeutic agent can include hormonal therapeutic agents or targeted therapeutic agents. Therapeutic agents can be used in conjunction with other treatments (e.g., cancer treatments), such as radiation therapy, surgery, or hyperthermia therapy.

Some chemotherapeutic agents can also be used to treat other conditions, including AL amyloidosis, ankylosing spondylitis, multiple sclerosis, Crohn's disease, psoriasis, psoriatic arthritis, systemic lupus erythematosus, rheumatoid arthritis, and scleroderma.

Chemotherapeutic agents can be cytotoxic. Cytotoxic agents can kill cells that divide rapidly, one property of most cancer cells. Chemotherapeutic agents can also harm cells that divide rapidly under normal circumstances: cells in the bone marrow, digestive tract, or hair follicles. This can result in the common side-effects of chemotherapy: myelosuppression (decreased production of blood cells, hence also immunosuppression), mucositis (inflammation of the lining of the digestive tract), or alopecia (hair loss).

Chemotherapeutic agents (e.g., various monoclonal antibodies) may also not be indiscriminately cytotoxic, but can target proteins that are abnormally expressed in cancer cells and are essential for their growth. Such chemotherapeutic agents can be referred to as targeted therapeutic agents (to distinguish from conventional chemotherapeutic agents) and can be used alongside traditional chemotherapeutic agents in antineoplastic treatment regimens.

Chemotherapeutic agents can be one drug (single-agent chemotherapy) or several drugs at once (e.g., combination chemotherapy or polychemotherapy). For example, the combination of chemotherapy and radiotherapy can be referred to as chemoradiotherapy. Chemotherapeutic agents using drugs that convert to cytotoxic activity only upon light exposure is called photochemotherapy or photodynamic therapy. A composition described herein can include a molecule or substrate coupled to two or more therapeutic agents.

Targeted therapeutic agents can overcome many issues seen with the use of cytotoxic agents. Targeted therapeutic agents can be localized or directed to a specific area or site of pathology. Targeted therapeutic agents can be small molecules or antibodies. The toxicity seen with the use of cytotoxics can be due to the lack of cell specificity of the drugs. Cytotoxic agents can kill a rapidly dividing cell, tumor cell, or normal cell. Targeted therapeutic agents can be designed to affect cellular proteins or processes that can be utilized by cancer cells. Targeted therapeutic agents can allow for a high dose to cancer tissues with a relatively low dose to other tissues. Targeted therapeutic agents can be used on a cancer-specific or patient-specific basis. Side effects can be often less severe than that of traditional methods of administering cytotoxic chemotherapeutic agents.

Targeted therapeutics can be selective for one protein. Targeted therapeutics can bind a range of protein targets. Targeted therapeutic agents can target the protein produced by the Philadelphia chromosome, a genetic lesion found commonly in chronic myelomonocytic leukemia. This fusion protein has enzyme activity that can be inhibited by imatinib, a small molecule drug.

Chemotherapeutic agents can be used in diseases other than cancer (e.g., autoimmune disorders, noncancerous plasma cell dyscrasia). Chemotherapeutic agents can be often used at lower doses, which can mean that the side effects are reduced or minimized. Chemotherapeutic agents, such as methotrexate, can be used in the treatment of rheumatoid arthritis (RA), psoriasis, ankylosing spondylitis, or multiple sclerosis. The anti-inflammatory response seen in RA is presently thought to be due to increases in adenosine, which can cause immunosuppression, effects on immuno-regulatory cyclooxygenase-2 enzyme pathways, reduction in pro-inflammatory cytokines, or anti-proliferative properties. Chemotherapeutic agents such as cyclophosphamide can be used to treat lupus nephritis, a common symptom of systemic lupus erythematosus. Chemotherapeutic agents such as dexamethasone, bortezomib, or melphalan (or combinations thereof) is commonly used as a treatment for AL amyloidosis. Chemotherapeutic agents such as bortezomid in combination with cyclophosphamide and dexamethasone can also treat AL amyloidosis. Chemotherapeutic agents such as lenalidomide can treat myeloma and AL amyloidosis.

A chemotherapeutic agent can be used in conditioning regimens prior to bone marrow transplant (e.g., hematopoietic stem cell transplant). Chemotherapeutic agents used in conditioning regimens can be used to suppress the recipient's immune system in order to allow a transplant to engraft. Chemotherapeutic agents such as cyclophosphamide is a common cytotoxic drug used in this manner, and can be used in conjunction with total body irradiation. Chemotherapeutic agents can be used at high doses to permanently remove the recipient's bone marrow cells (e.g., myeloablative conditioning) or at lower doses that will prevent permanent bone marrow loss (non-myeloablative and reduced intensity conditioning).

Treatment protocols described above can be adapted for compositions described herein (e.g., a molecule or substrate coupled to a therapeutic agent).

A therapeutic agent can be an antitumor antibiotic, anthracycline, platin, aziridine-containing composition, nucleoside analog, taxane, or diterpene.

As an example, a therapeutic agent can be a form of an antitumor antibiotic or anthracycline (e.g., bleomycin, bleomycin A2, bleomycin B2, actinomycin, plicamycin, mitomycin, Doxorubicin, daunorubicin, pirarubicin, aclarubicin, mitoxantrone, doxorubicin, myocet, adriamycin, Adriamycin PFS, Adriamycin RDF, rubex, doxil, caelyx, hydroxydaunorubicin, hydroxydaunomycin, AC (Adriamycin, cyclophosphamide), TAC (Taxotere, AC), ABVD (Adriamycin, bleomycin, vinblastine, dacarbazine), BEACOPP, CHOP (cyclophosphamide, hydroxydaunorubicin, vincristine, prednisone), FAC (5-fluorouracil, Adriamycin, cyclophosphamide). Antitumor antibiotics or anthracyclines can effect DNA intercalation (molecules insert between the two strands of DNA), generation of highly reactive free radicals that damage intercellular molecules, or topoisomerase inhibition. Antitumor antibiotics can effect DNA intercalation (molecules insert between the two strands of DNA), generation of highly reactive free radicals that damage intercellular molecules, or topoisomerase inhibition. Antitumor antibiotics or anthracyclines can be cytotoxic.

As another example, a therapeutic agent can be a form of a platin, a platinum-based antineoplastic (e.g., carboplatin, Paraplatin, Paraplatin-AQ, cisplatin, oxaliplatin, satraplatin, picoplatin, Nedaplatin, Triplatin, Lipoplatin). Platinum-based antineoplastic agents can cause crosslinking of DNA as monoadduct, interstrand crosslinks, intrastrand crosslinks, or DNA protein crosslinks. Platins can be cytotoxic.

As another example, a therapeutic agent can be a form of a nucleoside analog (e.g., analogue of pyrimidines, gemcitabine, cytarabine, fluorouracil, Adrucil, Carac, Efudex, Efudix, 5-FU, pyrimidine, floxuridine). Nucleotide analogues can replace a building blocks of nucleic acids (e.g. in this case of flurouracil, it replaces cytidine), during DNA replication, which can arrest tumor growth, as only one additional nucleoside can be attached to the "faulty" nucleoside, resulting in apoptosis. A nucleoside analog can be cytotoxic.

As another example, a therapeutic agent can be a form of aziridine-containing composition (e.g., mitomycin, mitomycin C, tamoxifen azidirine). Aziridine-containing composition can be a potent DNA cross-linker and can cause DNA replication arrest and cell death.

As another example, a therapeutic agent can be a form of taxane or diterpenes (e.g., paclitaxel, docetaxel, cabazitaxel, theotepa, AZQ, BZQ). Taxanes or diterpenes can disrupt of microtubule function, inhibiting the process of cell division. Taxanes or diterpenes can be cytotoxic.

A therapeutic agent can be an agent that can treat cancer. For example, a therapeutic agent can be Abiraterone Acetate; Abitrexate (Methotrexate); Abraxane (Paclitaxel Album instabilized Nanoparticle Formulation); ABVD; ABVE; ABVE-PC; AC; AC-T; Adcetris (Brentuximab Vedotin); ADE; Ado-Trastuzumab Emtansine; Adriamycin (Doxorubicin Hydrochloride); Adrucil (Fluorouracil); Afatinib Dimaleate; Afinitor (Everolimus); Akynzeo (Netupitant and Palonosetron Hydrochloride); Aldara (Imiquimod); Aldesleukin; Alemtuzumab; Alimta (Pemetrexed Disodium); Aloxi (Palonosetron Hydrochloride); Ambochlorin (Chlorambucil); Amboclorin (Chlorambucil); Aminolevulinic Acid; Anastrozole; Aprepitant; Aredia (Pam idronate Disodium); Arimidex (Anastrozole); Aromasin (Exemestane); Arranon (Nelarabine); Arsenic Trioxide; Arzerra (Ofatumumab); Asparaginase Erwinia chrysanthemi; Avastin (Bevacizumab); Axitinib; Azacitidine; BEACOPP; Becenum (Carmustine); Beleodaq (Belinostat); Belinostat; Bendamustine Hydrochloride; BEP; Bevacizumab; Bexarotene; Bexxar (Tositumomab and I 131 Iodine Tositumomab); Bicalutamide; BiCNU (Carmustine); Bleomycin; Blinatumomab; Blincyto (Blinatumomab); Bortezomib; Bosulif (Bosutinib); Bosutinib; Brentuximab Vedotin; Busulfan; Busulfex (Busulfan); Cabazitaxel; Cabozantinib-S-Malate; CAF; Campath (Alemtuzumab); Camptosar (Irinotecan Hydrochloride); Capecitabine; CAPDX; Carboplatin; CARBOPLATIN-TAXOL; Carfilzomib; Carmubris (Carmustine); Carmustine; Carmustine Implant; Casodex (Bicalutamide); CeeNU (Lomustine); Ceritinib; Cerubidine (Daunorubicin Hydrochloride); Cervarix (Recombinant HPV Bivalent Vaccine); Cetuximab; Chlorambucil; CHLORAMBUCIL-PREDNISONE; CHOP; Cisplatin; Clafen (Cyclophosphamide); Clofarabine; Clofarex (Clofarabine); Clolar (Clofarabine); CMF; Cometriq (Cabozantinib-S-Malate); COPP; COPP-ABV; Cosmegen (Dactinomycin); Crizotinib; CVP; Cyclophosphamide; Cyfos (Ifosfamide); Cyramza (Ramucirumab); Cytarabine; Cytarabine, Liposomal; Cytosar-U (Cytarabine); Cytoxan (Cyclophosphamide); Dabrafenib; Dacarbazine; Dacogen (Decitabine); Dactinomycin; Dasatinib; Daunorubicin Hydrochloride; Decitabine; Degarelix; Denileukin Diftitox; Denosumab; DepoCyt (Liposomal Cytarabine); DepoFoam (Liposomal Cytarabine); Dexrazoxane Hydrochloride; Dinutuximab; Docetaxel; Doxil (Doxorubicin Hydrochloride Liposome); Doxorubicin Hydrochloride; Doxorubicin Hydrochloride Liposome; Dox-SL (Doxorubicin Hydrochloride Liposome); DTIC-Dome (Dacarbazine); Efudex (Fluorouracil); Elitek (Rasburicase); Ellence (Epirubicin Hydrochloride); Eloxatin (Oxaliplatin); Eltrombopag Olamine; Emend (Aprepitant); Enzalutamide; Epirubicin Hydrochloride; EPOCH; Erbitux (Cetuximab); Eribulin Mesylate; Erivedge (Vismodegib); Erlotinib Hydrochloride; Erwinaze (Asparaginase Erwinia chrysanthemi); Etopophos (Etoposide Phosphate); Etoposide; Etoposide Phosphate; Evacet (Doxorubicin Hydrochloride Liposome); Everolimus; Evista (Raloxifene Hydrochloride); Exemestane; Fareston (Toremifene); Farydak (Panobinostat); Faslodex (Fulvestrant); FEC; Femara (Letrozole); Filgrastim; Fludara (Fludarabine Phosphate); Fludarabine Phosphate; Fluoroplex (Fluorouracil); Fluorouracil; Folex (Methotrexate); Folex PFS (Methotrexate); FOLFIRI; FOLFIRI-BEVACIZUMAB; FOLFIRI-CETUXIMAB; FOLFIRINOX; FOLFOX; Folotyn (Pralatrexate); FU-LV; Fulvestrant; Gardasil (Recombinant HPV Quadrivalent Vaccine); Gardasil 9 (Recombinant HPV Nonavalent Vaccine); Gazyva (Obinutuzumab); Gefitinib; Gemcitabine Hydrochloride; GEMCITABINE-CISPLATIN; GEMCITABINE-OXALIPLATIN; Gemtuzumab Ozogamicin; Gemzar (Gemcitabine Hydrochloride); Gilotrif (Afatinib Dimaleate); Gleevec (Imatinib Mesylate); Gliadel (Carmustine Implant); Gliadel wafer (Carmustine Implant); Glucarpidase; Goserelin Acetate; Halaven (Eribulin Mesylate); Herceptin (Trastuzumab); HPV Bivalent Vaccine, Recombinant; HPV Nonavalent Vaccine, Recombinant; HPV Quadrivalent Vaccine, Recombinant; Hycamtin (Topotecan Hydrochloride); Hyper-CVAD; Ibrance (Palbociclib); Ibritumomab Tiuxetan; Ibrutinib; ICE; Iclusig (Ponatinib Hydrochloride); Idamycin (Idarubicin Hydrochloride); Idarubicin Hydrochloride; Idelalisib; Ifex (Ifosfamide); Ifosfamide; Ifosfamidum (Ifosfamide); Imatinib Mesylate; Imbruvica (Ibrutinib); Imiquimod; Inlyta (Axitinib); Intron A (Recombinant Interferon Alfa-2b); Iodine 131 Tositumomab and Tositumomab; Ipilimumab; Iressa (Gefitinib); Irinotecan Hydrochloride; Istodax (Romidepsin); Ixabepilone; Ixempra (Ixabepilone); Jakafi (Ruxolitinib Phosphate); Jevtana (Cabazitaxel); Kadcyla (Ado-Trastuzumab Emtansine); Keoxifene (Raloxifene Hydrochloride); Kepivance (Paliferm in); Keytruda (Pembrolizumab); Kyprolis (Carfilzomib); Lanreotide Acetate; Lapatinib Ditosylate; Lenalidomide; Lenvatinib Mesylate; Lenvima (Lenvatinib Mesylate); Letrozole; Leucovorin Calcium; Leukeran (Chlorambucil); Leuprolide Acetate; Levulan (Aminolevulinic Acid); Linfolizin (Chlorambucil); LipoDox (Doxorubicin Hydrochloride Liposome); Liposomal Cytarabine; Lomustine; Lupron (Leuprolide Acetate); Lupron Depot (Leuprolide Acetate); Lupron Depot-Ped (Leuprolide Acetate); Lupron Depot-3 Month (Leuprolide Acetate); Lupron Depot-4 Month (Leuprolide Acetate); Lynparza (Olaparib); Marqibo (Vincristine Sulfate Liposome); Matulane (Procarbazine Hydrochloride); Mechlorethamine Hydrochloride; Megace (Megestrol Acetate); Megestrol Acetate; Mekinist (Trametinib); Mercaptopurine; Mesna; Mesnex (Mesna); Methazolastone (Temozolomide); Methotrexate; Methotrexate LPF (Methotrexate); Mexate (Methotrexate); Mexate-AQ (Methotrexate); Mitomycin C; Mitoxantrone Hydrochloride; Mitozytrex (Mitomycin C); MOPP; Mozobil (Plerixafor); Mustargen (Mechlorethamine Hydrochloride); Mutamycin (Mitomycin C); Myleran (Busulfan); Mylosar (Azacitidine); Mylotarg (Gemtuzumab Ozogamicin); Nanoparticle Paclitaxel (Paclitaxel Albumin-stabilized Nanoparticle Formulation); Navelbine (Vinorelbine Tartrate); Nelarabine; Neosar (Cyclophosphamide); Netupitant and Palonosetron Hydrochloride; Neupogen (Filgrastim); Nexavar (Sorafenib Tosylate); Nilotinib; Nivolumab; Nolvadex (Tamoxifen Citrate); Nplate (Romiplostim); Obinutuzumab; OEPA; Ofatumumab; OFF; Olaparib; Omacetaxine Mepesuccinate; Oncaspar (Pegaspargase); Ontak (Denileukin Diftitox); Opdivo (Nivolumab); OPPA; Oxaliplatin; Paclitaxel; Paclitaxel Albumin-stabilized Nanoparticle Formulation; PAD; Palbociclib; Paliferm in; Palonosetron Hydrochloride; Pamidronate Disodium; Panitumumab; Panobinostat; Paraplat (Carboplatin); Paraplatin (Carboplatin); Pazopanib Hydrochloride; Pegaspargase; Peginterferon Alfa-2b; PEG-Intron (Peginterferon Alfa-2b); Pembrolizumab; Pemetrexed Disodium; Perjeta (Pertuzumab); Pertuzumab; Platinol (Cisplatin); Platinol-AQ (Cisplatin); Plerixafor; Pomalidomide; Pomalyst (Pomalidomide); Ponatinib Hydrochloride; Pralatrexate; Prednisone; Procarbazine Hydrochloride; Proleukin (Aldesleukin); Prolia (Denosumab); Promacta (Eltrombopag Olamine); Provenge (Sipuleucel-T); Purinethol (Mercaptopurine); Purixan (Mercaptopurine); Radium 223 Dichloride; Raloxifene Hydrochloride; Ramucirumab; Rasburicase; R-CHOP; R-CVP; Recombinant Human Papillomavirus (HPV) Bivalent Vaccine; Recombinant Human Papillomavirus (HPV) Nonavalent Vaccine; Recombinant Human Papillomavirus (HPV) Quadrivalent Vaccine; Recombinant Interferon Alfa-2b; Regorafenib; R-EPOCH; Revlimid (Lenalidomide); Rheumatrex (Methotrexate); Rituxan (Rituximab); Rituximab; Rom idepsin; Rom iplostim; Rubidomycin (Daunorubicin Hydrochloride); Ruxolitinib Phosphate; Sclerosol Intrapleural Aerosol (Talc); Siltuximab; Sipuleucel-T; Somatuline Depot (Lanreotide Acetate); Sorafenib Tosylate; Sprycel (Dasatinib); STANFORD V; Sterile Talc Powder (Talc); Steritalc (Talc); Stivarga (Regorafenib); Sunitinib Malate; Sutent (Sunitinib Malate); Sylatron (Peginterferon Alfa-2b); Sylvant (Siltuximab); Synovir (Thalidomide); Synribo (Omacetaxine Mepesuccinate); TAC; Tafinlar (Dabrafenib); Talc; Tamoxifen Citrate; Tarabine PFS (Cytarabine); Tarceva (Erlotinib Hydrochloride); Targretin (Bexarotene); Tasigna (Nilotinib); Taxol (Paclitaxel); Taxotere (Docetaxel); Temodar (Temozolomide); Temozolomide; Temsirolimus; Thalidomide; Thalom id (Thalidomide); Thiotepa; Toposar (Etoposide); Topotecan Hydrochloride; Toremifene; Torisel (Temsirolimus); Tositumomab and I 131 Iodine Tositumomab; Totect (Dexrazoxane Hydrochloride); TPF; Trametinib; Trastuzumab; Treanda (Bendamustine Hydrochloride); Trisenox (Arsenic Trioxide); Tykerb (Lapatinib Ditosylate); Unituxin (Dinutuximab); Vandetanib; VAMP; Vectibix (Panitumumab); VeIP; Velban (Vinblastine Sulfate); Velcade (Bortezomib); Velsar (Vinblastine Sulfate); Vemurafenib; VePesid (Etoposide); Viadur (Leuprolide Acetate); Vidaza (Azacitidine); Vinblastine Sulfate; Vincasar PFS (Vincristine Sulfate); Vincristine Sulfate; Vincristine Sulfate Liposome; Vinorelbine Tartrate; VIP; Vismodegib; Voraxaze (Glucarpidase); Vorinostat; Votrient (Pazopanib Hydrochloride); Wellcovorin (Leucovorin Calcium); Xalkori (Crizotinib); Xeloda (Capecitabine); XELIRI; XELOX; Xgeva (Denosumab); Xofigo (Radium 223 Dichloride); Xtandi (Enzalutamide); Yervoy (Ipilimumab); Zaltrap (Ziv-Aflibercept); Zelboraf (Vemurafenib); Zevalin (Ibritumomab Tiuxetan); Zinecard (Dexrazoxane Hydrochloride); Ziv-Aflibercept; Zoladex (Goserelin Acetate); Zoledronic Acid; Zolinza (Vorinostat); Zometa (Zoledronic Acid); Zydelig (Idelalisib); Zykadia (Ceritinib); or Zytiga (Abiraterone Acetate).

For example, a therapeutic agent can be:

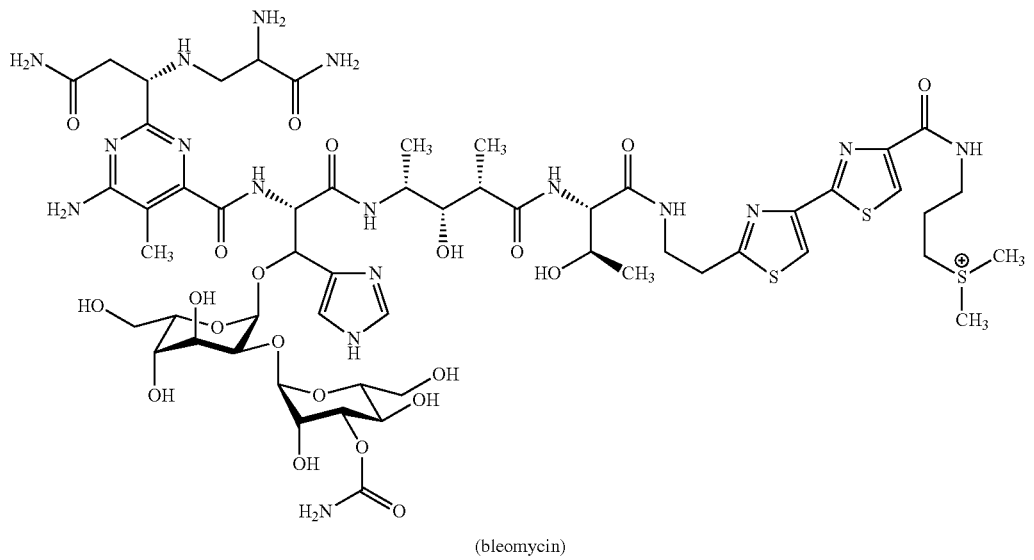

(bleomycin)

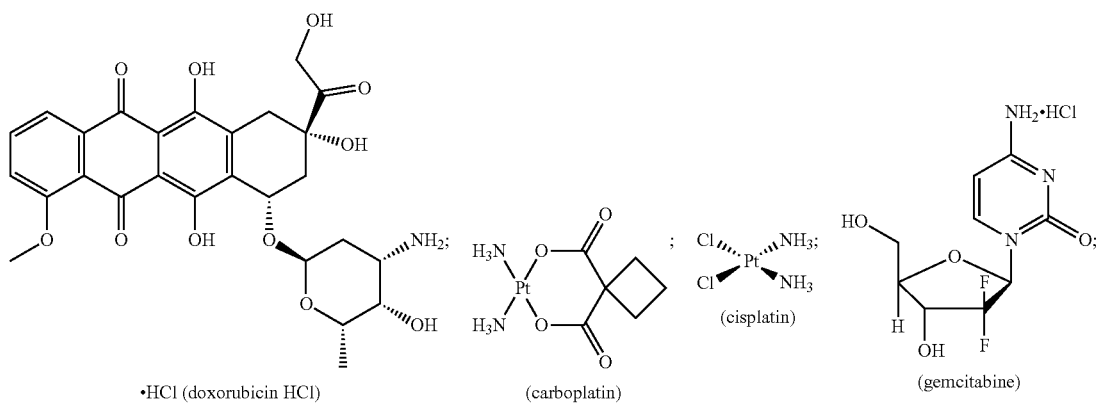

·HCl (doxorubicin HCl)    (carboplatin)    (cisplatin)    (gemcitabine)

-continued

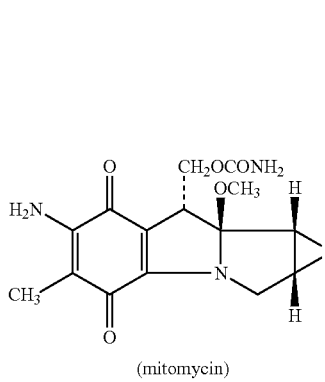

(mitomycin)

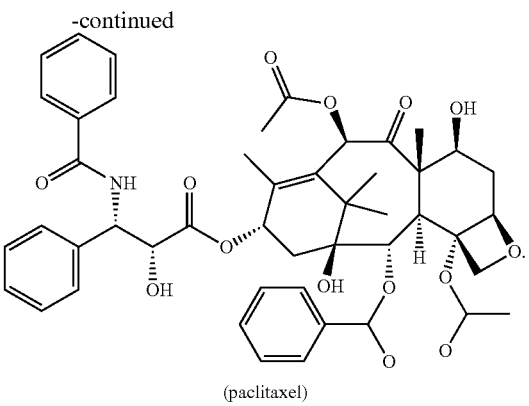

(paclitaxel)

Ligand

As described herein, a ligand (e.g., a streptavidin, an avidin) can be coupled to a molecule or substrate so as to attract a radioisotope coupled to a corresponding receptor. Such an approach can provide targeted radiotherapy in a subject via selective binding of the ligand and receptor. A ligand can be selective or non-selective for a receptor. A ligand can be preferably selective for a receptor (or vice versa, a receptor can be preferably selective for a ligand).

Streptavidin.

A ligand can be a streptavidin. A streptavidin can be a protein having a high affinity for biotin (e.g., $K_d$ of about $10^{-14}$ mol/L). A streptavidin or a nucleotide encoding such, can be isolated from the bacterium *Streptomyces* (e.g., *Streptomyces avidinii*). A streptavidin can be any commercially available streptavidin (e.g., Invitrogen; Qiagen; Thermo Scientific; Jackson ImmunoResearch; Sigma Aldrich; Cell Signaling Technology). A streptavidin can be a variant of a naturally occurring streptavidin having at least about 80%, 85%, 90%, 95%, or 99% sequence identity thereto and retaining or substantially retaining high affinity for biotin. A streptavidin can be a tetramer, with each subunit binding a biotin with equal or substantially equal affinity. A streptavidin can have a mildly acidic isoelectric point (pI) (e.g., about 5). A streptavidin can lack any carbohydrate modification. Where a streptavidin has no carbohydrate modification and a near-neutral pI, it can have substantially lower nonspecific binding compared to avidin.

A streptavidin can be an streptavidin coupled to a glycan. A streptavidin can be a glycol streptavidin (e.g., a, ethylene glycol streptavidin; or an streptavidin-poly (ethylene glycol) (PEG)). In some embodiments, a streptavidin be attached in a branched form incorporating polyethylene glycol (e.g., PEG-streptavidin), which can give the streptavidin a branched structure, allowing it to bind more biotin.

A streptavidin can be a streptavidin variant. For example, a streptavidin can be a monovalent, divalent, and trivalent variant. As another example, a variant streptavidin can have a near-neutral pI.

Avidin.

A ligand can be an avidin. An avidin can be a protein having a high affinity for biotin (e.g., $K_d$ of about $10^{-15}$ mol/L). An avidin or a nucleotide encoding such, can be isolated from egg white. Wild type avidin has about 30% sequence identity to wild type streptavidin, but highly similar secondary, tertiary and quaternary structure. An avidin can be glycosylated, positively charged, or have pseudo-catalytic activity (i.e., enhance alkaline hydrolysis of an ester linkage between biotin and a nitrophenyl group) or can have a higher tendency for aggregation as compared to a streptavidin. An avidin can be a tetramer of about 66-69 kDa in size. An avidin can have about 10% of molecular weight attributed to carbohydrate content composed of about 4 to 5 mannose or about three N-acetylglucosamine residues.

An avidin can be a streptavidin variant. For example, an avidin can be a non-glycosylated avidin. As another example, an avidin can be a deglycosylated avidin (e.g., Neutravidin), which can be more comparable to the size, pI or nonspecific binding of a wild type streptavidin. As another example, an avidin can be a deglycosylated avidin having modified arginines, exhibiting a more neutral isoelectric point (pI) and can better overcome problems of non-specific binding. Deglycosylated, neutral forms of avidin are commercially available (e.g., Extravidin, Sigma-Aldrich; Neutravidin, Thermo Scientific or Invitrogen; NeutraLite, Belovo). As another example, an avidin can be an avidin coupled to a glycan. As another example, an avidin can be a glycol avidin (e.g., a, ethylene glycol avidin; or an avidin-poly(ethylene glycol) (avidin-PEG)) (see generally, Caliceti et al., 2002, Journal of Controlled Release, 83, 97-108; Salmaso et al., 2005, Biochimica et Biophysica Acta, 1726, 57-66). In some embodiments, an avidin be attached in a branched form incorporating polyethylene glycol (e.g., PEG-avidin), which can give the avidin a branched structure, allowing it to bind more biotin.

An avidin can be a variant AvidinOX™, which can be obtained by 4-hydroxyazobenzene-2'-carboxylic acid-assisted sodium periodate oxidation of avidin (see generally De Santis et al., 2010, Cancer Biother Radiopharm, 25(2), 143-148; U.S. Pat. No. 8,562,947). This method can generate aldehyde groups from avidin carbohydrates, sparing biotin-binding sites from inactivation. An avidin variant, such as AvidinOX, can have an increased tissue half-life (e.g., one, two, or more weeks).

In some embodiments, avidin can be pegylated to produce a much larger molecule (e.g., MW>100 kDA) with more binding sites, and then periodation can be used to form Schiff bases, which could then bind tightly to the amino groups of proteins. The pegylated molecule would be too large to pass easily out of the peritoneal cavity; and it could be introduced in a large volume of solution, and be allowed to attach to surfaces, then flushed out, and biotinylated isotopes (e.g., tracer biotinylated isotopes) could then be introduced, which would likewise coat the surfaces, and allowed to remain.

An avidin can have reversible binding characteristics through nitration or iodination of a binding site tyrosine, or exhibit strong biotin binding characteristics at about pH 4 or biotin release at a pH of about 10 or higher. An avidin can be a monovalent, divalent, and trivalent variant of avidin.

Processes for linking a ligand, such as avidin or streptavidin, to a molecule or substrate are well known (see e.g. Savage, 1992, Avidin-Biotin Chemistry: A Handbook, Pierce Chemical Co, ISBN-10 0935940111, ISBN-13 978-0935940114; McMahon, 2010, Avidin-Biotin Interactions: Methods and Applications, Humana Press, ASIN B00GA4420E; Hermanson, 2010, Bioconjugate Techniques, Academic Press, ASIN B005YXETUU). Except as otherwise noted herein, therefore, the process of the present disclosure can be carried out in accordance with such processes.

In some embodiments, avidin can be coupled to talc, for example, using both Rhodamine and fluorescein avidin bound to talc then thrice washed, or using HRP-labeled avidin, which has shown saturation of binding (e.g., from 1:10 to 10:1 HRP to natural Avidin, e.g., 1:1). In some embodiments, talc can bind in excess of 2 nanograms of avidin per mg of talc (i.e., about 2 micrograms per gram). For context, about 2 grams of talc can be conventionally used for pleurodesis.

Molecularly Imprinted Polymer.

A ligand can be a molecularly imprinted polymer (MIP). A MIP is understood as a synthetic compound that can select, recognize or capture biological substances. MIPs can be generated via the polymerization of monomers in the presence of a template (see generally, Alvarez-Lorenzo and Concheiro, Ed., 2013, Handbook of Molecularly Imprinted Polymers, Smithers Rapra Technology, ISBN-10: 1847359604).

A MIP can be processed using a molecular imprinting technique that leaves cavities in polymer matrix with affinity to a chosen "template" molecule. The process can involve initiating polymerization of monomers in the presence of a template molecule that can be extracted afterwards, thus leaving complementary cavities behind. Such polymers can have affinity for the original molecule and have been used in applications such as chemical separations, catalysis, or molecular sensors. Binding activity of MIPs, or so called "plastic antibodies", can be about two orders of magnitude lower than specific antibodies but are still highly specific binding sites that can be made easily and are relatively inexpensive.

MIPs can be generated as specific for receptors described herein. For example, MIPs can be specific for biotin (see e.g., WO2014/030002). MIPs can be coupled to a molecule or substrate described herein.

Radioisotope

As described herein, a radioisotope can be coupled to a receptor so as to provide targeted radiotherapy via selective binding to a molecule or substrate coupled to a ligand. Systemic radioisotope therapy can be a form of targeted therapy. As described herein, targeting a radioisotope can be achieved by attaching it to one part of a ligand/receptor combination, where the other part can be attached to a target.

A radioisotope can be used to destroy or weaken cells associated with a proliferative disease, disorder, or condition. A radioisotope that generates radiation can be localized in a desired location (e.g., a tissue) according to approaches described herein. In some embodiments, beta radiation from the radioisotope can result in the destruction of cells, which is a process understood as radionuclide therapy (RNT) or radiotherapy. Short-range radiotherapy may be known as brachytherapy.

A radioisotope for use with compositions and methods described herein can be a strong beta emitter, optionally with sufficient gamma to enable imaging, such as lutetium-177. Lutetium-177 can be prepared from ytterbium-176, which is irradiated to become Yb-177, which decays rapidly to Lu-177. Lu-177 can emit sufficient beta radiation for therapy on small (e.g., endocrine) tumors.

Another exemplary radioisotope for use with compositions and methods described herein includes Yttrium-90, which can be conventionally used for treatment of cancer, particularly non-Hodgkin's lymphoma and liver cancer, and as a silicate colloid for the relieving the pain of arthritis in larger synovial joints.

Other exemplary radioisotopes for use with compositions and methods described herein include Iodine-131 or phosphorus-32. Iodine-131 has been conventionally used to treat the thyroid for cancers and other abnormal conditions such as hyperthyroidism (i.e., over-active thyroid). Iodine-131 is a strong gamma emitter, and can be conventionally used for beta therapy. Phosphorus-32 has been conventionally used to treat Polycythemia vera, in which an excess of red blood cells is produced in the bone marrow and Phosphorus-32 can be used to control this excess.

Another exemplary radioisotope for use with compositions and methods described herein includes boron-10. A subject administered a composition including Boron-10 can be irradiated with neutrons which are strongly absorbed by the boron, to produce high-energy alpha particles that can kill cells including those associated with a proliferative disease, disorder, or condition.

Another exemplary radioisotope for use with compositions and methods described herein includes Radium-223, which can be conventionally used for treatment of prostate cancer.

Another exemplary radioisotope for use with compositions and methods described herein includes bismuth-213. Bismuth-213, having a 46-minute half-life and high energy (8.4 MeV), can be formed from readily available Actinium-225 (via 3 alpha decays).

Another exemplary radioisotope for use with compositions and methods described herein includes lead-212, having a half-life of 10.6 hours. Lead-212 has been conventionally attached to monoclonal antibodies for cancer treatment. Such approaches can be adapted for methods and compositions described herein. The decay chain of lead-212 includes the short-lived isotopes bismuth-212 by beta decay, polonium-212 by beta decay, and thallium-208 by alpha decay of the bismuth, with further alpha and beta decays respectively to Pb-208, all over about an hour.

Other exemplary radioisotopes for use with compositions and methods described herein include Holmium-166, having a 26 hour half-life and conventionally used for treatment of liver tumor; Dysprosium-165, having a 2 hour half-life and conventionally used as aggregated hydroxide for synovectomy treatment of arthritis; Erbium-169, having a 9.4 day half-life and conventionally used for relieving arthritis pain in synovial joints; Holmium-166, having a 26 hour half-life and conventionally used for treatment of liver tumors; Iodine-125, having a 60 day half-life and conventionally used in cancer brachytherapy, including prostate and brain; Iridium-192, a beta emitter having a 74 day half-life; Rhenium-186, having a 3.8 day half-life, conventionally used for pain relief in bone cancer; Rhenium-188, having a 17 hour half-life, conventionally used to beta irradiate coronary arteries; Samarium-153, having a 47 hour half-life, conventionally used for relieving pain of secondary cancers lodged in the bone and for prostate and breast cancer; Strontium-89, having a 50 day half-life, conventionally used for reducing pain of prostate and bone cancer; and radioisotopes of caesium, gold or ruthenium.

Radioisotopes can be obtained from a variety or commercial or research sources including, but not limited to MDS Nordion, IRE, Covidien, NTP, ANSTO, and Isotop-NIIAR.

A conjugated radioisotope can be administered by any conventional route. For example, a conjugated radioisotope can be delivered through infusion (e.g., into the bloodstream) or ingestion.

In some embodiments, yttrium-90 radioactive glass or resin microspheres (e.g., SIR-Spheres and TheraSphere) coupled to a receptor, such as biotin, can be injected into the hepatic artery to radioembolize liver tumors or liver metastases. Such microspheres can be used in treatment approach known as selective internal radiation therapy. The microspheres can be approximately 30 μm in diameter and can be delivered directly into an artery supplying blood to the tumors. Such treatments can begin by guiding a catheter up through the femoral artery in the leg, navigating to the desired target site and administering treatment. A molecule or substrate coupled to a ligand, such as avidin or biotin, can be introduced into tissue at, in or near a tumor. Blood feeding the tumor can carry the microspheres directly to the tumor, allowing specific binding to the ligand-coupled molecule or substrate, thus providing a more selective approach than traditional systemic chemotherapy.

In some embodiments, a receptor (e.g., biotin) coupled to strontium-89 or samarium (153Sm) lexidronam can be used in the treatment of bone metastasis from cancer. The coupled radioisotopes can travel selectively to areas of damaged bone, in or around which have been introduced a ligand (e.g., avidin or streptavidin) coupled to a molecule or substrate, and spare normal undamaged bone.

In some embodiments, a receptor (e.g., biotin) can be coupled to ibritumomab tiuxetan (i.e., Zevalin), which is an FDA approved anti-CD20 monoclonal antibody conjugated to yttrium-90. In some embodiments, a receptor (e.g., biotin) can be coupled to one or more parts of tositumomab/ iodine ($^{131}$I) tositumomab regimen (Bexxar), which is a combination of an iodine-131 labeled and an unlabeled anti-CD20 monoclonal antibody. Such medications can be used for, e.g., the treatment of refractory non-Hodgkin's lymphoma according to approaches described herein.

Coupling can be any type attraction, link, or reaction that serves to immobilize a ligand on a molecule. Coupling can be via a bond. A radioisotope-receptor bond is understood as an attraction between atoms of a radioisotope and atoms of a receptor that allows the formation of a linkage between atoms of the biomolecule and the matrix material. A bond can be caused by an electrostatic force of attraction between opposite charges, either between electrons and nuclei, or as the result of a dipole attraction. A bond (e.g., between a biomolecule and a matrix material) can be, for example, a covalent bond, a coordinate covalent bond, an ionic bond, polar covalent, a dipole-dipole interaction, a London dispersion force, a cation-pI interaction, or hydrogen bonding.

Process for coupling a radioisotope to a receptor or ligand (e.g., biotin) are well known (see, e.g., Savage, 1992, Avidin-Biotin Chemistry: A Handbook, Pierce Chemical Co, ISBN-10 0935940111, ISBN-13 978-0935940114; McMahon, 2010, Avidin-Biotin Interactions: Methods and Applications, Humana Press, ASIN B00GA4420E; Hermanson, 2010, Bioconjugate Techniques, Academic Press, ASIN B005YXETUU; Bolzati et al., 2006, Nuclear Medicine and Biology, 34, 511-522; Runn-Dufault et al., 2000, Nuclear Medicine and Biology, 27, 803-807). Except as otherwise noted herein, therefore, the process of the present disclosure can be carried out in accordance with such processes.

Receptor

As described herein, a receptor (e.g., a biotin) can be coupled to a radioisotope so as to provide targeted radiotherapy via selective binding to a molecule or substrate coupled to a ligand. A receptor can be selective or nonselective for a ligand. A receptor can be preferably selective for a ligand (or vice versa, a ligand can be preferably selective for a receptor).

Biotin.

A receptor can be a biotin. A biotin can be a water soluble B-complex vitamin (e.g., vitamin $B_7$, vitamin H, or coenzyme R). A biotin can be a heterocyclic sulfur-containing (mono-)carboxylic acid. A biotin can comprise an imidazole ring and thiophene ring fused. A biotin can comprise a ureido (tetrahydroimidizalone) ring fused with a tetrahydrothiophene ring, optionally with a veleric acid substituent on a carbon of the tetrahydrothiophene ring.

Streptavidin or avidin can bind biotin with high affinity (e.g., $K_d$ of $10^{-14}$ mol/L to $10^{-15}$ mol/l) and specificity.

A biotin can be any commercially available biotin (e.g., Invitrogen; Qiagen; Thermo Scientific; Jackson ImmunoResearch; Sigma Aldrich; Cell Signaling Technology). A biotin can be a variant compound of a naturally occurring biotin that retains or substantially retaining high affinity for streptavidin.

A biotin can have a structural formula according to C10 H16 O3 N2 S. A biotin can have a structure as follows:

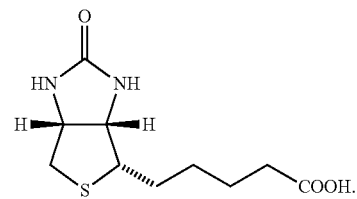 [SMILES: O=C(O)CCCC[C@@H]1SC[C@@H]2NC(=O)N[C@@H]21]

Biotin can be attached to a molecule or substrate by biotinylation. Biotinylated proteins of interest can be isolated from a sample by exploiting this highly stable interaction.

Biotinylation can be the process of covalently attaching a biotin to a molecule or substrate. Biotinylation can be generally rapid, specific and can be unlikely to perturb the natural function of the molecule or substrate to which it is attached given the small size of a biotin (e.g., MW=244.31 g/mol). Biotin can bind to streptavidin or avidin with an extremely high affinity, fast on-rate, and high specificity, and these interactions can be exploited as described herein. Biotin-binding to streptavidin or avidin can be resistant to extremes of heat, pH, or proteolysis, which can allow use of a biotinylated molecule or substrate in a wide variety of environments. Furthermore, multiple biotin molecules can be conjugated to a molecule or substrate, which can allow binding of multiple streptavidin, avidin, or Neutravidin. A large number of biotinylation reagents are know in the art and commercially available.

Various assays are available to determine extent of biotinylation.

The HABA (2-(4-hydroxyazobenzene) benzoic acid) assay can be used to determine the extent of biotinylation. HABA dye can be bound to avidin or streptavidin and yields a characteristic absorbance. When biotinylated proteins or other molecules are introduced, the biotin displaces the dye, resulting in a change in absorbance at 500 nm. This change can be directly proportional to the level of biotin in the sample. A HABA assay can require a relatively large amount of sample.

Extent of biotinylation can also be measured by streptavidin gel-shift, since streptavidin remains bound to biotin during agarose gel electrophoresis or polyacrylamide gel electrophoresis. The proportion of target biotinylated can be measured via the change in band intensity of the target with or without excess streptavidin, seen quickly and quantitatively by Coomassie Brilliant Blue staining.

Biotinylation, also called biotin labeling, can be most commonly performed through chemical means, although enzymatic methods are also available. Chemical biotinylation can use various conjugation chemistries to yield a nonspecific biotinylation of amines, carboxylates, sulfhydryls or carbohydrates (e.g., NHS-coupling gives biotinylation of a primary amines). Chemical biotinylation reagents can include a reactive group attached via a linker to the valeric acid side chain of biotin. Because the biotin binding pocket in avidin or streptavidin can be buried beneath the protein surface, a biotinylation reagent possessing a longer linker can be desirable, as such longer linker can enable the biotin molecule to be more accessible to binding avidin, streptavidin, or Neutravidin. A linker can also mediate the solubility of a biotinylation reagent. Linkers that incorporate poly(ethylene) glycol (PEG) can make water-insoluble reagents soluble or increase the solubility of biotinylation reagents that are already soluble to some extent.

Primary Amine Biotinylation.

Biotin can be conjugated to an amine group on the molecule or substrate. A primary amine group can be present as a lysine side chain epsilon-amine or N-terminal α-amine. Amine-reactive biotinylation reagents can be divided into two groups based on water solubility.

N-hydroxysuccinimide (NHS) esters have poor solubility in aqueous solutions. For reactions in aqueous solution, NHS can be first be dissolved in an organic solvent, then diluted into the aqueous reaction mixture. Commonly used organic solvents for this purpose can include dimethyl sulfoxide (DMSO) and dimethyl formamide (DMF). Because of the hydrophobicity of NHS-esters, NHS biotinylation reagents can also diffuse through the cell membrane, meaning that they will biotinylate both internal and external components of a cell.

Sulfo-NHS esters are more soluble in water and can be dissolved in water just before use because they hydrolyze easily. The water solubility of sulfo-NHS-esters can be due at least in part from a sulfonate group on the N-hydroxysuccinimide ring. Water solubility can eliminate a need to dissolve the reagent in an organic solvent. Sulfo-NHS-esters of biotin do not penetrate the cell membrane.

The chemical reactions of NHS- and sulfo-NHS esters can be identical, in that they can both react spontaneously with amines to form an amide bond. Because the target for the ester is a deprotonated primary amine, the reaction can be favored under basic conditions (above pH 7). Hydrolysis of the NHS ester can be a major competing reaction, and the rate of hydrolysis increases with increasing pH. NHS- and sulfo-NHS-esters have a half-life of several hours at pH 7 but only a few minutes at pH 9.

There can be additional flexibility in the conditions for conjugating NHS-esters to primary amines. Incubation temperatures can range from about 4-37° C., pH values in the reaction range from about 7-9, or incubation times range from a few minutes to about 12 hours. Buffers containing amines (e.g., Tris or glycine) can be avoided, because they compete with the reaction.

Sulfhydryl Biotinylation

An alternative to primary amine biotinylation can be to label sulfhydryl groups with biotin. Sulfhydryl-reactive groups such as maleimides, haloacetyls, or pyridyl disulfides, can require free sulfhydryl groups for conjugation; disulfide bonds can be first reduced to free up the sulfhydryl groups for biotinylation. If no free sulfhydryl groups are available, lysines can be modified with various thiolation reagents (Traut's Reagent, SAT(PEG4), SATA and SATP), resulting in the addition of a free sulfhydryl. Sulfhydryl biotinylation can be performed at a slightly lower pH (e.g., about 6.5-7.5) than labeling with NHS esters.

Carboxyl Biotinylation.

Biotinylation reagents that target carboxyl groups do not have a carboxyl-reactive moiety per se but instead rely on a carbodiimide crosslinker such as EDC to bind the primary amine on a biotinylation reagent to a carboxyl group on the target.

Biotinylation at carboxyl groups can occur at a pH of about 4.5-5.5. To prevent crossreactivity of the crosslinker with buffer constituents, buffers should not contain primary amines (e.g., Tris, glycine) or carboxyls (e.g., acetate, citrate).

Glycoprotein Biotinylation

Glycoproteins can be biotinylated by modifying the carbohydrate residues to aldehydes, which can then react with hydrazine- or alkoxyamine-based biotinylation reagents. Sodium periodate can oxidize a sialic acid on glycoproteins to aldehydes to form these stable linkages at a pH of about 4-6.

Antibodies can be heavily glycosylated, and because glycosylation does not interfere with the antibody activity, biotinylating the glycosyl groups can be an ideal strategy to generate biotinylated antibodies.

Biotinylation at carboxyl groups can occur at a pH of about 4.5-5.5. To prevent crossreactivity of the crosslinker with buffer constituents, buffers should not contain primary amines (e.g., Tris, glycine) or carboxyls (e.g., acetate, citrate).

Oligonucleotide Biotinylation.

Oligonucleotides can be readily biotinylated in the course of oligonucleotide synthesis by the phosphoramidite method using, e.g., commercial biotin phosphoramidite. Upon the standard deprotection, the conjugates obtained can be purified using reverse-phase or anion-exchange HPLC.

Non-Specific Biotinylation.

Photoactivatable biotinylation reagents can be useful when primary amines, sulfhydryls, carboxyls or carbohydrates are not available or not desired for labeling. A photoactivatable biotinylation reagent relies on aryl azides, which become activated by ultraviolet light (UV; >350 nm), which then react at C-H and N—H bonds. A photoactivatable biotinylation reagent can also be used to activate biotinylation at specific times by simply exposing the reaction to UV light at the specific time or condition.

Process for coupling a receptor or ligand (e.g., biotin) to a radioisotope are well known (see e.g., Savage, 1992, Avidin-Biotin Chemistry: A Handbook, Pierce Chemical Co, ISBN-10 0935940111, ISBN-13 978-0935940114; McMahon, 2010, Avidin-Biotin Interactions: Methods and Applications, Humana Press, ASIN B00GA4420E; Hermanson, 2010, Bioconjugate Techniques, Academic Press, ASIN B005YXETUU). Except as otherwise noted herein, therefore, the process of the present disclosure can be carried out in accordance with such processes.

Coupling

Coupling can be any type attraction, link, or reaction that serves to immobilize a therapeutic agent on a molecule/substrate; a ligand on a molecule/substrate; or a receptor on a radioisotope (or vice versa, a receptor on a molecule/substrate or ligand on a radioisotope). Coupling can be via a bond. A molecule-therapeutic agent bond is understood as an attraction between atoms of a molecule and atoms of a therapeutic agent that allows the formation of a linkage between atoms of the therapeutic agent and the matrix material. A molecule-ligand bond is understood as an attraction between atoms of a molecule and atoms of a ligand that allows the formation of a linkage between atoms of the biomolecule and the matrix material. A bond can be caused by an electrostatic force of attraction between opposite charges, either between electrons and nuclei, or as the result of a dipole attraction. A bond (e.g., between a biomolecule and a matrix material) can be, for example, a covalent bond, a coordinate covalent bond, an ionic bond, polar covalent, a dipole-dipole interaction, a London dispersion force, a cation-pi interaction, or hydrogen bonding. Coupling can be reversible or irreversible. One of ordinary skill will understand that coupling does not necessarily need to be irreversible and can be preferred to be reversible coupling.

Processes for coupling a molecule or substrate to a receptor or ligand (e.g., avidin or streptavidin) are well known (see e.g., Savage, 1992, Avidin-Biotin Chemistry: A Handbook, Pierce Chemical Co, ISBN-10 0935940111, ISBN-13 978-0935940114; McMahon, 2010, Avidin-Biotin Interactions: Methods and Applications, Humana Press, ASIN B00GA4420E; Hermanson, 2010, Bioconjugate Techniques, Academic Press, ASIN B005YXETUU). Except as otherwise noted herein, therefore, the process of the present disclosure can be carried out in accordance with such processes.

A ligand or therapeutic agent can be considered to be bound to a substrate (e.g., talc) if the ligand or therapeutic agent was detected on the substrate (e.g., via flow cytomoetry) after washing (e.g., with PBS).

Molecular Engineering

The following definitions and methods are provided to better define the present disclosure and to guide those of ordinary skill in the art in the practice of the present disclosure. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that can be endogenous to the particular host cell but has been modified through, for example, the use of DNA shuffling. The terms also include non-naturally occurring multiple copies of a naturally occurring DNA sequence. Thus, the terms refer to a DNA segment that can be foreign or heterologous to the cell, or homologous to the cell but in a position within the host cell nucleic acid in which the element is not ordinarily found. Exogenous DNA segments are expressed to yield exogenous polypeptides. A "homologous" DNA sequence can be a DNA sequence that is naturally associated with a host cell into which it can be introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule can be transcribed into a functional mRNA molecule that can be translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel, (2006), Condensed Protocols from Molecular Cloning: A Laboratory Manual, Cold Spring Harbor Laboratory Press, ISBN-10: 0879697717; Ausubel et al., (2002), Short Protocols in Molecular Biology, 5th ed., Current Protocols, ISBN-10: 0471250929; Sambrook and Russel, (2001), Molecular Cloning: A Laboratory Manual, 3d ed., Cold Spring Harbor Laboratory Press, ISBN-10: 0879695773; Elhai, J. and Wolk, C., P. 1988. Methods in Enzymology, 167, 747-754).

The "transcription start site" or "initiation site" can be the position surrounding the first nucleotide that can be part of the transcribed sequence, which can also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one can be affected by the other. For example, a regulatory DNA sequence can be said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA can be under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter can be operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that can be native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook, 1989; Innis, 1995; Gelfand, 1995; Innis & Gelfand, 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al., (2007), Nature Reviews, 5(9), 680-688; Sanger et al., (1991), Gene, 97(1), 119-123; Ghadessy et al., (2001), Proc Natl Acad Sci USA, 98(8), 4552-4557. Thus, one skilled in the art could generate a large number of nucleotide or polypeptide variants having, for example, at least 95-99% identity to the reference sequence described herein and screen such for desired phenotypes according to methods routine in the art.

Nucleotide or amino acid sequence identity percent (%) can be understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software can be used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity can be retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. Deletion can be the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6($\log_{10}$[Na$^+$])+0.41(fraction G/C content)−0.63(% formamide)−(600/l). Furthermore, the $T_m$ of a DNA:DNA hybrid is decreased by 1-1.5° C. for every 1% decrease in nucleotide identity (see, e.g., Sambrook and Russel, 2006).

Host cells can be transformed using a variety of standard techniques known to the art (see, e.g., Sambrook and Russel, (2006), Condensed Protocols from Molecular Cloning: A Laboratory Manual, Cold Spring Harbor Laboratory Press, ISBN-10: 0879697717; Ausubel et al., (2002), Short Protocols in Molecular Biology, 5th ed., Current Protocols, ISBN-10: 0471250929; Sambrook and Russel, (2001), Molecular Cloning: A Laboratory Manual, 3d ed., Cold Spring Harbor Laboratory Press, ISBN-10: 0879695773; Elhai, J. and Wolk, C., P. 1988. Methods in Enzymology, 167, 747-754). Such techniques include, but are not limited to, viral infection, calcium phosphate transfection, liposome-mediated transfection, microprojectile-mediated delivery, receptormediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" can be also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA can be intended to refer to any gene or DNA segment that can be introduced into a recipient cell, regardless of whether a similar gene may already be present in such a cell. The type of DNA included in the exogenous DNA can include DNA which can be already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see, e.g., Studier, (2005), Protein Expr Purif., 41(1), 207-234; Gellissen, ed. (2005), Production of Recombinant Proteins: Novel Microbial and Eukaryotic Expression Systems, Wiley-VCH, ISBN-10: 3527310363; Baneyx, (2004), Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds, (2006) Handb Exp Pharmacol., 173, 289-303G, describing hammerhead ribozymes and small hairpin RNA; Helene, C., et al., (1992), Ann. N.Y. Acad. Sci., 660, 27-36; Maher, (1992), Bioassays, 14(12): 807-15, describing targeting deoxyribonucleotide sequences; Lee et al., (2006), Curr Opin Chem Biol., 10, 1-8, describing aptamers; Reynolds et al., (2004), Nature Biotechnology, 22(3), 326-330, describing RNAi; Pushparaj and Melendez, (2006), Clinical and Experimental Pharmacology and Physiology, 33(5-6), 504-510, describing RNAi; Dillon et al., (2005), Annual Review of Physiology, 67, 147-173, describing RNAi; Dykxhoorn and Lieberman, (2005), Annual Review of Medicine, 56, 401-423, describing RNAi). RNAi molecules are commercially available from a variety of sources (e.g., Ambion, Tex.; Sigma Aldrich, Mo.; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinofrmatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Md., 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions can be contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein (e.g., molecule-ligand or radioisotope-receptor) can also be used in combination with other therapeutic modalities, as described further below. Thus, in addition to the therapies described herein, one may also provide to the subject other therapies known to be efficacious for treatment of the disease, disorder, or condition.

Therapeutic Methods

Another aspect provided herein is a process of treating a proliferative disease, disorder, or condition with a composition described herein.

For example, molecule or substrate coupled to a therapeutic agent can be used to treat a proliferative disease, disorder. Provided is a process of treating a proliferative disease, disorder, or condition in a subject in need administration of a therapeutically effective amount of a molecule or substrate coupled to a therapeutic agent, so as to provide targeted or selective therapy. The therapeutic method can include administration of a molecule or substrate coupled to a therapeutic agent.

For example, combination of a first composition including a ligand coupled to molecule or substrate and a second composition including a receptor coupled to a radioisotope (or vice versa, a receptor coupled to molecule or substrate and a ligand coupled to a radioisotope) can be used to treat a proliferative disease, disorder. Provided is a process of treating a proliferative disease, disorder, or condition in a subject in need administration of a therapeutically effective amount of the first composition and the second composition, so as to provide targeted or selective radiotherapy. The therapeutic method can include administration of a first composition including a ligand coupled to molecule or substrate and a second composition including a receptor coupled to a radioisotope.

Exemplary technology for rapidly delivering precisely calibrated and dispersed loads of microparticles into living tissue to depths of 2 cm include the use of air-powered injectors or sprays, and other methods known in the art. Such particles can be injected, e.g., directly into the walls or floor of the cavity created in breast tissue during lumpectomy for cancer, or in retroperitoneal tissues after excision of a pancreatic head cancer, or the cavity created in subcutaneous tissues of the thigh after radical excision of a sarcoma. Instead of conventional daily postoperative regimens of external beam radiation, a subject can be given, e.g., an intravenous dose of biotin-labeled radioisotope once monthly for one, two, three or more months until the recommended dose can be achieved.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

In some embodiments, administration can be according to conventional pleurodesis modified to incorporate compositions described herein.

Methods described herein are generally performed on a subject in need thereof. A subject in need of the therapeutic methods described herein can be a subject having, diagnosed with, suspected of having, or at risk for developing proliferative disease, disorder, or condition. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

Compositions, systems, or methods described herein can be used to treat proliferative diseases, disorders, or conditions. For example, compositions, systems, or methods described herein can be used (e.g., operatively or post-operatively) to treat mesothelioma, Meigs Syndrome, sarcoma, appendiceal carcinoma, pseudomyxoma peritonei, prostate cancer, prostate cancer lymph node dissection beds, rectovesical pouch tumor bed, ovarian cancer resection bed and peritoneal spread, uterine cancer resection cavities, pleural and peritoneal mesothelioma resection bed and peritoneal seeding, colorectal carcinoma, appendiceal carcinoma, pancreatic carcinoma, liver metastases, gastric carcinoma, renal carcinoma, retroperitoneal tumors (sarcomas, carcinomas), breast lumpectomy or breast lymph node dissection cavities, melanoma node dissection cavities, sarcoma resection cavities, head and neck cancer resection cavities, neck lymph node dissection cavities, scalp lesions, glioblastoma resection cavities, brain surface tumor lesions (resected, non resected), or trunk and extremity sarcoma resection cavities.

Compositions, systems, or methods described herein can be used at post-operative sites associated with a disease, disorder, or condition described herein. For example, an avidin-talc complex (followed by a receptor-radioisotope complex) can be used at postoperative sites associated with a disease, disorder, or condition described herein. As another example, an avidin-fibrin glue complex (followed by a receptor-radioisotope complex) can be used at postoperative sites associated with a disease, disorder, or condition described herein. As another example, an avidin-gelfoam complex (followed by a receptor-radioisotope complex) can be used at postoperative sites associated with a disease, disorder, or condition described herein.

Compositions, systems, or methods described herein can be used to treat proliferative diseases, disorders, or conditions. Examples of proliferative diseases, disorders, or conditions treatable with compositions described (e.g., molecule-ligand or radioisotope-receptor) include, but are not limited to, cancer; blood vessel proliferative disorders; fibrotic disorders; mesangial cell proliferative disorders; psoriasis; actinic keratoses; seborrheic keratoses; warts; keloid scars; eczema; and hyperproliferative diseases caused by virus infections, such as papilloma virus infection.

Cancer, or neoplasia, refers generally to any malignant neoplasm or spontaneous growth or proliferation of cells. A subject having "cancer", for example, may have a leukemia, lymphoma, or other malignancy of blood cells. In certain embodiments, the subject methods are used to treat a solid tumor. Exemplary solid tumors include but are not limited to non-small cell lung cancer (NSCLC), testicular cancer, lung cancer, ovarian cancer, uterine cancer, cervical cancer, pancreatic cancer, colorectal cancer (CRC), breast cancer, as well as prostate, gastric, colon, skin, stomach, esophageal, and bladder cancer. Systems and compositions described herein can be used in treatment methods for the above diseases or disorders.

Treatment of cancer or treating a subject having cancer can include inhibition of replication of cancer cells, inhibition of spread of cancer, reduction in tumor size, lessening or reducing the number of cancerous cells in the body of a subject, or amelioration or alleviation of symptoms of cancer. A treatment can be considered therapeutic if there can be or is a decrease in mortality or morbidity, and can be performed prophylactically, or therapeutically.

Methods described herein can be used to treat (e.g., reduce tumor size, decrease the vascularization, increase the permeability of, or reduce or prevent recurrence of tumor growth) an established tumor. An established tumor is generally understood as a solid tumor of sufficient size such that nutrients, e.g., oxygen, can no longer permeate to the center of the tumor from the subject's vasculature by osmosis and therefore the tumor requires its own vascular supply to receive nutrients. Methods described herein can be used to treat a solid tumor that is not quiescent and can be actively undergoing exponential growth.

A therapeutic protocol can be modified according to permeability of a solid tumor. Permeability of a solid tumor generally refers to the permeability of a solid tumor to a therapeutic. A solid tumor may be said to be permeable to a therapeutic if the therapeutic is able to reach cells at the center of the tumor. An agent that increases the permeability of a tumor may for example, normalize, e.g., maintain, the vasculature of a solid tumor. Tumor vascularization or tumor permeability can be determined by a variety of methods known in the art, such as, e.g. by immunohistochemical analysis of biopsy specimens, or by imaging techniques, such as sonography of the tumor, computed tomography (CT) or magnetic resonance imaging (MRI) scans.

For example, a ligand (e.g., therapeutic agent, avidin or streptavidin) can be conjugated to a biodegradable or non-biodegradable substrate, such as sutures, clips or meshes, implanted adjacent to or within delicate, relatively inaccessible surgically operated areas (e.g., pancreatic head, superior mesenteric artery region) or tumor-cell-contaminated surgical fields (e.g., surface of kidney in contact with a resected retroperitoneal sarcoma) to pre-target the region for postoperative chemotherapy while reducing the risk of radiation injury to the liver or kidney. As another example, a cancer treatment system can include avidin or streptavidin-conjugated biodegradable or non-biodegradable microspheres or other particles, introduced into a tumor-associated tissues (e.g., by air-powered needle-less injection) so to attract biotin-labeled alpha-emitting isotopes (e.g., Radium 223, Bismuth 212) for precisely targeted adjuvant radiotherapy of the surrounding marginal cavity of resected cancers (e.g., sarcoma, breast lumpectomy, pancreatic head, others) appropriate for such treatment, with at least one intent of forestalling local recurrence of tumor.

As another example, a therapeutic agent conjugated to a biodegradable or non-biodegradable substrate, such as silica or talc, can be placed into an area adjacent to a tumor of a subject or tumor-cell-contaminated area (e.g., a pleural space. surface of kidney in contact with a resected retroperitoneal sarcoma) to pre-target the region for postoperative chemotherapy while reducing the risk of additional effects to the tissue or organ (e.g., liver or kidney). As another example, a cancer treatment system can include therapeutic agent conjugated to biodegradable or non-biodegradable talc, introduced into a tumor-associated tissues (e.g., by air-powered needle-less injection) so to precisely targeted adjuvant therapy of the surrounding marginal cavity of resected cancers (e.g., sarcoma, breast lumpectomy, pancreatic head, others) appropriate for such treatment, with at least one intent of forestalling local recurrence of tumor.

Abdominal Cancer.

In some embodiments, a general pleurodesis approach using compositions, systems, or methods described herein described herein can be adapted for other indications. For example, a molecule-ligand combination (e.g., the talc-avidin) or a molecule-therapeutic agent combination mixed or suspended in matrix material (e.g., a fibrin/gelatin matrix), can be used during abdominal cancer surgery to spread over tissue surfaces, particularly the so called "bare area" of the liver between the liver and diaphragm, so as to pretarget that area for postoperative therapy (e.g., radiotherapy or chemotherapy), in a manner similar to its use in pleurodesis. It is understood that this area is conventionally difficult to completely clear of metastatic tumor, and that radiation therapy to this areas has been problematic.

Liver Metastasis.

In some embodiments, compositions, systems, or methods described herein (e.g., molecule-ligand-molecule or radio-isotope-receptor) can be used as a substitute or replacement for glass microspheres-yttrium 90 in indications such as ablating liver metastasis. Conventionally, radioactive glass spheres are directly injected into the liver vasculature, and because of their size, are held up in small arterioles and precapillaries, where they irradiate the surrounding tissue. The drawbacks of this conventional technique, among others, can be the difficulty of controlling the dose without repeat cannulation. Molecule-ligand compositions described herein (e.g., talc-avidin) of a specific size (e.g., graded by flow cytometery) can be used to similarly permeate hepatic metastases, thus pretargeting the tissue for repeated doses of therapeutic radioisotopes. This approaches imparts greater flexibility in treatment by separating the interventional procedure from the radioactive dose, not requiring radioactive precautions, or allowing choice of isotope and repeated dosing.

Peritoneal Carcinomatosis.

As another example, compositions, systems, or methods described herein can be used as treatment (e.g., adjuvant treatment) of peritoneal carcinomatosis. Peritoneal carcinomatosis can be a frequent complication of ovarian carcinoma, colorectal or especially appendiceal carcinoma, gastric carcinoma, pancreatic carcinoma, peritoneal mesothelioma, or pseudomyxoma peritonei. Conventional treatment of these conditions can employ cytoreductive surgery. In cytoreductive surgery, as much tumor as possible can be surgically resected (e.g., all tumor nodules greater than about 5.0 mm across) then intraoperative "heated" chemotherapy can be given using conventional drugs. Subjects are then observed, with or without additional systemic chemotherapy. In some instances, a catheter can be placed into the abdominal cavity and additional chemotherapy can be given repeatedly in the outpatient setting. But chemotherapy drugs, including small molecules such as cisplatin, do not penetrate deeper than 4 or 5 cell layers beneath the peritoneum, or cannot reach tumor cells that are lodged as deep as 2.5 mm below the surface. While intraperitoneal radioisotopes have been used for treatment of peritoneal malignancies in the past, results were unsatisfactory due to poor delivery of cytotoxic energy to the relevant target, excessive local fibrotic reactions and inflammation, necessity for protection and radioactive shielding of patients and personnel, and systemic effects on the bone marrow. Such conventional treatment can be adapted for use with compositions, systems, or methods described herein (e.g., as adjuvant treatment).

Various embodiments of the present disclosure provide an alpha-emitting cytotoxic isotope having short range radiation (usually under about 1 mm), with minimal marrow toxicity, and direct delivery of the isotope to the peritoneal surfaces. For example, avidin, which has a highly positive charged, can adhere to negatively charged normal peritoneal surfaces. When injected into the blood, avidin can be rapidly cleared (e.g., by about 5 hours) and can be cleared from the liver and circulation (e.g., by about 36 hours). Because of the structure of the peritoneal membrane, intraperitoneally injected avidin may also be taken up into the circulation or rapidly degraded in the reticuloendothelial system of the liver. In some embodiments, such as treatment of omentectomized patients, liver clearance may be slower (e.g., a few days). Using a branched polyethylene glycolavidin conjugate can slow its exit from the peritoneal compartment while retaining avidin's ability to bind biotin, and its ability to stick to peritoneal surfaces.

With avidin in place on the peritoneal surface, the unbound avidin can be washed off by peritoneal lavage. Biotinylated radioisotope can be directly introduced into the cavity by radiologically guided catheter, where it would bind to all exposed surfaces. Intravenous avidin can simultaneously be given to "clear" some or all isotope escaping from the peritoneal cavity. The above techniques can be accomplished with avidin alone, rather than conjugated to polyethylene glycol.

The above discussion references avidin as ligand and biotin as receptor, but one of ordinary skill will recognize such techniques can be performed with other ligands and receptors described herein.

When used in the treatments described herein, a therapeutically effective amount of a first composition (e.g., a ligand coupled to molecule or substrate) and a second composition (e.g., a receptor coupled to a radioisotope) can be employed in pure form or, where such forms exist, in pharmaceutically acceptable salt form and with or without a pharmaceutically acceptable excipient. For example, compounds, molecules, substrates, radioisotopes or other compositions or materials of the present disclosure can be administered, at a reasonable benefit/risk ratio applicable to any medical treatment, in a sufficient amount to provide a sufficient therapeutic outcome, as described further herein.

An effective amount of a compound described herein is generally that which can exhibit a therapeutic effect (e.g., an anti-proliferative therapeutic effect) to an extent such as to ameliorate the treated disease, disorder, or condition. In some embodiments, an effective amount of compositions described herein can be that amount sufficient to affect a desired result on a cancerous cell or tumor, including, but not limited to, for example, inhibiting spread of the disease, disorder, or condition, reducing tumor size, reducing tumor volume, decreasing vascularization of a solid tumor, increasing the permeability of a solid tumor to an agent, either in vitro or in vivo, reducing or eliminating recurrence of a tumor, reduce recurrence of tumor growth; prevent recurrence of tumor growth; reduce a number of cancerous cells in the subject; or ameliorate a symptom of the disease, disorder, or condition. In certain embodiments, an effective amount of therapy can be the amount that results in a percent tumor reduction or inhibition of more than about 55%, about 60%, about 65%, about 70%, about 75%, about 80%, about 85%, about 90%, about 95%, about 99%, or about 100%.

In certain embodiments, an effective amount of therapy can be sufficient to achieve a desired clinical result, including but not limited to, for example, ameliorating disease, stabilizing a subject, preventing or delaying the development of, or progression of, a proliferative disease, disorder, or condition in a subject. An effective amount of therapy can be determined based on one administration or repeated administration. Methods of detection and measurement of the indicators above are known to those of skill in the art. Such methods include, but are not limited to measuring reduction in tumor burden, reduction of tumor size, reduction of tumor volume, reduction in proliferation of secondary tumors, decreased solid tumor vascularization, expression of genes in tumor tissue, presence of biomarkers, lymph node involvement, histologic grade, and nuclear grade.

In some embodiments, tumor burden can be determined. Tumor burden, also referred to as tumor load, generally refers to a total amount of tumor material distributed throughout the body of a subject. Tumor burden can refer to a total number of cancer cells or a total size of tumor(s), throughout the body, including lymph nodes and bone barrow. Tumor burden can be determined by a variety of methods known in the art, such as, for example, by measuring the dimensions of tumor(s) upon removal from the subject, e.g., using calipers, or while in the body using imaging techniques, e.g., ultrasound, computed tomography (CT) or magnetic resonance imaging (MRI) scans. Tumor size can be determined, for example, by determining tumor weight or tumor volume.

The amount of a composition(s) described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects can be the therapeutic index that can be expressed as the ratio $LD_{50}/ED_{50}$, where large therapeutic indices are preferred.

The specific therapeutically effective dose level for any particular subject will depend upon a variety of factors including the disorder being treated and the severity of the disorder; activity of the specific compound employed; the specific composition employed; the age, body weight, general health, sex and diet of the patient; the time of administration; the route of administration; the rate of excretion of the composition employed; the duration of the treatment; drugs used in combination or coincidental with the specific compound employed; and like factors well known in the medical arts (see e.g., Koda-Kimble et al., (2004), Applied Therapeutics: The Clinical Use of Drugs, Lippincott Williams & Wilkins, ISBN 0781748453; Winter, (2003), Basic Clinical Pharmacokinetics, $4^{th}$ ed., Lippincott Williams & Wilkins, ISBN 0781741475; Sharqel, (2004), Applied Biopharmaceutics & Pharmacokinetics, McGraw-Hill/Appleton & Lange, ISBN 0071375503). For example, it is well within the skill of the art to start doses of agents at levels lower than those required to achieve the desired therapeutic effect and to gradually increase the dosage until the desired effect can be achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a subject that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of compositions described herein can occur as a single event, a periodic event, or over a time course of treatment. For example, agents can be administered daily, weekly, bi-weekly, or monthly. As another example, agents can be administered in multiple treatment sessions, such as 2 weeks on, 2 weeks off, and then repeated twice; or every 3rd day for 3 weeks. A first composition including a ligand coupled to molecule or substrate and a second composition including a receptor coupled to a radioisotope can have the same or different administration protocols. One of ordinary skill will understand these regimes to be exemplary and could design other suitable periodic regimes. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for a proliferative disease, disorder, or condition.

A combination of a first composition including a ligand coupled to molecule or substrate and a second composition including a receptor coupled to a radioisotope can be administered simultaneously or sequentially with another agent, such as an antibiotic, an anti-inflammatory, or another agent. Simultaneous administration can occur through administration of separate compositions, each containing one or more of a molecule or substrate, a ligand, a radioisotope, and receptor, an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006), Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to non-target tissues; decrease irritation caused by the agent; decrease toxicity due to high initial doses of the agent; alter the immunogenicity of the agent; decrease dosage frequency, improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components can include, but are not limited to a first composition including a ligand coupled to molecule or substrate and a second composition including a receptor coupled to a radioisotope (or vice versa, a receptor coupled to molecule or substrate and a ligand coupled to a radioisotope). Components can include, but are not limited to, a first composition including a ligand and a second composition including a substrate, wherein the ligand couples to the substrate. Components can include, but are not limited to, a therapeutic agent and a molecule or substrate, wherein the therapeutic agent couples to the substrate. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel, (2006), Condensed Protocols from Molecular Cloning: A Laboratory Manual, Cold Spring Harbor Laboratory Press, ISBN-10: 0879697717; Ausubel et al., (2002), Short Protocols in Molecular Biology, 5th ed., Current Protocols, ISBN-10: 0471250929; Sambrook and Russel, (2001), Molecular Cloning: A Laboratory Manual, 3d ed., Cold Spring Harbor Laboratory Press, ISBN-10: 0879695773; Elhai, J. and Wolk, C. P., 1988. Methods in Enzymology, 167, 747-754; Studier, (2005), Protein Expr Purif., 41(1), 207-234; Gellissen, ed. (2005) Production of Recombinant Proteins: Novel Microbial and Eukaryotic Expression Systems, Wiley-VCH, ISBN-10: 3527310363; Baneyx, (2004), Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have", or "include" are open-ended linking verbs. Any forms or tenses of one or more of these verbs, such as "comprises," "comprising," "has," "having," "includes", or "including," are also open-ended. For example, any method that "comprises," "has" or "includes" one or more steps is not limited to possessing only those one or more steps and can also cover other unlisted steps. Similarly, any composition or device that "comprises," "has", or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Binding Capacity of Biotin-Rhodamine and Anti-Avidin-FITC to Talc

The following Example determined if talc naturally binds to proteins without cross-linkers or chemical reactions.

Talc was used as nanoparticles to bind to Anti-Avidin FITC and Biotin Rhodamine. This combinant nanoparticle was observed under microscopy for efficiency and efficacy.

Materials used in this Example, include:
1. Sterile Talc powder (Bryan Corporation, Cat #: 1690, Lot #: 3M021, Exp. Date: December 2016)
2. Albumin solution from bovine serum (30%) (Sigma-Aldrich cat. #: A7284-50 mL, lot #: SLBD8234B
3. Monoclonal Anti-Avidin FITC conjugate, Clone WC19.10 (Sigma-Aldrich, cat. #: F1269)
4. Biotin Rhodamine 110 (Biotium, cat. #: 80022 at 5 mg in 311.4 µl DMSO; 20 mM or 16 µg/µl)
5. Tween 20 (Fisher, cat. #BP337-500, lot #145162)
6. PBS (10×) (Sigma cat. #: P5493, lot #: SLBH0296)

Day 1:
1. Take 30 mg of Talc and mix with 1 mL of 1×PBS
2. Centrifuge Talc at 1500 rpm 5 min
3. Remove supernatant liquid
4. Block Talc at RT using 1 mL blocking buffer 1 hour (Buffer soln.: 978.5 µL PBS+16.5 µL 30% BSA+5 µL 10% Tween20 or PBS+0.5% BSA+0.05% Tween20)
5. Remove blocking buffer and incubate talc overnight at 4° C. in 1 mL Blocking Buffer containing 1:500 dilution of Anti-Avidin FITC
*Protect reaction from light.

Day 2:
1. Centrifuge tube with overnight reaction at 1500 rpm 5 min.
2. Discard supernatant liquid.
3. Wash Talc 3× with 1 mL PBS+0.05% Tween20.
4. Incubate Talc again at RT in 1 mL of blocking buffer 1 hour (buffer soln. containing 2 µL Biotin Rhodamine).
*Protect from light.
5. Centrifuge tube.
6. Remove supernatant.
7. Wash Talc 5× with 1 mL washing buffer (buffer soln.: PBS+0.05% Tween20).
8. Mount onto slides.
9. Analyze under microscope using FITC filter and Rhodamine filter.

Figure 1B:
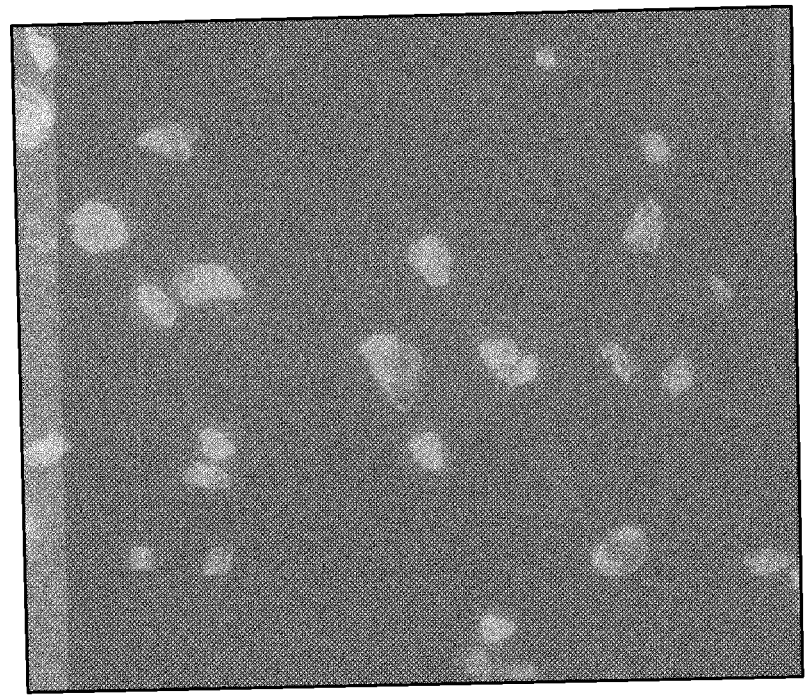
FIG. 1B shows Anti-Avidin FITC binding to talc.
Figure 2A:
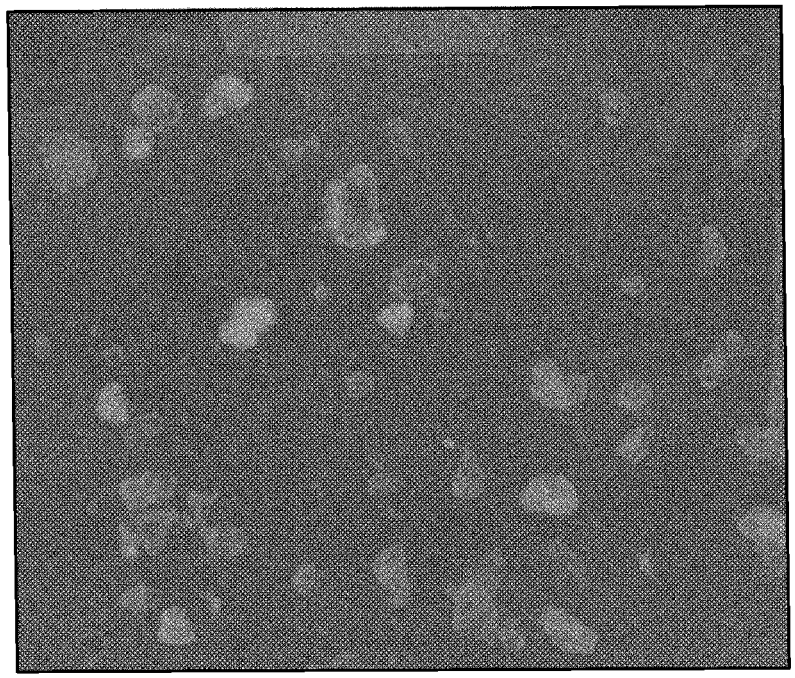
FIG. 2A-FIG. 2J are a series of microscopy images depicting Avidin and Avidin Rhodamine after washing.
Figure 2B:
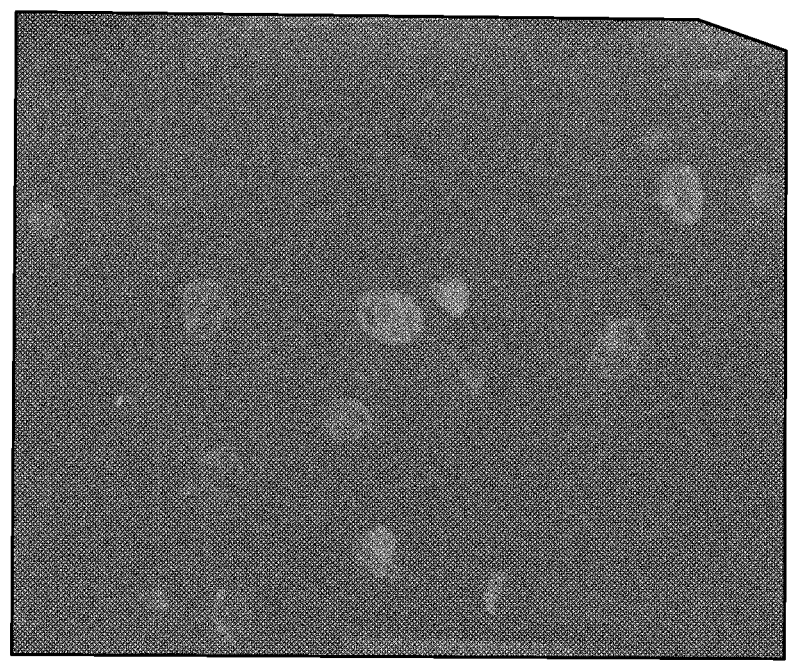
Figure 2C:
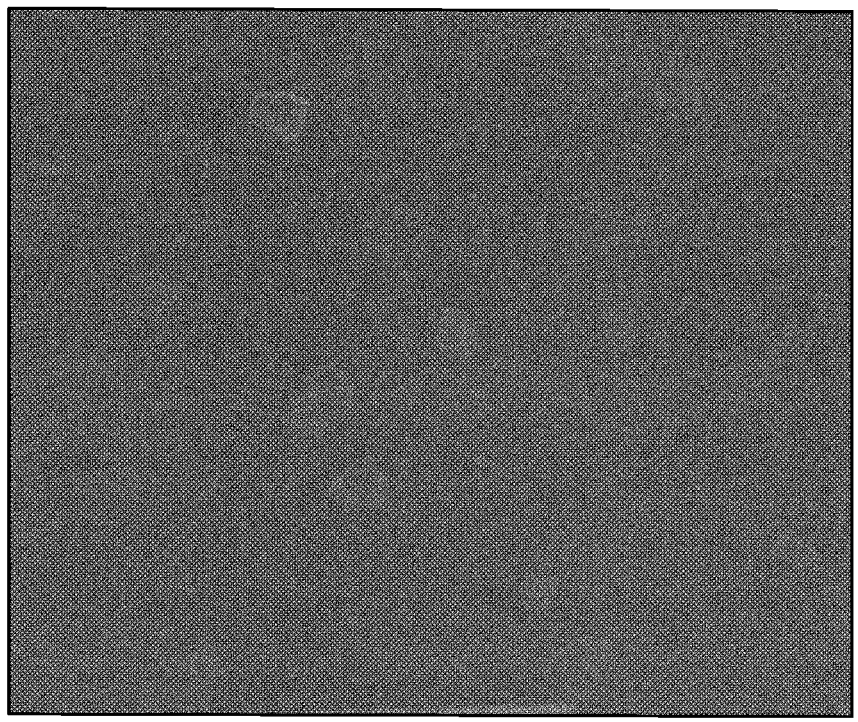
Figure 2D:
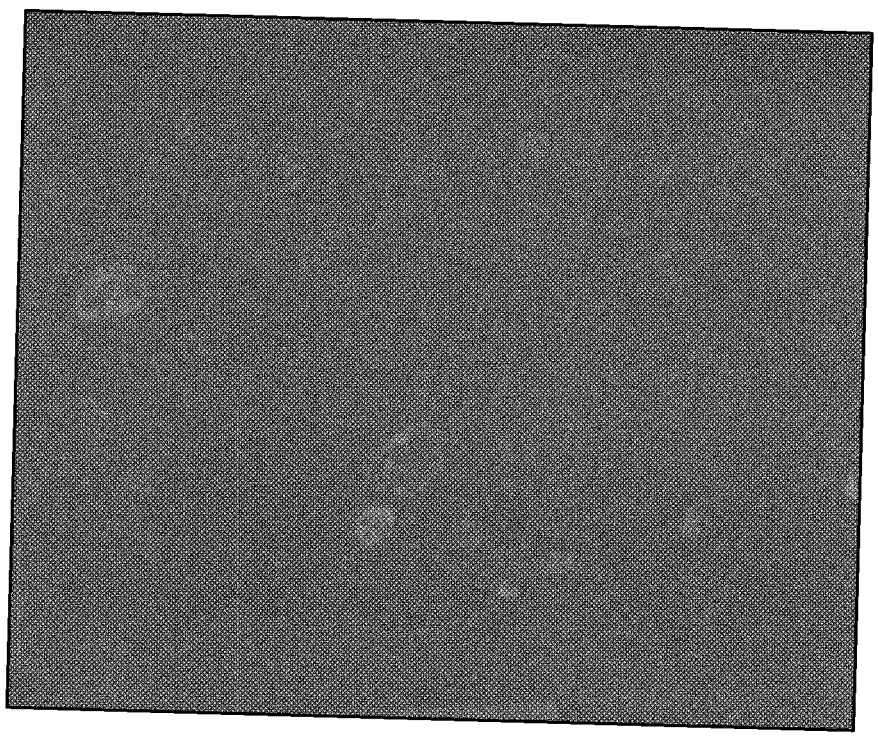
Figure 2E:
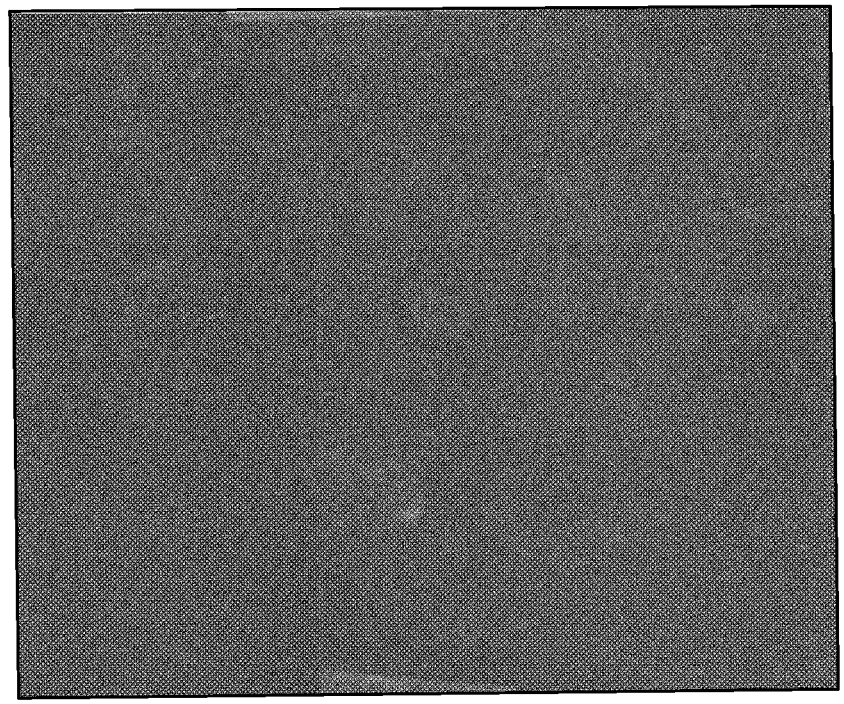
Figure 2F:
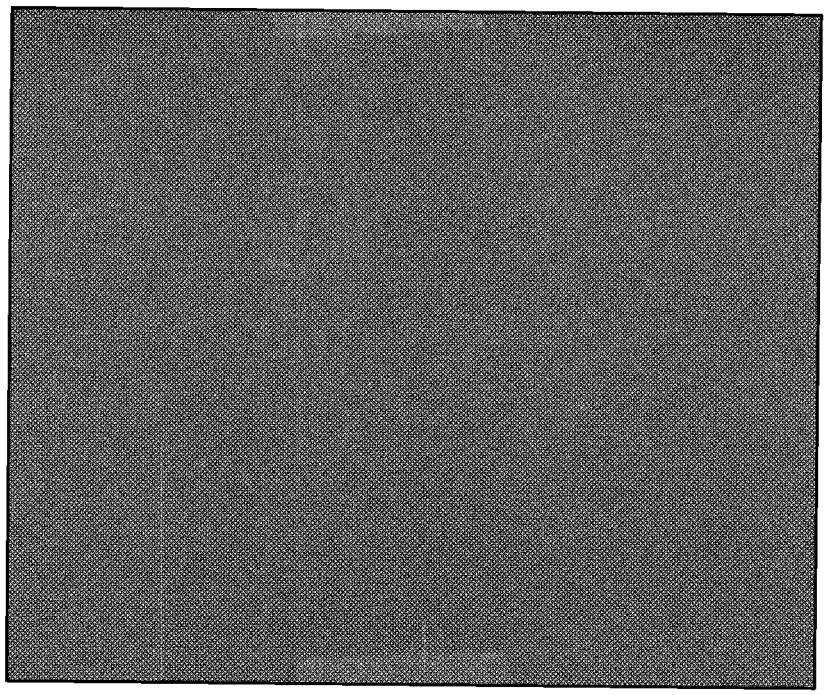
Figure 2G:
Figure 2H:
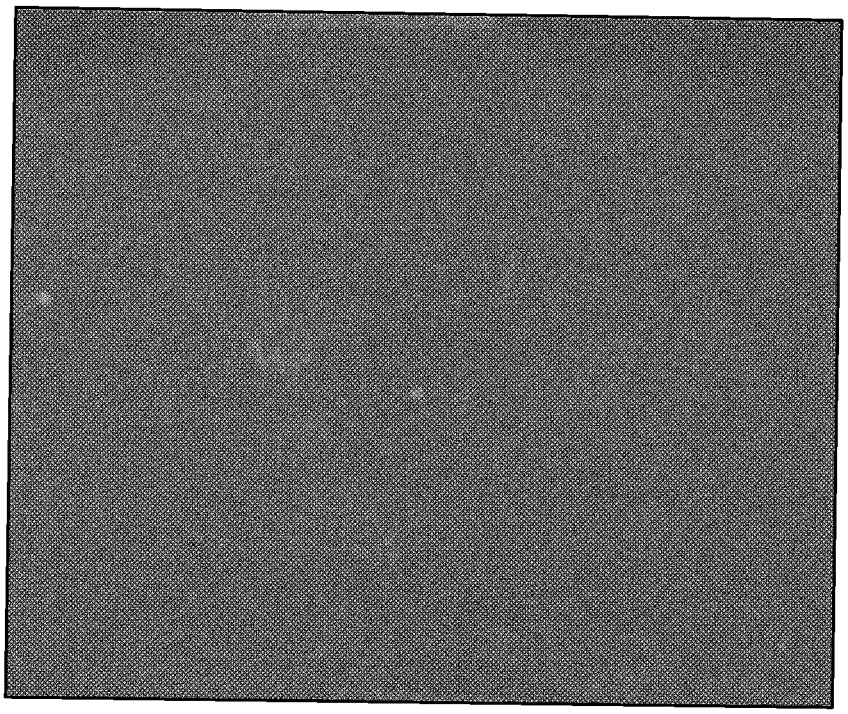
Figure 2I:
Figure 2J:
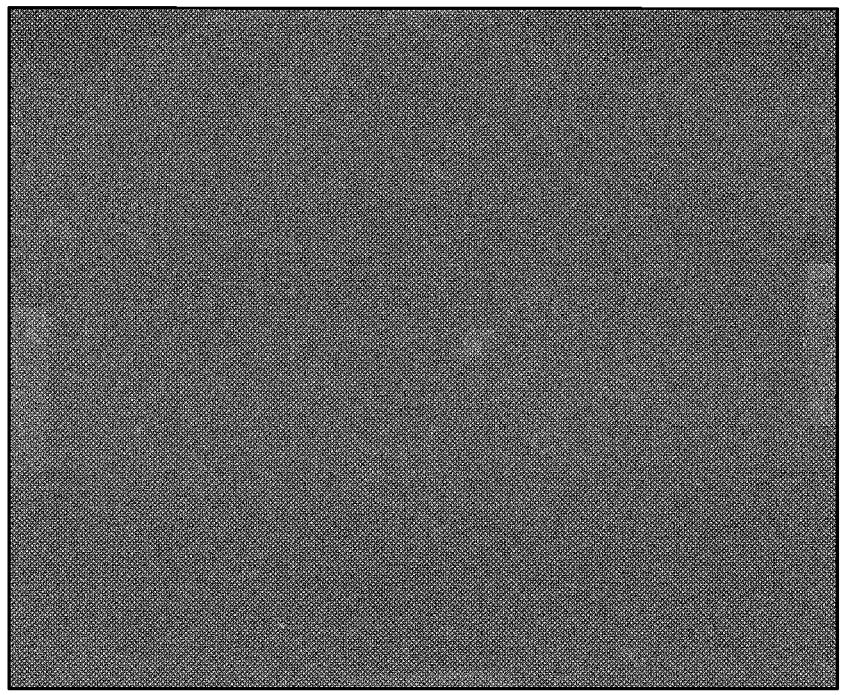

Photographs of results under microscopy filters are shown in FIG. 1A-B.

The study showed proteins binding to talc after incubation for several hours at 4° C.

Example 2: Avidin and Avidin-Rhodamine Binding to Talc

The following Example determined if the binding of Avidin and Avidin/Rhodamine to talc can be destroyed by washing with either PBS or PBS followed by 0.2% EDTA.

100 mg of talc was mixed with different levels of concentrations of Avidin and Avidin/Rhodamine overnight. The resulting mixtures were then washed with PBS and then washed with 0.2% EDTA.

Materials:
1. Avidin Rhodamine (Rhodamine Conjugated Avidin from Rockland, Cat. #: A 003-00, Lot #: 2496).
2. Avidin from egg white (Sigma, Cat. #: A 9275-100 mg, lot #: SLBB9685)
3. Sterile talc powder (Brian Corporation, Cat. #: 1690, Lot #: 3M021; exp. Date: December 2016)

Day 1:
1. Calculate the solutions for the experiment:
Avidin Rhodamine: Add 1 mL of water to 2 mg of Avidin producing a molecular weight of 66 kDa and a Molarity of 30.3 µM. Because the above was not enough to use for the experiment, it was mixed with pure Avidin and then added to the talc.
Avidin from egg white: 5 mL of 100 µM Avidin was prepared (33 mg Avidin+5 mL of PBS) and stored at 4° C. for one week.
Sterile Talc Powder
Make 1×PBS: 9 mL of water+1 mL of 10×PBS
Make 0.2% EDTA: First make stock solution of 2% EDTA=98.63 mL water+13.7 mL of 0.5 M EDTA. Then make a 1:10 dilution to get 0.2% EDTA.
2. Prepare 10 tubes with 100 mg of Talc in each labeled as in TABLE 1:

TABLE 1

10 samples with concentrations of Avidin/Avidin rhodamine.

| | | |
|---|---|---|
| 1-1a | 1-1b | Added: 100 µM Avidin/Avidin Rhod. |
| 1-2a | 1-2b | 10 µM |
| 1-3a | 1-3b | 1 µM |
| 1-4a | 1-4b | 100 nM |
| 1-5a | 1-5b | 10 nM |

All "a" tubes: Talc after last wash with only PBS collected for slides.

All "b" tubes: Talc after three washes with PBS and three washes with 0.2% EDTA transferred for slides.

3. Mix 1 mL of 100 µM of Avidin with 500 µL of 30.3 µM of Avidin Rhodamine (keep lights off).
4. Add 500 mL of mixed Avidin to Talc in tubes 1-1a and 1-1b. Mix well to bring the dry talc powder to evenly distributed reaction solution.
5. Prepare 1.5 mL of 10 µM mixed Avidin: 1.35 mL of PBS+150 µL of 100 µM mixed Avidin. Add 500 µL of 10 µM mixed Avidin to the tubes 1-2a and 1-2b. Mix well to bring the dry talc powder to evenly distributed reaction solution.

6. Continue step 5 in 1:10 dilutions until you get to the last and lowest concentration of Avidin.

7. Tightly cover the tubes with aluminum foil as to protect Rhodamine from the light.

8. Place tubes on the rotator and incubate overnight at 4° C.

Day 2:

1. Centrifuge all tubes at 3200 rpm for 3 min.
2. Discard the supernatant liquid.
3. Wash the talc in all tubes 3× in 1 mL PBS (discard the supernatant liquid after each wash).
4. Take all "a" labeled tubes and make slides, store them in the dark at 4° C.
5. Continue to wash all "b" labeled tubes with 0.2% EDTA. Wash 3× in 0.5 mL EDTA.
6. Take all "b" labeled tubes and make slides, store them in the dark at 4° C.
7. View slides under fluorescent microscope.
8. Photographs of results under microscopy filters are shown in FIG. 2A-J.

The study showed Avidin and Avidin-Rhodamine remained bound to talc despite multiple washes.

Example 3: Binding Avidin to Sterile Talc Powder

The following Example defined the Avidin plateau (i.e., concentration of Avidin which fully saturates 100 mg of talc) and determined the release of Avidin from talc surface during subsequent washings.

100 mg of sterile Talc was mixed with different concentrations of Avidin (i.e., 50 µM, 5 µM, 0.5 µM, 50 nM, 5 nM) overnight at 4° C. in 0.5 mL of PBS. After the incubation period, wash talc 3× with 1 mL PBS and 3× with 0.5 mL of 0.2% EDTA. Collect the supernatant liquid from two tubes containing the two highest concentrations of Avidin at varying points.

Materials:

1. Sterile Talc Powder (Bryan Corporation, Cat #: 1690, Lot #: 3M021, Exp. Date: December 2016)
2. Avidin from egg white (Sigma, Cat. #: A9275-100 mg, Lot #: SLBB9685)
3. PBS (Sigma, Cat. #:P5493-1L, Lot #: SLBH0296)
4. 0.5 M EDTA (Fischer Scientific)
5. Pierce 660 nm Protein Assay Kit (Thermo Scientific, Cat. #: 22662). Methods are based on the instructions provided in the kit.

Day 1:

1. Mix 100 mg of sterile talc with different concentrations of Avidin (50 µM, 5 µM, 0.5 µM, 50 nM, 5 nM) overnight at 4° C. in 0.5 mL of PBS.
2. After the incubation period, wash talc 3× with 1 mL PBS and 3× with 0.5 mL of 0.2% EDTA.
3. Collect the supernatant liquid from two tubes containing the two highest concentrations of Avidin at varying points:
   Before mixing with Talc
   Right after incubation
   After each wash with PBS
   After each wash with EDTA
   For other tubes, collect supernatant at points:
   Before mixing with Talc
   Right after incubation
   After last wash with PBS
   After last wash with EDTA
4. Run total protein assay using Pierce microplate kit and read plate in plate reader.

5. Calculate reaction:
To make 1 mL of 50 µM of Avidin=3.3 mg Avidin+1 mL of 1×PBS (the molecular weight of Avidin is 66,000 Da)

Reserve 0.5 mL of 50 µM Avidin for the first tube and make 1:10 dilution to get 5 µM Avidin solution (900 µL of PBS+100 µL of 50 µM stock solution, then use the same proportions going down)

Make 1×PBS=9 mL of water+1 mL of 10×PBS

Make 0.2% EDTA=make stock 2% EDTA=98.63 mL of water+13.7 mL of 0.5 M EDTA. Then make 1:10 dilution to get 0.2% EDTA.

6. Prepare five tubes with 100 mg of Talc in each tube.
7. Dampen the Talc powder with 1 mL of PBS and mix the two.
8. Centrifuge at 3200 rpm 5 min.
9. Remove supernatant liquid as much as possible.
10. Add the prepared concentrations of Avidin in each tube.
11. Mix Talc again with the solution of Avidin. Protect the tubes from light.
12. Mix overnight at 4° C.
13. Take 100 µL of different concentrations of Avidin and transfer to new tubes labeled as shown in TABLE 2.

TABLE 2

Avidin tube numbers and corresponding concentrations.

| | |
|---|---|
| 1-0 | 50 µM |
| 2-0 | 5 µM |
| 3-0 | 0.5 µM |
| 4-0 | 50 nM |
| 5-0 | 5 nM |

14. Store at 4° C.

Day 2:

1. Centrifuge all tubes at 3200 rpm for 3 min.
2. Collect supernatant liquid and distribute accordingly to tubes labeled as shown in TABLE 3.

TABLE 3

Supernatant collected and labeled.

| |
|---|
| 1-1 |
| 2-1 |
| 3-1 |
| 4-1 |
| 5-1 |

*Tube 1—has the highest concentration of Avidin, Tube 5—has the lowest concentration of Avidin.

*Keep on ice

3. Add 1 mL of 1×PBS and mix well.
4. Centrifuge all tubes at 3200 rpm for 3 min.
5. Collect supernatant to the tubes labeled as shown in TABLE 4.

TABLE 4

Supernatant collected to the below labeled tubes.

| | |
|---|---|
| 1-2a | 50 µM |
| 2-2a | 5 µM |
| 3-2a | 0.5 µM |
| 4-2a | 50 nM |
| 5-2a | 5 nM |

6. Wash all tubes in PBS two times, collecting the supernatant liquid from each wash ONLY from the two highest concentrations of Avidin (tubes labeled 1-2b, 1-2c, and 2-2b, 2-2c).

7. Continue to wash 3× with 0.5 mL of 0.2% EDTA.

8. Collect the supernatant from each wash and transfer to the new tubes only from the original tubes with the highest concentration of Avidin (50 µM and 5 µM). Collect only the FIRST wash with EDTA solution for the other tubes.

9. Keep the supernatant on ice.

10. Run the total protein assay (see e.g., Example 1) using all the collected supernatant liquid.

Day 3:

1. Check all the data from the previous day's protein assay.

2. One reading (e.g., sample 1-1) is more than the highest standard. Therefore, you need to repeat assay run in only two samples:

TABLE 5

Two samples ran.

| 1-0 | 1:10 dilution |
|---|---|
| 1-1 | 1:10 dilution |

3. See e.g., TABLE 6, TABLE 7, FIG. 3 and FIG. 4 for results.

4. Use reading from the last run in the final analysis of data.

TABLE 6

Figure 3:
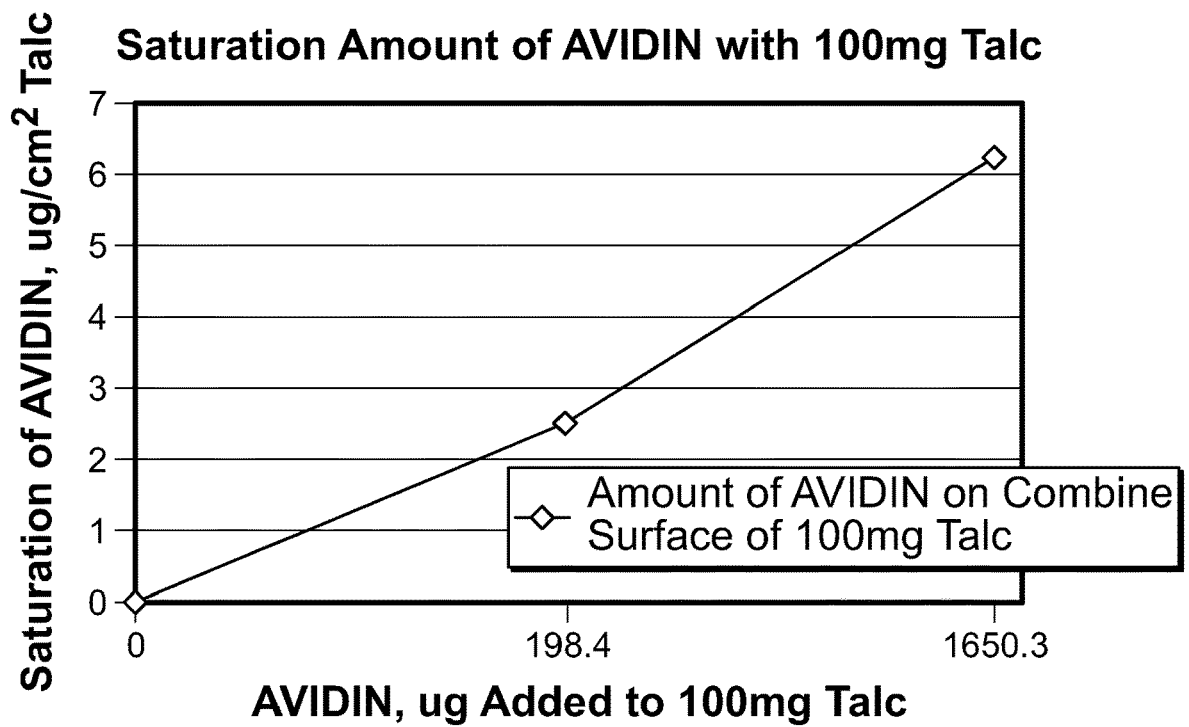
FIG. 3 is a scatter plot depicting the saturation amount of Avidin with 100 mg talc.
Figure 4:
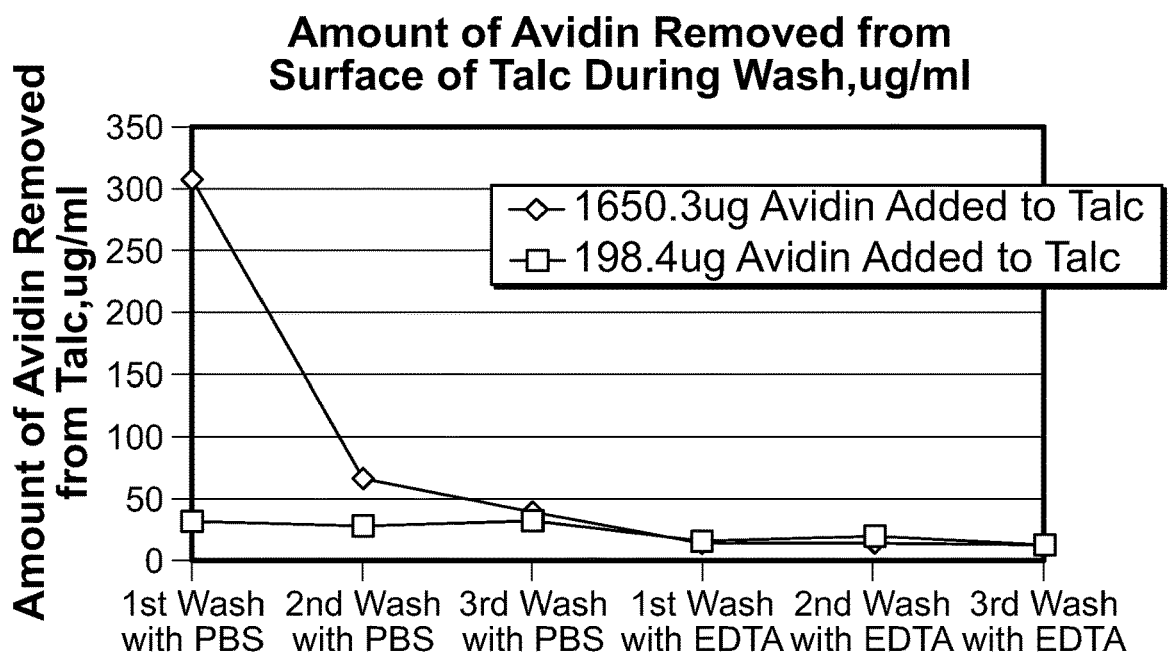
FIG. 4 is a scatter plot depicting the amount of Avidin removed from the surface of talc during wash.

Data for determining the saturation amount of Avidin with 100 mg talc (see e.g., FIG. 3).

| conc. AVIDIN µg/ml | 3300.6 | 396.8 |
|---|---|---|
| conc. AVIDIN in reaction (0.5 ml) | 1650.3 | 198.4 |
| AVIDIN in supernatant after incubation, µg/ml | 2370 | 27.4 |
| AVIDIN in supernatant after incubation, µg/0.5 ml | 1185 | 13.7 |
| Avidin binded to talc, µg | 465.3 | 184.7 |
| total surface area of 100 mg talc, cm² | 74.4 | 74.4 |
| Saturation of AVIDIN to the combine surface of 100 mg talc, µg/cm² | 6.25 | 2.48 |
| Saturation of AVIDIN to the combine surface of 100 mg talc | | |
| Amount Avidin added to reaction, µg | 0 | 198.4 | 1650.3 |
| Amount Avidin added to combine surface of 100 mg talc, µg/cm2 | | 2.7 | 22.2 |
| Saturation of AVIDIN to combine surface of 100 mg talc, µg/cm2 | 0 | 2.48 | 6.25 |

TABLE 7

Amount of Avidin, µg/ml removed by PBS and EDTA wash (see e.g., FIG. 4A, FIG. 4B, FIG. 4C).

| | 1650.3 µg | 198.4 µg |
|---|---|---|
| 1st wash with PBS | 307.4 | 31.4 |
| 2nd wash with PBS | 67.3 | 27.6 |
| 3rd wash with PBS | 40.3 | 32.7 |
| 1st wash with EDTA | 13.2 | 15.8 |
| 2nd wash with EDTA | 12.3 | 19.8 |
| 3rd wash with EDTA | 13.2 | 13 |

Estimation of Sphere Surface.

1. Talc particles

Bryan Corporation Talc is sterile and free of asbestos. The shape is similar to a nugget, and the calculations will substitute it's geometry with spheres. The Talc is calibrated to the distribution of 90% particles at size from 30 pm to 35 pm. Less than 5% is below that range, and above that range.

2. Volume and the surface area of the sphere $$V = \frac{\P \times d^3}{6} = [mm^3]$$

$$A = \P \times d^2 = [mm^2]$$

$$V = \P \times \frac{0.0303}{6} = 0.00014136 \text{ mm}^3$$

$$A = \P \times d^2 = \P \times 0.030^2 = 0.002827 \text{ mm}^2$$

3. Specific gravity of the talc is: $\rho = 2.75$ g/cm³ = 0.00275 g/mm³

4. Weight if each particle is: $G = v \times \rho$ [g],
$G = V \times r = 0.000014136 \times 0.00275 = 0.000\ 000\ 038$ g 5. Number of particles in 1 gram of Talc and total surface area $N_p = 1/0.000\ 000\ 038 = 26315789.47$ (particles)

The Total surface area of 1 gram of Talc is: $A_{Tot} = N_p \times A$ $A_{tot} = 26315789.47 \times 0.002827 = 74394.737$ mm²

$A_{tot} = 743.947$ cm²

The study showed that even at highest concentration of Avidin (50 µM), talc particles were not fully saturated. Only first wash removed quantifiable amounts of Avidin from talc surface.

Example 4: Optimization of Amount of Avidin which Completely Saturates Talc

The following Example determined the Avidin plateau by exposing 100 mg of talc to significantly higher concentrations of Avidin.

The below study describes the optimization of the amount of Avidin that was completely saturated in 100 mg of talc. This study's aim was to see the maximum ability of Talc saturation with Avidin by increasing the amount of Avidin added to 100 mg of Talc (see plateau in the curved slope).

Materials:

1. Sterile Talc Powder (Bryan Corporation, Cat #: 1690, Lot #: 3M021, Esp. Date: December 2016)

2. Avidin from egg white (Sigma, Cat. #: A9275-100 mg, Lot #: SLBB9685)

3. PBS (Sigma, Cat. #:P5493-1L, Lot #: SLBH0296)

Day 1:

1. Add 100 mg of Talc to each of the six Eppendorf tubes (round bottom).

2. Weigh Avidin and add the increments of varying weights of Avidin to the new tubes numerically labeled as in TABLE 8.

TABLE 8

| Tube labels. | |
|---|---|
| #1 | 9.9 mg |
| #2 | 6.6 mg |
| #3 | 3.3 mg |
| #4 | 3.3 mg |

3. Make solutions with the following calculations in TABLE 9.

TABLE 9

Solution calculations.

| | |
|---|---|
| #1 (300 μM or 19.8 mg/mL) | 0.5 mL 1x PBS + 9.9 mg Avidin |
| #2 (200 μM or 13.2 mg/mL) | 0.5 mL 1x PBS + 6/6 mg Avidin |
| #3 (100 μM or 6.6 mg/mL) | 0.5 mL 1x PBS + 3.3 mg Avidin |
| #4 (50 μM or 3.3 mg/mL) | 1.0 mL 1x PBS + 3.3 mg Avidin |
| #5 (25 μM or 1.5 mg/mL) | 0.5 mL 1x PBS + 0.5 mL of 50 μM Avidin |
| #6 (5 μM o r0.3 mg/mL) | 0.4 mL 1x PBS + 0.1 mL of 25 μM Avidin |

4. Dampen talc by adding 500 μL of 1×PBS. Mix well.
5. Centrifuge tubes at 3200 rpm for 5 min
6. Discard supernatant.
7. Add diluted Avidin (see above) and incubate Talc overnight at 4° C., constantly mixing.

Day 2:
1. Centrifuge all tubes with Avidin/Talc for 5 min and incubated overnight at 3200 rpm at 4° C.
2. Collect the supernatant from each tube but discard the pellet.
3. Run the Pierce total protein assay using the following dilutions of the collected supernatant.

TABLE 10

Dilutions for the Pierce protocol.

| | |
|---|---|
| #1 | 1:100 |
| #2 | 1:100 |
| #3 | 1:10 |
| #4 | 1:10 |
| #5 | Straight |
| #6 | Straight |

4. Read plate in the plate reader (absorbance assay) at 660 nm wavelength.
5. See e.g., TABLE 11, TABLE 12, and FIG. 6 for results.

TABLE 11

Figures 5, 6:
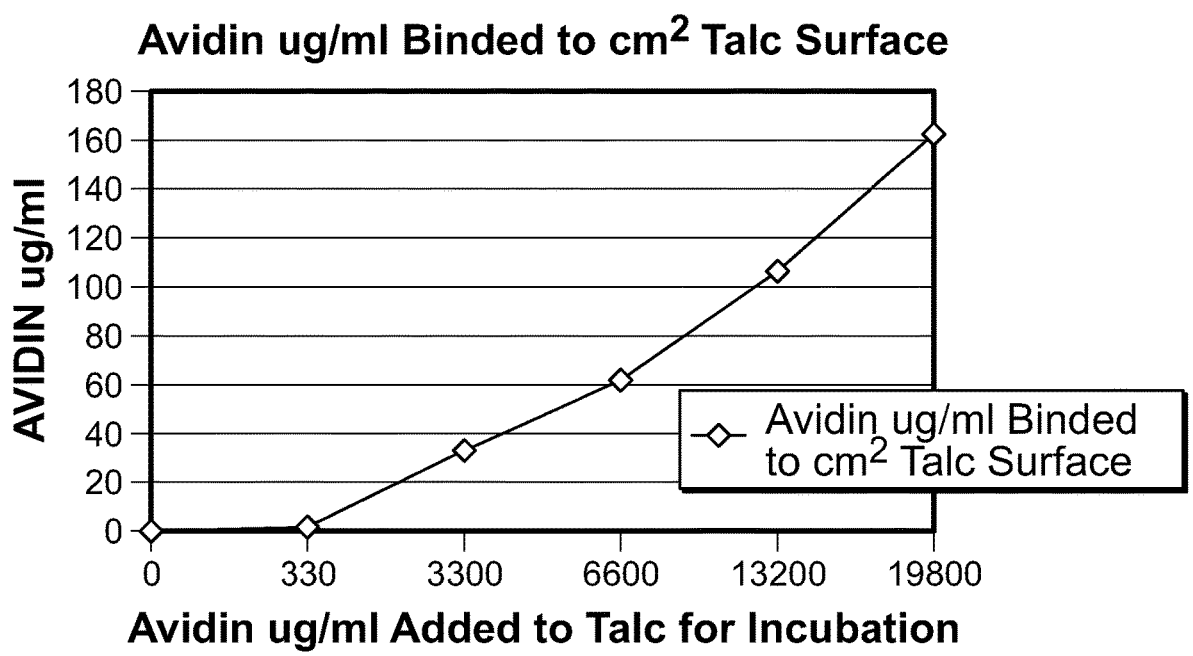
FIG. 5 shows the data points for the scatter plot in FIG. 4.
FIG. 6 is a scatter plot depicting Avidin bound to the surface of talc.

Data for Avidin binding to talc (see e.g., FIG. 6).

| ID | Avidin μg/ml added | Avidin μg, ml in supernatant | Avidin μg/ml binded with talc | Combine surface of 100 mg talc, cm2 | Avidin μg/cm2 talc surface |
|---|---|---|---|---|---|
| 1 | 19800 | 7633.3 | 12166.7 | 74.4 | 163.5 |
| 2 | 13200 | 5247.3 | 7952.7 | 74.4 | 106.9 |
| 3 | 6600 | 1968.5 | 4631.5 | 74.4 | 62.3 |
| 4 | 3300 | 847.3 | 2452.7 | 74.4 | 33.0 |
| 5 | 330 | 219.6 | 110.4 | 74.4 | 1.5 |

TABLE 12

Data for Avidin binding to talc (see e.g., FIG. 6).

| Avidin μg/ml added | Avidin μg/cm2 talc surface |
|---|---|
| 0 | 0 |
| 330 | 1.5 |
| 3300 | 33 |
| 6600 | 62.3 |
| 13200 | 106.9 |
| 19800 | 163.5 |

According to the above results, the plateau was not reached. It was determined that the concentration of Avidin needs to be increased. Thus, the study showed that even with increasing concentrations of Avidin, talc particles were not fully saturated. Therefore, subsequent experiment(s) used decreased amounts of talc.

Example 5: Determination of Flow Cytometry Ability to Analyze FITC- and Rhodamine-Labeled Talc The following Example determined if talc binding to FITC-Biotin/Rhodamine and anti-Avidin-FITC can be analyzed by Flow Cytometry. The following Example shows the size and shape of talc does not preclude analysis of talc samples by Flow Cytometry.

The aim of the below study was to determine if the Flow Cytometry can successfully analyze 50 mg of Talc added to Anti-Avidin FITC and Biotin Rhodamine.

Materials:
1. Monoclonal Anti-Avidin FITC conjugate, Clone WC19.10 (Sigma-Aldrich, Cat. #: F1269, Log #: 111M4813)
2. Biotin Rhodamine 110 Biotium (Cat. #: 80022); 5 mg/3.11.4 μL DMSO or 1.6 mg/mL or 20 mM
3. 10×PBS (Sigma, Cat. #: P5493, Lot #; SLBH0296)
4. Sterile Talc Powder (Bryan Corporation, Cat #: 1690, Lot #: 3M021, Exp. Date: December 2016)

Day 1:
1. Prepare three round bottom Eppendorf tubes with 50 mg of Talc in each.
2. Dampen two tubes with 1 mL of PBS
3. Centrifuge at 3200 rpm for 5 min
4. Discard supernatant
5. Prepare 1 mL solution of 1×PBS, containing 5 μL (or 9.5 μg) of Anti-Avidin (concentration of 1.9 mg/mL).
6. Prepare 1 mL of 1×PBS containing 2 μL (3.2 μg) of Biotin Rhodamine (concentration of 1.6 mg/mL).
7. Incubate Talc with above solutions overnight at 4° C. constantly mixing it.

Figure 7:
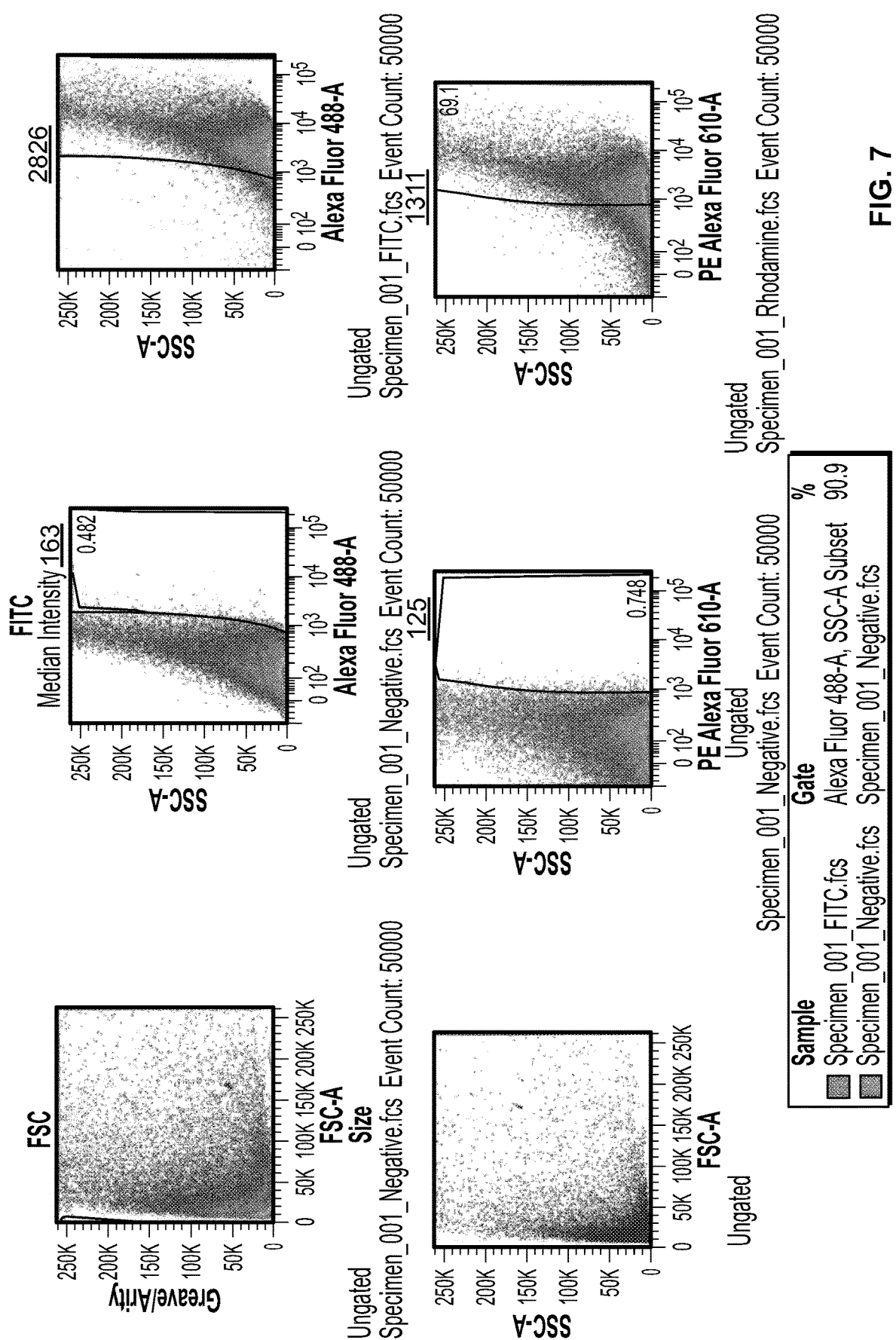
FIG. 7 are a series of flow cytometry data for FITC and Rhodamine labeled talc.

Day 2:
1. Centrifuge incubated tubes at 3200 rpm for 5 min
2. Discard the supernatant liquid.
3. Wash Talc 3× with 1 mL PBS.
4. Resuspend after last wash at 1 mL PBS.
5. Store at 4° C.
6. Dampen dry 50 mg of Talc in third tube with 1 mL PBS.
*Use this Talc as the negative control—request from the flow cytometry technician.
7. Transfer all three tubes to flow cytometry to perform an analysis of the samples.
8. See e.g., FIG. 7 for results.

The study showed that the size and shape of the talc samples can be successfully run through the Flow Cytometry instruments as the level of the dye is detectable. Thus, the study showed FITC and Rhodamine present on the surface of talc is detectable.

Example 6: Varying Concentrations of Talc Incubated with HRP-Avidin in 96-Well Plates to Determine the Plateau The following Example attempted to determine the plateau by using decreasing amounts of talc exposed to HRP-Avidin because increasing the amount of Avidin was not successful in determining the plateau (see e.g., Example 4).

1 mg, 5 mg, 10 mg, and 20 mg of Talc was incubated with HRP Avidin in 96 Well Plate To Find The Plateau.

The aim of this study was to define the plateau (the full saturation of Talc) by incubating small amounts of Talc in a 96 well plate with different concentrations of HRP Avidin.

Materials:
1. HRP Avidin
2. Talc
3. 10×PBS
4. TMB (ENZO, Cat. #: 80-0350, Lot #: 01071401)
5. Stop Solution 2 (ENZO, Cat. #: 80-0377, Lot #: 03191306)

Day 1:
1. This experiment uses the following concentrations of HRP Avidin (see TABLE 13).

TABLE 13

Concentrations of HRP Avidin.

40 ng/mL (260 pM)
20 ng/mL (130 pM)
10 ng/mL (65 pM)
5 ng/mL (32.5 pM)

2. Calculations of stock dilutions: 5.75 mg/mL or 5.75 µg/µL or 32.5 µM of HRP Avidin stock (see TABLE 14).

TABLE 14

Calculations of stock dilutions: 5.75 mg/mL or 5.75 µg/µL or 32.5 µM of HRP Avidin stock.

| | |
|---|---|
| 1:100 HRP Avidin stock dilution | 198 µL of PBS + 2 µL of HRP Avidin |
| 1:1000 HRP Avidin stock dilution | 198 µL of PBS + 2 µL of 1:100 HPR Avidin dilution |
| 1.5 mL of 40 ng/mL or 260 pM of solution | 1.488 mL of PBS + 12 µL of 1:1000 HRP Avidin dilution |
| 1:2 serial dilutions down* | 0.75 mL of PBS + 0.75 mL of the previous dilution* |

*Continued to dilute these solutions until the last concentration.

3. Weigh 200 mg of Talc and resuspend in 1 mL of PBS. This makes 200 mg/1000 µL or 0.2 mg/1 µL.
4. Follow the following calculations to get the proper amount of Talc in the wells (see TABLE 15).

TABLE 15

Calculations for concentration of Talc in the wells.

| | |
|---|---|
| 20 mg of Talc | 100 µL of Talc stock |
| 10 mg of Talc | 50 µL of Talc stock |
| 5 mg of Talc | 25 µL of Talc stock |
| 1 mg of Talc | 5 µL of Talc stock |

5. Follow the plate layout and calculations to fill up the plate with Talc.
6. Centrifuge plate at 3200 rpm for 3 min.
7. Take out supernatant liquid as much as possible.
*Do not touch pellet.
8. Fill up the plate with HRP solutions (see plate layout).
9. Incubate plate overnight at 4° C., constantly mixing it.
*sample was protected from light.

Day 2:
1. Finishing Day 1 experiment, wash wells with Talc 3× with 300 µL of PBS.
2. After final wash, resuspend Talc in 100 µL PBS.
3. Add 100 µL of TMB to all the wells used in the experiment.
4. Incubate at Room Temperature for 20 min
5. Add 100 µL Stop solution 2.
6. Read plate at absorbance setting of 450 nm.
7. See e.g., TABLE 16, TABLE 17, TABLE 18, and TABLE 19 for results.

TABLE 16

| | Concentration Avidin HRP. | | | |
|---|---|---|---|---|
| talc, mg | 40 ng/ml | 20 ng/ml | 10 ng/ml | 5 ng/ml |
| 1 | 2.741 | 1.5835 | 1.1545 | 0.798 |
| 5 | 2.7495 | 2.4425 | 1.4245 | 1.051 |
| 10 | 3.1785 | 3.6495 | 3.296 | 2.6405 |
| 20 | 3.5645 | 3.475 | 3.0635 | 2.617 |

TABLE 17

| Concentration Avidin HRP. | |
|---|---|
| average stock OD | |
| 40 ng/ml | 3.9855 |
| 20 ng/ml | 3.958 |
| 10 ng/ml | 3.826 |
| 5 ng/ml | 2.908 |

TABLE 18

| Combined surface of talc. | |
|---|---|
| talc, mg | Combine surface of talc, cm2 |
| 1 | 0.744 |
| 5 | 3.72 |
| 10 | 7.44 |
| 20 | 14.88 |

TABLE 19

| | HRP Avidin bound to cm$^2$ surface of talc, OD. | | | |
|---|---|---|---|---|
| talc, mg | 40 ng/ml | 20 ng/ml | 10 ng/ml | 5 ng/ml |
| 1 | 3.68 | 2.13 | 1.55 | 1.07 |
| 5 | 0.74 | 0.65 | 0.38 | 0.28 |
| 10 | 0.43 | 0.49 | 0.44 | 0.35 |
| 20 | 0.24 | 0.23 | 0.21 | 0.18 |

The results were unsuccessful in defining a plateau. The study showed HRP-Avidin readings were out of the range detectable by instrumentation. The experiment was repeated using a mixture of labeled and unlabeled Avidin.

Example 7: HRP Avidin: Determination of the Amount of Avidin Completely Saturating 1 Mg, 5 Mg, 10 Mg, and 20 Mg Talc The following Example attempted to determine the plateau by repeating the experiment in Example 6 with subsequent collection of plate supernatants followed by analysis of same.

The aim of the study was to minimize the amount of Talc in the 96 well microplates by using increments of 20 mg, 10 mg, 5 mg, and 1 mg of Talc added to HRP Avidin to determine the point of full saturation of Talc.

Materials:
1. HRP Avidin
2. Talc
3. 10×PBS

4. TMB (ENZO, Cat. #: 80-0350, Lot #: 01071401)

5. Stop Solution 2 (ENZO, Cat. #: 80-0377, Lot #: 03191306)

Day 1:

1. This experiment uses the following concentrations of HRP Avidin (see TABLE 20).

TABLE 20

| Concentrations of HRP Avidin. |
| --- |
| 40 ng/mL (260 pM) |
| 20 ng/mL (130 pM) |
| 10 ng/mL (65 pM) |
| 5 ng/mL (32.5 pM) |
| 2.5 ng/mL (16.25 pM) |
| 1.25 ng/mL (8.13 pM) |
| 0.63 ng/mL (4.05 pM) |

2. Calculations of the HRP stock dilutions: 5.75 mg/mL or 575 µg/µL or 32.5 µM (see TABLE 21).

TABLE 21

| Calculations of the HRP stock dilutions. | |
| --- | --- |
| 1:100 HRP Avidin stock dilution | 198 µL of PBS + 2 µL of HRP Avidin |
| 1:1000 HRP Avidin stock dilution | 90 µL of PBS + 10 µL of 1:100 HPR Avidin dilution |
| 3 mL of 40 ng/mL or 260 pM of solution | 3 mL of PBS + 24 µL of 1:1000 HRP Avidin dilution |
| 1:2 serial dilutions down* | 1.5 mL of PBS + 1.5 mL of the previous dilution* |

*Continue to dilute these solutions down until the last concentration.

3. Weigh 500 mg of Talc and resuspend it in 2.5 mL of PBS; resulting in a concentration of 200 mg/1000 µL.

4. Follow calculations to get the proper amount of Talc in the wells (see TABLE 22).

TABLE 22

| Calculations for Talc concentrations in the wells. | |
| --- | --- |
| 20 mg of Talc | 100 µL of Talc stock |
| 10 mg of Talc | 50 µL of Talc stock |
| 5 mg of Talc | 25 µL of Talc stock |
| 1 mg of Talc | 5 µL of Talc stock |

5. Fill up the plate with Talc.

6. Centrifuge plate at 3200 rpm for 3 min

7. Remove supernatant without touching the remaining pellet.

8. Fill up the plate with HRP solutions.

9. Mix Talc with the HRP solutions by pipetting up and down.

10. Incubate the plate overnight at 4° C., constantly mixing. Protect it from the light.

Day 2:

1. Complete Day 1 experiments, wash wells with Talc 3× with 300 µL of PBS.

2. After the final wash, resuspend Talc in 100 µL of PBS.

3. Add 100 µL of TMB to all the wells used in the experiment.

4. Incubate at room temperature for 20 min.

5. Add 100 µL of Stop Solution 2.

6. Read the plate at absorbance bandwidth of 450 nm.

7. Centrifuge plate at 3200 rpm for 3 min

8. Remove the supernatant and transfer onto a new clean plate.

9. Read absorbance of samples (supernatant) in new plate at 450 nm.

10. Obtain results for plate 1 and plate 2 (see e.g., FIG. 8, FIG. 9).

The study was unsuccessful in determining the plateau. Next experiments will increase the amount of HRP Avidin, and work only with 1 mg and 5 mg of Talc. Use min HRP Avidin+Cold Avidin to fill up surface of Talc. The study showed HRP-Avidin readings were out of the range detectable by instrumentation. The experiment was repeated using mixture of labeled and unlabeled Avidin with 1 and 5 mg talc.

Example 8: Saturation of Avidin to Talc
(Continuation of Experiment to Determine Plateau)

The following Example attempted to determine the plateau by utilizing small amounts of talc using mixtures of containing varying concentrations of labeled and unlabeled Avidin.

The aim of the following study was to optimize the concentration of Avidin to Talc by increasing the concentration of Avidin and to completely saturate 1 mg and 5 mg of Talc. Two experiments with different combinations of Avidin were designed as follows:

Experiment 1: Using a mixture of Horseradish Peroxidase (HRP) Avidin (hot Avidin) and cold Avidin.

Experiment 2: Using only a high concentration of HRP Avidin.

Materials:

1. Talc

2. HRP Avidin

3. Pure (cold) Avidin

4. TMB (ENZO, Cat. #: 80-0350, Lot #: 01071401)

5. Stop Solution 2 (ENZO, Cat. #: 80-0377, Lot #: 03191306)

6. 10×PBS

Day 1:

Experiment 1:

1. Calculate the amount of hot and cold Avidin that will be used to mix in Experiment 1.

TABLE 23

| Calculated amount of hot and cold Avidin used in Experiment 1. | | |
| --- | --- | --- |
| Hot Avidin | + | Cold Avidin |
| 40 ng/mL | + | 70 mg/mL |
| 20 ng/mL | + | 35 mg/mL |
| 10 ng/mL | + | 17.5 mg/mL |
| 5 ng/mL | + | 8.75 mg/mL |
| 2.5 ng/mL | + | 4.37 mg/mL |
| 1.25 ng/mL | + | 2.18 mg/mL |

2. Weigh 42 mg Avidin and resuspend it in 600 µL of PBS containing 40 ng/mL HRP Avidin (hot).

3. The following steps are the serial dilution preparations of the 40 ng/mL of hot Avidin:

1:100 dilution of HRP Avidin stock solution: 198 µL of PBS+2 µL of 32.5 µM HRP Avidin stock 1:1000 dilution of HRP Avidin stock solution: 90 µL of PBS+10 µL of 1:100 HRP Avidin stock Prepare 600 µL of 40 ng/mL of hot Avidin: 595.2 µL of PBS+4.8 µL of 1:1000 hot Avidin 4. Make 1:2 serial dilutions down to keep them above the planned concentrations of hot/cold Avidin mix:
   #1: 595.2 µL of PBS+4.8 µL of 1:1000 hot Avidin+42 mg of cold Avidin
   #2: 300 µL of PBS+300 µL of #1 solution
   Keep the same proportions down to the last planned concentration
5. Weigh 100 mg of Talc
6. Dampen Talc in 200 µL of PBS (100 mg/200 µL or 0.5 mg/µL) and mix gently until all the Talc is in solution.
7. Transfer Talc to the 96 well plate: Take 2 µL of Talc to get 1 mg of Talc in the well and 10 µL to get 5 mg of talc in the well following the plate layout (see TABLE 24).

TABLE 24

Experiment 1: mix of hot and cold Avidin. Avidin bound to talc, OD.

| Talc, mg/well | HRP AVIDIN + cold AVIDIN added | | | | | |
|---|---|---|---|---|---|---|
| | 40 ng/ml + 70 mg/ml | 20 ng/ml + 35 mg/ml | 10 ng/ml + 17.5 mg/ml | 5 ng/ml + 8.75 mg/ml | 2.5 ng/ml + 4.37 mg/ml | 1.25 ng/ml + 2.18 mg/ml |
| 1 | 0.465 | 0.482 | 0.365 | 0.21 | 0.332 | 0.312 |
| 5 | 1.839 | 1.41 | 1.196 | 1.019 | 1.152 | 0.992 |

TABLE 25

Experiment 1: remaining Avidin (not bound to talc) in supernatant, OD.

| Talc, mg/well | HRP AVIDIN + cold AVIDIN added | | | | | |
|---|---|---|---|---|---|---|
| | 40 ng/ml + 70 mg/ml | 20 ng/ml + 35 mg/ml | 10 ng/ml + 17.5 mg/ml | 5 ng/ml + 8.75 mg/ml | 2.5 ng/ml + 4.37 mg/ml | 1.25 ng/ml + 2.18 mg/ml |
| 1 | 4 | 4 | 4 | 3.576 | 1.938 | 1.01 |
| 5 | 4 | 4 | 4 | 3.46 | 1.869 | 1.177 |

*Repeat steps for experiment 2.

8. Mix the talc with 100 µL of Hot/Cold Avidin solutions prepared above (see plate layout).

Experiment 2:
1. This experiment only uses Hot HRP Avidin. Using the 1:1000 stock dilution that was used in Experiment 1, prepare the following concentrations of Hot Avidin:

TABLE 26 concentrations of Hot Avidin for Experiment 2.

300 ng/mL
150 ng/mL
75 ng/mL
37.5 ng/mL
18.75 ng/mL
9.375 ng/mL

2. Prepare the following calculations for dilution of hot Avidin:
   Take 600 µL of 300 ng/mL of Hot Avidin=564 µL of PBS+36 µL of 1:1000 HRP Avidin stock solution
   Make 600 µL of the next concentration: 300 µL of PBS+300 µL of 300 ng/mL of Hot Avidin.
   Use the same proportions to get the last planned concentration.
3. Transfer 100 µL of prepared solutions to the well.
4. Cover the plate with aluminum foil.
5. Incubate overnight at 4° C., constantly mixing the solutions.

Day 2:
1. Centrifuge plate at 3200 rpm for 3 min.
2. Using a new 96 well plate, transfer 80 µL of the supernatant to the new plate without disturbing the pellet of Talc.
3. Add 280 µL of PBS to the original plate with Talc and mix by pipetting up and down.
4. Centrifuge plate and discard the supernatant.
5. Repeat washing 2× with 300 µL of PBS and discard the supernatant.
6. After the last wash, resuspend the pellet in 100 µL PBS.
7. Add 100 µL of TMB solution to plate #1 with Talc.
8. Incubate Plate #1 at room temperature for 20 min.
9. Add 80 µL of TMB solution to the plate #2 (containing only the supernatant after overnight incubation).
10. Add 100 µL of Stop Solution 2 to the plate #1.
11. Add 80 µL of Stop Solution 2 to the plate #2.
12. Read absorbance at 450 nm.

TABLE 27

Experiment 2: Hot Avidin bound to talc, OD.

| Talc, mg/well | Amount of Hot AVIDIN added | | | | | |
|---|---|---|---|---|---|---|
| | 300 ng/ml | 150 ng/ml | 75 ng/ml | 37.5 ng/ml | 18.75 ng/ml | 9.375 ng/ml |
| 1 | 3.951 | 3.801 | 3.659 | 1.77 | 1.091 | 1.041 |
| 5 | 3.899 | 2.862 | 2.552 | 1.855 | 1.752 | 1.214 |

TABLE 28

Experiment 2: Remaining Avidin (not bound to talc) in supernatant, OD.

| Talc, mg/well | Amount of Hot AVIDIN added | | | | | |
|---|---|---|---|---|---|---|
| | 300 ng/ml | 150 ng/ml | 75 ng/ml | 37.5 ng/ml | 18.75 ng/ml | 9.375 ng/ml |
| 1 | 0.935 | 1.509 | 0.168 | 0.082 | 0.171 | 0.165 |
| 5 | 0.062 | 0.059 | 0.061 | 0.051 | 0.05 | 0.051 |

TABLE 29

OD of working solutions.

| hot AVIDIN | OD |
|---|---|
| 300 ng/mL | 3.608 |
| 150 ng/mL | 4 |
| 75 ng/mL | 3.938 |
| 37.5 ng/ml | 3.898 |
| 18.75 ng/ml | 2.212 |
| 9.375 ng/ml | 2.185 |

TABLE 30

OD of working solutions.

| Hot + cold AVIDIN | OD |
|---|---|
| 40 ng/ml + 70 mg/ml | 4 |
| 20 ng/ml + 35 mg/ml | 4 |
| 10 ng/ml + 17.5 mg/ml | 3.855 |
| 5 ng/ml + 8.75 mg/ml | 2.263 |
| 2.5 ng/ml + 4.37 mg/ml | 1.372 |
| 1.25 ng/ml + 2.18 mg/ml | 1.04 |

The study showed HRP-Avidin readings were out of the range detectable by instrumentation.

Example 9: Binding of Bleomycin to Talc

The following Example incubated talc with varying concentrations of bleomycin and determined the efficiency of binding with fluorescent microscopy.

50 mg of talc was incubated with different concentrations of bleomycin and the efficiency of binding was determined under the fluorescent microscope.

Materials:
1. Bleomycin Sulfate *Streptomyces verticillus* (Sigma-Aldrich, Cat. #: 15361-1 mg, Lot #: BCBK 1641V)
2. Water (Sigma Life Science, Cat. #: W3500, Lot #: RNBD1156)
3. Talc (same as in previous examples)
4. Vectashield Mounting Medium Day 1:
1. Reconstitute bleomycin by adding 100 μL of water to 1 mg of bleomycin. Get the concentration to 10 mg/mL and mix, keeping the drug at 4° C.
2. Prepare three identical tubes with 50 mg of talc in each.
3. Make 1 mL of 100 μg/mL solution: 990 μL of water+10 μL of 10 mg/mL of stock.
4. Make 1 mL of 1 μg/mL solution: 990 μL of water+10 μL of 100 μg/mL solution.
5. Add 1 mL of water to tube with talc and label it as #1.
6. Add 990 μL of 100 μg/mL solution to the other tube with talc and label it as Tube #2.
7. Add 1 mL of 1 μg/mL solution to remaining tube with talc and label it as Tube #3.
8. Mix Talc with added solutions and cover the tubes with aluminum foil.
9. Incubate overnight at 4° C., constantly mixing it.

Day 2:
1. Centrifuge tubes at 3200 rpm for 3 min.
2. Discard the supernatant.
3. Wash tubes 3× with 1 mL of water.
4. After last wash, complete, remove the water and resuspend the pellet in Vectashield mounting medium for fluorescence.
5. Take out ~45 μL of mixture from each tube to the glass slides.
6. Check slides under fluorescent microscope under DAPI filter.
7. There is no difference in image between the negative control (talc that did not incubate with bleomycin) and positive samples (talc that incubated with bleomycin).

Conclusion: It is presently thought that emission signals are very weak (see e.g., same results in publication Periasamy et al, Localization of bleomycin in single living cell using three-photon excitation microscopy, SPIE Proceedings, 2001, p. 348, Vol. 4262). The same experiment as designed above was repeated, but it did not use the microscope to check the binding. Rather, an experiment using Flow Cytometry with excitation at 290 nm will be conducted and with an expected emission of around 420 nm.

The study showed there is no difference in fluorescent imaging between negative control and talc incubated with bleomycin. It is presently thought that the emission filter is not adequate or that signal is very weak and, thus, a repeat experiment was planned to analyze the binding with a flow cytometer at excitation wavelength of 290 nm and emission wavelength at approximately 420 nm (see e.g., Example 11).

Example 10: "Hot" and "Cold" Avidin Mix Binds to Talc (Continuation of Plateau Definition)

The following Example verified the difference in absorbance between "cold" (unlabeled) Avidin binding to talc by utilizing a fixed amount (40 ng/ml) of "hot" (labeled) HRP-Avidin and adding different amounts of "cold" Avidin.

Materials:
1. Sterile talc powder (Bryan Corporation, Cat. #: 1690, Lot #: 3M021, Exp. Date: December 2016)
2. Avidin from egg white (Sigma, Cat. #: A9275-100 mg, Lot #: SLBB9685)
3. 10×PBS (Sigma, Cat. #: P5493-1L, Lot #: SLBB9685)
4 Immunopure Avidin, Horseradish Peroxidase, Conjugated (Thermo Scientific, Cat. #: 21123, Lot #: OJ193825)
5. Water (Sigma Life Science, Cat. #: 3500, Lot #: RNBD1156)
6. Fetal Bovine Serum (ATCC, Cat. #: 30-2020, Lot #: 60353051, Bottle #: 2692)
7. TMB Substrate (ENZO, Cat. #: 80-0350, Lot #: 01071401)
8. Stop Solution 2 (ENZO, Cat. #: 80-0377, Lot #: 02241430)

Day 1:
Preparation of HRP (Hot) Avidin:
1. Prepare 10 mL of 40 ng/mL (or 260 μM) HRP Avidin in 1×PBS using 5.75 mg/mL or 32.5 μM of HRP Avidin stock solution.
2. Make 1:100 dilution from HRP Avidin stock solution: 198 μL of PBS+2 μL HRP Avidin.
3. Make 1:1000 dilution: 90 μL of PBS+10 μL of 1:100 HRP Avidin stock solution dilution.

4. Make 10 mL of 40 ng/mL or 260 µM solution: 10 mL of PBS+80 µL of 1:1000 dilution.

5. Keep solution on ice.

Preparation of Diluted Cold Avidin:

6. Weighed 12 mg of Avidin (cold Avidin), then resuspend it in 3 mL of PBS that contained 40 ng/mL of "hot" Avidin. So the solution will now be 40 ng/mL hot Avidin+4 mg/mL of Cold Avidin. Labeled this tube as #1.

7. Make 3 mL of 1:10 dilution of solution in Tube #1 and make labeled Tube #2 containing 2.7 mL of 40 ng/mL in PBS+300 µL of tube #1. The solution in the tube will contain 40 ng/mL of Hot Avidin+400 µg of Cold Avidin.

8. Make 1:2 dilution of solution in Tube #2 using as a diluted solvent of 4 ng/mL of Hot Avidin in PBS. The final concentration will be 40 ng/mL of Hot Avidin+200 µg/mL of Cold Avidin. Label this tube as Tube #3.

9. Prepare 3 mL of solution from step 8: 1.5 mL of 40 ng/mL of Hot Avidin in PBS+1.5 mL of Tube #2.

10. Make 1:2 dilution of solution in Tube #3, using as a solvent of 40 ng/mL Hot Avidin in PBS. The final concentration will be 40 ng/mL of hot Avidin+100 µg/mL of Cold Avidin. Label this tube as Tube #4.

11. Prepare 3 mL of solution: 1.5 mL of 40 ng/mL of Hot Avidin in PBS+1.5 mL of Tube #3.

12. Keep solutions on ice.

Preparation of Talc:

13. Weight 100 mg of Talc.

14. Resuspend Talc in 200 µL of PBS making 0.5 mg/µL.

15. This experiment will be using 1 mg and 5 mg of Talc. To get the correct amount of 1 mg of Talc into the 96 well microplate, 2 µL of Talc/PBS mixture will be transferred. To get 5 mg of Talc, 10 µL of Talc/PBS mixture will be taken.

16. Plate will be loaded as shown in TABLE 31.

TABLE 31

Plate design.

| | 1 | 2 | 3 | 4 | 5 | 6 | 7 | 8 | 9 | 10 | 11 | 12 |
|---|---|---|---|---|---|---|---|---|---|---|---|---|
| 1 mg Talc | | | | | | | | | | | | |
| 5 mg Talc | | | | | | | | | | | | |

TABLE 32

Plate loading protocol.

| Columns: | Solutions Added: |
|---|---|
| 1, 2, 3 | 40 ng/mL of Hot Avidin + 100 µg of Cold Avidin |
| 4, 5, 6 | 40 ng/mL of Hot Avidin + 200 µg/mL of Cold Avidin |
| 7, 8, 9 | 40 ng/mL of Hot Avidin + 400 µg/mL of Cold Avidin |
| 10, 11, 12 | 40 ng/mL of Hot Avidin + 4 mg/mL of Cold Avidin |

17. Add Talc mixture to proper wells.

18. Add 100 µL of Prepared hot/cold Avidin solutions stored on ice to the Talc following the design of the plate (see e.g., FIG. 7).

19. Using the pipetter, mix the Talc and Avidin mixture well by pumping up and down.

20. Cover the plate with Aluminum foil.

21. Incubate plate overnight at 4° C., constantly mixing it on the rocker.

Day 2:

1. Transfer the plate to room temperature.

2. Centrifuge it at 1500 rpm for 3 min.

3. Wash the plate 3× with 300 µL PBS containing 10% FBS.

4. After the final wash, resuspend Talc in 100 µL of PBS.

5. Add 100 µL of TMB.

6. Incubate at room temperature in no light for 20 min

7. Add 100 µL of Stop Solution 2.

8. Read absorbance at 450 nm using the plate reader.

9. See e.g., TABLE 32 for results.

TABLE 32

Efficiency of binding talc to different combinations of "hot" and "cold" Avidin, OD.

| Amount of talc (mg) | 4 ng/ml hot Avidin + 100 µg/ml cold Avidin | 40 ng/ml hot Avidin + 200 µg/ml cold Avidin | 40 ng/ml hot Avidin + 400 µg/ml cold Avidin | 40 ng/ml hot Avidin + 4 mg/ml cold Avidin |
|---|---|---|---|---|
| 1 mg | 1.91 | 1.65 | 1.21 | 1.07 |
| 5 mg | 2.92 | 3.18 | 3.17 | 2.18 |

The study successfully obtained the plateau. The above experiment was repeated to verify results and included additional negative and positive controls (see e.g., Example 12).

Example 11: Binding of Bleomycin to Talc: A Repeated Experiment to Check the Efficiency with Flow Cytometry The following Example verified the binding efficiency of bleomycin to talc by incubating 25 mg talc with varying concentrations of bleomycin with subsequent reading by flow cytometry.

Binding Bleomycin to Talc (A Repeated Experiment): Checking The Efficiency Of The Flow Cytometry Purpose: incubate 25 mg talc with different concentration of BLEOMYCIN and check efficiency of binding under flow cytometry.

Materials:

1. Bleomycin sulfate *Streptomyces verticillus* (Sigma-Aldrich, cat #15361-1 mg, lot #BCBK 1641V).

2. Talc, (same as used in previous Examples)

3. 10×PBS (Sigma, Cat. #: P5493-1L, Lot #: SLBH0296)

Day 1:

1. Prepare four identical tubes with 25 mg talc in each one.

2. Make 0.5 mL of 500 µg/mL Bleomycin solution: 475 µL PBS+25 µL of 10 mg/mL bleomycin stock solution.

3. Make 0.5 ml of 100 µg/ml Bleomycin solution: 475 µL PBS+5 µL of 10 mg/ml solution.

4. Make 0.5 mL of 1 µg/mL Bleomycin solution: 495 µL PBS+5 µL of 100 µg/mL solution.

5. Make the negative control: 500 µL of PBS+25 mg of Talc.

6. Mix all tubes well.

7. Incubate overnight at 4° C. on the 360 rotator and protected from light.

Day 2:

1. Centrifuge all tubes at 3200 rpm. 3 min

2. Discard the supernatant liquid.

3. Wash tubes 3× with 1 ml of PBS.

4. After last wash completely remove PBS and resuspend pellet in 500 µL PBS.

5. Transfer tubes for flow cytometry for analysis.

6. Flow cytometry with bleomycin:
   a. 25 µL of each concentration was transferred into a glass falcon tube as shown in TABLE 33.

TABLE 33

Bleomycin sample concentration.

25 μL control no bleomycin + 0.5 ml of PBS
25 μL of 1 mg/ml bleomycin + 0.5 ml of PBS
25 μL of 100 mg/ml bleomycin + 0.5 ml of PBS
25 μL of 500 mg/ml bleomycin + 0.5 ml of PBS b. The control sample was placed in the flow cytometer to determine the control light scatter.
c. The emissions were set for 353 and 405 with excitation wavelength set between 244-248 mm and 289-294 mm.
d. Each concentration was placed in the flow cytometer and the data was uploaded.
e. The emissions and excitation wavelength was changed to the values shown in TABLE 34.

TABLE 34

Emission and excitation wavelengths (nm).

Figure 10:
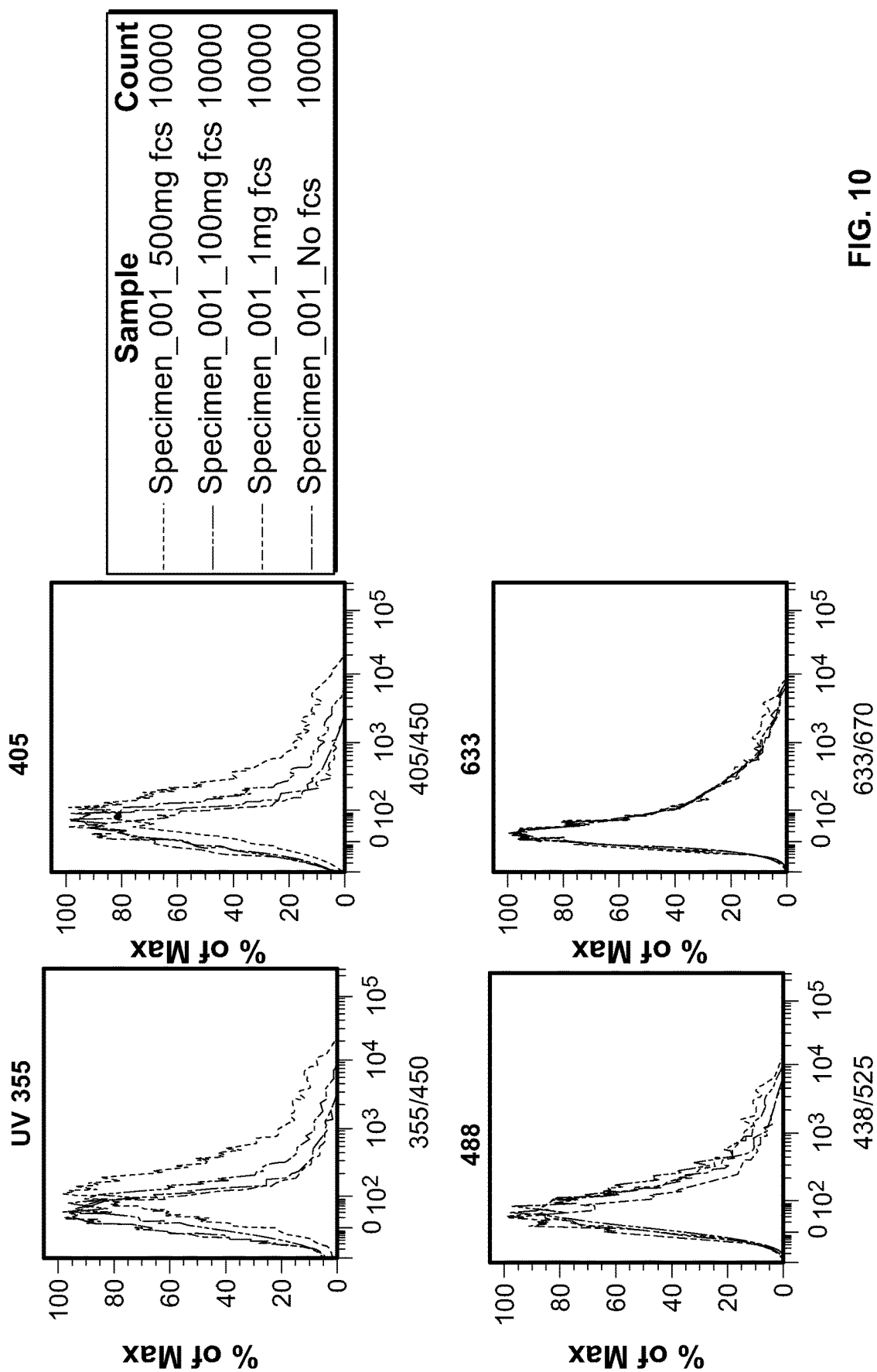
FIG. 10 are a series of flow cytometry data for bleomycin and talc at various excitation and emission wavelengths.
Figure 10:
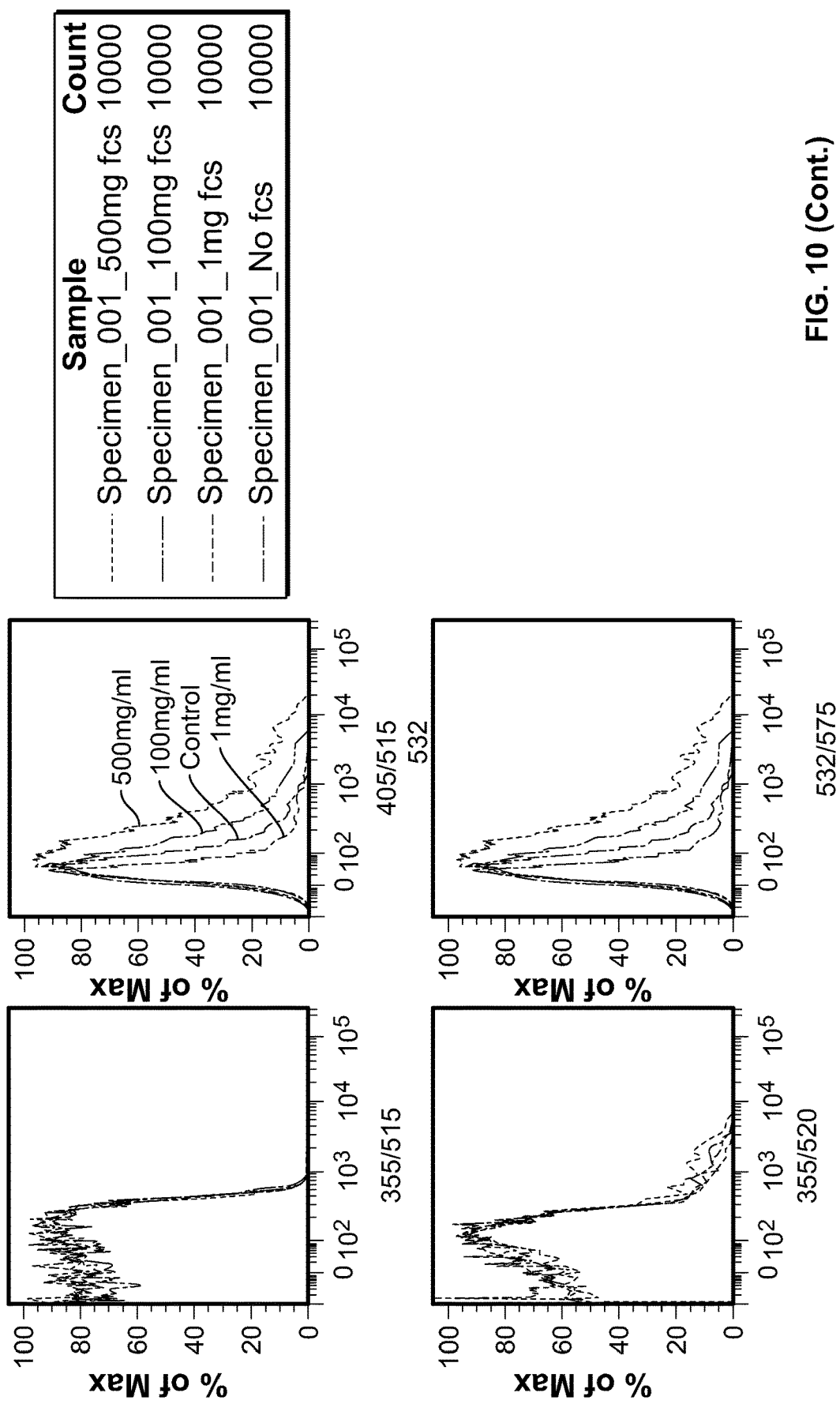
Figure 11:
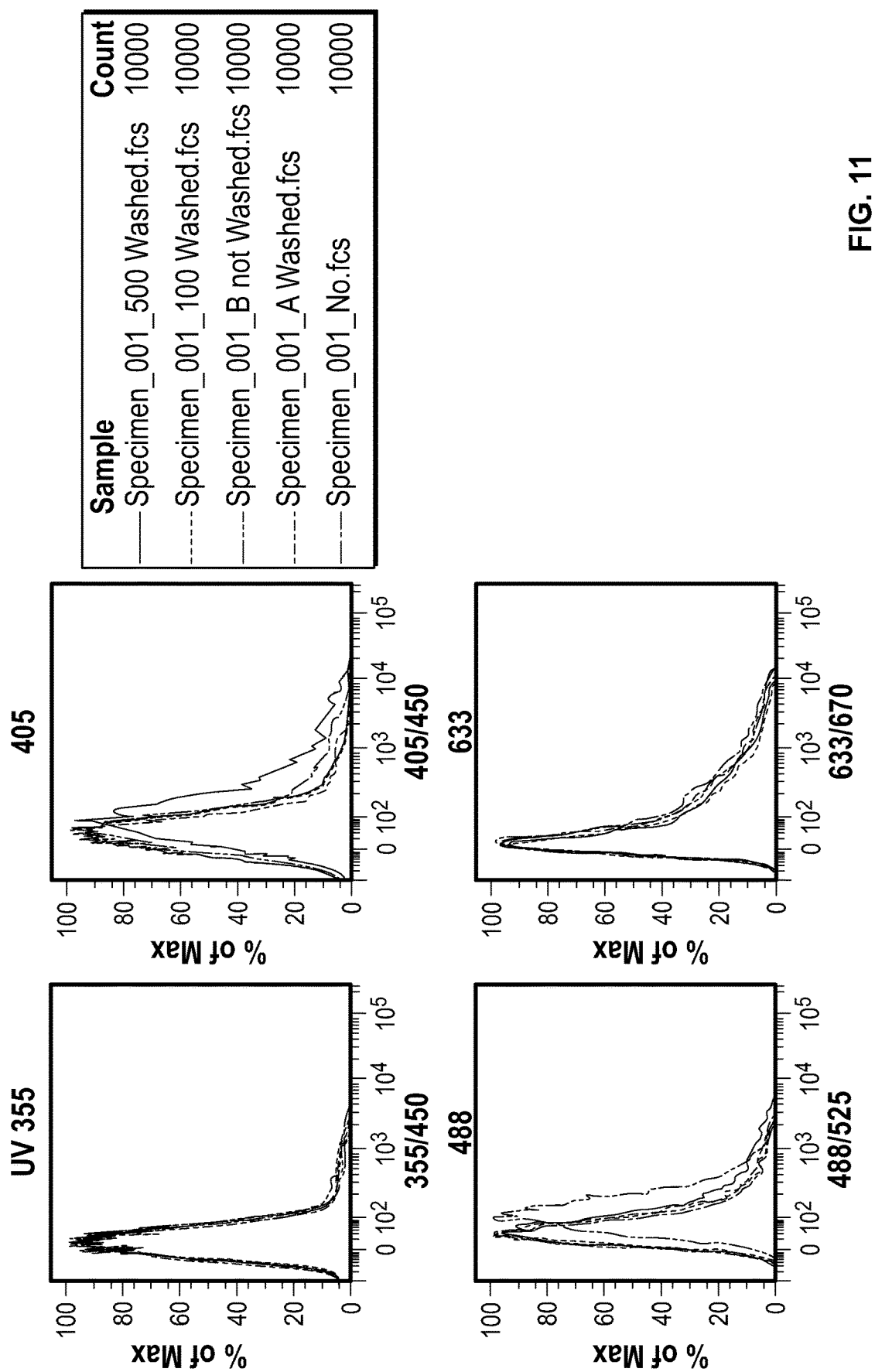
FIG. 11 are a series of flow cytometry data for bleomycin and talc at various excitation and emission wavelengths (repeated study).
Figure 11:
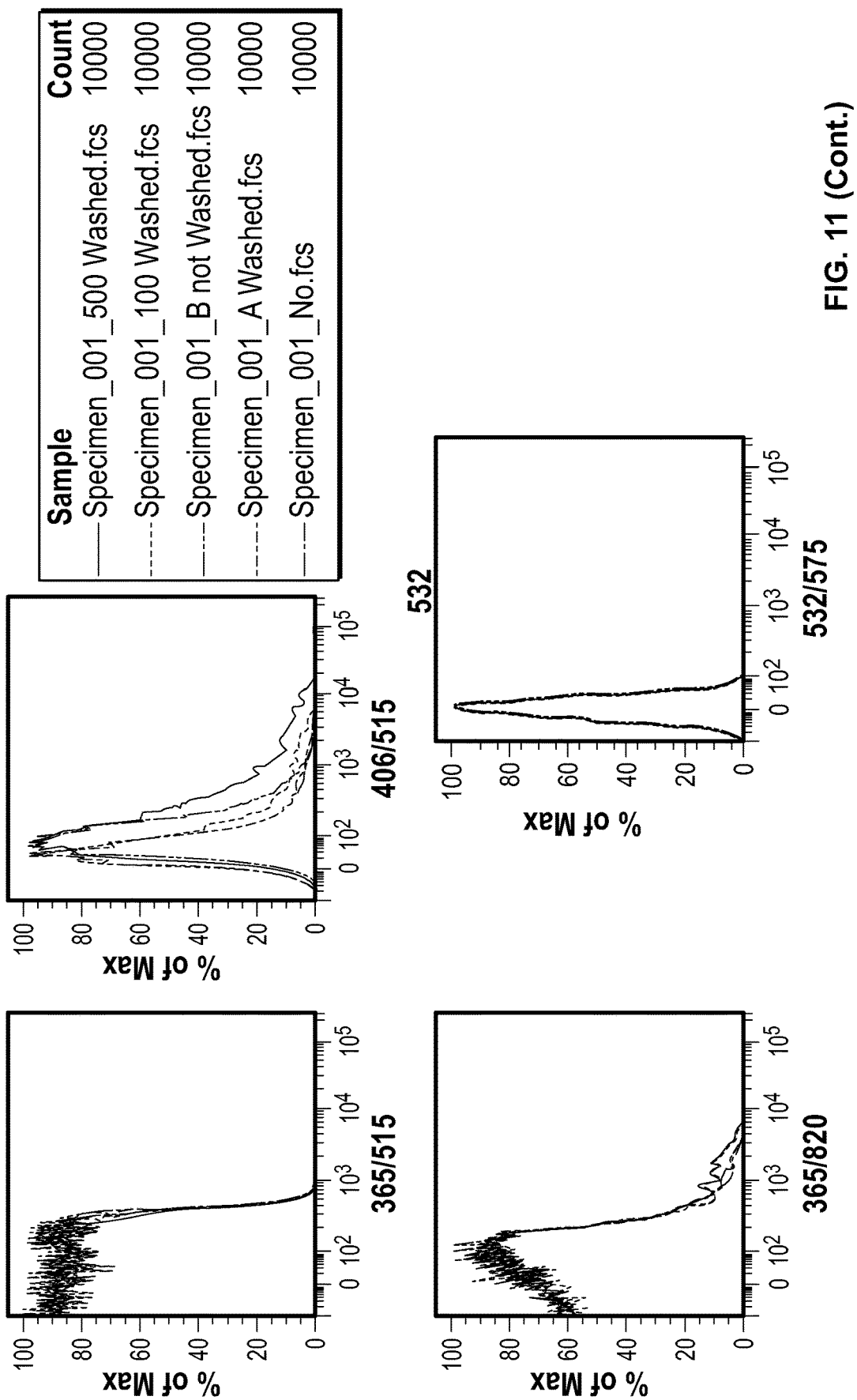
Figure 12:
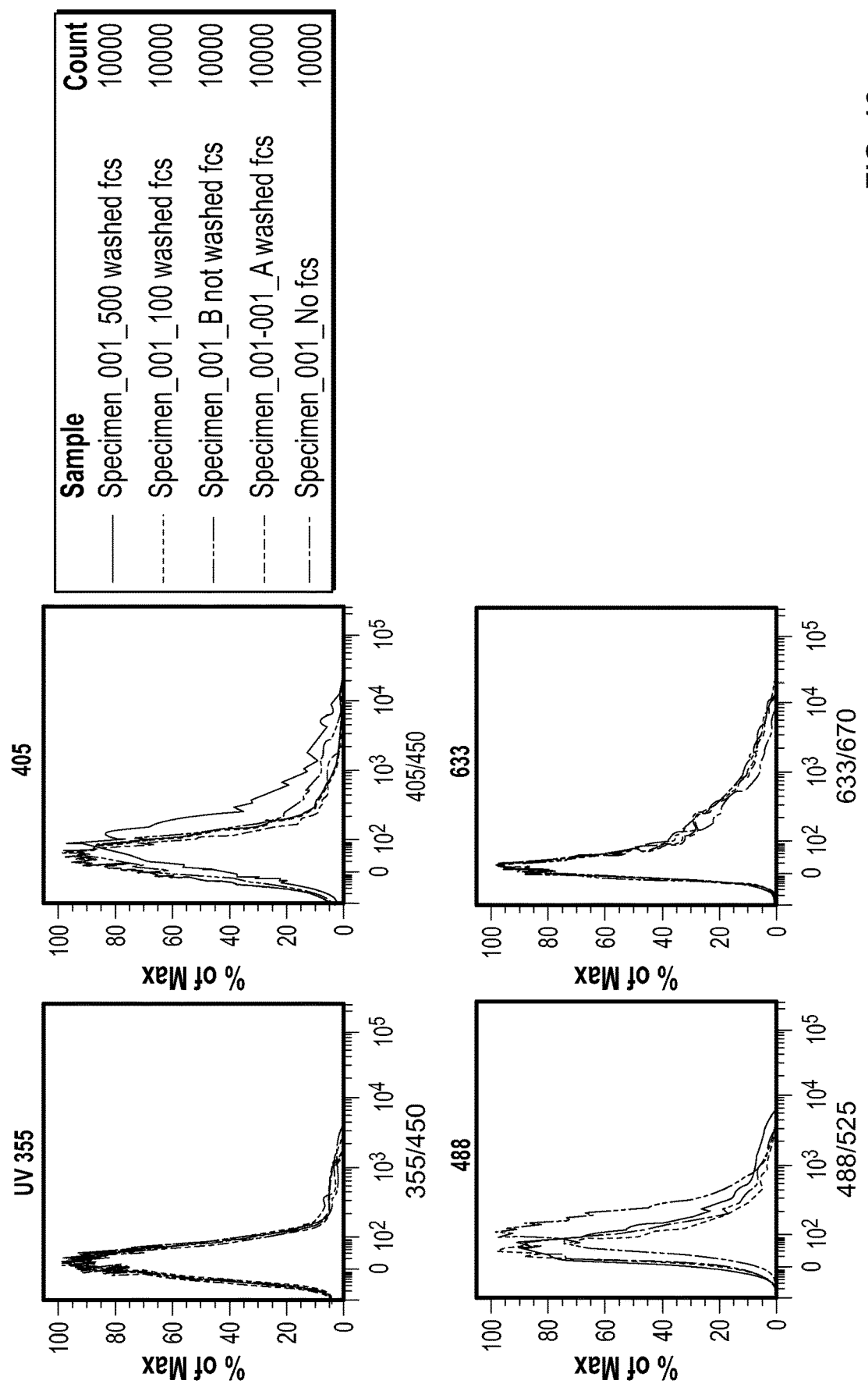
FIG. 12 are a series of flow cytometry data for bleomycin and talc at various excitation and emission wavelengths (repeated study).
Figure 12:
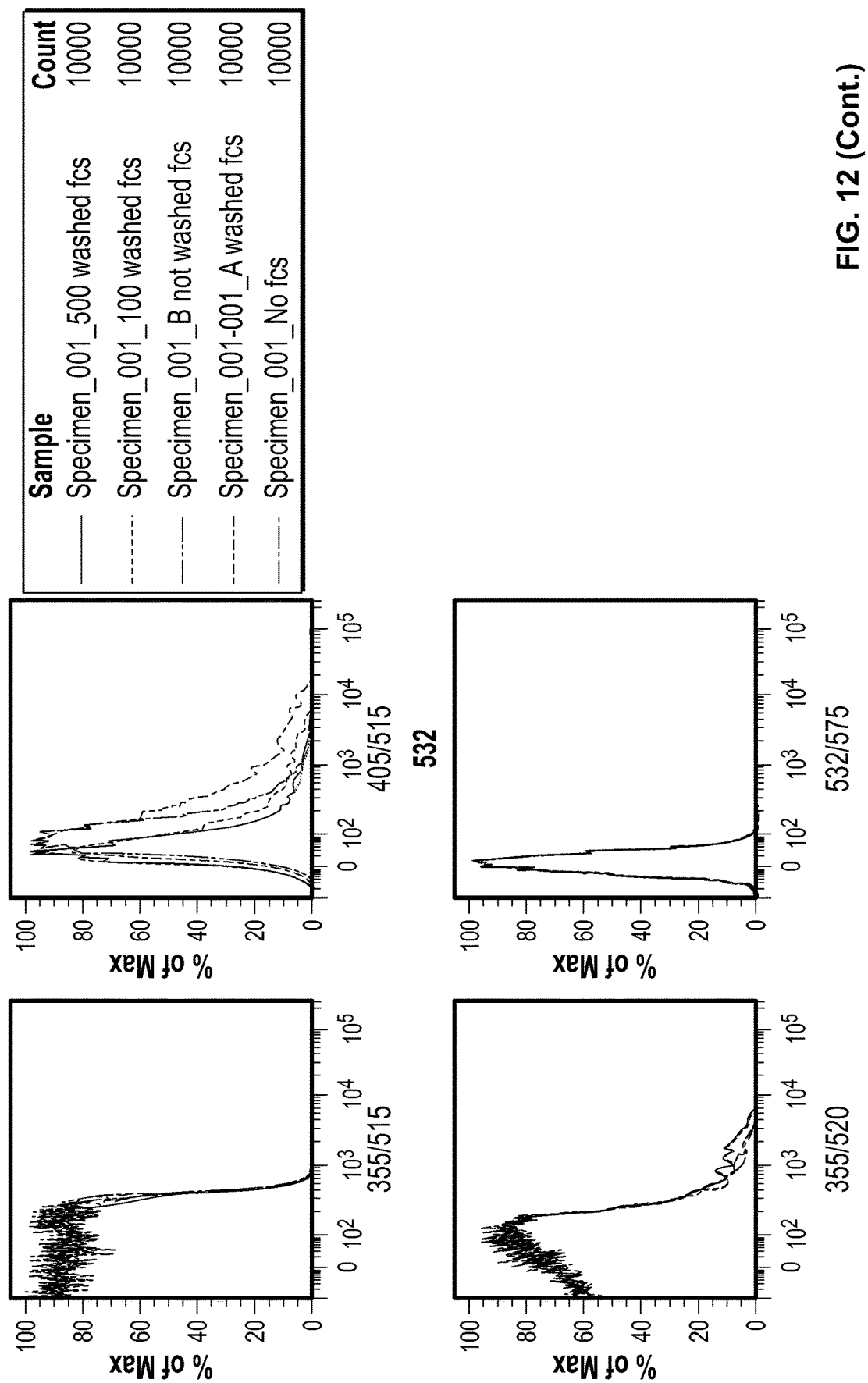

| UV/ Excitation (Gray Laser) | UV/ Excitation (Violet Laser) | UV/ Excitation (blue laser) | UV/ Excitation (green laser) | UV/ Excitation (Red laser) |
|---|---|---|---|---|
| 355/450 | 405/450 | 488/525 | 532/575 | 633/670 |
| 355/515 | 405/515 | | | |
| 355/620 | | | | | g. The data was placed into a graph and exported to a PDF.
7. Flow Cytometry Results showed that 1 mg/ml appeared below the control in each graph. It is presently thought that this could be due to too little amount remaining after washing to be detected by the sensor. 500 mg/ml showed the greatest excitation with every laser (see e.g., FIG. 10 and TABLE 35).

TABLE 35

Excitation of 1 mg, 100 mg, 500 mg, and control samples at various wavelengths.

| Sample | 488/525 | Ratio | 633/670 | Ratio | 405/515 | Ratio | 355/450 | Ratio | 355/515 | Ratio | 405/450 | Ratio | 532/575 | Ratio | 355/620 | Ratio |
|---|---|---|---|---|---|---|---|---|---|---|---|---|---|---|---|---|
| 1 mg | 194.0 | 0.9 | 57.5 | 1.1 | 74.4 | 0.6 | 109.0 | 1.0 | 42.4 | 1.0 | 77.1 | 0.8 | 158.0 | 1.1 | 112.0 | 1.3 |
| 100 mg | 345.0 | 1.7 | 52.8 | 1.0 | 299.0 | 2.5 | 256.0 | 2.3 | 47.4 | 1.2 | 216.0 | 2.4 | 233.0 | 1.6 | 140.0 | 1.6 |
| 500 mg | 435.0 | 2.1 | 62.2 | 1.1 | 781.0 | 8.8 | 782.0 | 7.0 | 55.1 | 1.3 | 666.0 | 7.3 | 428.0 | 3.0 | 221.0 | 2.5 |
| No | 208.0 | 1.0 | 54.7 | 1.0 | 119.0 | 1.0 | 112.0 | 1.0 | 40.9 | 1.0 | 91.6 | 1.0 | 143.0 | 1.0 | 86.8 | 1.0 |

Flow Cytometry was able to detect the presence of bleomycin on talc. Additionally, there is a one and a half log difference between the negative control and the highest concentration of Avidin incubated 500 μg/mL of talc. Following experiments concentrate on excitation from the UV range of 355-405 nm and the experiments were repeated to verify prior data.

The study showed bleomycin binds to talc and remains on surface of talc even following multiple PBS washes.

Example 12: "Hot" and "Cold" Avidin Mix Binds to Talc (Repeat of Experiment)

The following Example repeated the hot/cold experiment shown in Example 10, with the addition of multiple controls.

Materials:
1. Sterile Talc Powder (Bryan Corporation, Cat. #: 1690, Lot #: 3M021, Exp. Date: December 2016)
2. Avidin from egg white (Sigma, Cat. #: A9275-100 mg, Lot #: SLBB9685)
3. 10×PBS (Sigma, Cat. #: P5493-1L, Lot #: SLBB9685)
4. Immunopure Avidin, Horseradish Peroxidase, Conjugated
5. Water (Sigma Life Science, Cat. #: 3500, Lot #: RNBD1156)
6. Fetal Bovine Serum (ATCC, Cat. #: 30-2020, Lot #: 60353051, Bottle #: 2692)
7. TMB Substrate (ENZO, Cat. #: 80-0350, Lot #: 01071401)
8. Stop Solution 2 (ENZO, Cat. #: 80-0377, Lot #: 02241430)

Day 1:
Preparation of HRP (Hot) Avidin:
1. Prepare 10 mL of 40 ng/mL (or 260 mM) HRP Avidin in 1×PBS using 5.75 mg/mL or 32.5 μM of HRP Avidin stock solution.
2. Make 1:100 dilution from HRP Avidin stock solution: 198 μL of PBS+2 μL HRP Avidin.
4. Make 10 mL of 40 ng/mL or 260 μM solution: 10 mL of PBS+80 μL of 1:1000 dilution.
5. Keep solution on ice.

Preparation of Diluted Cold Avidin:
6. Weigh 8 mg of Avidin (cold Avidin), then resuspend it in 2 mL of PBS that contains 40 ng/mL of "hot" Avidin. So the solution will now be 40 ng/mL hot Avidin+4 mg/mL of Cold Avidin. Label this tube as #1.
7. Make 3 mL of 1:10 dilution of solution in Tube #1 and make labeled Tube #2 containing 2.7 mL of 40 ng/mL in Hot Avidin solution in PBS+300 μL of Tube #1. The solution in the tube will contain 40 ng/mL of Hot Avidin+400 μg of Cold Avidin.
8. Make 1:2 dilution of solution in Tube #2 using as a diluted solvent of 4 ng/mL of Hot Avidin in PBS. Added 1 mL of Hot Avidin+1 mL of Tube #2. The final concentration will be 40 ng/mL of Hot Avidin+200 μg/mL of Cold Avidin. Label this tube as Tube #3.
9. Make 1:2 dilution of solution in Tube #3, using as a solvent of 40 ng/mL Hot Avidin in PBS Prepare 2 mL of solution: 1 mL of 40 ng/mL of Hot Avidin in PBS+1 mL of Tube #3 The final concentration will be 40 ng/mL of hot Avidin+100 μg/mL of Cold Avidin. Label this tube as Tube #4.
10. Keep solutions on ice.

Preparation of Talc:
11. Weigh 100 mg of Talc.
12. Resuspend Talc in 200 μL of PBS making 0.5 mg/μL.
13. This experiment will be using 1 mg and 5 mg of Talc. To get the correct amount of 1 mg of Talc into the 96 well microplate, 2 μL of Talc/PBS mixture will be transferred. To get 5 mg of Talc 10 μL of Talc/PBS mixture will be taken.
14. Design of the plate in TABLE 36.

TABLE 36

Plate design.

| | 1 | 2 | 3 | 4 | 5 | 6 |
|---|---|---|---|---|---|---|
| 1 mg Talc: | 40 ng/mL Hot + 100 ug/mL Cold | 40 ng/mL Hot + 100 ug/mL Cold | 40 ng/mL Hot + 100 ug/mL Cold | 40 ng/mL Hot + 200 ug/mL Cold | 40 ng/mL Hot + 200 ug/mL Cold | 40 ng/mL Hot + 200 ug/mL Cold |
| 5 mg Talc: | 40 ng/mL Hot + 100 ug/mL Cold | 40 ng/mL Hot + 100 ug/mL Cold | 40 ng/mL Hot + 100 ug/mL Cold | 40 ng/mL Hot + 200 ug/mL Cold | 40 ng/mL Hot + 200 ug/mL Cold | 40 ng/mL Hot + 200 ug/mL Cold |
| | 1 mg Talc incubated with 40 ng/mL of only HRP in PBS | 1 mg Talc incubated with 40 ng/mL of only HRP in PBS | 1 mg Talc incubated with 40 ng/mL of only HRP in PBS | 5 mg Talc incubated with 40 ng/mL of only HRP in PBS | 5 mg Talc incubated with 40 ng/mL of only HRP in PBS | 5 mg Talc incubated with 40 ng/mL of only HRP in PBS |
| | 1 mg Talc incubated with 40 ng/mL of only HRP in PBS | 1 mg Talc incubated with 40 ng/mL of only HRP in PBS | 1 mg Talc incubated with 40 ng/mL of only HRP in PBS | 5 mg Talc incubated with 40 ng/mL of only HRP in PBS | 5 mg Talc incubated with 40 ng/mL of only HRP in PBS | 5 mg Talc incubated with 40 ng/mL of only HRP in PBS |
| | 1 mg Talc in PBS (no proteins included) | 1 mg Talc in PBS (no proteins included) | 1 mg Talc in PBS (no proteins included) | 5 mg Talc in PBS (no proteins included) | 5 mg Talc in PBS (no proteins included) | 5 mg Talc in PBS (no proteins included) |
| 1 mg of Talc: | Incubated with 100 ug/mL of only Cold Avidin in PBS | Incubated with 100 ug/mL of only Cold Avidin in PBS | Incubated with 100 ug/mL of only Cold Avidin in PBS | Incubated with 200 ug/mL of only Cold Avidin in PBS | Incubated with 200 ug/mL of only Cold Avidin in PBS | Incubated with 200 ug/mL of only Cold Avidin in PBS |
| 5 mg of Talc: | Incubated with 100 ug/mL of only Cold Avidin in PBS | Incubated with 100 ug/mL of only Cold Avidin in PBS | Incubated with 100 ug/mL of only Cold Avidin in PBS | Incubated with 200 ug/mL of only Cold Avidin in PBS | Incubated with 200 ug/mL of only Cold Avidin in PBS | Incubated with 200 ug/mL of only Cold Avidin in PBS |

| | 7 | 8 | 9 | 10 | 11 | 12 |
|---|---|---|---|---|---|---|
| 1 mg Talc: | 40 ng/mL Hot + 400 ug/mL Cold | 40 ng/mL Hot + 400 ug/mL Cold | 40 ng/mL Hot + 400 ug/mL Cold | 40 ng/mL Hot + 4 mg/mL Cold | 40 ng/mL Hot + 4 mg/mL Cold | 40 ng/mL Hot + 4 mg/mL Cold |
| 5 mg Talc: | 40 ng/mL Hot + 400 ug/mL Cold | 40 ng/mL Hot + 400 ug/mL Cold | 40 ng/mL Hot + 400 ug/mL Cold | 40 ng/mL Hot + 4 ug/mL Cold | 40 ng/mL Hot + 4 ug/mL Cold | 40 ng/mL Hot + 4 ug/mL Cold |
| | 1 mg Talc incubated with 40 ng/mL of HRP Avidin in PBS with 10% FBS | 1 mg Talc incubated with 40 ng/mL HRP Avidin in PBS with 10% FBS | 1 mg Talc incubated with 40 ng/mL HRP Avidin in PBS with 10% FBS | 5 mg Talc incubated with 40 ng/mL of HRP Avidin in PBS with 10% FBS | 5 mg Talc incubated with 40 ng/mL of HRP Avidin in PBS with 10% FBS | 5 mg Talc incubated with 40 ng/mL of HRP Avidin in PBS with 10% FBS |
| 1 mg of Talc: | Incubated with 400 ug/mL of only Cold Avidin in PBS | Incubated with 400 ug/mL of only Cold Avidin in PBS | Incubated with 400 ug/mL of only Cold Avidin in PBS | Incubated with 4 mg/mL of only Cold Avidin in PBS | Incubated with 4 mg/mL of only Cold Avidin in PBS | Incubated with 4 mg/mL of only Cold Avidin in PBS |
| 5 mg of Talc: | Incubated with 400 ug/mL of only Cold Avidin in PBS | Incubated with 400 ug/mL of only Cold Avidin in PBS | Incubated with 400 ug/mL of only Cold Avidin in PBS | Incubated with 4 mg/mL of only Cold Avidin in PBS | Incubated with 4 mg/mL of only Cold Avidin in PBS | Incubated with 4 mg/mL of only Cold Avidin in PBS |

15. Add Talc mixture to proper wells.
16. Add 100 µL of prepared hot/cold Avidin solutions stored on ice to the Talc following the design of the plate (see TABLE 36).
17. Using the pipetter, mix the Talc and Avidin mixture well by pumping up and down.
18. Cover the plate with Aluminum foil.
19. Incubate plate overnight at 4° C., constantly mixing it on the rocker.

Day 2:
1. Transfer the plate to room temperature.
2. Centrifuge it at 1500 rpm for 3 min.
3. Wash the plate 3× with 300 µL PBS containing 10% FBS.
4. After the final wash, resuspend Talc in 100 µL of PBS.
5. Add 100 µL of TMB.
6. Incubate at room temperature in no light for 20 min.
7. Add 100 µL of Stop Solution 2.
8. Read absorbance at 450 nm using the plate reader.
9. See data in TABLE 37.

TABLE 37

Efficiency of binding hot/cold Avidin mixture, OD.

| sample | OD |
|---|---|
| CONTROLS: | |
| 1 mg talc in PBS only: | 0.48 |
| 5 mg talc in PBS only: | 1.32 |
| 1 mg talc incubated with only 40 ng/mL HRP Avidin in PBS | 2.55 |
| 5 mg talc incubated with only 40 ng/mL HRP Avidin in PBS | 2.33 |
| 1 mg talc in in 40 ng/mL HRP Avidin in PBS containing 10% FBS: | 0.56 |
| 5 mg talc in in 40 ng/mL HRP Avidin in PBS containing 10% FBS: | 0.76 |
| 1 mg of Talc incubated with Cold Avidin only: | |
| 100 ug/mL | 0.31 |
| 200 ug/mL | 0.27 |
| 400 ug/mL | 0.3 |
| 4 mg/Ml | 0.33 |
| 5 mg of Talc incubated with Cold Avidin only: | |
| 100 ug/mL | 1.38 |
| 200 ug/mL | 1.4 |
| 400 ug/mL | 1.01 |
| 4 mg/mL | 1.23 |
| 1 mg Talc incubated: | |
| 40 ng/mL of Hot Avidin + 100 ug/mL of Cold Avidin: | 1.45 |
| 40 ng/mL of Hot Avidin + 200 ug/mL of Cold Avidin: | 1.45 |
| 40 ng/mL of Hot Avidin + 400 ug/mL of Cold Avidin: | 1.31 |
| 40 ng/mL of Hot Avidin + 4 mg/mL of Cold Avidin: | 1.06 |
| 5 mg Talc incubated: | |
| 40 ng/mL of Hot Avidin + 100 ug/mL of Cold Avidin: | 2.85 |
| 40 ng/mL of Hot Avidin + 200 ug/mL of Cold Avidin: | 2.7 |
| 40 ng/mL of Hot Avidin + 400 ug/mL of Cold Avidin: | 2.65 |
| 40 ng/mL of Hot Avidin + 4 mg/mL of Cold Avidin: | 1.6 |

TABLE 38

Raw data from microplate of TABLE 36.

| 1 | 2 | 3 | 4 | 5 | 6 | 7 | 8 | 9 | 10 | 11 | 12 |
|---|---|---|---|---|---|---|---|---|---|---|---|
| 1.4128 | 1.5969 | 1.3492 | 1.3182 | 1.6409 | 1.395 | 1.1787 | 1.5351 | 1.2049 | 1.0529 | 1.0769 | 1.0381 |
| 2.6693 | 2.8218 | 2.9528 | 2.4959 | 2.8141 | 2.7906 | 3.082 | 3.0227 | 1.86 | 1.5939 | 1.5378 | 1.6533 |
| 2.1669 | 2.0477 | 2.216 | 2.0499 | 2.2032 | 1.7009 | 0.7017 | 0.4947 | 0.4826 | 0.7828 | 0.7434 | 0.7407 |
| 2.8453 | 2.962 | 3.0786 | 2.7933 | 2.8299 | 2.4302 | 0.0537 | 0.0513 | 0.0547 | 0.0491 | 0.0514 | 0.0522 |
| 0.0516 | 0.048 | 0.0466 | 0.0504 | 0.0521 | 0.0542 | 0.0537 | 0.0543 | 0.0504 | 0.048 | 0.052 | 0.0569 |
| 0.4827 | 0.4734 | 0.4752 | 1.2381 | 1.1888 | 1.5445 | 0.0495 | 0.0523 | 0.0505 | 0.0498 | 0.0496 | 0.0525 |
| 0.4373 | 0.2746 | 0.2226 | 0.2701 | 0.2684 | 0.2574 | 0.2408 | 0.3108 | 0.354 | 0.2618 | 0.3584 | 0.3743 |
| 1.4221 | 1.4705 | 1.2587 | 1.3784 | 1.4737 | 1.3586 | 0.9944 | 1.357 | 0.6924 | 1.4221 | 0.9106 | 1.3512 |

TABLE 39

Average OD from triplicate loading of samples.

| 1 | 2 | 3 | 4 |
|---|---|---|---|
| 1.45 | 1.45 | 1.31 | 1.06 |
| 2.81 | 2.70 | 2.65 | 1.60 |
| 2.55 | 2.33 | 0.56 | 0.76 |
| 0.48 | 1.32 | | |
| 0.31 | 0.27 | 0.30 | 0.33 |
| 1.38 | 1.40 | 1.01 | 1.23 |

The study determined the full saturation of talc and completion of the plateau determination.

Example 13: Binding of Bleomycin to Talc: Flow Cytometry

The following Example repeated the experiments shown in Example 11 and determined the best excitation and emission parameters for flow cytometry in order to analyze the bleomycin-talc conjugate.

The study's aim was to incubate 25 mg talc with different concentrations of bleomycin and determine the efficiency of binding under flow cytometry.

Materials:
1. Bleomycin sulfate *Streptomyces verticillus* (Sigma-Aldrich, cat #15361-1 mg, lot #BCBK 1641V)
2. Talc (same as previous Examples).
3. 10×PBS (Sigma, Cat. #: P5493-1L, Lot #: SLBH0296)

Day 1:
1. Prepare four identical tubes with 25 mg talc in each one.

2. Make 0.5 ml of 500 µg/mL Bleomycin solution: 475 µL PBS+25 µL of 10 mg/mL bleomycin stock solution.

3. Make 0.5 ml of 100 µg/ml Bleomycin solution: 475 µL PBS+5 µL of 10 mg/ml solution.

4. Make 0.5 mL of 1 µg/mL bleomycin solution: 495 µL PBS+5 µL of 100 µg/mL solution.

5. Make the negative control: 500 µL of PBS+25 mg of Talc.

6. Mix all tubes well.

7. Incubate overnight at 4° C. on the 360° rotator. Protect from light.

Day 2:

1. Split talc in tube containing 1 µg/ml solution in half; label tubes as 1 µg/ml (a) and 1 µg/ml (b). Keep tube (b) on ice. Not wash tube 1 µg/ml (b).

2. Centrifuge all other tubes at 3200 rpm. 3 min 3. Discard the supernatant liquid.

4. Wash tubes 3× with 1 ml of PBS.

5. After last wash completely remove PBS and resuspend pellet in 500 µL PBS.

6. Transfer tubes for flow cytometry for analysis.

Flow Cytometry with Bleomycin 1. 25 µL of each concentration was transferred into a glass falcon tube:

TABLE 40

Bleomycin samples.

25 µL control no bleomycin + 2 ml of PBS
25 µL of 1 mg/µL bleomycin + 2 ml of PBS
25 µL of 100 mg/µL bleomycin + 2 ml of PBS
25 µL of 500 mg/µL bleomycin + 2 ml of PBS 2. The control sample was placed in the flow cytometer to determine the control light scatter.

3. The emissions was set for 353 and 405 with excitation wavelength set between 244-248 mm and 289-294 mm.

4. Each concentration was placed in the flow cytometer and the data was uploaded.

5. The emissions and excitation wavelength was changed to values as shown in TABLE 41.

6.

TABLE 41

Emissions and excitation wavelength.

| UV/ Excitation (Gray Laser) | UV/ Excitation (Violet Laser) | UV/ Excitation (blue laser) | UV/ Excitation (green laser) | UV/ Excitation (Red laser) |
|---|---|---|---|---|
| 355/450 | 405/450 | 488/525 | 532/575 | 633/670 |
| 355/515 | 405/515 | | | |
| 355/620 | | | | |

7. The date was put into a graph and exported to a PDF (see e.g., FIG. 11A-H).

The study showed analysis utilizing different flow cytometry lasers. The data showed 1 mg/µL appears below the control in each graph. 500 mg/µL showed the greatest excitation with every laser.

Example 14: Talc Bound to HRP- and Cold-Avidin, Incubation for 48 Hours in PBS Containing 10% FBS The following Example determined stability of talc binding to Avidin at 48 hours.

Purpose: To check how strong the conjugate of hot/cold Avidin to Talc is. This is then washed (incubate) talc/Avidin conjugate for 48 hours with PBS containing 10% FBS solution. Absorbance will be checked twice—once before washing with PBS containing 10% FBS and after 48 hours, washing will be done.

Hypothesis: The presence of FBS will not destroy the conjugate talc/AVIDIN.

Materials:

1. Sterile Talc Powder (Bryan Corporation, Cat. #: 1690, Lot #: 3M021, Exp. Date: December 2016)

2. Avidin from egg white (Sigma, Cat. #: A9275-100 mg, Lot #: SLBB9685)

3. 10×PBS (Sigma, Cat. #: P5493-1L, Lot #: SLBB9685)

4. Immunopure Avidin, Horseradish Peroxidase, Conjugated (Thermo Scientific, Cat. #: 21123, Lot #: OJ193825)

5. Water (Sigma Life Science, Cat. #: 3500, Lot #: RNBD1156)

6. Fetal Bovine Serum (ATCC, Cat. #: 30-2020, Lot #: 60353051, Bottle #: 2692)

7. TMB Substrate (ENZO, Cat. #: 80-0350, Lot #: 01071401)

8. Stop Solution 2

(ENZO, Cat. #: 80-0377, Lot #: 02241430)

Day 1: Preparation of HRP (Hot) Avidin:

1. Prepare 10 mL of 40 ng/mL (or 260 µM) HRP Avidin in 1×PBS using 5.75 mg/mL or 32.5 uM of HRP Avidin stock solution.

2. Make 1:100 dilution from HRP Avidin stock solution: 198 µL of PBS+2 µL HRP Avidin.

3. Make 1:1000 dilution: 90 µL of PBS+10 µL of 1:100 HRP Avidin stock solution dilution.

4. Make 10 mL of 40 ng/mL or 260 µM solution: 10 mL of PBS+80 µL of 1:1000 dilution.

5. Keep solution on ice.

Preparation of Diluted Cold Avidin:

6. Weigh 8 mg of Avidin (cold Avidin), then resuspend it in 2 mL of PBS containing 40 ng/mL of "hot" Avidin. So the solution will now be 40 ng/mL hot Avidin+4 mg/mL of Cold Avidin. Label this tube as #1.

7. Make 3 mL of 1:10 dilution of solution in Tube #1 and make labeled Tube #2 containing 2.7 mL of 40 ng/mL in Hot Avidin solution in PBS+300 µL of Tube #1. The solution in the tube will contain 40 ng/mL of Hot Avidin+400 µg of Cold Avidin.

8. Make 1:2 dilution of solution in Tube #2 using as a diluted solvent of 4 ng/mL of Hot Avidin in PBS. Added 1.5 mL of Hot Avidin+1.5 mL of Tube #2. The final concentration will be 40 ng/mL of Hot Avidin+200 µg/mL of Cold Avidin. Label this tube as Tube #3.

9. Make 1:2 dilution of solution in Tube #3, using as a solvent of 40 ng/mL Hot Avidin in PBS. Prepare 2 mL of solution: 1 mL of 40 ng/mL of Hot Avidin in PBS+1 mL of Tube #3. The final concentration will be 40 ng/mL of hot Avidin+100 µg/mL of Cold Avidin. Label this tube as Tube #4.

10. Keep solutions on ice.

Preparation of Talc:

11. Weight 200 mg of Talc.

12. Resuspend Talc in 400 µL of PBS, making 0.5 mg/µL.

13. This experiment will be using 1 mg and 5 mg of Talc. To get the correct amount of 1 mg of Talc into the 96 well microplate, 2 µL of Talc/PBS mixture will be transferred. To get 5 mg of Talc, 10 µL of Talc/PBS mixture will be taken.

14. OD data of samples before 48 hrs incubation of binded talc with PBS+10% FBS and after incubation with FBS is over is needed to be required for the purpose of the experiment. Two identical microplates need to be set up, labeling them as: plate #1 and plate #2. Design of the plate:

15. Add Talc mixture to proper wells.

16. Add 100 μL of Prepared hot/cold Avidin solutions stored on ice to the Talc following the design of the plate (see above).

17. Using the pipetter, mix the Talc and Avidin mixture well by pumping up and down.

18. Cover the plates with Aluminum foil.

19. Incubate plates overnight at 4° C., constantly mixing it on the rocker.

Day 2:
1. Transfer the plates to room temperature.
2. Centrifuge them at 1500 rpm. 3 min
3. Wash both plates 3× with 300 μL PBS.
4. After the final wash, resuspend Talc in plate #1, that will be read for absorbance, in 100 μL of PBS.
5. Add 150 μL of PBS contains 10% FBS to talc in plate #2 and return plate to 4° C. to continue incubation for another 48 hrs. Mix constantly, cover plate with Aluminum foil.
6. Add 100 μL of TMB to samples in plate #1.
7. Incubate at room temperature in no light. 20 min
8. After incubation with TMB is over, add 100 μL of Stop Solution 2.
9. Read absorbance at 450 nm using the plate reader.

Day 3:
1. Continue incubation of plate #2

Day 4:
1. Transfer plate #2 to room temperature.
2. Centrifuge it at 1500 rpm.
3. Collect 100 μL supernatant from samples except native controls and load on same plate.
4. Wash plate except supernatant samples 3× with 300 μL PBS.
5. After the final wash, resuspend Talc in plate #2, that will be read for absorbance, in 100 μL of PBS.
6. Add 100 μL of TMB to all samples in plate #2.
7. Incubate at room temperature in no light for 20 min.
8. After incubation with TMB is over add 100 μL of Stop Solution 2.
9. Read absorbance at 450 nm using the plate reader.
10. See data in TABLE 42.

TABLE 42

Comparison of absorbance right after incubation of talc with hot/cold Avidin and after 48 hrs wash with FBS, OD.

| sample | right after o/n incubation with AVIDIN | after 48 hrs of wash in PBS containted 10% FBS |
|---|---|---|
| 1 mg Talc incubated: | | |
| 40 ng/mL of Hot Avidin + 100 ug/mL of Cold Avidin: | 1.79 | 1.35 |
| 40 ng/mL of Hot Avidin + 200 ug/mL of Cold Avidin: | 1.45 | 1.14 |
| 40 ng/mL of Hot Avidin + 400 ug/mL of Cold Avidin: | 1.27 | 0.92 |
| 40 ng/mL of Hot Avidin + 4 mg/mL of Cold Avidin: | 0.91 | 0.83 |
| 1 mg talc in PBS only(neg.control) | 0.52 | 0.7 |
| 5 mg Talc incubated: | | |
| 40 ng/mL of Hot Avidin + 100 ug/mL of Cold Avidin: | 3.37 | 2.9 |
| 40 ng/mL of Hot Avidin + 200 ug/mL of Cold Avidin: | 3.24 | 3.07 |
| 40 ng/mL of Hot Avidin + 400 ug/mL of Cold Avidin: | 2.66 | 2.49 |
| 40 ng/mL of Hot Avidin + 4 mg/mL of Cold Avidin: | 1.98 | 2.28 |
| 5 mg talc in PBS only(neg.control) | 1.24 | 1.33 |

TABLE 43

Supernatant after 48 hrs wash (PBS + 10% FBS).

| Supernatant after 48 hrs wash (PBS + 10% FBS) | OD |
|---|---|
| 1 mg Talc binded: | |
| 40 ng/mL of Hot Avidin + 100 ug/mL of Cold Avidin: | 2.94 |
| 40 ng/mL of Hot Avidin + 200 ug/mL of Cold Avidin: | 2.66 |
| 40 ng/mL of Hot Avidin + 400 ug/mL of Cold Avidin: | 2.41 |
| 40 ng/mL of Hot Avidin + 4 mg/mL of Cold Avidin: | 2.55 |
| 5 mg Talc binded: | |
| 40 ng/mL of Hot Avidin + 100 ug/mL of Cold Avidin: | 2.9 |
| 40 ng/mL of Hot Avidin + 200 ug/mL of Cold Avidin: | 3.07 |
| 40 ng/mL of Hot Avidin + 400 ug/mL of Cold Avidin: | 2.49 |
| 40 ng/mL of Hot Avidin + 4 mg/mL of Cold Avidin: | 2.28 |

The study showed binding of Avidin to talc is unchanged at 48 hours.

Example 15: Binding of Bleomycin to Talc: Flow Cytometry

The following Example repeated the experiments shown in Example 11 and determined the best excitation and emission parameters for flow cytometry in order to analyze bleomycin-talc conjugate.

The aim of the study was to incubate 25 mg talc with different concentration of bleomycin and check efficiency of binding under flow cytometry.

Materials:
1. Bleomycin sulfate *Streptomyces verticillus* (Sigma-Aldrich, cat #15361-1 mg, lot #BCBK 1641V)
2. Talc (same as previous Examples)
3. 10×PBS (Sigma, Cat. #: P5493-1L, Lot #: SLBH0296)

Day 1:
1. Prepare four identical tubes with 25 mg talc in each one.
2. Make 0.5 ml of 500 μg/mL Bleomycin solution: 475 μL PBS+25 μL of 10 mg/mL bleomycin stock solution.
3. Make 0.5 ml of 100 μg/ml bleomycin solution: 475 μL PBS+5 μL of 10 mg/ml solution.
4. Make 0.5 mL of 1 μg/mL Bleomycin solution: 495 μL PBS+5 μL of 100 μg/mL solution.
5. Make the negative control: 500 μL of PBS+25 mg of Talc.
6. Mix all tubes well.

7. Incubate overnight at 4° C. on the 360° rotator. Protect from light.

Day 2:

1. Split talc in tube containing 1 μg/ml solution in half; label tubes as 1 μg/ml (a) and 1 μg/ml (b). Keep tube (b) on ice. Not wash tube 1 μg/ml (b).
2. Centrifuge all other tubes at 3200 rpm for 3 min
3. Discard the supernatant liquid.
4. Wash tubes 3× with 1 ml of PBS.
5. After last wash completely remove PBS and resuspend pellet in 500 μL PBS.
6. Transfer tubes for flow cytometry for analysis.

Flow cytometry with Bleomycin 1. 25 μL of each concentration was transferred into a glass falcon tube as shown in TABLE 45.

TABLE 45

Bleomycin samples.

25 μL control no bleomycin + 2 ml of PBS
25 μL of 1 mg/μL bleomycin + 2 ml of PBS
25 μL of 100 mg/μL bleomycin + 2 ml of PBS
25 μL of 500 mg/μL bleomycin + 2 ml of PBS 2. The control sample was placed in the flow cytometer to determine the control light scatter.
3. The emissions were set for 353 and 405 with excitation wavelength set between 244-248 mm and 289-294 mm.
4. Each concentration was placed in the flow cytometer and the data was uploaded.
5. The emissions and excitation wavelength was changed to values as shown in TABLE 46.
6.

TABLE 46

Emission and excitation wavelengths.

| UV/ Excitation (Gray Laser) | UV/ Excitation (Violet Laser) | UV/ Excitation (blue laser) | UV/ Excitation (green laser) | UV/ Excitation (Red laser) |
|---|---|---|---|---|
| 355/450 | 405/450 | 488/525 | 532/575 | 633/670 |
| 355/515 | 405/515 | | | |
| 355/620 | | | | |

TABLE 47

Raw data.

| Sample | 488/525 | Ratio | 633/670 | Ratio | 405/515 | Ratio | 355/450 | Ratio | 355/515 |
|---|---|---|---|---|---|---|---|---|---|
| 1: 100 washe | 56.3 | 0.9 | 72.4 | 1.3 | 67.1 | 1.3 | 20.1 | 1.2 | −4.57 |
| 2: 500 washe | 77.7 | 1.2 | 56.6 | 1 | 130 | 2.5 | 13.3 | 0.8 | 3.26 |
| 3: A washed.f | 66.6 | 1.1 | 68.6 | 1.3 | 51.4 | 1 | 22.3 | 1.3 | −5.66 |
| 4: B not wash | 125 | 2 | 65.8 | 1.2 | 97.8 | 1.9 | 19 | 1.1 | −1.3 |
| 5: No. fcs | 62.4 | 1 | 54.7 | 1 | 52.3 | 1 | 16.8 | 1 | −4.57 |

| Sample | Ratio | 405/450 | Ratio | 532/575 | Ratio | 355/620 | Ratio |
|---|---|---|---|---|---|---|---|
| 1: 100 washe | 1 | 65.1 | 1.6 | 0 | 0 | 65.8 | 1.3 |
| 2: 500 washe | −0.7 | 117 | 2.9 | −1.09 | 1 | 51.4 | 1 |
| 3: A washed.f | 1.2 | 44.4 | 1.1 | −1.09 | 1 | 53.7 | 1 |
| 4: B not wash | 0.3 | 57.3 | 1.4 | −1.09 | 1 | 51.4 | 1 |
| 5: No. fcs | 1 | 40.5 | 1 | −1.09 | 1 | 51.4 | 1 |

7. The date was placed into a graph and exported to a PDF (see e.g., FIG. 12A-H).

The study showed analysis utilizing different flow cytometry lasers. Results showed that 1 mg/μL appeared below the control in each graph. 500 mg/μL showed the greatest excitation with every laser.

Example 16: Cytotoxicity Assay of NCI-28H Cells Treated with Compounds-Bleomycin, Talc, and Talc Bound to Bleomycin The following Example determined which of the above three compounds (bleomycin, talc, or talc bound to bleomycin) is more cytotoxic to NCI-28H cells after 72 hours of treatment.

The study added different type of compounds to NCI-28H cells: only bleomycin, only talc, and talc that was previously incubated with bleomycin. Read absorbance (MTS assay) and calculate cells survival rate.

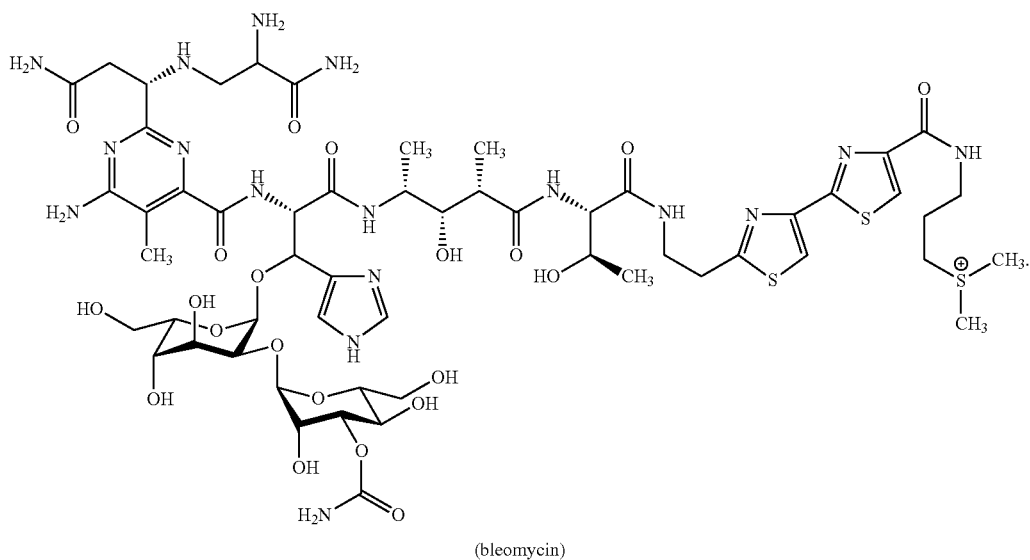

(bleomycin)

Materials:
1. Bleomycin sulfate *Streptomyces verticillus* (Sigma-Aldrich, cat #15361-1 mg, lot # BCBK 1641V)
2. Sterile Talc Powder (Bryan Corporation, cat. # NDC 63256-200-05; lot
   #: 3M021; exp. December 2016)
3. DPBS, 1× (ATCC, Cat. #: 30-2200, Lot #: 61443818)
4. NCI-28H (ATCC, cat. #: CRL-5820, lot #: 7379248)
5. RPMI-1640 media (ATCC cat. #30-2001, lot #62027197).
6. Trypsin-EDTA (ATCC cat. #30-2101, lot #61618818).
7. Fetal Bovine serum (ATCC cat. #3022).
8. CellTiter 96 AQueous One Solution cell proliferation assay (Promega cat # G3581)

DAY 1

Cells Preparation:
1. Set up 1 cytotoxicity plate for tomorrow experiment: trypsinize NCI-28H cells (T-75 flask, passage 7):
   Remove old medium, wash cells with 7 ml DPBS, remove DPBS, add 2 ml trypsin, incubate plates for 1-2', when cells detached add 6 ml fresh medium, mix cells and medium.
   Count cells under the microscope using the glass slide. Average # of cells in slide is 67; average in 1 ml of mix is 67×10,000=670,000 cells/ml;
   Count how much cell/medium stock needed: use 1 plate (60 wells) in the assay; count extra wells for safety reason. If we need 100 wells, in each well will be 5,000 cells in 0.1 ml; so total we need 500,000 cells in 10 ml. 500,000 cells/670,000=0.75 ml of cells/media mix need to take from flask and transfer to 9.25 ml media. In 50 ml Falcon tube combine 9.25 ml fresh medium and 0.75 ml cells. Gently mix.
2. Transfer 100 µL of prepared cells/medium mix to proper wells, keep overnight at 37° C., 5% $CO_2$.

Talc Preparation:
1. Under the hood open new bottle of sterile talc and transfer approximately 25 mg of talc to each of 2 sterile Eppendorf tubes. Close tubes and weigh talc added to each tube. Result: tube #1-56.2 mg; tube #2-63.3 mg.
2. Reconstitute the bleomycin 1 mg powder with 100 µL water; solution will be 10 mg/ml or 6.25 mM (mw=1600).
3. Make 400 µL of 1 mg/ml Bleomycin solution using 360 µL DPBS+40 µL of 10 mg/ml stock of drug. Final concentration was 1 mg/ml or 625 µM.
4. Mix 56.2 mg talc in tube #1 with 400 µL of 625 µM bleomycin.
5. Mix 63.3 mg talc with 400 µL DPBS.
6. Protect tubes from light, tape them on rotator and incubate overnight at 4° C.

DAY 2

Preparation of Talc
1. Bring back tubes from cold room to laboratory. Centrifuge 3200 rpm for 3 min. Take out supernatant. Wash pellet 3 times with 1.0 ml of DPBS (sterile) after last wash add to tube #1: contains 56.2 mg talc, 112.4 µL of media; final concentration talc in tube will be 0.5 mg/µL. Add to tube #2 contains 63.3 mg talc, 126.6 µL of media; final concentration talc in tube will be 0.5 mg/µL.
2. Keep tubes with talc at 4° C.
3. Prepare first dilution of each of the above tubes by adding 540 µL media+60 µL of tube #1 or tube #2 solution.
4. After preparation of the above solution, prepare 3 subsequent 1:2 serial dilutions of each of the above preparations (300 µL media+300 µL of previous dilution).
5. Add 100 µL of the above preparations in steps #3, #4 to the proper wells as indicated in the 96-well plate. The resultant preparation added to each well will give presence of talc in the wells as following: 0.6 mg talc/well, 1.25 mg talc/well, 2.5 mg talc/well, and 5.0 mg talc/well after sequential dilutions (1:2) across plate.
6. The above procedure was again utilized for the second tube (#1) which contains bleomycin bound to talc.

Preparation of Bleomycin:
Prepare the following dilutions of bleomycin
(1) 1 mg/ml (625 µM),
(2) 250 µg/ml (156.3 µM),
(3) 62.5 µg/ml (39 µM),
(4) 15.6 µg/ml (9.75 µM),
(5) 3.9 µg/ml (2.43 µM),
(6) 0.97 µg/ml (0.6 µM),
(7) 0.24 µg/ml (0.15 µM),
(8) 0.06 µg/ml (0.038 µM),
(9) 0.015 µg/ml (0.009 µM),

(10) 0.004 µg/ml (0.002 µM)
Prepare 500 µL stock solution of 625 µM Bleomycin as follows:
1. 450 µL media+50 µL of stock (6.25 mM bleomycin).
2. Following preparation of above solution prepare the above 9 sequential serial dilutions using the following formula: 375 µL media+125 µL of prior dilution.
3. Add 100 µL of each 10 preparations of diluted bleomycin (step 1 and 2) to the proper wells according to a plate layout.
4. Add 100 µL of media for untreated cells that will use as a control and not contain any drug or any kind of talc.
5. Check the plate and start incubation at 37° C./5% $CO_2$ DAY 3
1. Check plate under microscope, no visible sign of contamination is present.
2. Mix by pipetting up and down media in the wells containing talc.
3. Continue incubation plate at 37° C./5% $CO_2$ DAY 4
1. Check plate under microscope, no visible sign of contamination is present.
2. Mix by pipetting up and down media in the wells containing talc.
3. Continue incubation plate at 37° C./5% $CO_2$.

DAY 5
1. Check plate under microscope, no visible sign of contamination is present.
2. Mix talc/media liquid in the wells. Using needle/vacuum system remove all liquid from all wells.
3. Wash cells 2×300 µL DPBS, remove final wash.
4. Add 120 µL fresh media to all wells.
5. Add 20 µL of CellTiter 96 Aqueous One solution to each well.
6. Incubate plate 1 hr at 37° C., 5% $CO_2$.
7. Read absorbance in plate reader at 490 nm.
8. See e.g., TABLE 48, TABLE 49, TABLE 50, FIG. 13, and FIG. 14 for results.

TABLE 48

Cells treated with talc.

| | amount of talc added to cells, mg | | | | |
|---|---|---|---|---|---|
| | 0 | 0.62 | 1.25 | 2.5 | 5 |
| talc only, no BLEOMYCIN | 1.87 | 1.01 | 0.82 | 0.90 | 1.36 |
| Talc binded to 1 mg/ml BLEOMYCIN | 1.87 | 0.47 | 0.45 | 0.51 | 0.60 |

TABLE 49

% survival after incubation with talc.

| | amount of talc added to cells, mg | | | | |
|---|---|---|---|---|---|
| | 0 | 0.62 | 1.25 | 2.5 | 5 |
| talc only, no BLEOMYCIN | 100 | 53.87 | 43.97 | 48.20 | 72.31 |
| Talc binded to 1 mg/ml BLEOMYCIN | 100 | 25.23 | 24.11 | 27.24 | 31.81 |

TABLE 50

% survival NCI-28H cells after treatment with bleomycin.

| % survival NCI-28H cells after treatment with BLEOMYCIN Bleomycin, ug/ml | | | | | | | | | | |
|---|---|---|---|---|---|---|---|---|---|---|
| 0 | 0.004 | 0.015 | 0.06 | 0.24 | 0.97 | 3.9 | 15.6 | 62.5 | 250 | 1000 |
| 100 | 92.41 | 88.25 | 93.38 | 91.86 | 86.19 | 71.05 | 74.60 | 68.76 | 47.13 | 24.92 |

The above data suggests a clear toxic effect on NCI-28H cells with talc alone and an even more toxic effect when cells were exposed to talc bound to bleomycin. Toxicity of talc and talc bound to bleomycin was even higher than when cells were exposed to pure bleomycin.

Figure 13:
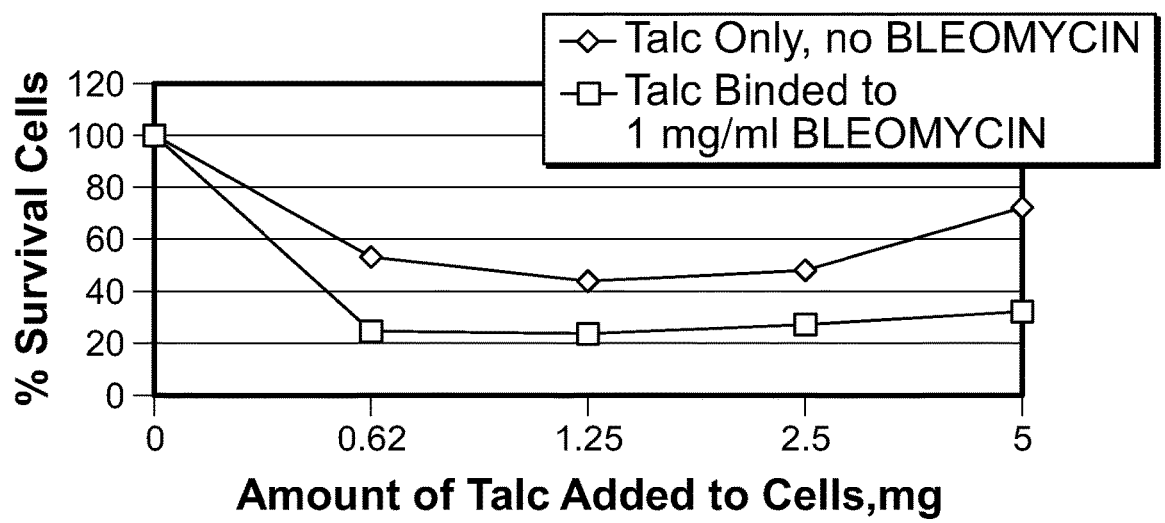
FIG. 13 is a scatter plot depicting % survival NCI-28H cells after incubation for 72 hrs with talc and talc bound to bleomycin.
Figure 14:
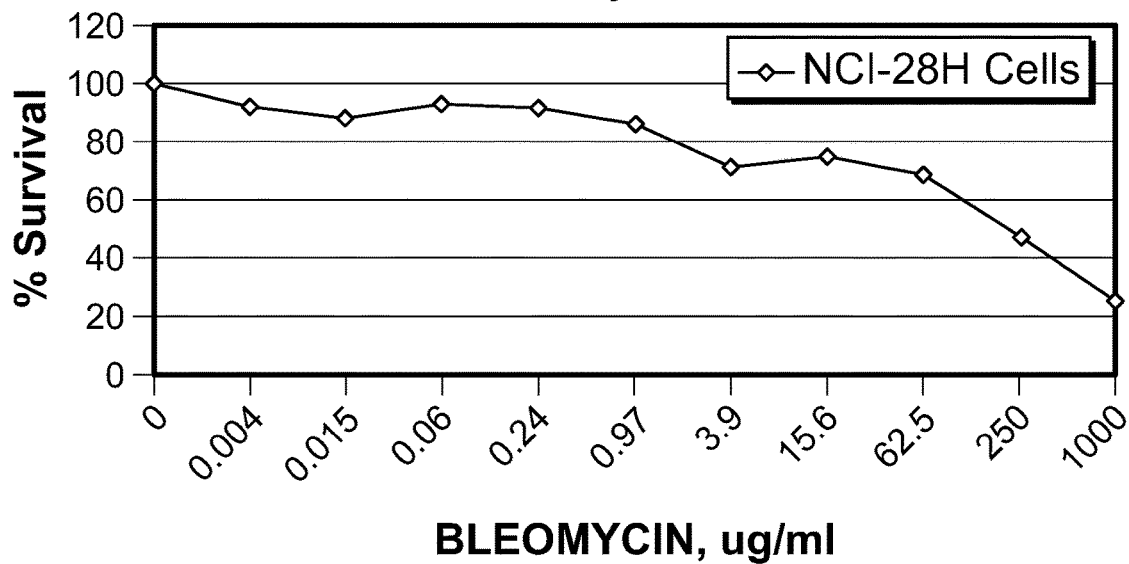
FIG. 14 is a scatter plot depicting % survival NCI-28H cells after 72 hours of bleomycin treatment.
Figure 15:
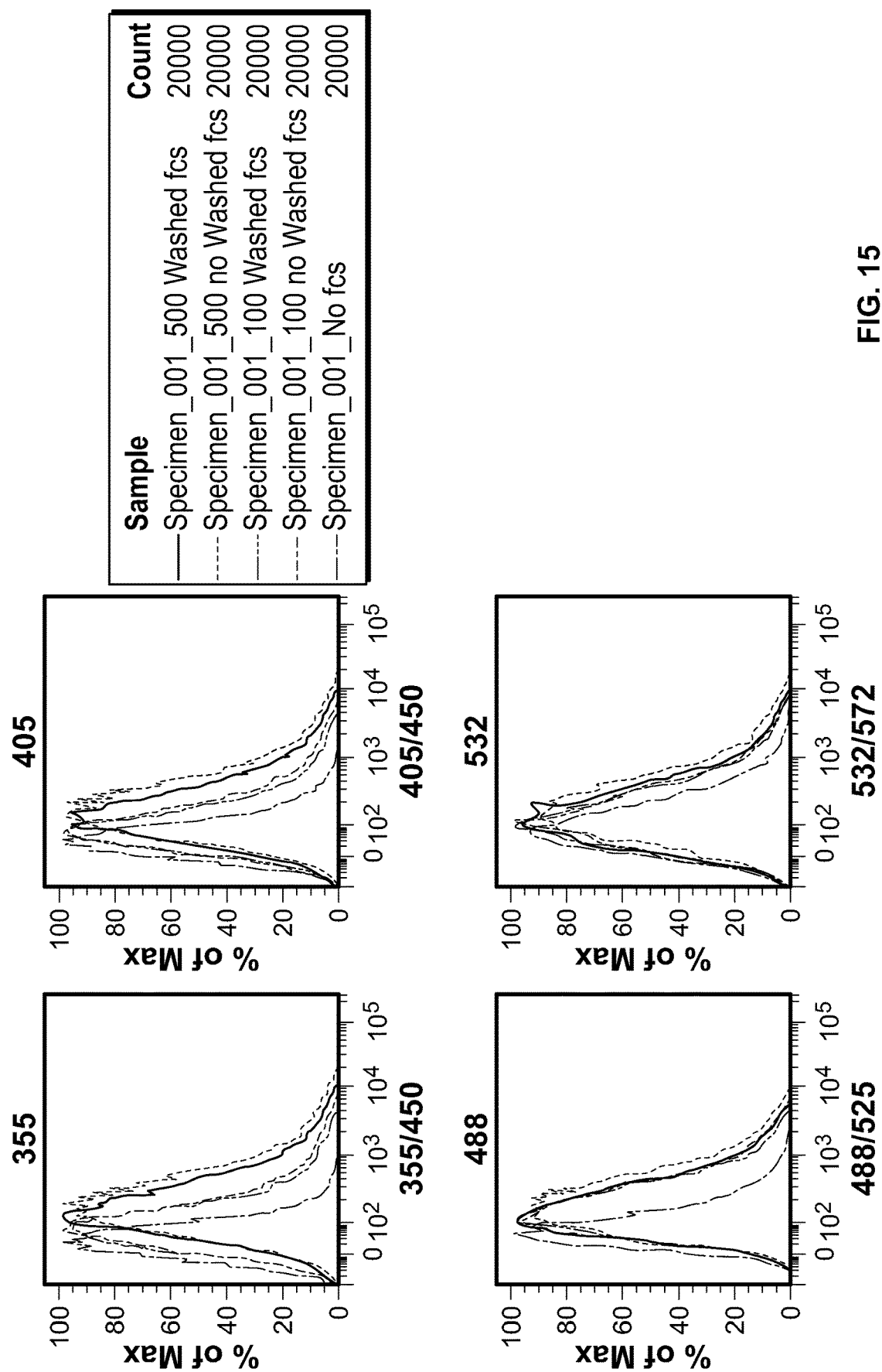
FIG. 15 are a series of flow cytometry data for washed samples of bleomycin and talc at various excitation and emission wavelengths.
Figure 15:
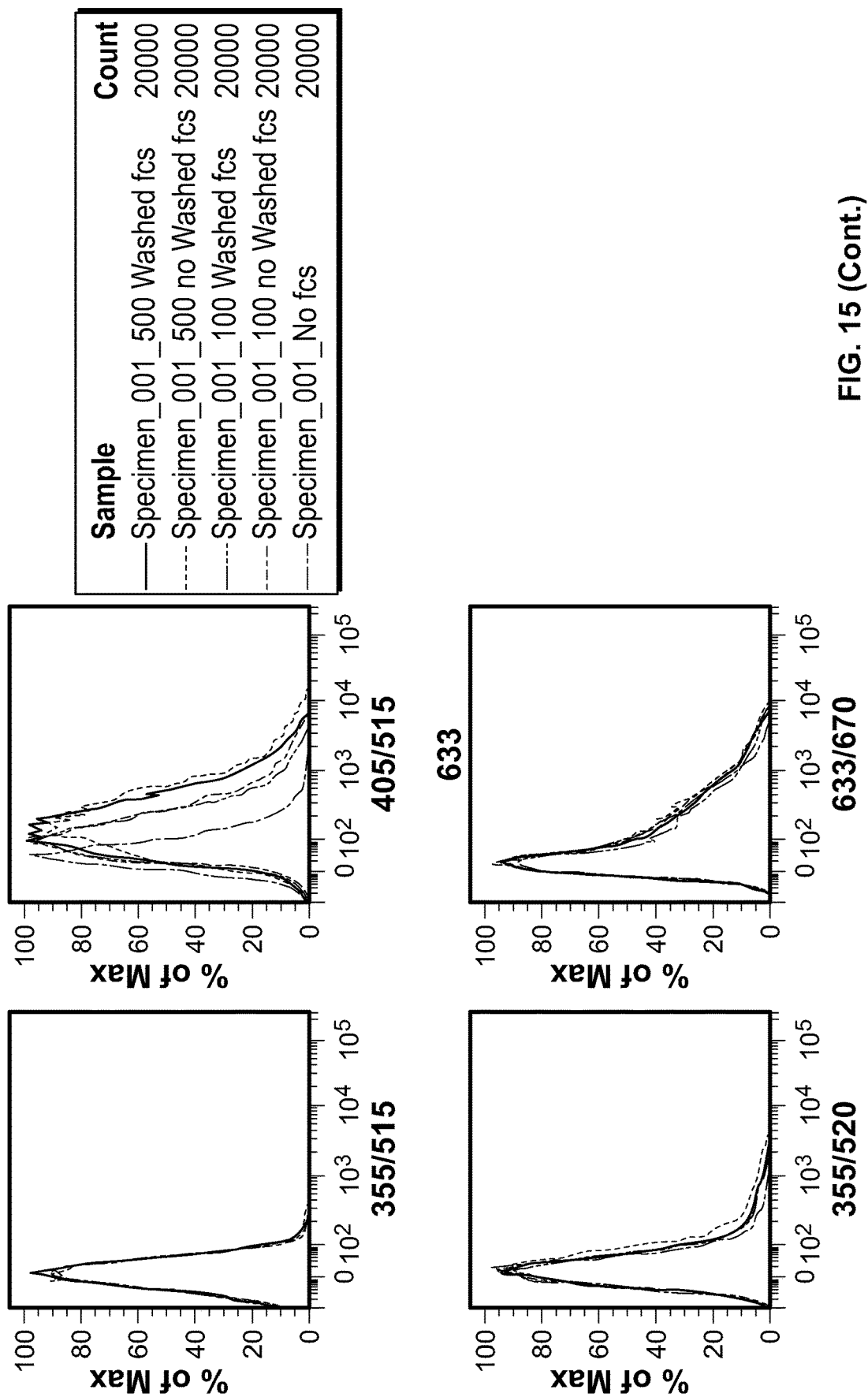

Thus, the study showed that following exposure of NCI-28H cells to the above compounds, it was found that talc-bleomycin was more toxic than talc alone, and talc alone is more toxic than bleomycin alone (see e.g., FIG. 13, FIG. 14).

Example 17: Biotin-HRP: Determination of Concentration Range for Absorbance Assay The following Example determined the maximum detection range for absorbance at 440 nm by utilizing varying concentrations of Biotin-HRP.
BIOTIN HRP: determination of concentration range for absorbance assay.
Plan: make different concentration of BIOTIN HRP to find out the maximum detection range for absorbance assay (450 nm).
MATERIAL:
Biotinylated Peroxidase; Invitrogen, cat. #432040, lot #1482487A.
TMB substrate; ENZO, cat. #80-0350 lot #01071401.
Stop Solution 2; ENZO, cat. #80-0377, lot #02241430.
10×PBS; (Sigma, Cat. #: P5493-1L, Lot #: SLBB9685).
Water; (Sigma Life Science, Cat. #: 3500, Lot #: RNBD1156)
DAY 1
1. Prepare dilution (1:5) of Biotin HRP (2.5 mg/ml) stock in following range: 5 µg/ml-1 mg/ml-200 ng/ml-40 ng/ml-8 ng/ml-1.6 ng/ml-0.3 ng/ml-0.06 ng/ml.
2. Make first dilution (5 µg/ml): 998 µL PBS+2 µL of stock 2.5 mg/ml Biotin HRP.
3. Make serial dilution (1:5) down using formula: 800 µL PBS+200 µL of previous dilution of Biotin HRP.
4. Add 100 µL of each dilution (2 wells for each dilution) to the proper wells in 96 wells microplate.
5. Add 100 µL TMB substrate, incubate at RT for 20 min.
6. Add 100 µL Stop Solution 2.
7. Read absorbance in plate reader using 450 nm setting.
CONCLUSION: for further experiments, concentrations of BIOTIN HRP more than 1.6 ng/ml was shown to be not optimal. The working range was shown to be optimal between 0.3 ng/ml to 1.6 ng/ml.

The study showed a concentration of 1.6 ng/ml was the preferred maximum concentration of Biotin-HRP for detection. Therefore, for future experimentation, a range of 0.3 ng/ml-1.6 ng/ml is appropriate for the absorbance assay.

Example 18: Binding of Bleomycin to Talc: Flow Cytometry Analysis of Washed and Unwashed Bleomycin-Talc Particles The following Example determined if repeated washing removes bleomycin from surface of talc by flow cytometry analysis of particles prior to and following PBS washing.

Purpose: incubate 25 mg talc with different concentration of BLEOMYCIN and check efficiency of binding under flow cytometry using washed and not washed talc Materials:
1. Bleomycin sulfate *Streptomyces verticillus* Sigma-Aldrich, cat #15361-1 mg, lot # BCBL 5313V
2. Talc, same as before; see previous experiments
3. 10×PBS
Sigma, Cat. #: P5493-1L, Lot #: SLBH0296
Day 1:
1. Prepare 3 identical tubes with 25 mg talc in each one.
2. Reconstitute Bleomycin with 100 µL water, making final dilution as 1 g/ml.
3. Make 0.5 ml of 500 µg/mL Bleomycin solution: 475 µL PBS+25 µL of 10 mg/mL Bleomycin stock solution.
4. Make 0.5 ml of 100 µg/ml Bleomycin solution: 475 µL PBS+5 µL of 10 mg/ml solution.
5. Make the negative control: 500 µL of PBS+25 mg of Talc.
6. Mix all tubes well.
7. Incubate overnight at 4° C. on the 360° rotator. Protect from light.
Day 2:
1. Split talc in tubes containing 100 µg/ml and 500 µg/ml solution in half. Keep one tube from each dilution of drug on ice. Not wash it.
2. Centrifuge all other tubes at 3200 rpm. 3 min
3. Discard the supernatant liquid.
4. Wash tubes 3× with 1 ml of PBS.
5. After last wash completely remove PBS and resuspend pellet in 250 µL PBS.
6. Transfer tubes for flow cytometry for analysis.
Flow Cytometry with Bleomycin
1. 25 µL of each concentration was transferred into a glass falcon tube (see TABLE 51).

TABLE 51

Sample concentration.

25 µL control no bleomycin + 0.5 ml of PBS
25 µL of 100 mg/ml not washed bleomycin + 0.5 ml of PBS
25 µL of 100 mg/ml washed bleomycin + 0.5 ml of PBS
25 µL of 500 mg/ml not washed bleomycin + 0.5 ml of PBS
25 µL of 500 mg/ml washed bleomycin + 0.5 ml of PBS 2. The control sample was placed in the flow cytometer to determine the control light scatter.
3. The emissions was set for 353 and 405 with excitation wavelength set between 244-248 mm and 289-294 mm.
4. Each concentration was placed in the flow cytometer and the data was uploaded.
5. The emissions and excitation wavelength was changed to 6.

TABLE 51

Emission and excitation wavelengths.

| UV/ Excitation (Gray Laser) | UV/ Excitation (Violet Laser) | UV/ Excitation (blue laser) | UV/ Excitation (green laser) | UV/ Excitation (Red laser) |
|---|---|---|---|---|
| 355/450 | 405/450 | 488/525 | 532/575 | 633/670 |
| 355/515 | 405/515 | | | |
| 355/620 | | | | |

7. The data was put into a graph and exported to a PDF (see e.g., FIG. 15A-H).

TABLE 52

Raw data.

| Sample | 488/525 | ratio | 633/670 | ratio | 405/515 | ratio | 355/450 | ratio | 355/515 | ratio | 405/450 | ratio |
|---|---|---|---|---|---|---|---|---|---|---|---|---|
| not washed 100 mg | 155 | 2.29 | 91.1 | 1.95 | 132 | 2.87 | 95.2 | 4.11 | 8.7 | 47.5 | 98.9 | 3.04 |
| washed 100 mg | 152 | 2.24 | 75.4 | 1.91 | 124 | 2.81 | 87.5 | 4.03 | 6.53 | 46.6 | 91.9 | 2.98 |
| not washed 500 mg | 199 | 2.94 | 95 | 2.5 | 222 | 3.68 | 205 | 5.27 | 12.2 | 61 | 191 | 3.9 |
| washed 500 mg | 164 | 2.42 | 82.2 | 2.06 | 190 | 3.03 | 168 | 4.35 | 9.79 | 50.3 | 159 | 3.22 |
| Control | 67.6 | 1 | 79.3 | 0.85 | 54 | 1 | 37.7 | 1 | 3.26 | 1 | 50.9 | 1 |

| 532/575 | ratio | 355/620 | ratio |
|---|---|---|---|
| 143 | 1.61 | 28.7 | 8.24 |
| 142 | 1.58 | 26.5 | 8.08 |
| 199 | 2.07 | 29.8 | 10.5 |
| 173 | 1.7 | 37.7 | 8.72 |
| 96.1 | 0.7 | 18.8 | 3.59 |

Thus, the study showed that there is very little difference in washed and unwashed bleomycin-talc as shown by analysis at 405 nm and 488 nm excitation and emission. It is presently thought that the agent (bleomycin) is absorbed or bound by talc.

Example 19: Talc Bound to Cold Avidin/Biotin HRP and Only to Biotin/HRP

The following Example determined if there is a difference in binding of Biotin/HRP to talc which has or does not have Avidin on its surface.

Plan: prepare two different kind of particles: talc bound with different amounts of cold AVIDIN and talc that did not exposed to cold Avidin. Incubate both particles to 1 ng/ml biotin HRP and find difference in binding.

MATERIAL:

Biotinylated Peroxidase; Invitrogen, cat. #432040, lot #1482487A.
Avidin from egg white. (Sigma, Cat. #: A9275-100 mg, Lot #: SLBB9685)
TMB substrate; ENZO, cat. #80-0350 lot #01071401.
Stop Solution 2; ENZO, cat. #80-0377, lot #02241430.
10×PBS; (Sigma, Cat. #: P5493-1L, Lot #: SLBB9685).
Sterile Talc Powder, Bryan Corporation, cat. # NDC 63256-200-05; lot #: 3M021; exp. December 2016

DAY 1

Preparation of Diluted Cold Avidin:

1. Weight 6 mg of Avidin (cold Avidin), then resuspend it in 1.5 mL of PBS. So the solution will now be 4 mg/mL of Cold Avidin. Label it as tube #1.
2. Make 1.5 mL of 1:2 dilution of solution in Tube #1 and make labeled Tube #2 containing 750 µL PBS+750 µL of Tube #1. The solution in the tube will contain 2 mg/ml of Cold Avidin.
3. Make 1:2 dilution of solution in Tube #2. Added 750 µL PBS+750 µL of Tube #2. The final concentration 1 mg/mL of Cold Avidin. Label this tube as Tube #3.
4. Make 1:2 dilution of solution in Tube #3 in PBS. Prepare 1.5 mL of solution: 750 µL of PBS+750 µL of Tube #3. The final concentration will be 0.5 mg/ml of Avidin. Label this tube as Tube #4.
5. Keep solutions on ice.

Preparation of Talc:

6. Weight 150 mg of Talc.
7. Resuspend Talc in 300 µL of PBS making 0.5 mg/µL.
8. This experiment will be using 1 mg and 5 mg of Talc. To get the correct amount of 1 mg of Talc into the 96 well microplate, 2 µL of Talc/PBS mixture will be transferred. To get 5 mg of Talc, 10 µL of Talc/PBS mixture will be taken.
9. Design plate.
10. Add Talc mixture to proper wells.
11. Add 100 µL of Prepared cold Avidin or PBS to the Talc following the design of the plate.
12. Using the pipette, mix the Talc with Avidin mixture or PBS well by pumping up and down.
13. Cover the plate with Aluminum foil.
14. Incubate plate overnight at 4° C., constantly mixing it on the rocker.

DAY 2

1. Transfer the plate to room temperature.
2. Centrifuge it at 1500 rpm. For 3 min and discard supernatant from wells containing Avidin only.
3. Wash those wells 3× with 300 µL PBS.
4. After the final wash, centrifuge plate and remove all PBS from all wells except controls.
5. Prepare 4 ml of 1 ng/ml biotin HRP:
   make 1 ml of 5 µg/ml Biotin=998 µL PBS+2 µL of Biotin HRP stock 2.5 mg/ml;
   make 1:100 dilution of 5 µg/ml=990 µL PBS+10 µL of above dilution;
   make 4 ml of 1 ng/ml Biotin HRP=3.92 ml PBS+80 µL of 1:100 dilution.
6. Add 100 µL of 1 ng/ml solution to all wells (pre-incubated with Avidin and not exposed to Avidin) except controls.
7. Cover the plate with Aluminum foil.
8. Incubate plate for 1 hr at 4° C., constantly mixing it on the rocker.
9. Transfer the plate to room temperature.
10. Centrifuge it at 1500 rpm 3 min and discard supernatant from all wells except control.
11. Wash wells 3× with 300 µL PBS.
12. After the final wash, centrifuge plate and remove all PBS from all wells except controls.
13. Add 100 µL PBS to wells.
14. Add 100 µL TMB subtract to all wells, incubate 20 min at RT.
15. Add 100 µL Stop Solution 2 to the wells and read absorbance in plate reader at 450 nm setting.
16. See e.g., TABLE 53 for results.

TABLE 53

Absorbance Biotin HRP bound to Avidin/talc complex.

| talc, mg | AVIDIN preincubation, mg/ml | | | | |
| --- | --- | --- | --- | --- | --- |
| | 0 | 0.5 | 1 | 2 | 4 |
| 1 | 0.19 | 0.81 | 0.83 | 0.83 | 0.86 |
| 5 | 1.05 | 2.66 | 2.21 | 1.70 | 1.60 |

The study showed talc having an Avidin on its surface binds greater amounts of Biotin/HRP than talc alone.

Example 20: Absorbance of Talc Bound to Avidin-HRP

The following Example determined effect of vacuum-drying and −20° C. storage of Avidin-talc conjugate.

Plan: check stability of Avidin HRP bound to talc if talc is completely dry and powder stored at −20° C.

Material:

1. Sterile Talc Powder (Bryan Corporation, Cat. #: 1690, Lot #: 3M021, Exp. Date: December 2016)
2. 10×PBS (Sigma, Cat. #: P5493-1L, Lot #: SLBB9685)
3. Water (Sigma Life Science, Cat. #: 3500, Lot #: RNBD1156)
4. TMB Substrate (ENZO, Cat. #: 80-0350, Lot #: 01071401)
5. Stop Solution 2 (ENZO, Cat. #: 80-0377, Lot #: 02241430)
6. Immunopure Avidin, Horseradish Peroxidase, Conjugated (Thermo Scientific, Cat. #: 21123, Lot #: OJ193825).

Equipment:

1. Desi-Vac container. (Fischer Scientific; cat. #08-664-5A
2. Rotator for 2 ml tubes (360°)

DAY 1

1. Weigh 6 tubes with 25 mg talc in each.
2. Prepare 5 ml of 40 ng/ml AVIDIN HRP:
   Make 1:100 dilution of stock
   198 µL of PBS+2 µL of Avidin HRP
   Make 1:1000 dilution
   90 µL of PBS+10 µL of 1:100 dilution
   Make 5 mL of 40 ng/mL
   5 mL PBS+40 µL of 1:1000 dilution
3. Mix each tube with 1 mL of 40 ng/mL Avidin HRP solution. Add to tube #6 1 mL of PBS (negative control)
4. Incubate overnight at 4° C. Rotate tubes.

Day 2

1. Centrifuge all tubes. 3200 rpm for 3 minutes.
2. Discard the supernatant.

3. Wash all tubes with 1 mL PBS 3×.
4. Take negative control and 1 tube bound Avidin HRP. Resuspend both tubes in 500 µL of PBS.
5. Run absorbance:
   Using the 96 well micro-plate, transfer and split each tube into five wells in equal portions of 100 µL.
   Add 100 µL of TMB substrate to each well.
   Incubate for 20 min at RT.
   Add 100 µL of Stop solution #2 and measure absorbance in 450 nm.
6. See e.g., TABLE 54, TABLE 55, and FIG. 15 for results.

TABLE 54

Average OD: 5 mg talc binds to Avidin HRP (powder format).
AVERAGE OD: 5 mg talc binds to AVIDIN HRP (powder format)

| samples | no AVIDIN added | after o/n incubation | after vacuum dry | 24 hrs at −20 C. | 48 hrs at −20 C. | 7 days at −20 C. |
|---|---|---|---|---|---|---|
| 5 mg talc with drug | 1.97 | 3.06 | 2.08 | 2.306 | 1.92 | 2.162 |

TABLE 55

% from OD of pure talc.
% from OD of pure talc

| negative control (no AVIDIN added, not dry) | after o/n incubation with AVIDIN | talc bound to AVIDIN: after vacuum dry | powder stored for 24 hrs at −20 C. | 48 hrs at −20 C. | 7 days at −20 C. |
|---|---|---|---|---|---|
| 100 | 155.33 | 105.58 | 117.06 | 97.46 | 109.75 |

TABLE 56

Average reading (Absorbance assay), OD Day 1.

| | |
|---|---|
| 5 mg talc binded to AVIDIN HRP DAY 1, right after incubation | 3.06 |
| 5 mg talc, no AVIDIN HRP added | 1.97 |

TABLE 57

Average Absorbance of 5 mg Talc to Avidin HRP; Day 2, OD.

| | right after making powder, 24 hrs after binding |
|---|---|
| 5 mg talc with 40 ng/ml Avidin HRP | 2.08 |

7. Take all the supernatant from the experimental four tubes and place them into four new tubes with tops open in the vacuum o/n in 4° C. The end result is the protein powder containing the bound Talc/Avidin HRP.

Day 3
1. Take one tube and run absorbance assay to check the presence of the Avidin HRP.

2. Resuspend powder in the one tube in 500 μL of PBS.

3. Run absorbance:

Using the 96 well micro-plate, transfer and split 500 μL tube into five wells in equal portions of 100 μL.

Add 100 μL of TMB substrate to each well.

Incubate for 20 min at RT.

Add 100 μL of Stop solution #2 and measure absorbance in 450 nm.

4.

TABLE 58

Average Absorbance of 5 mg Talc bound to 40 ng/mL Avidin HRP; Day 3, OD.

| | 24 hrs after powder stored in −20 C. |
|---|---|
| OD | 2.306 |

5. The other three tubes: transfer immediately into −20° C.

Day 4

1. Take one tube from the −20° C. and run absorbance assay to check the presence of the Avidin HRP.

2. Resuspend powder in the one tube in 500 μL of PBS.

3. Run absorbance: split 500 μL tube into five wells in equal.

Using the 96 well micro-plate, transfer and split 500 μL tube into five wells in equal portions of 100 μL.

Add 100 μL of TMB substrate to each well.

Incubate for 20 min at RT.

Add 100 μL of Stop solution #2 and measure absorbance in 450 nm.

4.

TABLE 59

Average Absorbance of 5 mg Talc to Avidin HRP; Day 4, OD.

| | AVERAGE ABSORBANCE OF 5 mg TALC TO AVIDIN HRP; DAY 4, OD |
|---|---|
| OD | 1.92 |

Day 5

1. Take one tube from the −20° C. and run absorbance assay to check the presence of the Avidin HRP.

2. Resuspend powder in the one tube in 500 μL of PBS.

3. Run absorbance:

Using the 96 well micro-plate, transfer and split 500 μL tube into five wells in equal portions of 100 μL.

Add 100 μL of TMB substrate to each well.

Incubate for 20 min at RT.

Add 100 μL of Stop solution #2 and measure absorbance in 450 nm.

4.

Day 6

1. Take one tube from the −20° C. and run absorbance assay to check the presence of the Avidin HRP.

2. Resuspend powder in the one tube in 500 μL of PBS.

3. Run absorbance:

Using the 96 well micro-plate, transfer and split 500 μL tube into five wells in equal portions of 100 μL.

Add 100 μL of TMB substrate to each well.

Incubate for 20 min at RT.

Add 100 μL of Stop solution #2 and measure absorbance in 450 nm.

4.

TABLE 60

Average absorbance of 5 mg Talc to Avidin HRP, Day 7, OD.

| AVERAGE ABSORBANCE OF 5 mg TALC TO AVIDIN HRP:DAY 7; OD |
|---|
| OD 2.162 |

The study showed that dry vacuum procedure is not optimal to reverse talc-Avidin HRP to powder again. Further studies optimize the procedure to store binding talc for longer periods of time.

The study showed both vacuum-drying and −20° C. storage did not show optimum stability preservation of Avidin-talc conjugate.

Example 21: Cytotoxicity Assay of NCI-28H Cells Treated with Doxorubicin, Cisplatin, Paclitaxel, Talc, and Talc Bound to Doxorubicin, Cisplatin, and Paclitaxel The following Example determined which of the above compounds (doxorubicin, cisplatin, paclitaxel, talc alone, or talc bound to doxorubicin, cisplatin, and paclitaxel) is more cytotoxic to NCI-28H.

The following study exposed NCI-28H cells to different types of formulations: only drugs, only talc, and talc that was previously incubated with doxorubicin, cisplatin, or paclitaxel.

Experimental Plan:

Add to NCI-281-1 cells to different types of compounds: only drugs, only talc and talc that previously incubated with doxorubicin, cisplatin, and paclitaxel.

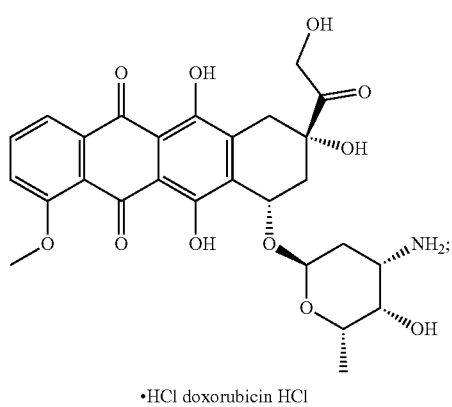

·HCl doxorubicin HCl

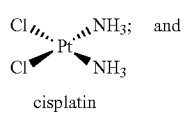

cisplatin

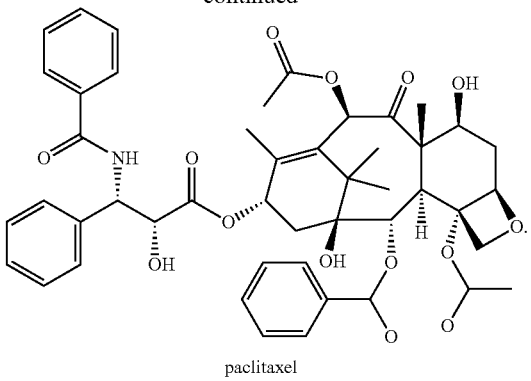

paclitaxel

Read absorbance (MTS assay) and calculate cells survival rate. Compare survival rate between each formulation.

Materials:
1. Doxorubicin Hydrochloride, 50 mg/25 ml; Amneal-Agila LLC, cat. # NDC 53150-315-01; lot #7800982; exp. March 2015.
2. Cisplatin 100 mg/ml; TEVA, cat. # NDC 0703-5748-11; lot #13J04LA, exp. April 2015.
3. Paclitaxel, 300 mg/ml; Sagent, cat. # NDC 25021-213-50; lot #38J0111; exp. April 2015.
4. Sterile Talc Powder, Bryan Corporation, cat. # NDC 63256-200-05; lot #: 3M021; exp. December 2016
5. DPBS, 1×
ATCC, Cat. #: 30-2200, Lot #: 61443818.
6. NCI-28H,
ATCC, cat. #: CRL-5820, lot #: 7379248
7. RPMI-1640 media; ATCC cat. #30-2001, lot #62027197.
8. Trypsin-EDTA; ATCC cat. #30-2101, lot #61618818.
9. Fetal Bovine serum, ATCC cat. #3022
10. CellTiter 96 AQueous One Solution cell proliferation assay; Promega cat # G3581.

DAY 1

Cells Preparation:
1. Set up 3 cytotoxicity plates for Day 2 experiment: trypsinize NCI-28H cells (T-75 flask, passage 12):
Remove old medium, wash cells with 7 ml DPBS, remove DPBS, add 2 ml trypsin, incubate plates for 1-2', when cells detached add 6 ml fresh medium, mix cells and medium.
Count cells under the microscope using the glass slide. Average # of cells in slide is 29.3; average in 1 ml of mix is 29.3×10,000=293,000 cells/ml;
Count how much cell/medium stock needed: use 3 plates (60 wells) in the assay; count extra wells for safety reason. If we need 200 wells, in each well will be 5,000 cells in 0.1 ml; so total we need 1,000,000 cells in 20 ml. 1,000,000 cells/293,000=3.4 ml of cells/media mix need to take from flask and transfer to 16.6 ml media. In 50 ml Falcon tube, combine 16.6 ml fresh medium and 3.4 ml cells. Gently mix.
2. Transfer 100 µL of prepared cells/medium mix to proper wells, keep overnight at 37° C., 5% CO₂.

Talc Preparation:
1. Under the hood transfer sterile talc approximately 25 mg of talc to each of 3 sterile Eppendorf tubes, and approximately 100 mg of sterile talc to one tube. Total tubes are 4. Close tubes and weigh how much exactly talc added to each tube. Result: tube #1=110 mg; tube #2 (dox)=35.8 mg, tube #3(CIS)=43.1 mg, tube #4 (Paclitaxel)=45.2 mg.

2. Talc/doxorubicin preparation: to make 500 µL of 1 µM doxorubicin solution use stock 3.45 mM; dilute stock 1:100=495 µL DPBS+5 µL stock; combine 485.5 µL DPBS+ 14.5 µL of 1:100 dilution of doxorubicin stock. Final solution is 500 µL of 1 µM doxorubicin. Mix talc in tube #2 with this solution.

3. Talc/cisplatin preparation: to make 500 µL of 20 µM CISPLATIN solution use stock 3.33 mM; dilute stock 1:10=90 µL DPBS+10 µL stock; combine 470.0 µL DPBS+ 30 µL of 1:10 dilution of CISPLATIN stock. Final solution is 500 µL of 20 µM.

cisplatin. Mix talc in tube #3 with this solution.

4. Talc/paclitaxel preparation: to make 500 µL of 1 µM paclitaxel solution use stock 7.03 mM; dilute stock 1:100=495 µL DPBS+5 µL stock; combine 482 µL DPBS+ 18.0 µL of 1:100 dilution of paclitaxel stock. Final solution is 500 µL of 1 µM paclitaxel. Mix talc in tube #4 with this solution.

5. Protect tubes from light, tape them on rotator and incubate overnight at RT.

DAY 2

Preparation of Talc

1. Centrifuge tubes at 3200 rpm for 3 min. Take out supernatant. Wash pellet 3 times with 1.0 ml of DPBS (sterile) after last wash add to tube #1: contains 110 mg talc, 220 µL of media; final concentration talc in tube will be 0.5 mg/µL. Add to tube #2 contains 35.8 mg talc, 71.6 µL of media; to tube #3 contains 43.1 mg talc add 86.2 µL media and for tube #4 contains.

45.2 mg talc add 90.4 µL media; final concentration talc in all tubes will be 0.5 mg/µL.

2. Keep tubes with talc at RT.

3. Prepare first working solution of talc from tube #1: 1.26 ml media+140 µL of 0.5 mg/µL talc. Total concentration will be 5 mg/100 µL. Make dilutions 1:2 (700 µL media+700 µL previous dilution) to make following concentration talc in well 2.5 mg talc/100 µL media; 1.25 mg/100 µL; 0.6 mg/100 µL.

4. Prepare first dilution of each of the above tubes #2, #3, #4 by adding 540 µL media+60 µL of prepared above 0.5 mg talc and drug/µL.

5. After preparation of the above solution, prepare 3 subsequent 1:2 serial dilutions of each of the above preparations (300 µL media+300 µL of previous dilution).

6. Add 100 µL of the above preparations in steps #3, #4, #5 to the proper wells as indicated in a 96-well plate layout. The resultant preparation added to each well will give presence of talc in the wells as following: 0.6 mg talc/well, 1.25 mg talc/well, 2.5 mg talc/well, and 5.0 mg talc/well after sequential dilutions (1:2) across plate.

Preparation of doxorubicin (stock 3.4 5 mM): Prepare the following dilutions (1:5) of drug:

(1) 5 µM
(2) 1 µM
(3) 0.2 µM
(4) 0.04 µM
(5) 0.008 µM
(6) 0.0016 µM
(7) 0.00032 µM
(8) 0.000064 µM

Prepare 600 µL of 10 µM doxorubicin solution (double concentration to keep 5 µM drug in total volume 200 µL media in well) as follows:

1. 582.6 µL media+17.4 µL of 1:10 dilution of doxorubicin stock.

2. Following preparation of above solution prepare the above 7 sequential serial dilutions using the following formula: 480 µL media+120 µL of prior dilution.

3. Add 100 µL of each 8 preparations of diluted doxorubicin (step 1 and 2) to the proper wells according to a plate layout.

Preparation of cisplatin (stock 3.33 mM):

Prepare the following dilutions (1:5) of drug:

(1) 100 µM
(2) 20 µM
(3) 4 µM
(4) 0.8 µM
(5) 0.16 µM
(6) 0.032 µM
(7) 0.0064 µM
(8) 0.0013 µM

1. Prepare 600 µL of 200 µM CISPLATIN solution (double concentration to keep 100 µM drug in total volume 200 µL media in well) as follows: 564.0 µL media+36.0 µL of cisplatin stock.

2. Following preparation of above solution prepare the above 7 sequential serial dilutions using the following formula: 480 µL media+120 µL of prior dilution.

3. Add 100 µL of each 8 preparations of diluted CISPLATIN to the proper wells according to a prepared plate layout.

Preparation of paclitaxel (stock 7.03 mM): 1. Prepare the following dilutions (1:5) of drug:

(1) 10 µM
(2) 2 µM
(3) 0.4 µM
(4) 0.08 µM
(5) 0.016 µM
(6) 0.0032 µM
(7) 0.00064 µM
(8) 0.00013 µM

2. Prepare 600 µL of 20 µM paclitaxel solution (double concentration to keep 10 µM drug in total volume 200 µL media in well) as follows: 582.9 µL media+17.1 µL of 1:10 dilution of paclitaxel stock.

3. Following preparation of above solution prepare the above 7 sequential serial dilutions using the following formula: 480 µL media+120 µL of prior dilution.

4. Add 100 µL of each 8 preparations of diluted paclitaxel (step 1, 2, 3) to the proper wells according to a plate layout.

5. Add 100 µL of media for untreated cells that will use as a control and not contain any drug or any kind of talc.

6. Check the plate and start incubation at 37° C./5% $CO_2$

DAY 3

1. Continue incubation plate at 37° C./5% $CO_2$

DAY 4

1. Continue incubation plate at 37° C./5% $CO_2$.

DAY 5

1. Check plate under microscope, no visible sign of contamination is present.

2. Mix talc/media liquid in the wells. Using needle/vacuum system, remove all liquid from all wells.

3. Wash cells 1×300 µL media, remove final wash.

4. Add 120 µL fresh media to all wells.

5. Add 20 µL of CellTiter 96 Aqueous One solution to each well.

6. Incubate plate 1 hr at 37° C., 5% $CO_2$.

7. Read absorbance in plate reader at 490 nm.

8. Data is shown below and in FIG. 16, FIG. 17, FIG. 18, FIG. 19, FIG. 20, FIG. 21, FIG. 22, and FIG. 23.

TABLE 61

Data for NCI-28H cells treated with Dox/Talc.

| 0 talc | 0.6 mg | 1.25 mg | 2.5 mg | 5 mg |
|---|---|---|---|---|
| 1.49 | 0.72 | 0.72 | 0.78 | 1.55 |

% survival from untreated by DOX cells(cells + talc)

| | | | | |
|---|---|---|---|---|
| 100 | 48.7 | 48.7 | 52.4 | 104.1 |

Average: cells + talc binded to 1 µM DOXORUBICIN

| 1.38 | 0.83 | 1.16 | 1.21 | 1.72 |
|---|---|---|---|---|

% survival from untreated by DOX cells(cells + talc binded to 1 µM DOX)

| | | | | |
|---|---|---|---|---|
| 100 | 59.8 | 83.4 | 87.4 | 124.6 |

% survival NCI-28H cells after different treatment(compare to untreated cells)
cells + 125 nM DOX 70
cells + 0.6 mg talc 48.7
cells + 0.6 mg talc/125 nM DOX 59.5

TABLE 62

Data for NCI-28H cells treated and untreated by Doxorubicin.

AVERAGE: cells + DOX
DOX, µM

| 0 | 0.000064 | 0.00032 | 0.0016 | 0.008 | 0.04 | 0.2 | 1 | 5 |
|---|---|---|---|---|---|---|---|---|
| 1.37 | 1.18 | 1.10 | 1.11 | 1.14 | 1.06 | 0.89 | 0.67 | 0.63 |

% survival from untreated by DOX cells
Dox, nM

| 0 | 0.064 | 0.32 | 1.6 | 8 | 40 | 200 | 1000 | 5000 |
|---|---|---|---|---|---|---|---|---|
| 100 | 86.3 | 80.0 | 80.7 | 83.4 | 77.4 | 65.0 | 48.6 | 46.2 |

TABLE 63

Average reading: cells + cisplatin
Cisplatin, µM

| 0 | 0.0013 | 0.0064 | 0.032 | 0.16 | 0.8 | 4 | 20 | 100 |
|---|---|---|---|---|---|---|---|---|
| 1.50 | 1.37 | 1.19 | 1.15 | 1.20 | 1.23 | 1.18 | 0.48 | 0.59 |

TABLE 64

% survival from untreated cells (cells + cisplatin)

| 0 | 0.0013 | 0.0064 | 0.032 | 0.16 | 0.8 | 4 | 20 | 100 |
|---|---|---|---|---|---|---|---|---|
| 100 | 91.07 | 79.21 | 76.66 | 79.74 | 82.09 | 78.41 | 31.99 | 39.35 |

TABLE 65

Average reading: cells + talc only.
talc, mg

| 0 | 0.6 mg | 1.25 mg | 2.5 mg | 5 mg |
|---|---|---|---|---|
| 1.3545 | 0.7295 | 0.6255 | 0.7745 | 1.221 |

TABLE 66

% survival from untreated cells: cells + talc only.

| 0 | 0.6 mg | 1.25 mg | 2.5 mg | 5 mg |
|---|---|---|---|---|
| 100 | 53.86 | 46.18 | 57.18 | 90.14 |

TABLE 67

Average readings: cells + talc incubated with 20 µM Cisplatin.

| 0 | 0.6 mg | 1.25 mg | 2.5 mg | 5 mg |
|---|---|---|---|---|
| 1.354 | 0.697 | 0.7415 | 1.1475 | 1.6665 |

TABLE 68

% survival from untreated: cells + talc/20 µM cisplatin.

| 0 | 0.6 mg/2.5 µM | 1.25 mg/5 µM CIS | 2.5 mg/10 µM | (5 mg/20 µM CIS |
|---|---|---|---|---|
| 100 | 51.48 | 54.76 | 84.75 | 123.08 |

TABLE 69

Paclitaxel, talc, cell data.
Average readings: cells + drug

| 0 | 0.13 | 0.68 | 3.5 | 16 | 80 | 400 | 2000 | 10,000 |
|---|---|---|---|---|---|---|---|---|

Paclitaxel, nM

| 1.52 | 1.56 | 1.33 | 1.37 | 1.29 | 1.10 | 1.01 | 0.95 | 0.93 |
|---|---|---|---|---|---|---|---|---|

% survival (cells + drug)

| 100 | 102.50 | 86.98 | 89.85 | 84.47 | 71.81 | 66.39 | 62.43 | 60.71 |
|---|---|---|---|---|---|---|---|---|

TABLE 70

Paclitaxel, talc, cell data.
Average reading: cells + talc

| 0 | 0.6 mg | 1.25 mg | 2.5 mg | 5 mg |
|---|---|---|---|---|
| 1.62 | 1.01 | 1.20 | 1.20 | 1.59 |

TABLE 70-continued

Paclitaxel, talc, cell data.
Average reading: cells + talc

% survival from untreated cells: cells + talc only

| 100 | 62.40 | 74.09 | 74.09 | 98.58 |

Average reading: cells + talc binded to 1 µM Paclitaxel

| 1.4835 | 0.725 | 0.43 | 0.6875 | 1.011 |

% survival from untreated cells: cells + talc binded to 1 µM Taxol

| 100 | 48.87 | 28.99 | 46.34 | 68.15 |

% survival from untreated cells: combine data

|  | 0 mg | 0.6 mg | 1.25 mg | 2.5 mg | 5 mg |
| --- | --- | --- | --- | --- | --- |
| cells + talc | 100 | 62.40 | 74.09 | 74.09 | 98.58 |
| cells + talc binded to 1 µM Taxol | 100 | 48.87 | 28.99 | 46.34 | 68.15 |

Figure 21:
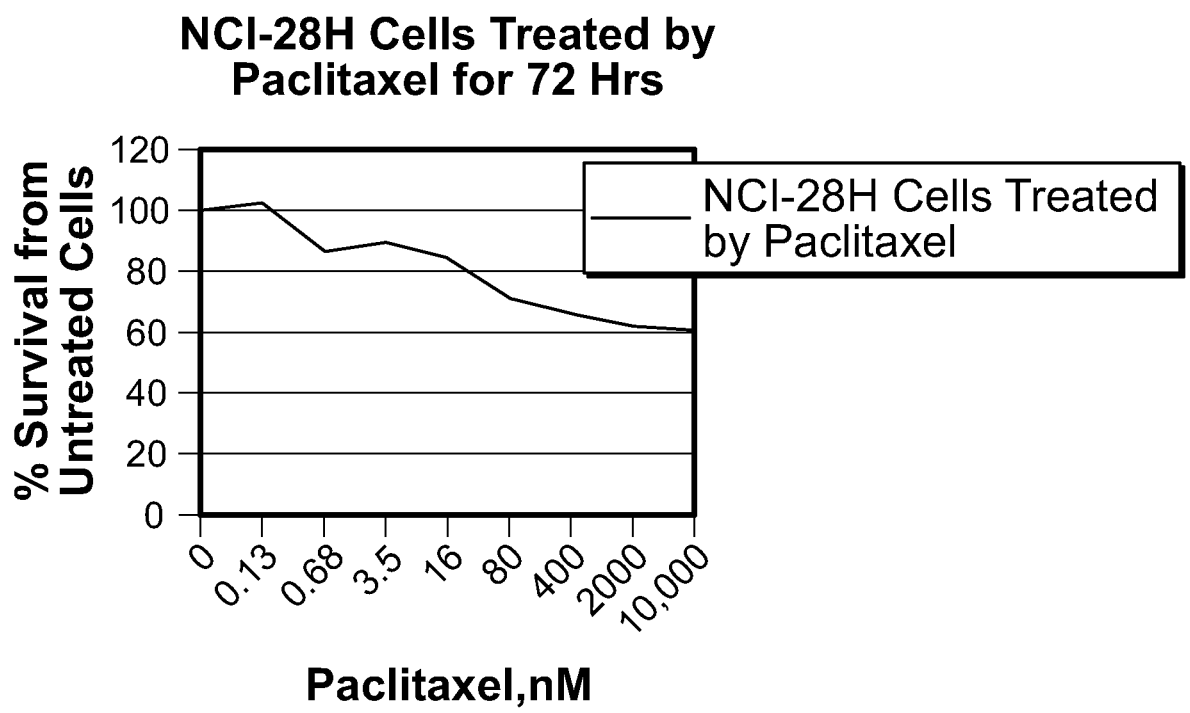
FIG. 21 is a scatter plot depicting % NCI-28H cells survival after 72 hours of paclitaxel treatment.
Figure 22:
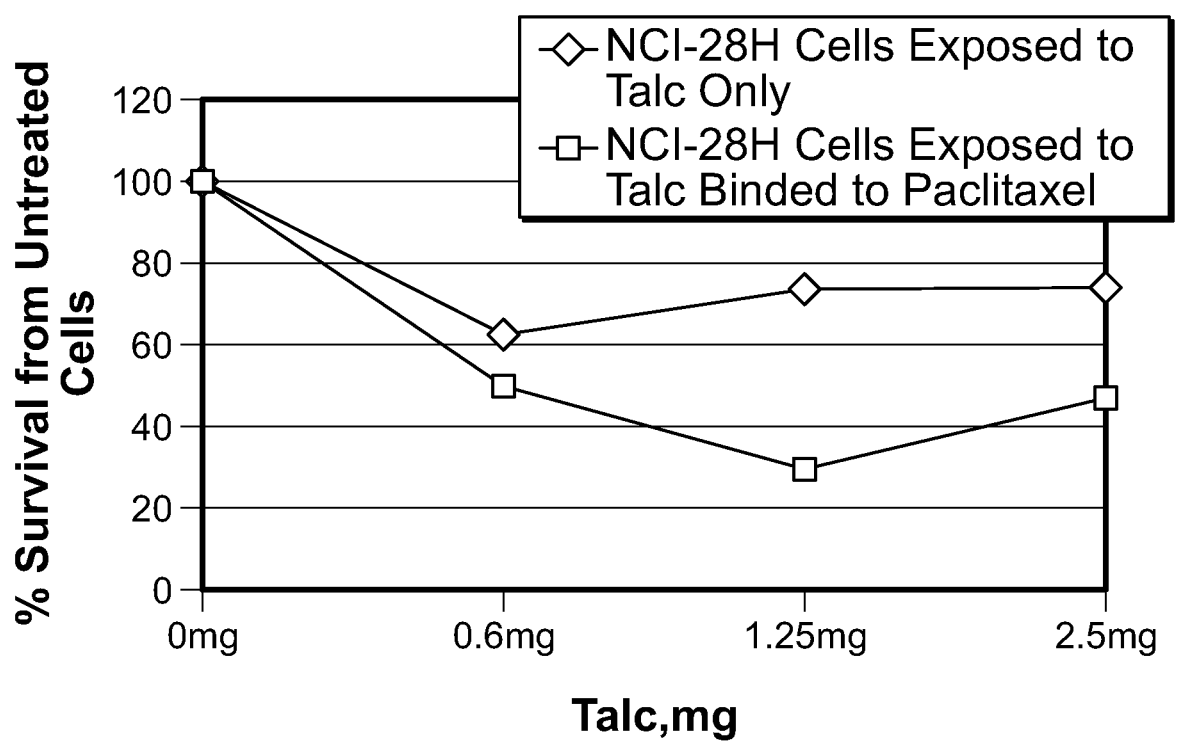
FIG. 22 is a scatter plot depicting % NCI-28H cells survival after exposure to talc or talc bound to paclitaxel.
Figure 23:
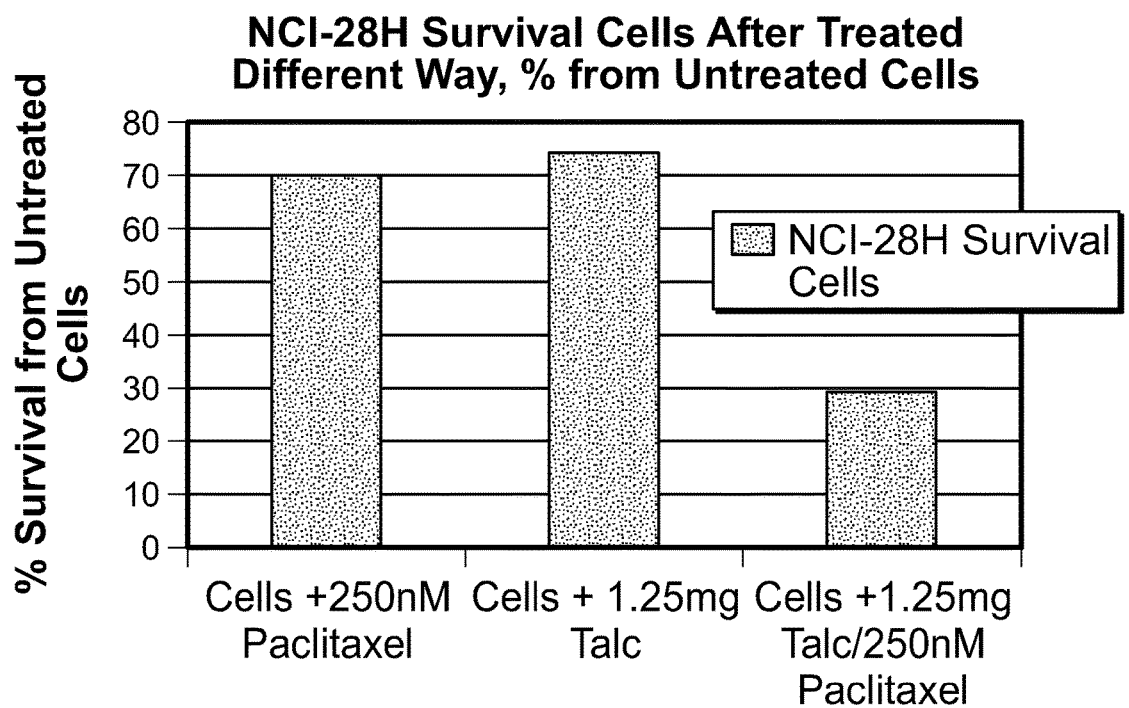
FIG. 23 is the data and a bar graph showing the comparison of survival NCI-28H cells with different treatments.
Figure 24:
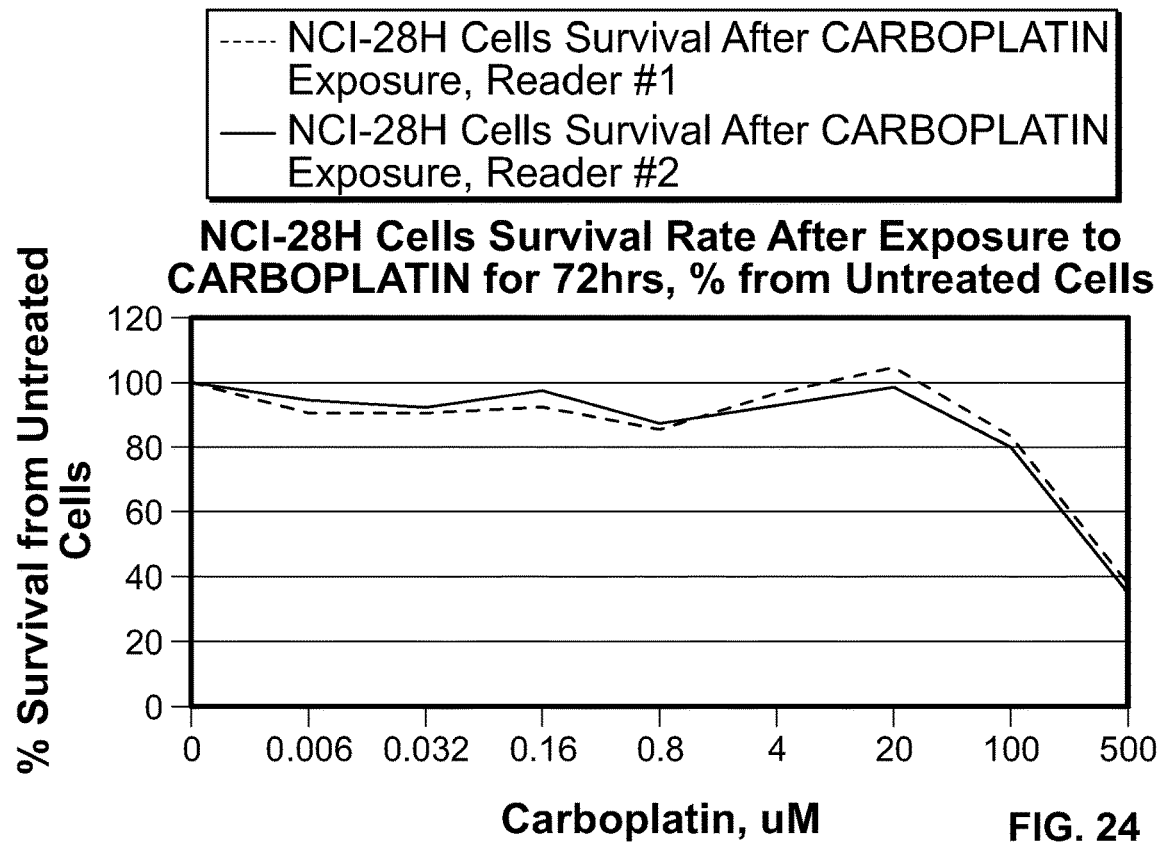
FIG. 24 is a scatter plot depicting % NCI-28H cells survival after exposure to carboplatin.
Figure 25:
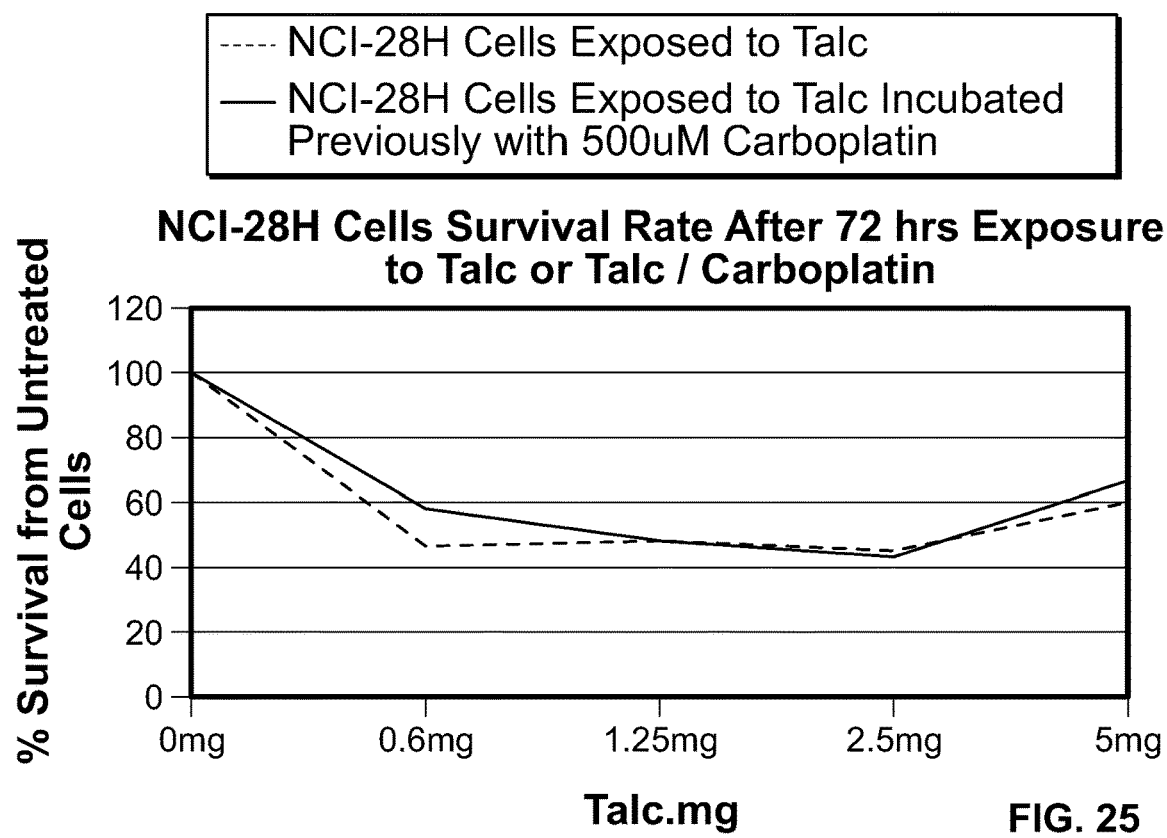
FIG. 25 is a scatter plot depicting % NCI-28H cells survival after 72 hours exposure to talc or talc/carboplatin.
Figure 26:
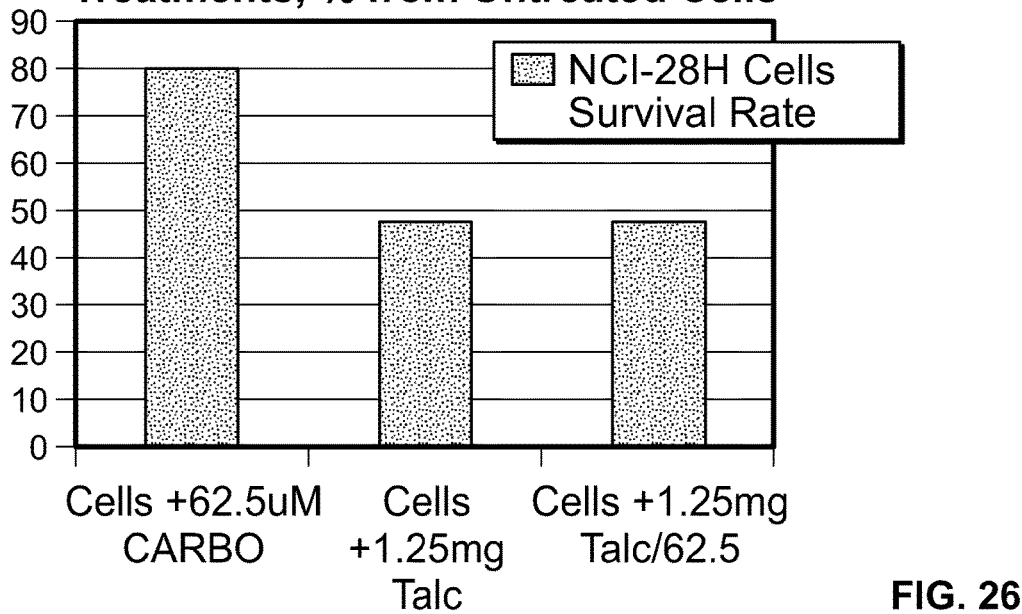
FIG. 26 is the data and a bar graph showing the comparison of survival NCI-28H cells with different treatments.

The data shows that talc bound to paclitaxel has a greater cytotoxic effect than paclitaxel or talc alone (see e.g., FIG. 21, FIG. 22, FIG. 23).

Figure 16:
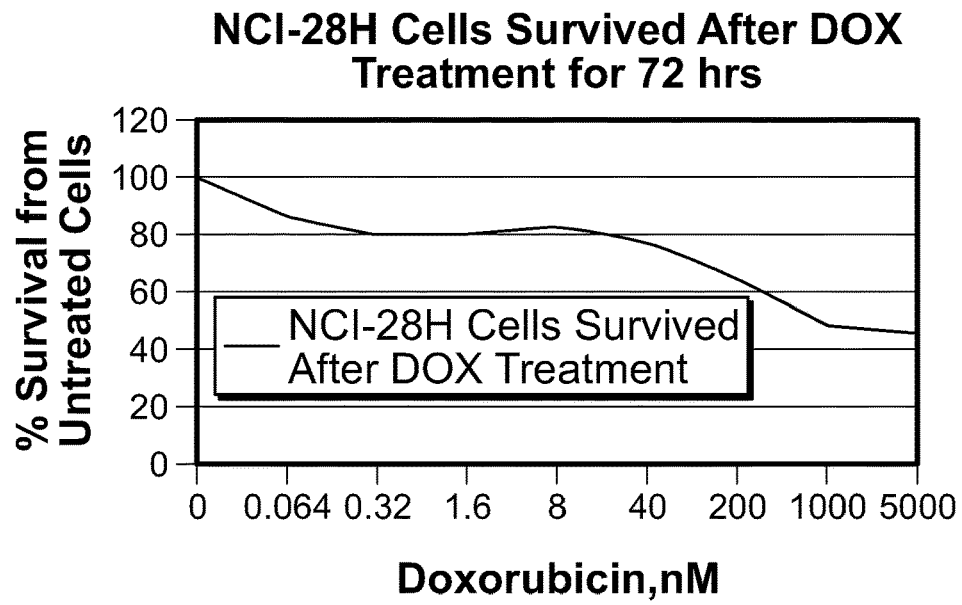
FIG. 16 is a scatter plot depicting % NCI-28H cells survival after 72 hours of doxorubicin treatment.
Figure 17:
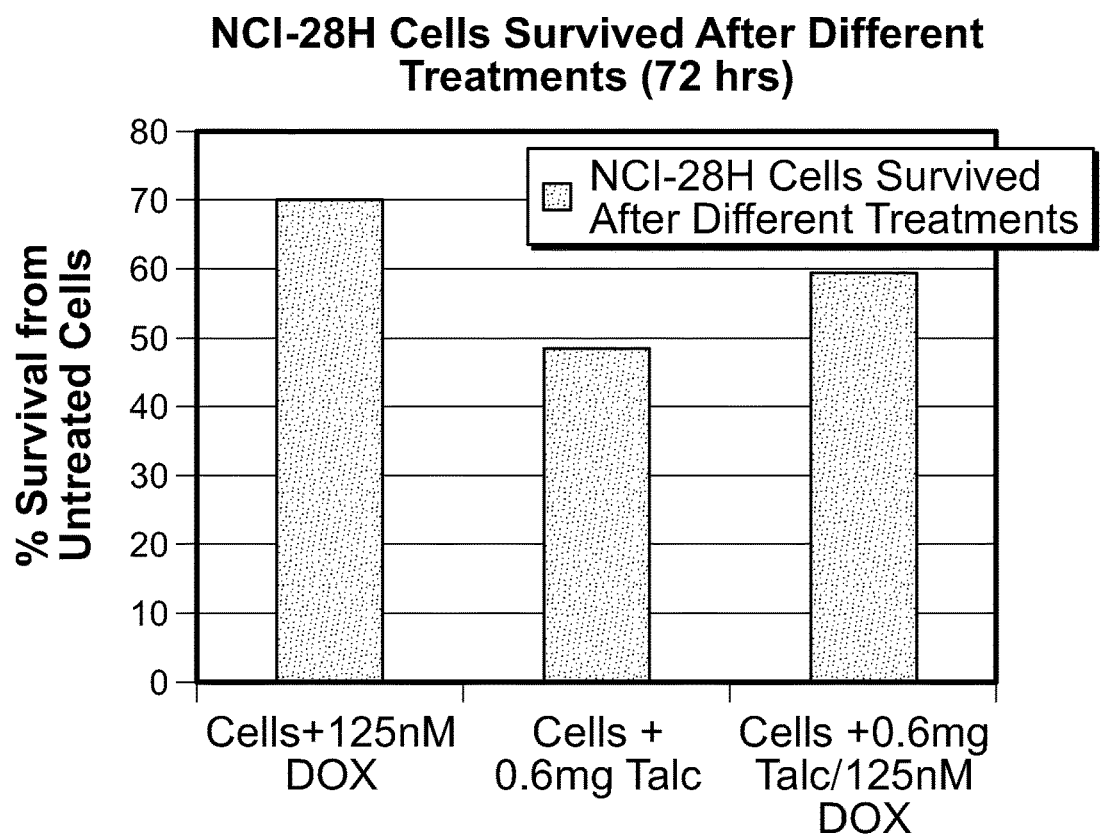
FIG. 17 is a bar graph of % NCI-28H cells survival after various treatments.
Figure 18:
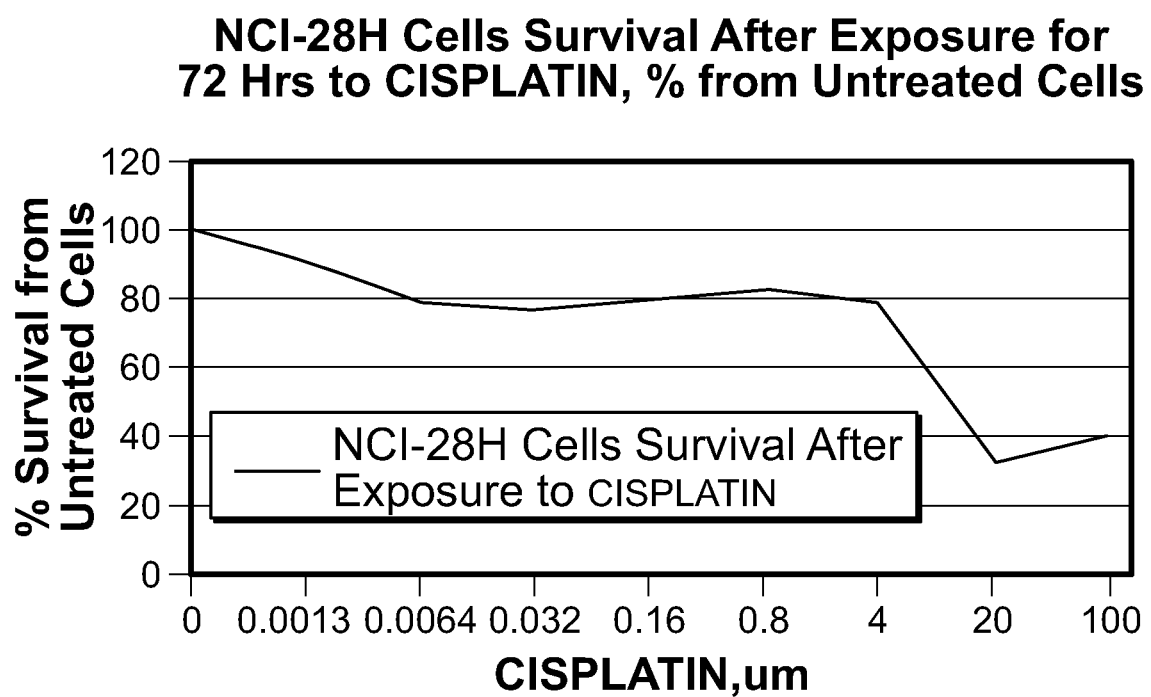
FIG. 18 is a scatter plot depicting % NCI-28H cells survival after 72 hours of exposure to cisplatin.
Figure 19:
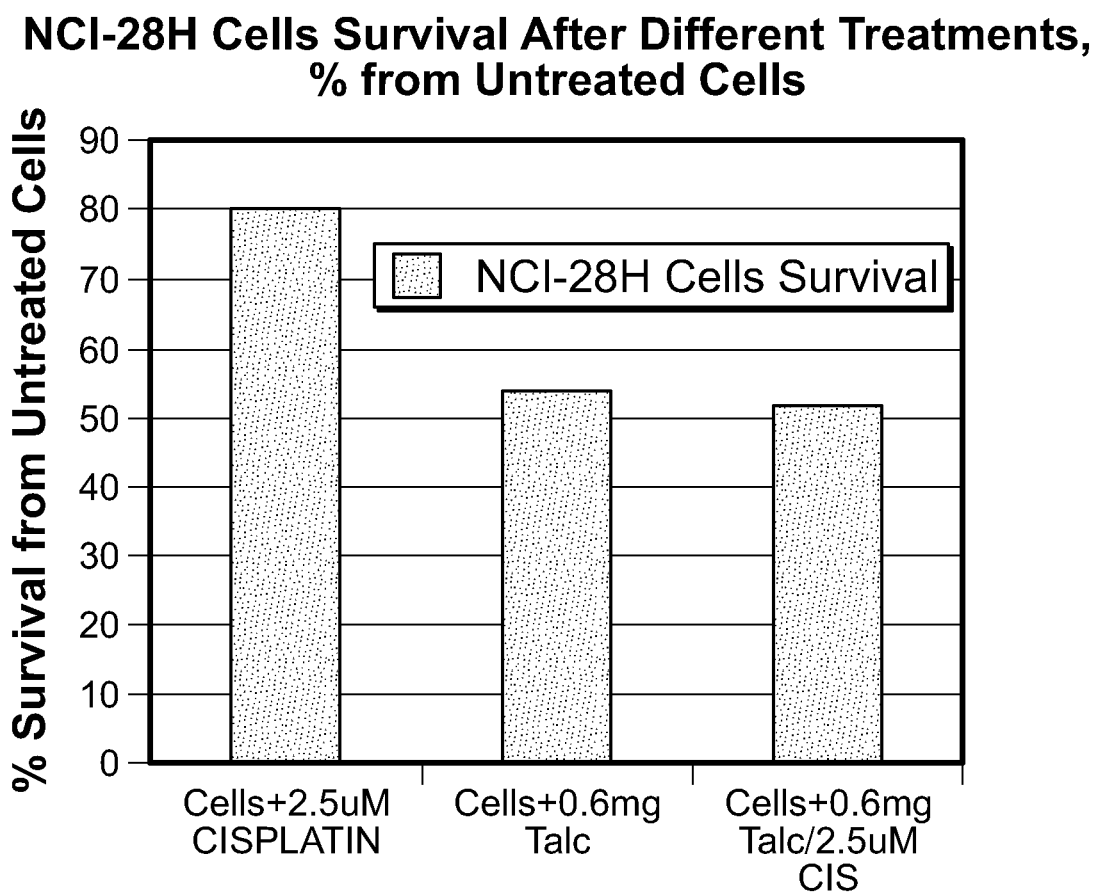
FIG. 19 is the data and a bar graph showing the comparison of survival NCI-28H cells with different treatments.
Figure 20:
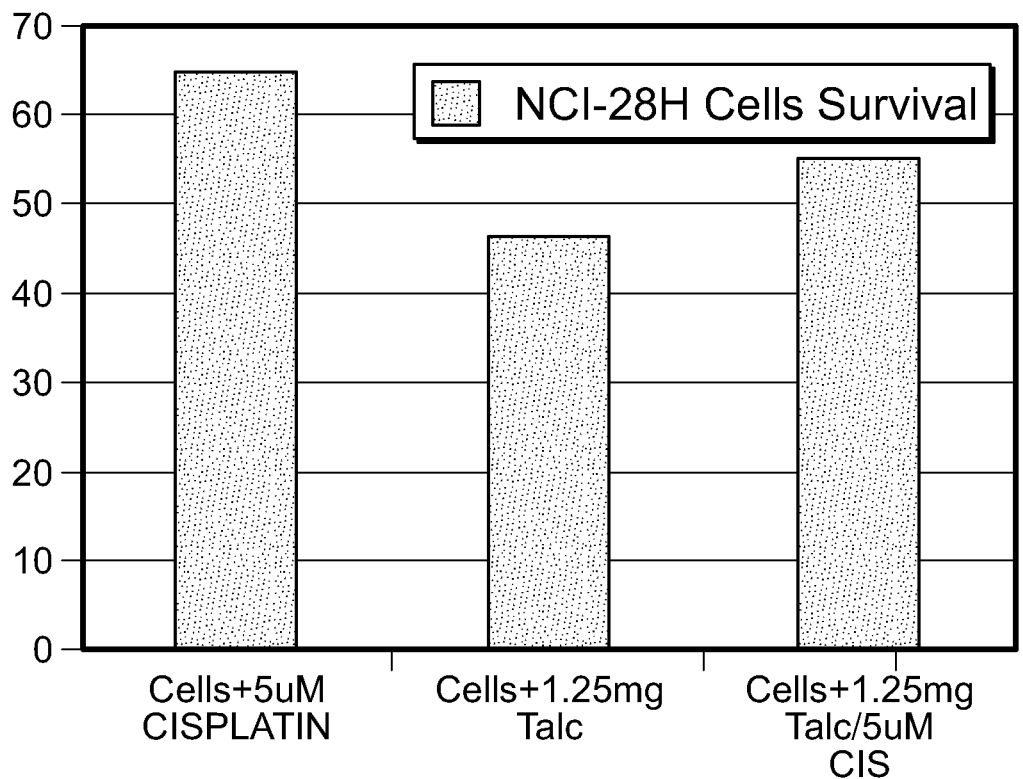
FIG. 20 is the data and a bar graph showing the comparison of survival NCI-28H cells with different treatments.

The data shows that talc bound to doxorubicin has a greater cytotoxic effect than doxorubicin or talc alone (see e.g., FIG. 16, FIG. 17).

The study showed clear cytotoxic effect on NCI-28H cells with talc alone. But when talc is bound to doxorubicin and paclitaxel, toxicity is enhanced over either of these cytotoxic agents used alone. In contrast, there was no noticeable difference in toxicity of cisplatin when bound or unbound to talc. Therefore, it is presently thought that cisplatin may not be effective because it may not bind to talc.

Example 22: Cytotoxicity Assay of NCI-28H Cells Treated with Compounds-Carboplatin, Mitomycin, Gemcitabine, Talc Alone, and Talc Bound to Carboplatin, Mitomycin, and Gemcitabine The following Example determined which of the above compounds (carboplatin, mitomycin, gemcitabine, or talc bound to carboplatin, mitomycin, or gemcitabine) is more cytotoxic to NCI-28H.

Carboplatin, Mitomycin, Gemcitabine, talc, and talc bound to the drugs.

Experimental Plan:
Add to NCI-28H cells different type of compounds: only drugs, only talc and talc that previously incubated with Carboplatin, Mitomycin, or Gemcitabine.

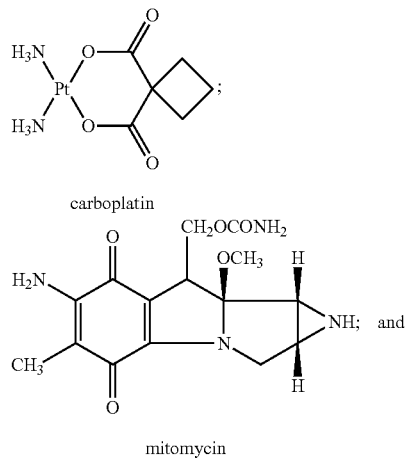

carboplatin mitomycin

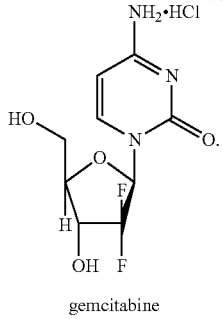

gemcitabine

Read absorbance (MTS assay) and calculate cells survive rate. Compare survival rate Materials:
1. Carboplatin 450 mg/45 ml; Hospira, cat # NDC 61703-339-50, lot #A011711AA, exp. September 2014.
2. Mitomycin 20 mg; Accord, cat. # NDC 16729-108-11, lot #PP01516, exp. July 2015
3. Gemcitabine 200 mg; SUN pharmaceutical industries LTD, cat. # NDC 47335-153-40, lot #JKL4371A, exp. August 2015.
4. Sterile Talc Powder,
Bryan Corporation, cat. # NDC 63256-200-05; lot #: 3M021; exp. December 2016
5. DPBS, 1×
ATCC, Cat. #: 30-2200, Lot #: 61443818.
6. NCI-28H,
ATCC, cat. #: CRL-5820, lot #: 7379248
7. RPMI-1640 media; ATCC cat. #30-2001, lot #62027197.
8. Trypsin-EDTA; ATCC cat. #30-2101, lot #61618818.
9. Fetal Bovine serum, ATCC cat. #3022
10. CellTiter 96 AQueous One Solution cell proliferation assay; Promega cat # G3581.
11. 0.9% Sodium Chloride 50 ml; BAXTER cat. #2131306, NDC 03380049-41, lot # P300574, exp. April 2014.

DAY 1
Cells Preparation:
1. Set up 3 cytotoxicity plates for tomorrow experiment: trypsinize NCI-28H cells (T-75 flask, passage 12):
Remove old medium, wash cells with 7 ml DPBS, remove DPBS, add 2 ml trypsin, incubate plates for 1-2', when cells detached add 6 ml fresh medium, mix cells and medium.
Count cells under the microscope using the glass slide. Average # of cells in slide is 31; average in 1 ml of mix is 31×10,000=310,000 cells/ml;
Count how much cell/medium stock needed: will use 3 plates (60 wells) in the assay; count extra wells for safety reason. If we need 200 wells, in each well will be 5,000 cells in 0.1 ml; so total we need 1,000,000 cells in 20 ml.
1,000,000 cells/310,000=3.2 ml of cells/media mix need to take from flask and transfer to 16.8 ml media. In 50 ml Falcon tube, combine 16.8 ml fresh medium and 3.2 ml cells. Gently mix.
2. Transfer 100 µL of prepared cells/medium mix to proper wells, keep overnight at 37° C., 5% $CO_2$.

Talc Preparation:
1. Under the hood transfer sterile talc approximately 25 mg of talc to each of 3 sterile Eppendorf tubes, and approximately 100 mg of sterile talc to one tube. Total tubes are 4.

Close tubes and weigh how much exactly talc added to each tube. Result: tube #1=89.1 mg; tube #2 (CARBO)=32.0 mg, tube #3 (MITOMYCIN)=32.5 mg, tube #4 (GEM)=28.8 mg.

2. Talc/Carboplatin preparation: to make 500 µL of 500 µM carboplatin solution use stock 26.9 mM; dilute stock 1:10=90 µL DPBS+10 µL stock; combine 407.0 µL DPBS+93.0 µL of 1:10 dilution of carboplatin stock. Final solution is 500 µL of 500 µM carboplatin. Mix talc in tube #2 with this solution.

3. Talc/mitomycin preparation: reconstitute 20 mg powder of drug with 20 ml sterile water, molarity of stock solution will be 2.99 mM to make 500 µL of 200 µM Mitomycin solution use stock 2.99 mM; combine 466.6 µL DPBS+33.4 µL stock. Final solution is 500 µL of 200 µM Mitomycin. Mix talc in tube #3 with this solution.

4. Talc/Gemcitabine preparation: to make 500 µL of 200 µM Gemcitabine, reconstitute drug with 5 ml of 0.9% Sodium Chloride; stock will be 133.48 mM; dilute stock 1:10=90 µL DPBS+10 µL stock; combine 462.6 µL DPBS+37.4 µL of 1:10 dilution of stock. Final solution is 500 µL of 200 µM Gemcitabine. Mix talc in tube #4 with this solution.

5. Protect tubes from light, tape them on rotator and incubate o/n at RT.

DAY 2

Preparation of Talc

1. Centrifuge tubes at 3200 rpm for 3 min. Take out supernatant. Wash pellet 3 times with 1.0 ml of DPBS (sterile) after last wash add to tube #1: contains 89.1 mg talc, 178.2 µL of media; final concentration talc in tube will be 0.5 mg/µL. Add to tube #2 contains 32.0 mg talc, 64.0 µL of media; to tube #3 contains 32.5 mg talc add 65.0 µL media and for tube #4 contains 28.8 mg talc add 57.6 µL media; final concentration talc in all tubes will be 0.5 mg/µL.

2. Keep tubes with talc at RT.

3. Prepare first working solution of talc from tube #1: 1.35 ml media+150 µL of 0.5 mg/µL talc. Total concentration will be 5 mg/100 µL. Make dilutions 1:2 (750 µL media+750 µL previous dilution) to make following concentration talc in well 2.5 mg talc/100 µL media; 1.25 mg/100 µL; 0.6 mg/100 µL.

4. Prepare first dilution of each of the above tubes #2, #3, #4 by adding 540 µL media+60 µL of prepared above 0.5 mg talc and drug/µL.

5. After preparation of the above solution, prepare 3 subsequent 1:2 serial dilutions of each of the above preparations (300 µL media+300 µL of previous dilution).

6. Add 100 µL of the above preparations in steps #3, #4, #5 to the proper wells as indicated in a 96-well plate layout. The resultant preparation added to each well will give presence of talc in the wells as following: 0.6 mg talc/well, 1.25 mg talc/well, 2.5 mg talc/well, and 5.0 mg talc/well after sequential dilutions (1:2) across plate.

Preparation of carboplatin (stock 26.9 mM): Prepare the following dilutions (1:5) of drug:
(1) 500 µM
(2) 100 µM
(3) 20 µM
(4) 4 µM
(5) 0.8 µM
(6) 0.16 µM
(7) 0.032 µM
(8) 0.0064 µM Prepare 600 µL of 1 mM carboplatin solution (double concentration to keep 500 µM drug in total volume 200 µL media in well) as follows:

1. 577.7 µL media+22.3 µL of carboplatin stock.

2. Following preparation of above solution prepare the above 7 sequential serial dilutions using the following formula: 480 µL media+120 µL of prior dilution.

3. Add 100 µL of each 8 preparations of diluted carboplatin (step 1 and 2) to the proper wells according to a plate layout.

Preparation of mitomycin (stock 2.99 mM): Prepare the following dilutions (1:5) of drug:
(1) 200 µM
(2) 40 µM
(3) 8 µM
(4) 1.6 µM
(5) 0.32 µM
(6) 0.064 µM
(7) 0.013 µM
(8) 0.0026 µM 1. Prepare 600 µL of 400 µM Mitomycin solution (double concentration to keep 100 µM drug in total volume 200 µL media in well) as follows: 520.0 µL media+80.2 µL of stock.

2. Following preparation of above solution prepare the above 7 sequential serial dilutions using the following formula: 480 µL media+120 µL of prior dilution.

3. Add 100 µL of each 8 preparations of diluted mitomycin to the proper wells according to a plate layout.

Preparation of gemcitabine (stock 133.48 mM):

1. Prepare the following dilutions (1:5) of drug:
(1) 200 µM
(2) 40 µM
(3) 8 µM
(4) 1.6 µM
(5) 0.32 µM
(6) 0.064 µM
(7) 0.013 µM
(8) 0.0026 µM 2. Prepare 600 µL of 400 µM drug solution (double concentration to keep 200 µM drug in total volume 200 µL media in well) as follows:

582.0 µL media+18.0 µL of 1:10 dilution of stock.

3. Following preparation of above solution prepare the above 7 sequential serial dilutions using the following formula: 480 µL media+120 µL of prior dilution.

4. Add 100 µL of each 8 preparations of diluted Gemcitabine (step 1, 2, 3) to the proper wells according to a plate layout.

5. Add 100 µL of media for untreated cells that will use as a control and not contain any drug or any kind of talc.

6. Check the plate and start incubation at 37° C./5% $CO_2$.

DAY 3

1. Mix talc in wells by pipetting up and down. Continue incubation plate at 37° C./5% $CO_2$.

DAY 4

1. Mix talc in wells by pipetting up and down. Continue incubation plate at 37° C./5% $CO_2$.

DAY 5

1. Check plate under microscope, no visible sign of contamination is present.

2. Mix talc/media liquid in the wells. Using needle/vacuum system remove all liquid from all wells.

3. Wash all cells 1×300 µL DPBS, remove final wash.

4. Add 120 µL fresh media to all wells.

5. Add 20 µL of CellTiter 96 Aqueous One solution to each well.

6. Incubate plate 1 hr at 37° C., 5% $CO_2$.

7. Read absorbance in plate reader at 490 nm.

TABLE 71

Average reading: cells + drug, carboplatin, μM.

| 0 | 0.006 | 0.032 | 0.16 | 0.8 | 4 | 20 | 100 | 500 |
|---|---|---|---|---|---|---|---|---|
| 1.65593 | 1.504233 | 1.514967 | 1.5334 | 1.4238 | 1.605067 | 1.7355 | 1.388067 | 0.618933 |

TABLE 72

% survival from untreated cells: cells + drug, carboplatin, μM.

| 0 | 0.006 | 0.032 | 0.16 | 0.8 | 4 | 20 | 100 | 500 |
|---|---|---|---|---|---|---|---|---|
| 100 | 90.84 | 91.49 | 92.60 | 85.98 | 96.93 | 104.81 | 83.82 | 37.38 |
| 100 | 94.28 | 92.95 | 97.48 | 87.53 | 93.62 | 99.20 | 79.53 | 35.14 |

TABLE 73

Average absorbance reading talc + cells and cells + talc incubated with 500 μM.

| | 0 mg | 0.6 mg | 1.25 mg | 2.5 mg | 5 mg |
|---|---|---|---|---|---|
| cells + talc | 1.65593 | 0.771 | 0.78895 | 0.74915 | 0.9812 |
| cells + talc/500 μMCarbo | 1.65593 | 0.9763 | 0.7927 | 0.7154 | 1.0903 |

TABLE 74

% survival cells after talc and talc bound to carboplatin added.

| | 0 mg | 0.6 mg | 1.25 mg | 2.5 mg | 5 mg |
|---|---|---|---|---|---|
| Cells + talc | 100 | 46.56 | 47.64 | 45.24 | 59.25 |
| Cells + talc/500 μMCarbo | 100 | 58.95 | 47.87 | 43.20 | 65.84 |

TABLE 73

Average reading: cells + drug, gemcitabine, μM.

| 0 | 0.0026 | 0.013 | 0.064 | 0.32 | 1.6 | 8 | 40 | 200 |
|---|---|---|---|---|---|---|---|---|
| 1.77441 | 2.033633 | 1.913633 | 1.430167 | 1.388733 | 1.1977 | 1.00395 | 1.0663 | 0.9352 |

TABLE 74

% survival from untreated cells: cells + drug, gemcitabine, μM.
Gemcitabinem, μM

| 0 | 0.0026 | 0.013 | 0.064 | 0.32 | 1.6 | 8 | 40 | 200 |
|---|---|---|---|---|---|---|---|---|
| 100 | 114.61 | 107.85 | 80.60 | 78.26 | 67.50 | 56.58 | 60.09 | 52.70 |

TABLE 75

Average absorbance readings: cells + drug, mitomycin, μM.

| 0 | 0.0026 | 0.013 | 0.064 | 0.32 | 1.6 | 8 | 40 | 200 |
|---|---|---|---|---|---|---|---|---|
| 1.91438 | 2.031533 | 1.965033 | 1.8766 | 1.827167 | 1.036467 | 0.3451 | 0.520033 | 0.246367 |

TABLE 76

% survival cells after exposure to drug for 72 hrs (cells + drug only), mitomycin, μM.

| 0 | 0.0026 | 0.013 | 0.064 | 0.32 | 1.6 | 8 | 40 | 200 |
|---|---|---|---|---|---|---|---|---|
| 100 | 106.12 | 102.65 | 98.03 | 95.44 | 54.14 | 18.03 | 27.16 | 12.87 |

TABLE 77

Average absorbance readings: survival cells after talc incubated to mitomycin added.

| | 0 mg | 0.6 mg | 1.25 mg | 2.5 mg | 5 mg |
|---|---|---|---|---|---|
| Cells + talc | 1.91438 | 1.7976 | 2.1208 | 1.99815 | 2.1156 |
| Cells + talc/Mitomycin | 1.91438 | 0.6719 | 0.6604 | 0.7877 | 1.22415 |

TABLE 78

% survival cells after talc and talc/mitomycin treatment.

| | 0 mg | 0.6 mg | 1.25 mg | 2.5 mg | 5 mg |
|---|---|---|---|---|---|
| Cells + talc | 100 | 93.90 | 110.78 | 104.38 | 110.51 |
| Cells + talc/Mitomycin | 100 | 35.10 | 34.50 | 41.15 | 63.94 |

TABLE 79

Average absorbance reading: cells + drug, gemcitabine, μM.

| Gemcitabine, uM | | | | | | | | |
|---|---|---|---|---|---|---|---|---|
| 0 | 0.0026 | 0.013 | 0.064 | 0.32 | 1.6 | 8 | 40 | 200 |
| 1.77441 | 2.033633 | 1.913633 | 1.430167 | 1.388733 | 1.1977 | 1.00395 | 1.0663 | 0.9352 |

TABLE 80

% survival cells: cells + drug only.

| Gemcitabine, uM | | | | | | | | |
|---|---|---|---|---|---|---|---|---|
| 0 | 0.0026 | 0.013 | 0.064 | 0.32 | 1.6 | 8 | 40 | 200 |
| 100 | 114.61 | 107.85 | 80.60 | 78.26 | 67.50 | 56.58 | 60.09 | 52.70 |

TABLE 81

Average absorbance reading: cells + talc.

| | 0 mg | 0.6 mg | 1.25 mg | 2.5 mg | 5 mg |
|---|---|---|---|---|---|
| Cells + talc only | 1.77441 | 1.10175 | 1.0486 | 1.12035 | 1.20865 |
| Cells + talc/Gemcitabine | 1.77441 | 0.9357 | 0.7983 | 0.70395 | 0.84505 |

TABLE 82

% survival cells: cells + talc/drug; % from untreated cells.

| | 0 mg | 0.6 mg | 1.25 mg | 2.5 mg | 5 mg |
|---|---|---|---|---|---|
| Cells + talc only | 100 | 62.09 | 59.10 | 63.14 | 68.12 |
| Cells + talc/Gemcitabine | 100 | 52.73 | 44.99 | 39.67 | 47.62 |

Figure 27:
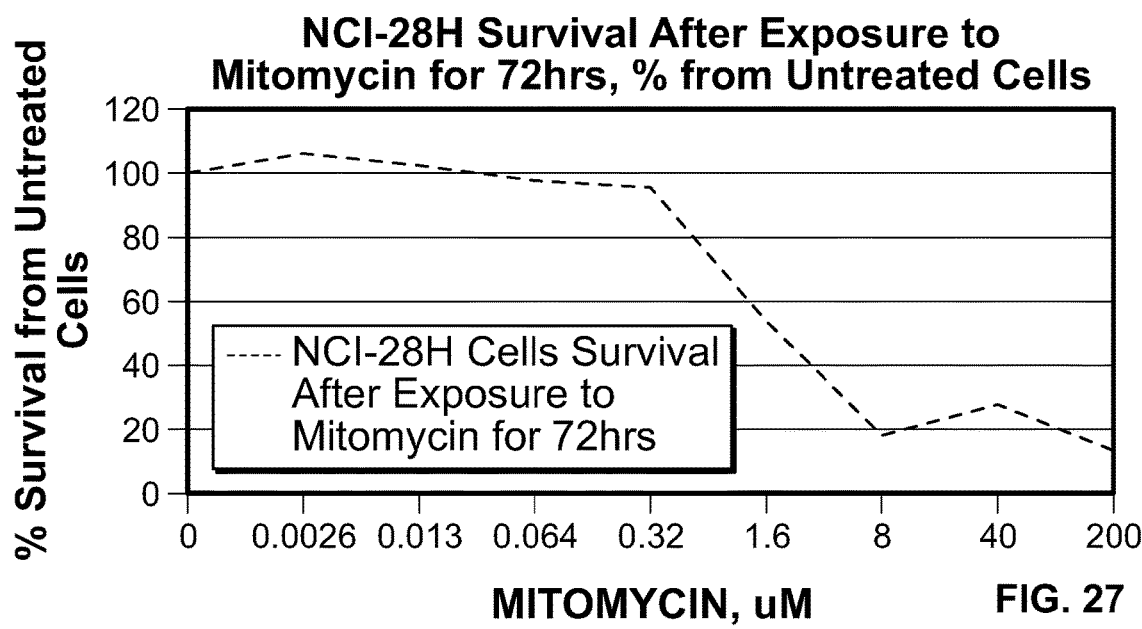
FIG. 27 is a scatter plot depicting % NCI-28H cells survival after 72 hours exposure to mitomycin.
Figure 28:
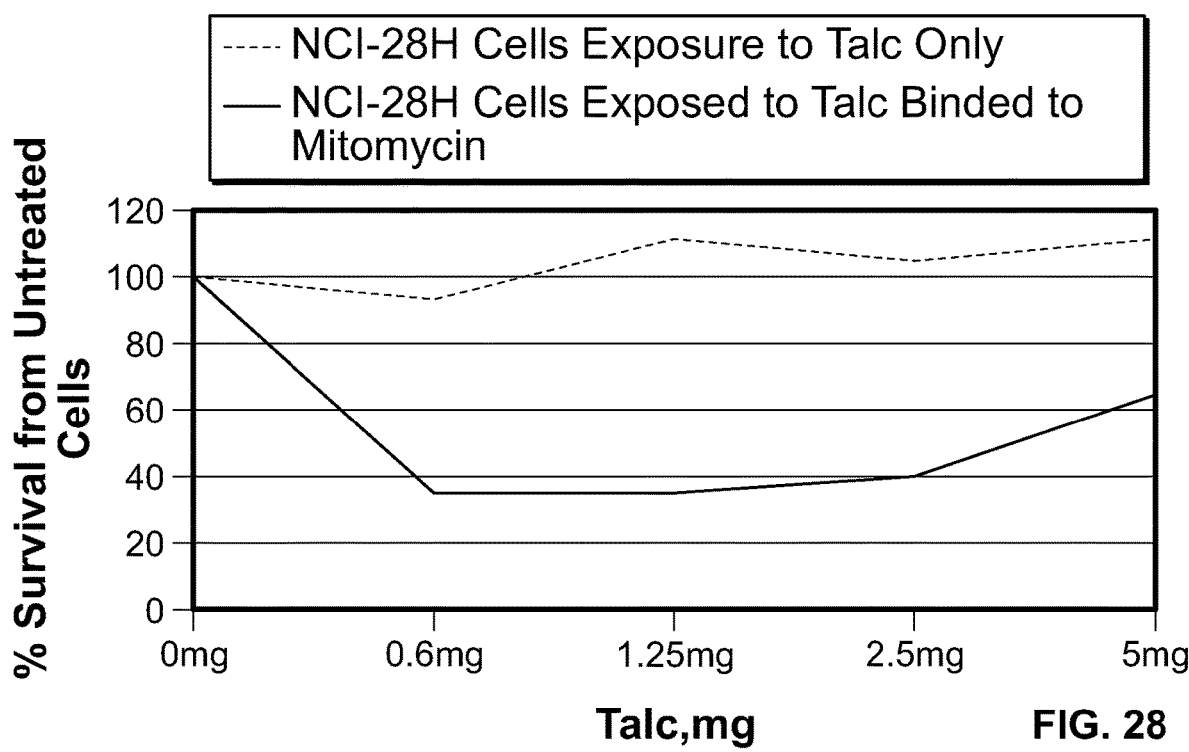
FIG. 28 is a scatter plot depicting % NCI-28H cells survival after exposure to talc or talc bound to mitomycin.
Figure 29:
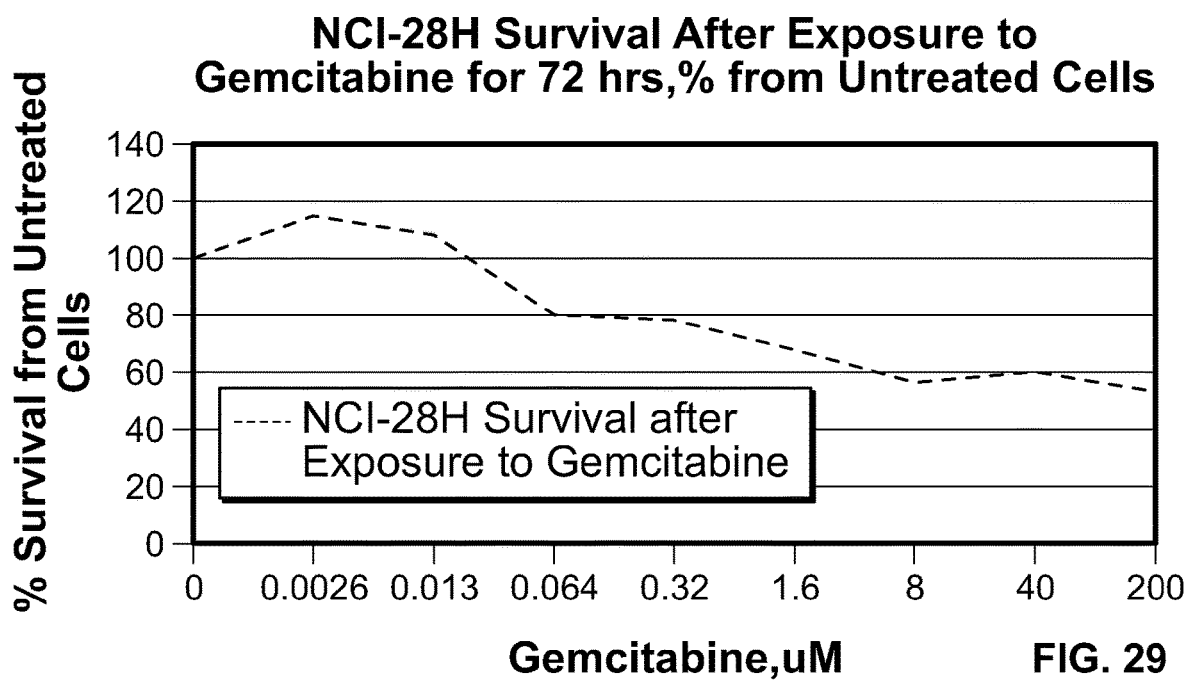
FIG. 29 is a scatter plot depicting % NCI-28H cells survival after 72 hours exposure to talc or talc bound to gemcitabine.
Figure 30:
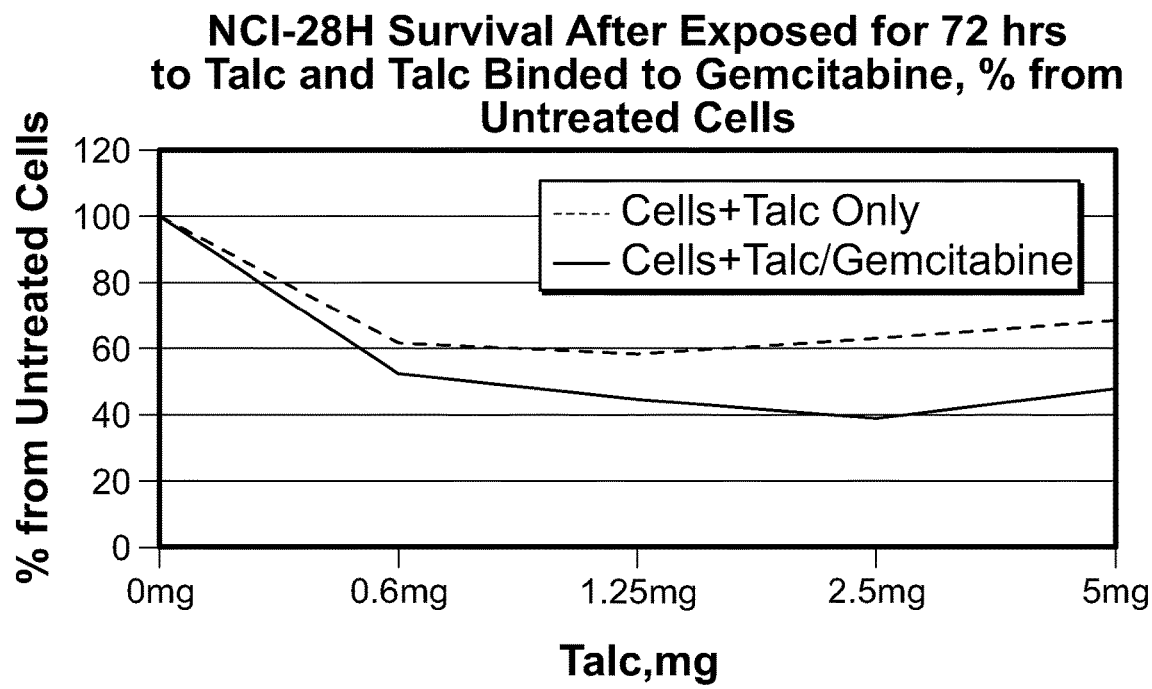
FIG. 30 is a scatter plot depicting % NCI-28H cells survival after 72 hours exposure to talc or talc bound to gemcitabine.

The data showed that talc bound to mitomycin has a greater cytotoxic effect than mitomycin or talc alone (see e.g., FIG. 27, FIG. 28).

The study showed clear cytotoxic effect on NCI-28H cells with talc, mitomycin, and gemcitabine when used as single-agents. However, when talc is bound to mitomycin or gemcitabine, toxicity is greatly enhanced over any of these agents when used alone. In contrast, there was no noticeable difference in toxicity of carboplatin-talc or talc alone on NCI-28H cells. Based on these findings, it is presently thought that carboplatin may not bind to talc or talc does not absorb carboplatin.

Example 23: Cytotoxicity Assay: NCI-2052H Cells Treated with Different Compounds-Bleomycin, Mitomycin, Doxorubicin, Paclitaxel, Talc Alone and Talc Bound to Each of these Compounds The following Example determined if cytotoxicity would also occur when another cell line was exposed to similar conditions, based on above experimental results with NCI-28H. Therefore, a similar experiment was designed utilizing NCI-2052H to determine if different compounds (talc, chemotherapy drugs, and talc conjugated to chemotherapy agents) would also be cytotoxic to NCI-2052H cells.

Plan: add to NCI-2052H cells different type of compounds: only drugs, only talc and talc that previously incubated with Bleomycin, Mitomycin, Doxorubicin, or Paclitaxel.

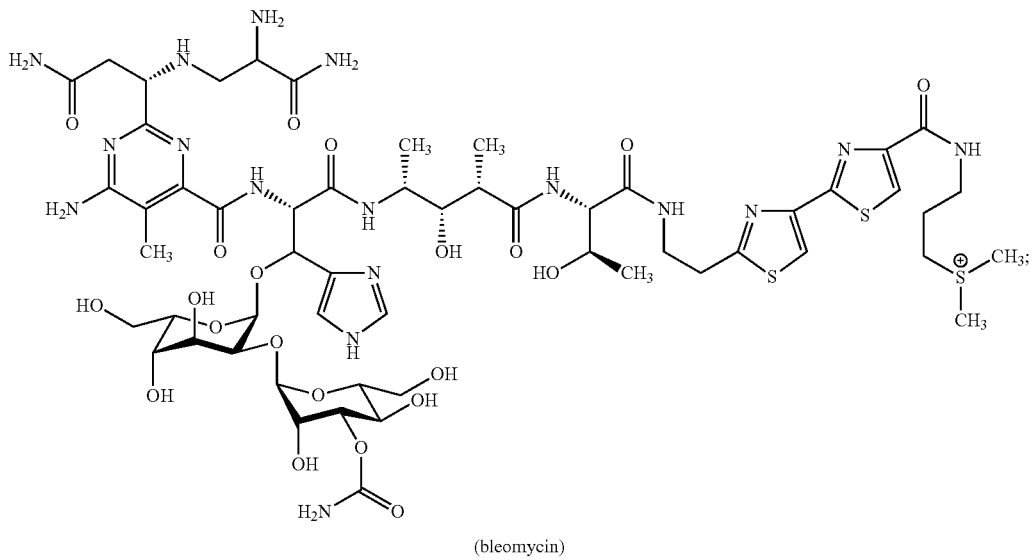

(bleomycin)

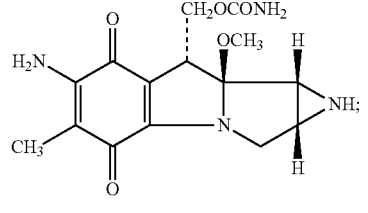

mitomycin

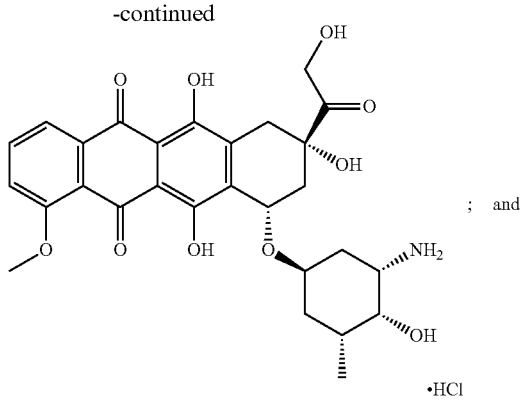

doxorubicin

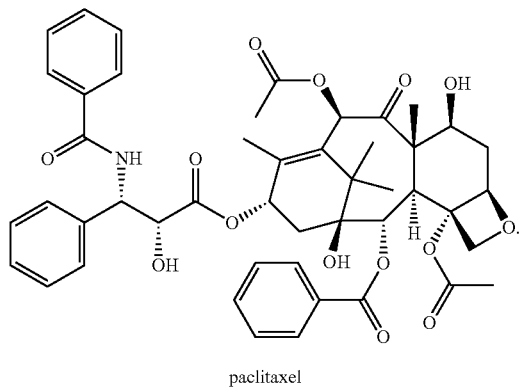

paclitaxel

Read absorbance (MTS assay) and calculate cells survival rate. Compare survival rate Materials:
1. Bleomycin sulfate from *Streptomyces verticillus*; Sigma, cat #15361-10 mg, lot # BCBL0535V.
2. Mitomycin 20 mg; Accord, cat. # NDC 16729-108-11, lot #PP01516, exp. July 2015.
3. Doxorubicin Hydrochloride, 50 mg/25 ml; Amneal-Agila LLC, cat. #NDC 53150-315-01; lot #7800982; exp. March 2015.
4. Paclitaxel, 300 mg/ml; Sagent, cat. # NDC 25021-213-50; lot #38J0111; exp. April 2015.
5. Sterile Talc Powder, Bryan Corporation, cat. # NDC 63256-200-05; lot #: 3M021; exp. December 2016
6. DPBS 1×; ATCC, Cat. #: 30-2200, Lot #: 61443818.
7. NCI-2052H cell line, ATCC, cat. #: CRL-5915, lot #: 57608140.
8. RPMI-1640 media; ATCC cat. #30-2001, lot #62027197.
9. Trypsin-EDTA; ATCC cat. #30-2101, lot #61618818.
10. Fetal Bovine serum, ATCC cat. #3022
11. CellTiter 96 AQueous One Solution cell proliferation assay; Promega cat # G3581.

DAY 1

Cells Preparation:
1 Set up 4 cytotoxicity plates for tomorrow experiment: trypsinize NCI-28H cells (T-75 flask, passage 6):
  Remove old medium, wash cells with 7 ml DPBS, remove DPBS, add 2 ml trypsin, incubate plates for 1-2 min., when cells detached add 6 ml fresh medium, mix cells and medium. —Count cells under the microscope using the glass slide. Average # of cells in slide is 44; average in 1 ml of mix is 44×10,000=440,000 cells/ml;

Count how much cell/medium stock needed: will use 4 plates (60 wells) in the assay; count extra wells for safety reason. If we need 300 wells, in each well will be 5,000 cells in 0.1 ml media; so total we need 1,500,000 cells in 30 ml media. 1,500,000 cells/440,000=3.4 ml of cells/media mix need to take from flask and transfer to 26.6 ml media. In 50 ml Falcon tube, combine 26.6 ml fresh medium and 3.4 ml cells. Gently mix.

2 Transfer 100 µL of prepared cells/medium mix to proper wells, keep overnight at 37° C., 5% $CO_2$.

Talc Preparation;
1. Under the hood transfer sterile talc approximately 25 mg of talc to each of 4 sterile Eppendorf tubes, and approximately 150 mg of sterile talc to one tube. Total tubes are 5. Close tubes and weigh exactly how much talc added to each tube. Result: tube #1 (Bleomycin)=52.0 mg; tube #2(Mitomycin)=35.2 mg, tube #3(Dox)=42.4 mg, tube #4 (Paclitaxel)=44.0 mg. Tube #5(no drugs)=133.6 mg.
2. Talc/Bleomycin preparation: need to make 400 µL of 1 mg/ml solution. Reconstitute powder of drug in 100 µL of sterile water; stock of drug will be 100 mg/ml. To make 400 µL of 1 mg/ml Bleomycin, combine 396.0 µL DPBS+4.0 µL of Bleomycin stock. Final solution is 400 µL of 1 mg/ml of Bleomycin. Mix talc in tube #1 with this solution.
3. Talc/Mitomycin preparation: use stock solution 2.99 mM to make 500 µL of 200 µM Mitomycin solution use stock 2.99 mM; combine 466.6 µL DPBS+33.4 µL stock. Final solution is 500 µL of 200 µM Mitomycin. Mix talc in tube #2 with this solution.
4. Talc/Doxorubicin preparation: to make 500 µL of 1 µM Doxorubicin use stock 3.45 mM; dilute stock 1:100=495.0

µL DPBS+5 µL stock; combine 485.5 µL DPBS+14.5 µL of 1:100 dilution of stock. Mix talc in tube #3 with this solution.

5. Talc/PACLITAXEL preparation: to make 500 µL of 1 µM paclitaxel solution use stock 7.03 mM; dilute stock 1:100=495 µL DPBS+5 µL stock; combine 482 µL DPBS+18.0 µL of 1:100 dilution of paclitaxel stock. Final solution is 500 µL of 1 µM paclitaxel. Mix talc in tube #4 with this solution.

6. Add 1 ml DPBS in tube #5, mix talc with DPBS.

7. Protect tubes from light, tape them on rotator and incubate o/n at RT.

DAY 2

Preparation of Talc

1. Centrifuge tubes at 3200 rpm for 3 min. Take out supernatant. Wash pellet in tubes #1, #2, #3, #4 3 times with 1.0 ml of DPBS (sterile) after last wash add to tube #1: contains 52.0 mg talc, 104.0 µL of media; final concentration talc in tube will be 0.5 mg/µL. Add to tube #2 contains 35.2 mg talc, 70.4 µL of media; to tube #3 contains 42.4 mg talc add 84.8 µL media; for tube #4 contains 44.0 mg talc add 88.8 µL media; for tube #5 contains 133.6 mg talc add 267.2 µL media; final concentration talc in all tubes will be 0.5 mg/µL.

2. Keep tubes with talc at RT.

3. Prepare first working solution of talc from tube #5: 1.8 ml media+200 µL of 0.5 mg/µL talc. Total concentration will be 5 mg/100 µL. Make dilutions 1:2 (900 µL media+900 µL previous dilution) to make following concentration talc in well 2.5 mg talc/100 µL media; 1.25 mg/100 µL; 0.6 mg/100 µL.

4. Prepare first dilution of each of the above tubes #1, #2, #3, #4 by adding 540 µL media+60 µL of prepared above 0.5 mg (talc and drug)/µL media 5. After preparation of the above solution, prepare 3 subsequent 1:2 serial dilutions of each of the above preparations (300 µL media+300 µL of previous dilution).

6. Add 100 µL of the above preparations in steps #3, #4, #5 to the proper wells as indicated in a 96-well plate layout. The resultant preparation added to each well will give presence of talc in the wells as following: 0.6 mg talc/well, 1.25 mg talc/well, 2.5 mg talc/well, and 5.0 mg talc/well after sequential dilutions (1:2) across plate.

Preparation of Bleomycin:

Prepare the Following Dilutions of Bleomycin (1) 1 mg/ml (625 µM),
(2) 250 µg/ml (156.3 µM),
(3) 62.5 µg/ml (39 µM),
(4) 15.6 µg/ml (9.75 µM),
(5) 3.9 µg/ml (2.43 µM),
(6) 0.97 µg/ml (0.6 µM),
(7) 0.24 µg/ml (0.15 µM),
(8) 0.06 µg/ml (0.038 µM).

Prepare 500 µL stock solution of 625 µM
Bleomycin as follows:

1. 450 µL media+50 µL of stock (6.25 mM bleomycin).

2. Following preparation of above solution prepare the above 7 sequential serial dilutions using the following formula: 375 µL media+125 µL of prior dilution.

3. Add 100 µL of each 8 preparations of diluted bleomycin (step 1 and 2) to the proper wells according to a plate layout.

4. Add 100 µL of media for untreated cells that will use as a control and not contain any drug or any kind of talc.

5. Preparation of mitomycin (stock 2.99 mM):
Prepare the Following Dilutions (1:5) of Drug:
(1) 200 µM
(2) 40 µM
(3) 8 µM
(4) 1.6 µM
(5) 0.32 µM
(6) 0.064 µM
(7) 0.013 µM
(8) 0.0026 µM 6. Prepare 600 µL of 400 µM Mitomycin solution (double concentration to keep 200 µM drug in total volume 200 µL media in well) as follows: 520.0 µL media+80.2 µL of stock.

7. Following preparation of above solution prepare the above 7 sequential serial dilutions using the following formula: 480 µL media+120 µL of prior dilution.

8. Add 100 µL of each 8 preparations of diluted MITOMYCIN to the proper wells according to a plate layout.

Preparation of DOXORUBICIN (stock 3.45 mM): Prepare the following dilutions (1:5) of drug:
(1) 10 µM
(2) 2 µM
(3) 0.4 µM
(4) 0.08 µM
(5) 0.016 µM
(6) 0.0032 µM
(7) 0.00064 µM
(8) 0.000128 µM Prepare 600 µL of 20 µM doxorubicin solution (double concentration to keep 10 µM drug in total volume 200 µL media in well) as follows:

1. 565.2 µL media+34.8 µL of 1:10 dilution of doxorubicin stock.

2. Following preparation of above solution prepare the above 7 sequential serial dilutions using the following formula: 480 µL media+120 µL of prior dilution.

3. Add 100 µL of each 8 preparations of diluted doxorubicin (step 1 and 2) to the proper wells according to a plate layout. Preparation of paclitaxel (stock 7.03 mM):

1. Prepare the following dilutions (1:5) of drug:
(1) 20 µM
(2) 4 µM
(3) 0.8 µM
(4) 0.16 µM
(5) 0.032 µM
(6) 0.0064 µM
(7) 0.00128 µM
(8) 0.000256 µM 2. Prepare 600 µL of 40 µM paclitaxel solution (double concentration to keep 20 µM drug in total volume 200 µL media in well) as follows:

565.8 µL media+34.2 µL of 1:10 dilution of
Paclitaxel Stock.

3. Following preparation of above solution prepare the above 7 sequential serial dilutions using the following formula: 480 µL media+120 µL of prior dilution.

4. Add 100 µL of each 8 preparations of diluted paclitaxel (step 1, 2, 3) to the proper wells according to a plate layout.

5. Add 100 µL of media for untreated cells that will use as a control and not contain any drug or any kind of talc.

6. Check the plates and start incubation for 72 hrs at 37° C./5% $CO_2$.

DAY 3
1. Mix talc in wells by pipetting up and down. Continue incubation plate at 37° C./5% $CO_2$.

DAY 4
1. Mix talc in wells by pipetting up and down. Continue incubation plate at 37° C./5% $CO_2$.

DAY 5
1. Check plate under microscope, no visible sign of contamination is present.
1. Mix talc/media liquid in the wells. Using needle/vacuum system, remove all liquid from all wells.
2. Wash all cells 1×300 μL DPBS, remove final wash.
3. Add 120 μL fresh media to all wells.
4. Add 20 μL of CellTiter 96 Aqueous One solution to each well.
5. Incubate plate 1 hr at 37° C., 5% $CO_2$.
6. Read absorbance in plate reader at 490 nm.
7.

TABLE 83

Figure 31:
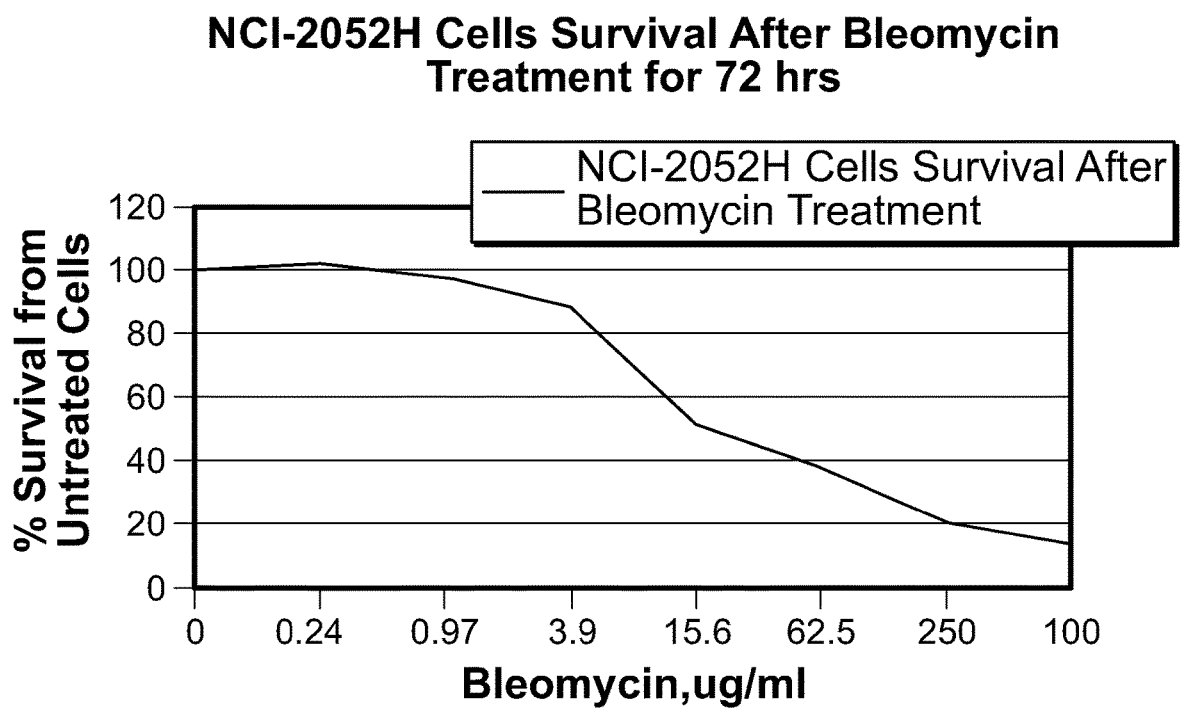
FIG. 31 is a scatter plot depicting % NCI-2052H cells survival after 72 hours exposure to bleomycin.

Average readings: cells + drug, bleomycin, μg/ml (see e.g., FIG. 31).

| 0 | 0.24 | 0.97 | 3.9 | 15.6 | 62.5 | 250 | 1000 |
|---|---|---|---|---|---|---|---|
| 1.32366 | 1.3454 | 1.2884 | 1.1733 | 0.684633 | 0.507533 | 0.276567 | 0.193467 |

TABLE 84

% survival from untreated cells (see e.g., FIG. 31).

Bleomycin, ug/ml

| 0 | 0.24 | 0.97 | 3.9 | 15.6 | 62.5 | 250 | 1000 |
|---|---|---|---|---|---|---|---|
| 100 | 101.64 | 97.34 | 88.64 | 51.72 | 38.34 | 20.89 | 14.62 |

TABLE 85

Figure 32:
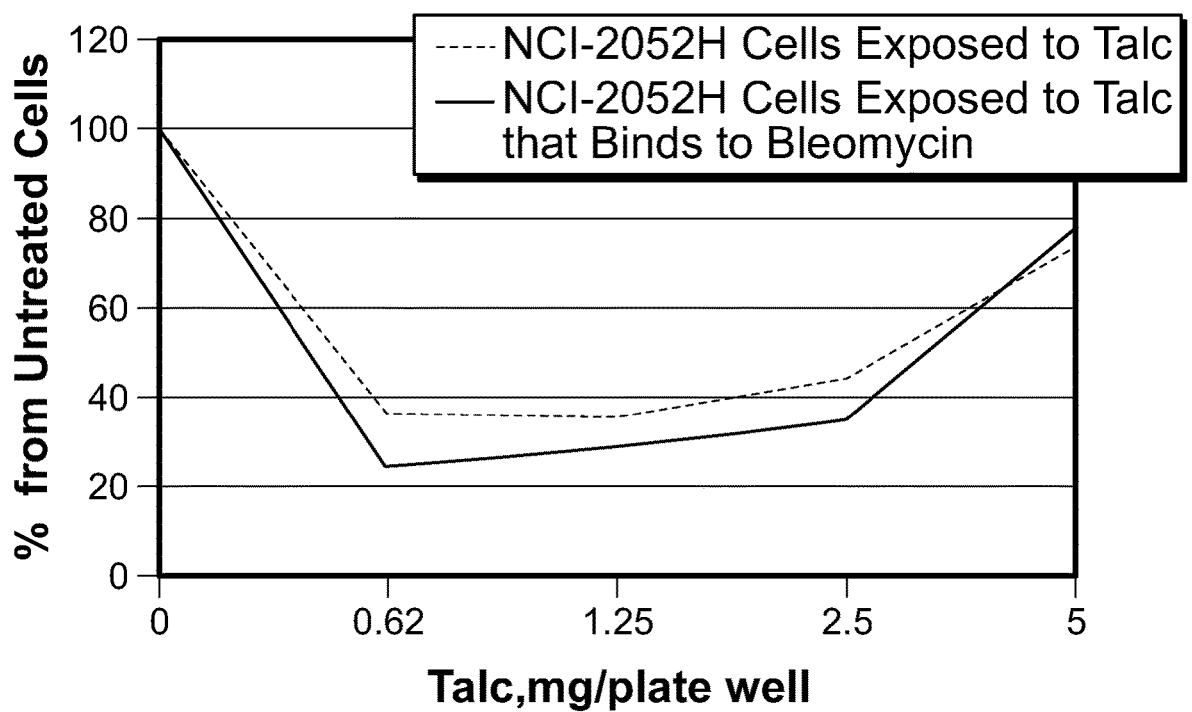
FIG. 32 is a scatter plot depicting % NCI-2052H cells survival after exposure to talc or talc/bleomycin.
Figure 33:
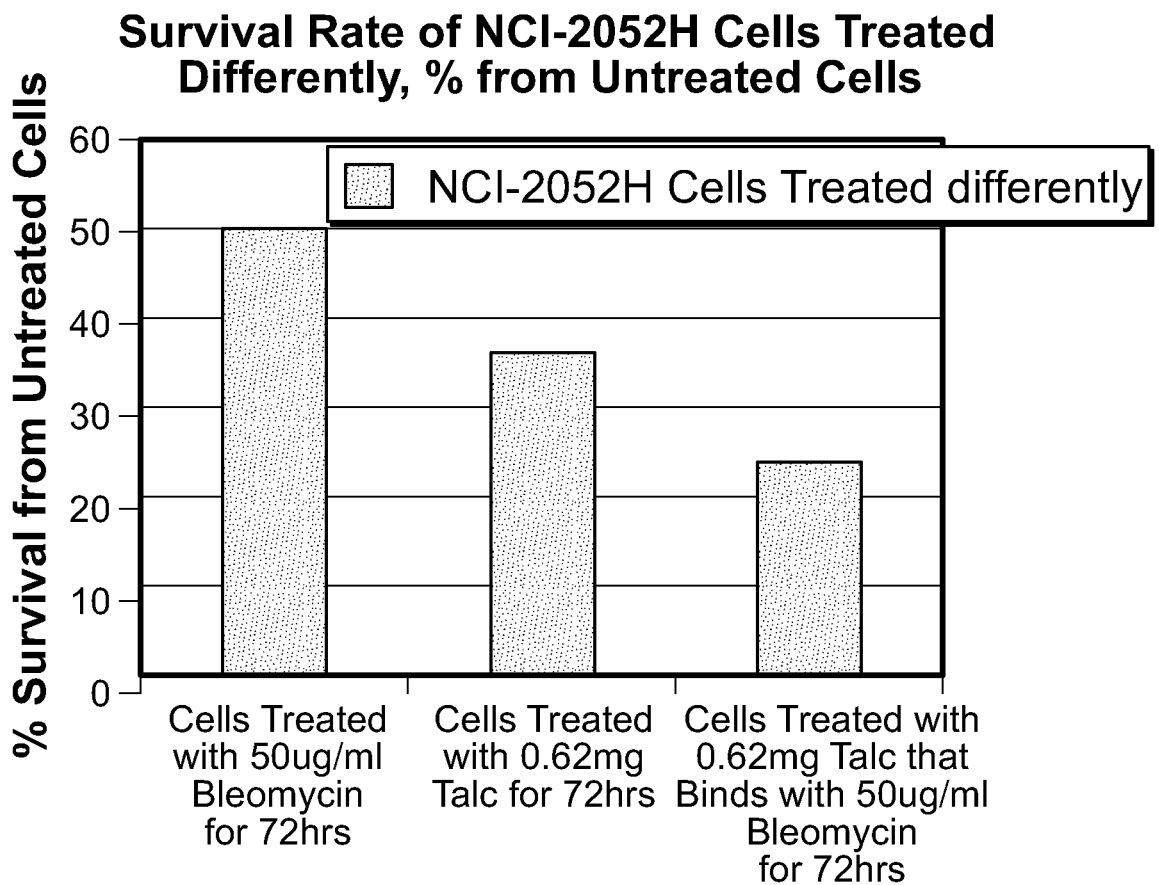
FIG. 33 is the data and a bar graph showing the comparison of survival NCI-2052H cells with different treatments.

Average readings: talc, talc + drug (see e.g., FIG. 32).
talc, mg/well

| | 0 | 0.62 | 1.25 | 2.5 | 5 |
|---|---|---|---|---|---|
| talc only | 1.32366 | 0.4757 | 0.47085 | 0.5883 | 0.97375 |
| talc + Bleo | 1.32366 | 0.3168 | 0.3819 | 0.46465 | 1.0287 |

TABLE 86

% survival from untreated cells (see e.g., FIG. 32).
talc, mg/well

| | 0 | 0.62 | 1.25 | 2.5 | 5 |
|---|---|---|---|---|---|
| talc only | 100 | 35.94 | 35.57 | 44.44 | 73.56 |
| talc + Bleo | 100 | 23.93 | 28.85 | 35.10 | 77.72 |

TABLE 87

Figure 34:
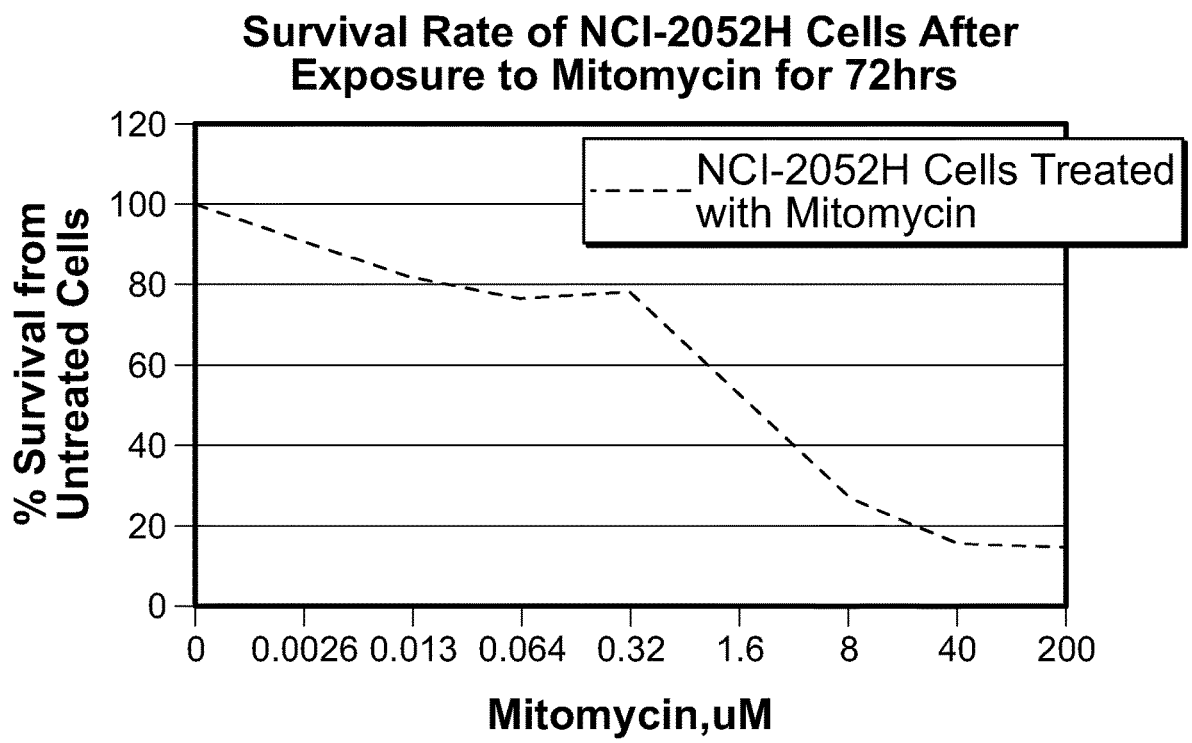
FIG. 34 is a scatter plot depicting % NCI-2052H cells survival after 72 hours exposure to mitomycin.

Average reading: cells + drug, mitomycin, μM (see e.g., FIG. 34).

| 0 | .0026 | 0.013 | 0.064 | 0.32 | 1.6 | 8 | 40 | 200 |
|---|---|---|---|---|---|---|---|---|
| 1.57579 | 1.423967 | 1.283633 | 1.199233 | 1.2222 | 0.813767 | 0.4142 | 0.2305 | 0.209833 |

TABLE 88

Average reading: cells + talc/mitomycin.
talc, mg/well

|  | 0 | 0.62 | 1.25 | 2.5 | 5 |
|---|---|---|---|---|---|
| cells + talc | 1.57579 | 0.359 | 0.4202 | 0.5906 | 1.26305 |
| cells + talc/Mitomycin | 1.57579 | 0.4339 | 0.51025 | 0.79055 | 1.0963 |

TABLE 89

% survival from untreated cells.
talc, mg/well

|  | 0 | 0.62 | 1.25 | 2.5 | 5 |
|---|---|---|---|---|---|
| cells + talc | 100 | 22.78 | 26.67 | 37.48 | 80.15 |
| cells + talc/Mitomycin | 100 | 27.54 | 32.38 | 50.17 | 69.57 |

TABLE 90

Figure 35:
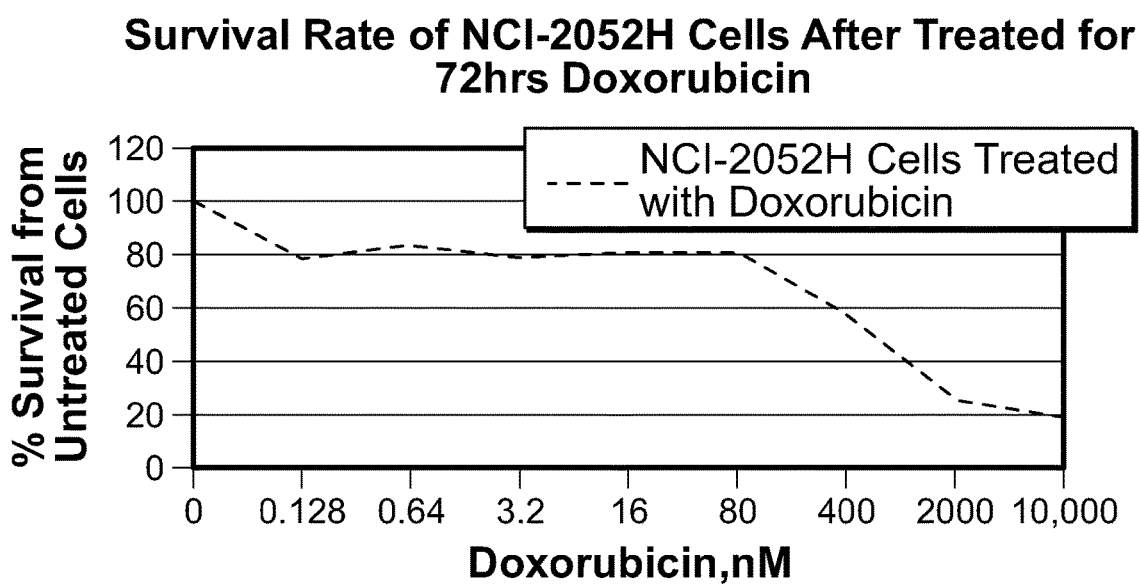
FIG. 35 is a scatter plot depicting % NCI-2052H cells survival after 72 hours exposure to doxorubicin.

Average reading: cells after treated for 72 hrs with doxorubicin, nM (see e.g., FIG. 35).

| 0 | 0.128 | 0.64 | 3.2 | 16 | 80 | 400 | 2000 | 10,000 |
|---|---|---|---|---|---|---|---|---|
| 1.37733 | 1.082267 | 1.149067 | 1.084133 | 1.1113 | 1.1153 | 0.795533 | 0.352467 | 0.2605 |

TABLE 91

% survival from untreated cells, doxorubicin, nM (see e.g., FIG. 35).

| 0 | 0.128 | 0.64 | 3.2 | 16 | 80 | 400 | 2000 | 10,000 |
|---|---|---|---|---|---|---|---|---|
| 100 | 78.58 | 83.43 | 78.71 | 80.69 | 80.98 | 57.76 | 25.59 | 18.91 |

TABLE 92

Figure 36:
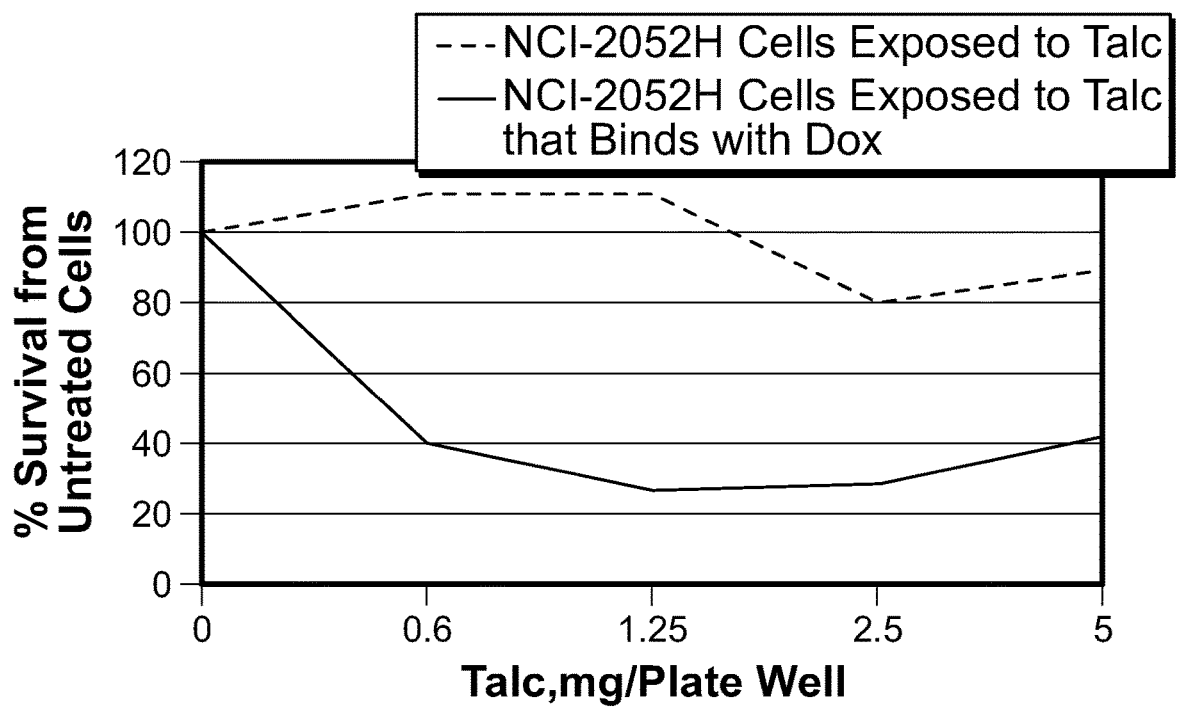
FIG. 36 is a scatter plot depicting % NCI-2052H cells survival after exposure to talc or talc/doxorubicin.

Average readings: cells + talc/doxorubicin (see e.g., FIG. 36).
talc, mg/well

|  | 0 | 0.6 | 1.25 | 2.5 | 5 |
|---|---|---|---|---|---|
| cells + talc | 1.37733 | 1.52825 | 1.5293 | 1.1036 | 1.2317 |
| cells + talc/Dox | 1.37733 | 0.5573 | 0.37065 | 0.3926 | 0.5758 |

TABLE 93

% survival from untreated cells (see e.g., FIG. 36).
talc, mg/well

|  | 0 | 0.6 | 1.25 | 2.5 | 5 |
|---|---|---|---|---|---|
| cells + talc | 100 | 110.96 | 111.03 | 80.13 | 89.43 |
| cells + talc/Dox | 100 | 40.46 | 26.91 | 28.50 | 41.81 |

TABLE 94

Figure 37:
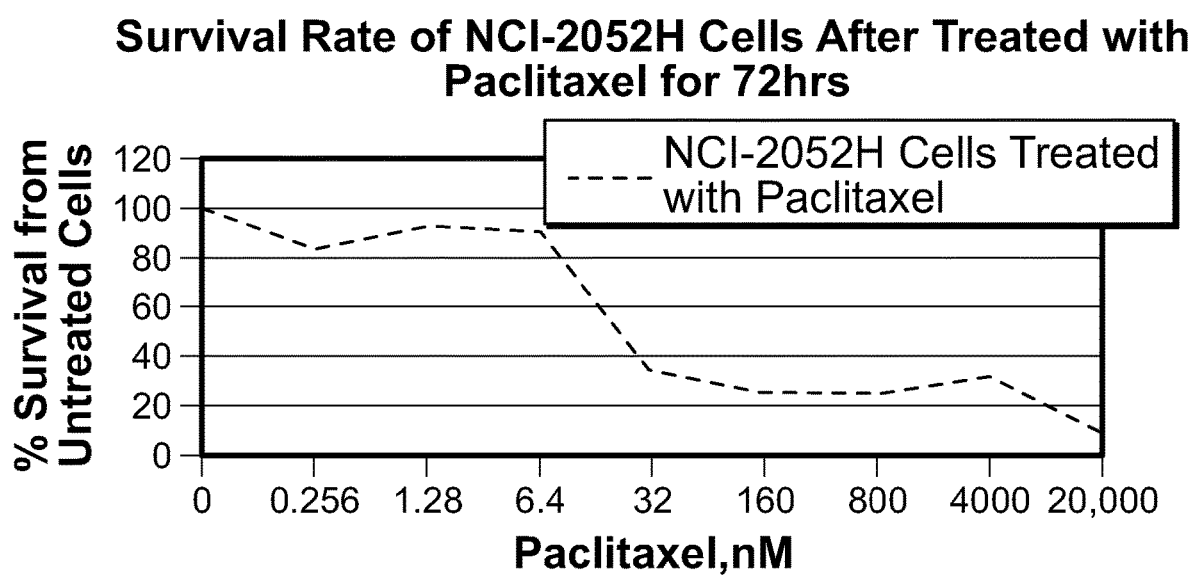
FIG. 37 is a scatter plot depicting % NCI-2052H cells survival after 72 hours exposure to paclitaxel.

Average reading: cells + drug, paclitaxel, nM (see e.g., FIG. 37).
Paclitaxel, nM

| 0 | 0.256 | 1.28 | 6.4 | 32 | 160 | 800 | 4000 | 20,000 |
|---|---|---|---|---|---|---|---|---|
| 1.70244 | 1.4273 | 1.5873 | 1.539567 | 0.581767 | 0.436067 | 0.4326 | 0.552967 | 0.1647 |

TABLE 95

% survival from untreated cells (see e.g., FIG. 37).

| 0 | 0.256 | 1.28 | 6.4 | 32 | 160 | 800 | 4000 | 20,000 |
|---|---|---|---|---|---|---|---|---|
| 100 | 83.84 | 93.24 | 90.43 | 34.17 | 25.61 | 25.41 | 32.48 | 9.67 |

TABLE 96

Average absorbance reading: cells + talc; cells + talc binds to paclitaxel.
Talc, mg/well (see e.g., FIG. 38).

|  | 0 | 0.62 | 1.25 | 2.5 | 5 |
|---|---|---|---|---|---|
| cells + talc | 1.70244 | 0.6172 | 0.96435 | 0.29925 | 0.4724 |
| cells + talc, that binds to Taxol | 1.70244 | 0.20145 | 0.2091 | 0.3997 | 0.54495 |

TABLE 97

Figure 38:
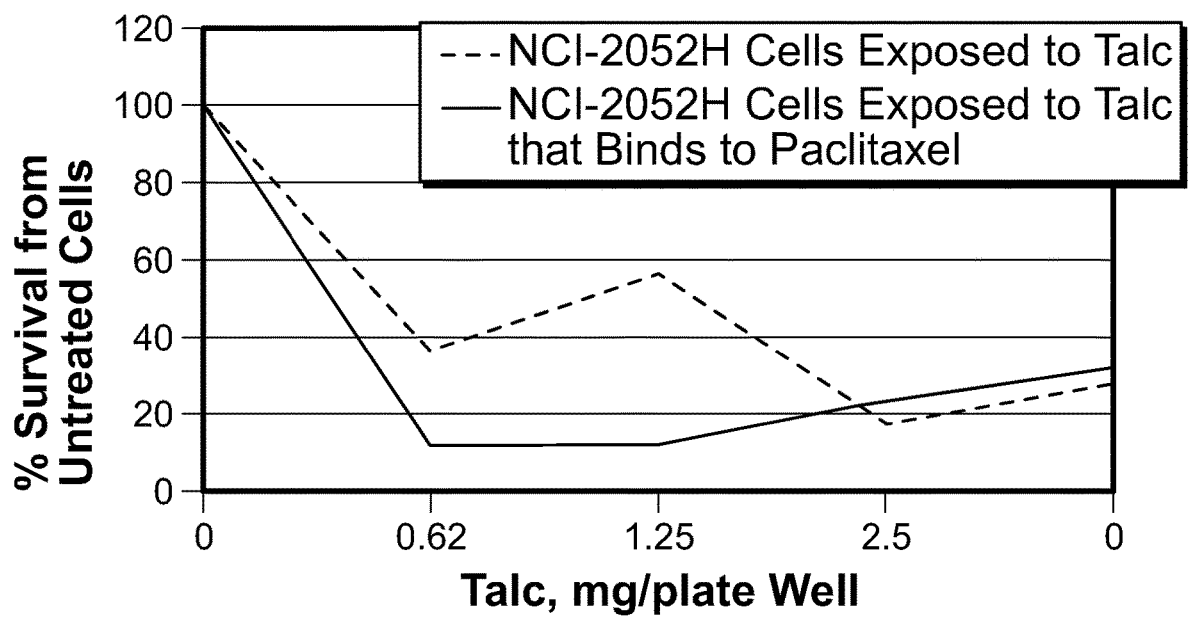
FIG. 38 is a scatter plot depicting % NCI-2052H cells survival after 72 hours exposure to talc or talc/paclitaxel.
Figure 39:
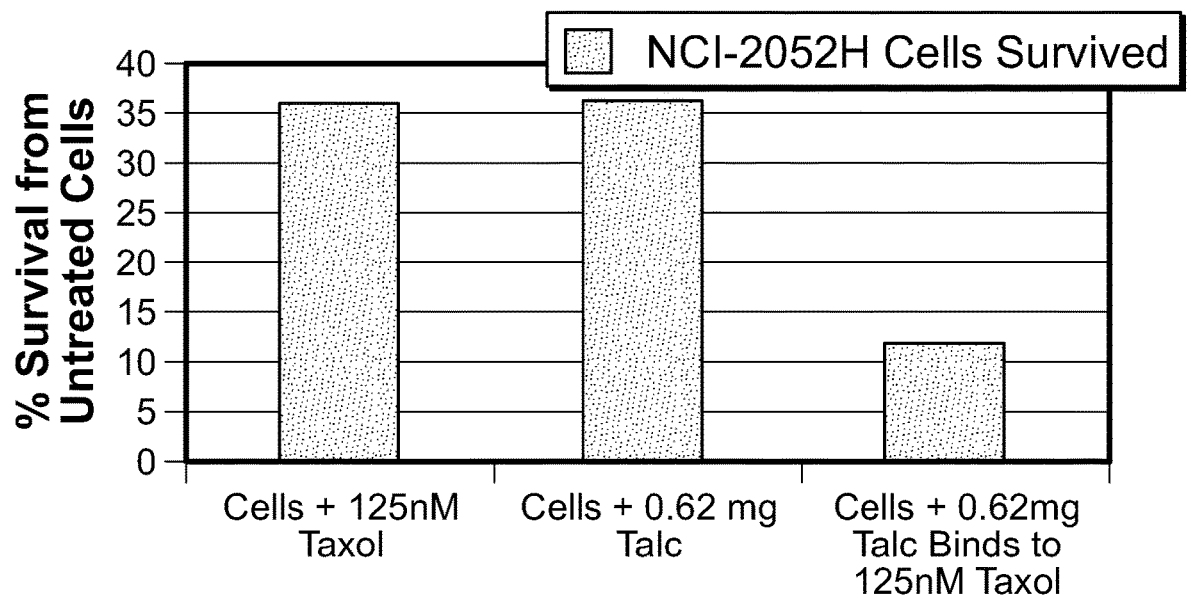
FIG. 39 is the data and a bar graph showing the comparison of survival NCI-2052H cells with different treatments.

% survival from untreated cells (see e.g., FIG. 38).

|  | 0 | 0.62 | 1.25 | 2.5 | 5 |
|---|---|---|---|---|---|
| cells + talc | 100 | 36.25 | 56.65 | 17.58 | 27.75 |
| cells + talc, that binds to Taxol | 100 | 11.83 | 12.28 | 23.48 | 32.01 |

The study showed enhanced cytotoxicity on NCI-2052H cells when cells are exposed to talc conjugated to the following chemotherapy drugs: bleomycin, doxorubicin, and paclitaxel vs. talc alone. But the talc-mitomycin conjugate demonstrated less cytotoxicity than talc alone. The result was not expected, thus, additional experiments for mitomycin and NCI-2052H were performed to test if the results were correct.

Example 24: Repeated Cytotoxicity Experiment: NCI-2052H Cells Treated with Mitomycin, Talc Alone and Talc Bound to Mitomycin The following Example repeated the experiment in Example 23 with NCI-2052H and mitomycin.

Plan: repeat one more time experiment when NCI-2052H cells exposed for 72 hrs to Mitomycin, talc and talc bound to Mitomycin. Compare survival rate of cells.

Materials:
1. Mitomycin 20 mg; Accord, cat. # NDC 16729-10811, lot #PP01516, exp. July 2015.
2. Sterile Talc Powder, Bryan Corporation, cat. # NDC 63256-200-05; lot #: 3M021; exp. December 2016.
3. DPBS 1×; ATCC, Cat. #: 30-2200, Lot #: 61443818.
4. NCI-2052H cell line, ATCC, cat. #: CRL-5915, lot #: 57608140.
5. RPMI-1640 media; ATCC cat. #30-2001, lot #62027197.
6. Trypsin-EDTA; ATCC cat. #30-2101, lot #61618818.
7. Fetal Bovine serum, ATCC cat. #3022.
8. CellTiter 96 AQueous One Solution cell proliferation assay; Promega cat # G3581.

DAY 1
1. Use NCI-2052H cells, passage 9 to fill up 96 well microplate with 5,000 cells per well. Protocol how to do that see in previous cytotoxicity experiment.
2. Incubate plate overnight at 37° C., 5% $CO_2$.
3. Prepare talc: under the hood transfer sterile talc approximately 25 mg of talc to each of 2 sterile Eppendorf tubes. Close tubes and weigh how much exactly talc added to each tube. Result: tube #1=48.1 mg; tube #2=44.5 mg.
4. Add 500 µL DPBS (sterile) to tube #1, add 500 µL DPBS containing 200 µM Mitomycin to tube #2.
5. Talc/mitomycin preparation: use Mitomycin stock 2.99 mM. To make 500 µL of 200 uM Mitomycin combine 466.6 µL DPBS+33.4 µL stock. Mix talc in tube #2 with this solution.
6. Incubate both tubes overnight at 4° C., on rotator.

DAY 2
Preparation of Talc.
1. Centrifuge tubes at 3200 rpm for 3 min. Take out supernatant. Wash pellet in tubes #1 and #2 3 times with 1.0 ml of DPBS (sterile) after last wash add to tube #1: contains 48.1 mg talc, 96.2 µL of media; final concentration talc in tube will be 0.5 mg/µL. Add to tube #2 contains 44.5 mg talc 89.0 µL of media; final concentration talc in the tube will be 0.5 mg/µL.
2. Keep tubes with talc at RT.
3. Prepare first dilution of talc from tube #1: 540 µL media+60 µL of 0.5 mg/µL talc. Total concentration will be 5 mg/100 µL. Make dilutions 1:2 (300 µL media+300 µL previous dilution) to make following concentration talc in well 2.5 mg talc/100 µL media; 1.25 mg/100 µL; 0.6 mg/100 µL.
4. Prepare dilutions from tube #2 by adding 540 µL media+60 µL of prepared above 0.5 mg (talc bound to drug)/µL media.
5. After preparation of the above solution, prepare 3 subsequent 1:2 serial dilutions (300 µL media+300 µL of previous dilution).
6. Add 100 µL of the above preparations to the proper wells as indicated in a 96-well plate layout. The resultant preparation added to each well will give presence of talc in the wells as following: 0.6 mg talc/well, 1.25 mg talc/well, 2.5 mg talc/well, and 5.0 mg talc/well after sequential dilutions (1:2) across plate.

Preparation of mitomycin (stock 2.99 mM): Prepare the following dilutions (1:5) of drug:
(1) 200 µM
(2) 40 µM
(3) 8 µM
(4) 1.6 µM
(5) 0.32 µM
(6) 0.064 µM
(7) 0.013 µM
(8) 0.0026 µM 1. Prepare 600 µL of 400 µM Mitomycin solution (double concentration to keep 200 µM drug in total volume 200 µL media in well) as follows: 519.8 µL media+80.2 µL of stock.
2. Following preparation of above solution prepare the above 7 sequential serial dilutions using the following formula: 480 µL media+120 µL of prior dilution.
3. Add 100 µL of each 8 preparations of diluted mitomycin to the proper wells according to a plate layout.

Incubation
1. Incubate plate for 72 hrs at 37° C., 5% $CO_2$.

DAY 3
1. Check plate under microscope. Continue incubation plate at 37° C./5% $CO_2$.

DAY 4
1. Check plate under microscope. Continue incubation plate at 37° C./5% $CO_2$.

DAY 5
1. Check plate under microscope, no visible sign of contamination is present.
2. Mix talc/media liquid in the wells. Using needle/vacuum system, remove all liquid from all wells.
3. Wash all wells 1×300 µL DPBS, remove final wash.
4. Add 120 µL fresh media to all wells.
5. Add 20 µL of CellTiter 96 Aqueous One solution to each well.
6. Incubate plate 1 hr at 37° C., 5% $CO_2$.
7. Read absorbance in plate reader at 490 nm.
8. Results and Data:

TABLE 98

Figure 40:
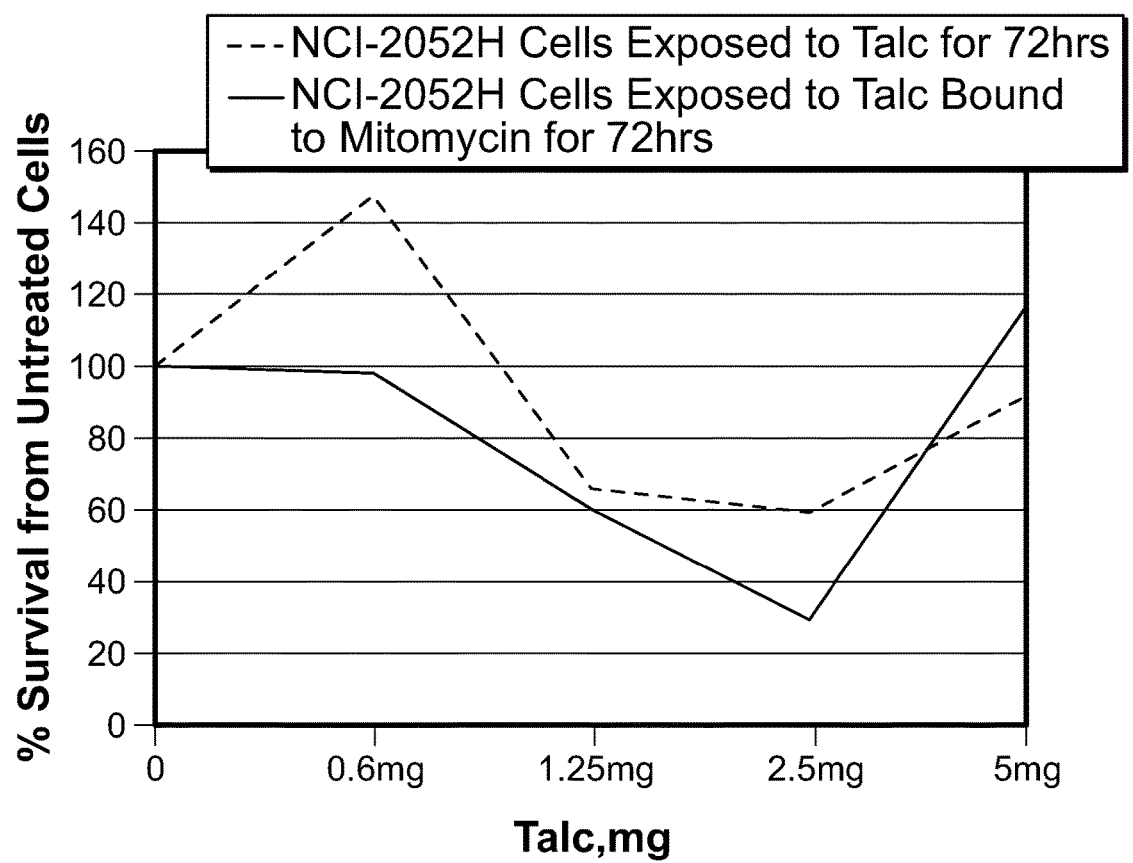
FIG. 40 is a scatter plot depicting % NCI-2052H cells survival after 72 hours exposure to talc or talc/mitomycin.

Average absorbance reading: cells + talc + talc/drug (see e.g., FIG. 40).

| | Talc, mg | | | | |
|---|---|---|---|---|---|
| | 0 | 0.6 mg | 1.25 mg | 2.5 mg | 5 mg |
| cells + talc | 1.095 | 1.615 | 0.72 | 0.6485 | 1.0035 |
| cells + talc/Mitomycin | 1.095 | 1.076 | 0.659 | 0.316 | 1.28 |

TABLE 99

% survival from untreated cells (see e.g., FIG. 40).

| | Talc, mg | | | | |
|---|---|---|---|---|---|
| | 0 | 0.6 mg | 1.25 mg | 2.5 mg | 5 mg |
| cells + talc | 100 | 147.49 | 65.75 | 59.22 | 91.64 |
| cells + talc/Mitomycin | 100 | 98.26 | 60.18 | 28.86 | 116.89 |

TABLE 100

Figure 41:
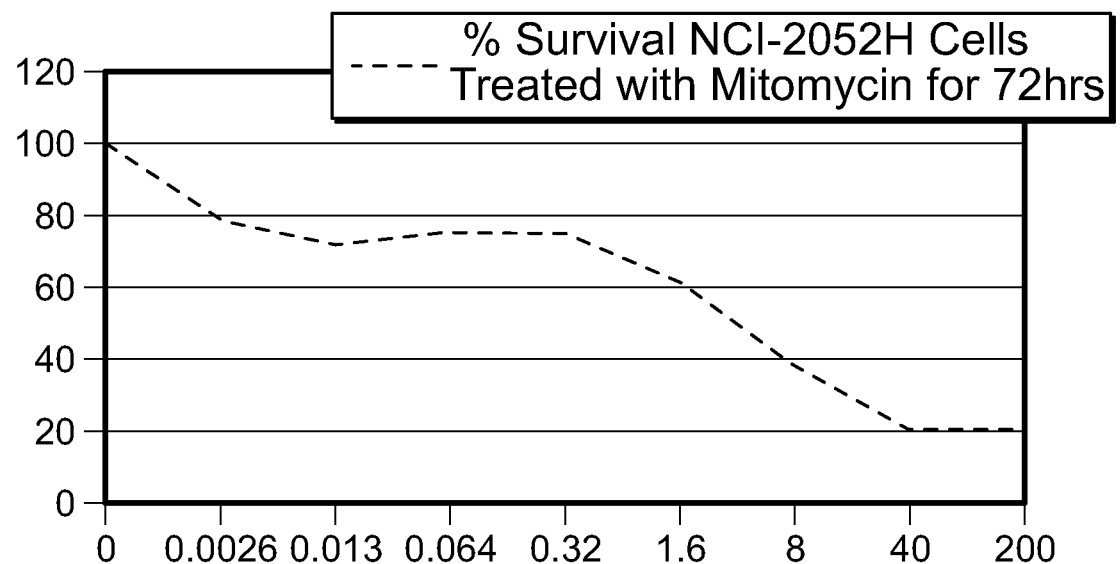
FIG. 41 is a scatter plot depicting % NCI-2052H cells survival after 72 hours exposure to mitomycin.

| Average reading: drug + cells (see e.g., FIG. 41). Mitomycin, uM | | | | | | | | |
|---|---|---|---|---|---|---|---|---|
| 0 | .0026 | 0.013 | 0.064 | 0.32 | 1.6 | 8 | 40 | 200 |
| 1.095 | 0.863667 | 0.790667 | 0.826667 | 0.822333 | 0.677 | 0.421667 | 0.225667 | 0.224333 |

TABLE 101

| % survival from untreated cells (see e.g., FIG. 41). | | | | | | | | |
|---|---|---|---|---|---|---|---|---|
| 0 | 0.0026 | 0.013 | 0.064 | 0.32 | 1.6 | 8 | 40 | 200 |
| 100 | 78.87 | 72.21 | 75.49 | 75.10 | 61.83 | 38.51 | 20.61 | 20.49 |

The study showed clear cytotoxic effect on NCI-2052H cells with talc alone. Further, when talc is bound to mitomycin, toxicity was enhanced.

Example 25: Inhibition of Non-Specific Binding of Biotin-Rhodamine to Talc by Washing with Low and High pH Buffers The following Example determined if various buffers of varying pH (4.8-8.0) effect the binding of Biotin-Rhodamine to talc particles.

Plan: incubate talc with Biotin Rhodamine. Make washings using different pH buffers: PBS, TBS (pH 8.0), Citrate buffer (pH 4.8). Run fluorescent assay.

Materials:
1. Sterile Talc Powder (Bryan Corporation, Cat. #: 1690, Lot #: 3M021, Exp. Date: December 2016)
2. 10×PBS (Sigma, Cat. #: P5493-1L, Lot #: SLBB9685)
3. Water (Sigma Life Science, Cat. #: 3500, Lot #: RNBD1156)
4. Water deionized; Sigma-Aldrich, cat. #38796-1L; lot # BCBM0010V
5. Biotin rhodamine 110; Biotium, cat. #80022.
6. Tris Buffered Saline pH 8.0, powder; Sigma cat. #T6664-10 pak; lot #SLBK8366V.
7. Citrate Buffer solution, 0.09 M; Sigma, cat. # C2488-500 ml, lot # SLBD8857V DAY 1
1. Add 25 mg talc to the each of 4 eppendorf tubes (round bottom). Label tubes as #1, #2, #3, #4.
2. Add to each tube 500 µL 1×PBS.
3. Add 5 µL of Biotin Rhodamine (concentration: 16 µg/µL) to the tubes #1, #2, #3, but not to tube #4.
4. Mix well, incubate all tubes for 1 hr at 4° C., rotator. Protect from light.
5. Wash talc in tube #1 three times with 500 µL TBS; in tube #2 three times with 500 µL Citrate buffer and in tube #3 three times with PBS. (Centrifuge speed –3200 rpm for 3 min)
6. Centrifuge talc in tube #4 and remove supernatant.
7. Add to all tubes 200 µL PBS, mix well.
8. Transfer 50 µL talc mix from each tube to fluorescent assay 96 well plate. Then add to each well 100 µL PBS to keep talc in equal distribution around well.
9. Run fluorescent assay using settings excitation/emission as 496 nm/520 nm.

TABLE 102

| Average fluorescent signal (Rhodamine 110). | |
|---|---|
| | Average fluorescent signal (RHODAMINE 110) |
| talc/Biotin washed with TBS, pH 8.0 | 12868.68 |
| talc/Biotin washed with Citrate buffer, pH 4.8 | 14027.61 |
| talc/Biotin washed with PBS | 13760.41 |
| Talc in PBS, no Biotin | 715.75 |

The evidence strongly suggests the presence of Biotin-Rhodamine on talc. Changing pH of washing buffers did not change amount of Biotin Rhodamine that nonspecifically bound with talc. Thus, the study showed strong evidence that pH does not affect the binding of Biotin-Rhodamine to talc particles.

The invention claimed is:

1. A method of treating abdominal cancer in a subject comprising administering to a subject in need thereof a composition comprising:
 a therapeutic agent; and
 a substrate;
 wherein,
  the therapeutic agent is contained in or on the substrate;
  the substrate comprises gelfoam loaded with avidin-poly(ethylene glycol); and
  the therapeutic agent is bound to the substrate prior to administration to the subject.

2. The method of claim 1, wherein the abdominal cancer comprises at least one of bladder cancer, ovarian cancer, uterine cancer, malignant pleural mesothelioma, peritoneal carcinomatosis, colorectal cancer, liver cancer, pancreatic carcinoma, peritoneal mesothelioma, gastric cancer, renal carcinoma, colon cancer, stomach cancer, esophageal cancer, or appendiceal cancer.

3. The method of claim 1, wherein the abdominal cancer comprises stomach cancer.

4. The method of claim 1, wherein the abdominal cancer comprises uterine cancer.

5. The method of claim 1, wherein the abdominal cancer comprises bladder cancer.

* * * * *